US012448444B2

(12) United States Patent
Chauchet et al.

(10) Patent No.: US 12,448,444 B2
(45) Date of Patent: Oct. 21, 2025

(54) BISPECIFIC ANTIBODIES TARGETING CD47 AND PD-L1 AND METHODS OF USE THEREOF

(71) Applicant: NovImmune SA, Geneva (CH)

(72) Inventors: Xavier Chauchet, Geneva (CH); Krzysztof Masternak, Mollens (CH); Limin Shang, Bellevue (CH); Giovanni Magistrelli, Cessy (FR); Nicolas Fischer, Lancy (CH)

(73) Assignee: Novimmune SA, Geneva (CH)

( * ) Notice: Subject to any disclaimer, the term of this patent is extended or adjusted under 35 U.S.C. 154(b) by 0 days.

(21) Appl. No.: 17/701,573

(22) Filed: Mar. 22, 2022

(65) Prior Publication Data

US 2022/0315655 A1 Oct. 6, 2022

Related U.S. Application Data

(60) Provisional application No. 63/317,899, filed on Mar. 8, 2022, provisional application No. 63/164,329, filed on Mar. 22, 2021.

(51) Int. Cl.
*C07K 16/28* (2006.01)
*A61K 39/00* (2006.01)
*A61P 35/00* (2006.01)

(52) U.S. Cl.
CPC .......... *C07K 16/2803* (2013.01); *A61P 35/00* (2018.01); *C07K 16/2827* (2013.01); *A61K 2039/505* (2013.01); *C07K 2317/31* (2013.01); *C07K 2317/73* (2013.01); *C07K 2317/76* (2013.01); *C07K 2317/92* (2013.01)

(58) Field of Classification Search
CPC ............ C07K 16/2803; C07K 16/2827; C07K 2317/31; C07K 2317/73; C07K 2317/76; C07K 2317/92; A61P 35/00; A61K 2039/505
See application file for complete search history.

(56) References Cited

U.S. PATENT DOCUMENTS 3,773,919 A 11/1973 Boswell et al.
4,485,045 A 11/1984 Regen
(Continued)

FOREIGN PATENT DOCUMENTS

EP 1810979 B1 6/2012
EP 3722322 A1 10/2020
(Continued)

OTHER PUBLICATIONS

Baldrick, P., "Pharmaceutical excipient development: the need for preclinical guidance," Regulatory Toxicology and Pharmacology, Oct. 2000, 32(2), pp. 210-218.
(Continued)

*Primary Examiner* — Aurora M Fontainhas
*Assistant Examiner* — Selam Berhane
(74) *Attorney, Agent, or Firm* — Fenwick & West LLP; Matthew Pavao

(57) ABSTRACT

This disclosure provides novel bispecific antibodies that specifically bind to CD47 and Programmed Death-Ligand 1 (PD-L1). The disclosure further relates to methods of making the bispecific antibodies and nucleic acids encoding the antibodies. The disclosure further relates to therapeutic methods for use of the bispecific antibodies in the treatment of a condition associated with malignant cells expressing CD47 and/or PD-L1.

35 Claims, 18 Drawing Sheets

Specification includes a Sequence Listing.

(56) References Cited

U.S. PATENT DOCUMENTS

| | | | |
|---|---|---|---|
| 4,522,811 | A | 6/1985 | Eppstein et al. |
| 4,544,545 | A | 10/1985 | Ryan et al. |
| 4,676,980 | A | 6/1987 | Segal et al. |
| 4,816,567 | A | 3/1989 | Cabilly et al. |
| 5,013,556 | A | 5/1991 | Woodle et al. |
| 5,030,719 | A | 7/1991 | Umemoto et al. |
| 5,225,539 | A | 7/1993 | Winter |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,916,771 | A | 6/1999 | Hori et al. |
| 5,939,598 | A | 8/1999 | Kucherlapati et al. |
| 6,075,181 | A | 6/2000 | Kucherlapati et al. |
| 6,150,584 | A | 11/2000 | Kucherlapati et al. |
| 6,528,624 | B1 | 3/2003 | Idusogie et al. |
| 9,334,331 | B2 | 5/2016 | Igawa et al. |
| 10,421,807 | B2 | 9/2019 | Gonzales et al. |
| 11,260,117 | B2 | 3/2022 | Masternak et al. |
| 2012/0184716 | A1 | 7/2012 | Fischer et al. |
| 2022/0315654 | A1 | 10/2022 | Chauchet et al. |
| 2023/0355796 | A1 | 11/2023 | Chao et al. |
| 2023/0365682 | A1 | 11/2023 | Chao et al. |

FOREIGN PATENT DOCUMENTS

| | | | |
|---|---|---|---|
| WO | WO-9100360 | A1 | 1/1991 |
| WO | WO-9220373 | A1 | 11/1992 |
| WO | WO-9308829 | A1 | 5/1993 |
| WO | WO-9402602 | A1 | 2/1994 |
| WO | WO-9411026 | A2 | 5/1994 |
| WO | WO-9522618 | A1 | 8/1995 |
| WO | WO-9627011 | A1 | 9/1996 |
| WO | WO-9633735 | A1 | 10/1996 |
| WO | WO-9634096 | A1 | 10/1996 |
| WO | WO-9953049 | A1 | 10/1999 |
| WO | WO-2010135558 | A1 | 11/2010 |
| WO | WO-2011084255 | A2 | 7/2011 |
| WO | WO-2012023053 | A2 | 2/2012 |
| WO | WO-2013088259 | A2 | 6/2013 |
| WO | WO-2014087248 | A2 | 6/2014 |
| WO | WO-2018215835 | A1 | 11/2018 |
| WO | WO-2019016411 | A1 | 1/2019 |
| WO | WO-2019234576 | A1 | 12/2019 |
| WO | WO-2022200387 | A1 | 9/2022 |
| WO | WO-2022200389 | A1 | 9/2022 |

OTHER PUBLICATIONS

Bobo et al. "Convection-enhanced delivery of macromolecules in the brain", Proceedings of the National Academy of Sciences, Mar. 1994, 91(6), pp. 2076-2080.

Bowie et al., "A method to identify protein sequences that fold into a known three-dimensional structure", Science. Jul. 12, 1991; 253(5016): 164-70.

Brodeur et al., "Mouse-Human Myeloma Partners for the Production of Heterohybridomas," Monoclonal Antibody Production Techniques and Applications, Marcel Dekker, Inc., Mar. 1987, pp. 51-63.

Caron et al., "Engineered Humanized Dimeric Forms of IgG Are More Effective Antibodies" the Journal of Experimental Medicine, Oct. 1992, 176(4), pp. 1191-1195.

Chappell, S. et al., "A 9-nt segment of a cellular mRNA can function as an internal ribosome entry site (IRES) and when present in linked multiple copies greatly enhances IRES activity," Proceedings of the National Academy of Sciences, Feb. 2000, 97(4), pp. 1536-1541.

Charman, W.N., "Lipids, lipophilic drugs, and oral delivery-some emerging concepts," Journal of Pharmaceutical Sciences, Aug. 2000, 89(8), pp. 967-978.

Chothia, C. et al., "Canonical Structures for the Hypervariable Regions of Immunoglobins", Journal of Molecular Biology, Aug. 1987, vol. 196, No. 4, pp. 901-917.

Cole, S. et al. "The EBV-Hybridoma Technique and Its Application to Human Lung Cancer," Monoclonal Antibodies and Cancer Therapy 27, Jan. 1985, pp. 77-96.

Cote, R. et al., "Generation of human monoclonal antibodies reactive with cellular antigens," Proceedings of the National Academy of Sciences, Apr. 1983, vol. 80, pp. 2026-2030.

Davidson, B.L. et al., "A model system for in vivo gene transfer into the central nervous system using an adenoviral vector," Nature Genetics, Mar. 1993, vol. 3, pp. 219-223.

Davies et al., "Antibody-Antigen Complexes," Annual Review Biochemistry, Jul. 1990, vol. 59, pp. 439-473.

Davis, J.H et al., "SEEDbodies: fusion proteins based on strand-exchange engineered domain (SEED) CH3 heterodimers in an Fc analogue platform for asymmetric binders or immunofusions and bispecific antibodies," Protein Engineering, Design & Selection, Apr. 2010, vol. 23, No. 4, pp. 195-202.

Deuse, T., et al., "The SIRPα-CD47 immune checkpoint in NK cells," Journal of Experimental Medicine, Mar. 2021, vol. 218, No. 3, 25 pages.

Dumet et al., "Insights into the LgG heavy chain engineering patent landscape as applied to LgG4 antibody development," mAbs, Published: Sep. 2019, vol. 11, No. 8, pp. 1341-1350.

Eppstein et al., "Biological activity of liposome-encapsulated murine interferon y is mediated by a cell membrane receptor," Proceedings of the National Academy of Sciences, Jun. 1985, 82(11), pp. 3688-3692.

Fishwild et al., "High-avidity human IgGk monoclonal antibodies from a novel strain of minilocus transgenic mice," Nature Biotechnology, Jul. 1996, 14(7), pp. 845-851.

Geller, A.I. et al., "An HSV-1 Vector Expressing Tyrosine Hydroxylase Causes Production and Release of L-DOPA from Cultured Rat Striatal Cells," Journal of Neurochemistry, Feb. 1995, 64(2), pp. 487-496.

Geller, A.I. et al., "Infection of cultured central nervous system neurons with a defective herpes simplex virus 1 vector results in stable expression of *Escherichia coli* B-galactosidase," Proceedings of the National Academy of Sciences, Feb. 1990, 87(3), pp. 1149-1153.

Geller, A.I. et al., "Long-term increases in neurotransmitter release from neuronal cells expressing a constitutively active adenylate cyclase from a herpes simplex virus type 1 vector," Proceedings of the National Academy of Sciences, Aug. 1993, 90(16), pp. 7603-7607.

Goding, J.W. (Ed.) "Production of Monoclonal Antibodies", in Monoclonal Antibodies: Principles and Practice, 2nd Edition, Academic Press, pp. 59-103 (1986).

Goulet R.G. and Atkins W.M., "Considerations for the Design of Antibody-Based Therapeutics," Journal of Pharmaceutical Sciences, Jan. 2020, 109(1), pp. 74-103.

Gramer et al., "Production of stable bispecific IgG1 by controlled Fab-arm exchange: Scalability from bench to large-scale manufacturing by application of standard approaches," mAbs, Nov. 2013, 5(6), pp. 962-973.

Gruber et al., "Efficient Tumor Cell Lysis Mediated by a Bispecific Single Chain Antibody Expressed in *Escherichia coli,*" The Journal of Immunology, Jun. 1994, 152(11), pp. 5368-5374.

Gunasekaran et al., "Enhancing antibody Fe heterodimer formation through electrostatic steering effects: applications to bispecific molecules and monovalent IgG," Journal of Biological Chemistry, Jun. 2010, 285(25), p. 19637-19646.

Hellen, C.U. and Sarnow, P., "Internal ribosome entry sites in eukaryotic mRNA molecules," Genes & Development, Jul. 2001, 15(13), pp. 1593-1612.

Holliger et al., "'Diabodies': Small bivalent and bispecific antibody fragments," Proceedings of the National Academy of Sciences, Jul. 1993, 90(14), pp. 6444-6448.

Honegger et al., "Yet another numbering scheme for immunoglobulin variable domains: An automatic modeling and analysis tool," Journal of Molecular Biology, Jun. 2001, 309(3), pp. 657-670.

Hoogenboom, H.R. and Winter, G., "By-passing Immunisation. Human Antibodies from Synthetic Repertoires of Germline VH Gene Segments Rearranged in Vitro," Journal of Molecular Biology, Sep. 1992, 227(2), pp. 381-388.

(56) References Cited

OTHER PUBLICATIONS

Husain, B., et al., "Expanding the boundaries of biotherapeutics with bispecific antibodies," BIODRUGS, vol. 12, No. 5, Aug. 21, 2018, pp. 441-464, XP55655206.
Hwang et al., "Hepatic uptake and degradation of unilamellar sphingomyelin/cholesterol liposomes: A kinetic study," Proceedings of the National Academy of Sciences, Jul. 1980, 77(7), pp. 4030-4034.
Jansen et al., "Immunotoxins: Hybrid Molecules Combining High Specificity and Potent Cytotoxicity," Immunological Reviews, Feb. 1982, 62(1), pp. 185-216.
Jones et al., "Replacing the complementary-determining regions in a human antibody with those from a mouse," Nature, vol. 321, May 1986, pp. 522-525.
Kaplitt, M. G. et al., "Long-term gene expression and phenotypic correction using adeno-associated virus vectors in the mammalian brain," Nature Genetics, Oct. 1994, 8(2), pp. 148-154.
Killen and Lindstrom, "Specific killing of lymphocytes that cause experimental autoimmune myasthenia gravis by ricin toxin-acetylcholine receptor conjugates," The Journal of Immunology, Nov. 1984, 133(5), pp. 2549-1553.
Klein, C. et al. "Progress in overcoming the chain association issue in bispecific heterodimeric IgG antibodies," InMAbsm, Nov. 2012, 4(6), pp. 653-663.
Kohler G. and Milstein C., "Continuous cultures of fused cells secreting antibody of predefined specificity," Nature, Aug. 1975, 256(5517), pp. 495-497.
Kontermann, R. et al., "Complement recruitment using bispecific diabodies," Nature Biotechnology, Jul. 1997, 15(7), pp. 629-631.
Kostelny et al., "Formation of a Bispecific Antibody by the Use of Leucine Zippers," The Journal of Immunology, Mar. 1992, 148(5), pp. 1547-1553.
Kozbor et al., "A human hybrid myeloma for production of human monoclonal antibodies," The Journal of Immunology, Dec. 1984, 133(6), pp. 3001-3005.
Kozbor et al., "The production of monoclonal antibodies from human lymphocytes," Immunology Today, Mar. 1983, 4(3), pp. 72-79.
La Salle et al., "An Adenovirus Vector for Gene Transfer into Neurons and Glia in the Brain," Science, Feb. 1993, 259(5097), pp. 988-990.
Lefranc, M-P., et al., "IMGT, the international ImMunoGeneTics database," Nucleic Acids Research, Jan. 1999, 27(1), pp. 209-212.
Lefranc, M-P., "Immunoglobulins: 25 Years of Immunoinformatics and IMGT-Ontology," Biomolecules, Dec. 2014, 4(4), pp. 1102-1139; doi: 10.3390/biom4041102.
Lim, F., et al., in DNA Cloning: Mammalian Systems, D. Glover, Ed. (Oxford Univ. Press, Oxford England, (1995), 23 pages.
Lonberg and Huszar, "Human Antibodies from Transgenic Mice," International Reviews of Immunology, Jan. 1995, 13(1), pp. 65-93.
Lonberg et al., "Antigen-specific human antibodies from mice comprising four distinct genetic modifications," Nature, Apr. 1994, 368(6474), pp. 856-859.
Lopez-Beltran, A., et al., "Immune checkpoint inhibitors for the treatment of bladder cancer," CANCERS, vol. 13, No. 1, 131, Jan. 3, 2021, XP055941080, DOI: 10.3390/cancers13010131, 16 pages.
Malmqvist, M., "Biosepcific interaction analysis using biosensor technology," Nature, Jan. 1993, 361(6408), pp. 186-187.
Marasco et al., "Design, intracellular expression, and activity of a human anti- human immunodeficiency virus type 1 gpl20 single-chain antibody," Proceedings of the National Academy of Sciences, Aug. 1993, 90(16), pp. 7889-7893.
Marks et al., "By-passing Immunization: Building High Affinity Human Antibodies by Chain Shuffling," Bio/Technology, Jul. 1992, 10(7), pp. 779-783.
Marks et al., "By-passing Immunization. Human Antibodies from V-gene Libraries Displayed on Phage," Journal of Molecular Biology, Dec. 1991, 222(3), pp. 581-597.
Martin et al., "Irreversible Coupling of Immunoglobulin Fragments to Preformed Vesicles," The Journal of Biological Chemistry, Jan. 1992, 257(1), pp. 286-288.
Milstein, C. & Cuello, A. C., "Hybrid hybridomas and their use in immunohistochemistry," Nature, Oct. 1983, 305(5934), pp. 537-540.
Moore et al., "Application of dual affinity retargeting molecules to achieve optimal redirected T-cell killing of B-cell lymphoma," Blood, The Journal of the American Society of Hematalogy, Apr. 2011, 117(17), pp. 4542-4551.
Morrison et al., "High-flow microinfusion: tissue penetration and pharmacodynamics," American Journal of Physiology—Regulatroy, Intensive and Comparative Physiology, Jan. 1994, 266(1), pp. R292-R305.
Morrison, S. L., "Success in specification," Nature, Apr. 1994, 368(6474), pp. 812-813.
Munson et al., "Ligand: A Versatile Computerized Approach for Characterization of Ligand-Binding Systems," Analytical Biochemistry, Sep. 1980, 107(1), pp. 220-239.
Namisaki et al., "R409K Mutation prevents acid-induced aggregation of human LgG4," Plos One, Mar. 17, 2020, 15(3), e0229027, 20 pages.
Neuberger, M., "Generating high-avidity human Mabs in mice," Nature Biotechnology, Jul. 1996, 14(7), pp. 826.
Presta, L.G., "Antibody engineering," Current Opinion in Structural Biology, Aug. 1992, 2(4), pp. 593-596.
Pörtner, L et al., "T and NK cells of B cell NHL patients exert cytotoxicity against lymphoma cells following binding of bispecific tetravalent antibody CD19×CD3 or CD19×CD16," Cancer Immunology, Immunotherapy, Oct. 2012, 61(10), pp. 1869-1875.
Ramakrishnan, S. and Houston, L.L., "Comparison of the Selective Cytotoxic Effects of Immunotoxins Containing Ricin A Chain or Pokeweed Antiviral Protein and Anti-Thy 1.1 Monoclonal Antibodies," Cancer Research, Jan. 1984, 44(1), pp. 201-208.
Ridgway et al., "'Knobs-into-holes' engineering of antibody CH3 domains for heavy chain heterodimerization," Protein Engineering, Design and Selection, Jul. 1996, 9(7), pp. 617-621.
Riechmann, L. et al. (Mar. 1988), "Reshaping human antibodies for therapy," Nature, vol. 332, No. 6162, pp. 323-327.
Ruiz et al., "IMGT, the international ImMunoGeneTics database," Nucleic Acids Research, Jan. 2000, 28(1), pp. 219-221.
Shopes, B., "A genetically engineered human IgG mutant with enhanced cytolytic activity," The Journal of Immunology, May 1992, 148(9), pp. 2918-2922.
Stevenson et al., "A chimeric antibody with dual Fc regions (bisFabFc) prepared by manipulations at the IgG hinge," Anti-Cancer Drug Design, Mar. 1989, 3(4), pp. 219-230.
Strohl, W.R., "Optimization of Fc-mediated effector functions of monoclonal antibodies," Current Opinion in Biotechnology, Dec. 2009, 20(6), pp. 685-691.
Suresh et al., "Bispecific Monoclonal Antibodies from Hybrid Hybridomas," Methods in Enzymology, Jan. 1986, vol. 121, pp. 210-228.
Thornton et al. "Prediction of progress at last", Nature, Nov. 1991, 354(6349), pp. 105-106.
Traunecker et al., "Bispecific single chain molecules (Janusins) target cytotoxic lymphocytes on HIV infected cells," The EMBO Journal, Dec. 1991, 10(12), pp. 3655-3659.
Tutt et al., "Trispecific F(ab')3 Derivatives that Use Cooperative Signaling via the TCR/CD3 Complex and CD2 to Activate and Redirect Resting Cytotoxic T Cells," The Journal of Immunology, Jul. 1991, 147(1), pp. 60-69.
Vaughan et al., "Human antibodies with sub-nanomolar affinities isolated from a large non-immunized phage display library," Nature Biotechnology, Mar. 1996, 14(3), pp. 309-314.
Verhoeyen, M., et al., "Reshaping human antibodies: grafting an antilysozyme activity", Science, Mar. 1988, 239(4847), pp. 1534-1536.
Vitetta et al., "Redesigning Nature's Poisons to Create Anti-Tumor Reagents," Science, Nov. 1987, 238(4830), pp. 1098-1104.
Von Kreudenstein, T. et al., "Improving biophysical properties of a bispecific antibody scaffold to aid developability: quality by molecular design," InMAbs, Sep. 2013, 5(5), pp. 646-654.

(56) References Cited

OTHER PUBLICATIONS

Wang, W., "Lyophilization and development of solid protein pharmaceuticals," International Journal of Pharmaceutics, Aug. 2000, 203(1-2), pp. 1-60.
Wang, Y., et al., "Tumor-selective blockade of CD47 signaling with a CD47/PD-L1 bispecific antibody for enhanced anti-tumor activity and limited toxicity," Cancer Immunology Immunotherapy, vol. 70, No. 2, Aug. 6, 2020, pp. 365-376, XP55779288.
Wilkinson, D., "Ultimate Abs," The Scientist 25, Apr. 17, 2000, vol. 14, No. 8, pp. 25-28.
Wolf, E. et al., "BiTEs: bispecific antibody constructs with unique anti-tumor activity," Drug Discovery Today, Sep. 2005, 10(18), pp. 1237-1244.
Yang, et al., "Cellular and Humoral Immune Responses to Viral Antigens Create Barriers to Lung-Directed Gene Therapy with Recombinant Adenoviruses," Journal of Virology, Apr. 1995, 69(4), pp. 2004-2015.
Akbar, R., et al.; "A compact vocabulary of paratope-epitope interactions enables predictability of antibody-antigen binding," Cell Rep., 34(11):108856, pp. 1-21; (Mar. 16, 2021).
Lo, Y-T, et al.; "Conformational epitope matching and prediction based on protein surface spiral features," BMC Genomics; 22(Suppl 2)116, pp. 1-16 (2021).
Marks, C., et al.; "How repertoire data are changing antibody science," J Biol Chem., 295(29):9823-9837 (2020).
Tang, I., et al.; "Generation of a potent anti-PD-L1-CD47 bispecific antibody with a strong therapeutic and safety profile for cancer immunotherapy," Front. Drug Discov., 3:1-16; (May 8, 2023).
Vajda, S., et al.; "Progress toward improved understanding of antibody maturation," Curr Opin Struct Biol., 67:226-231 (2021).
Dheilly, E., et al., "Tumor-Directed Blockade of CD47 with Bispecific Antibodies Induces Adaptive Antitumor Immunity," Antibodies (Basel) (2018); 7(1):3, 15 pages.
Fischer, N. et al., "Exploiting light chains for the scalable generation and platform purification of native human bispecific IgG," Nature Communications 6, Article No. 6113, Feb. 12, 2015, 6(1), https://doi: 10.1038/ncomms7113, 12 pages.

BISPECIFIC ANTIBODIES TARGETING CD47 AND PD-L1 AND METHODS OF USE THEREOF

RELATED APPLICATIONS

This application claims the benefit of and priority to U.S. Provisional Application No. 63/317,899, filed on Mar. 8, 2022, and U.S. Provisional Application No. 63/164,329 filed on Mar. 22, 2021, each of which is incorporated herein by reference in its entirety.

FIELD

This disclosure relates to bispecific antibodies that specifically bind to CD47 and Programmed Death-Ligand 1 (PD-L1), methods of making the bispecific antibodies and nucleic acids encoding the antibodies. The disclosure further relates to therapeutic methods for use of the bispecific antibodies in the treatment of a condition associated with malignant cells expressing CD47 and/or PD-L1 (e.g. cancer).

REFERENCE TO SEQUENCE LISTING

This application is being filed electronically via EFS-Web and includes an electronically submitted sequence listing in .txt format. The .txt file contains a sequence listing entitled "NOVI_048_001US_SeqList_ST25.txt" created on Nov. 20, 2024, and having a size of 174,906 bytes. The sequence listing contained in this .txt file is part of the specification and is incorporated herein by reference in its entirety.

BACKGROUND OF THE INVENTION

CD47 or Integrin-Associated-Protein (IAP) is a ubiquitous 50 kDa transmembrane glycoprotein with multiple functions in cell-cell communication. It interacts with multiple ligands, such as integrins, SIRPα (Signal Regulatory Protein alpha), SIRPγ and thrombospondins.

The widespread expression of CD47 in healthy tissues brings the question of treatment safety and efficacy: First, targeting CD47 with a neutralizing monoclonal antibody (Mab) could affect healthy cells, resulting in severe toxicities as shown in preclinical studies with mice and cynomolgus monkeys Second, even if severe toxicities could be avoided or mitigated by using alternative formats broad expression of CD47 could still cause a rapid elimination of CD47-binding molecules through target-mediated drug disposition resulting in poor pharmacokinetics and decreased efficacy.

Programmed cell death ligand-1 (PD-L1), also referred to as B7-H1 and CD274, is a transmembrane protein constitutively expressed on both hematopoietic cells, in particular myeloid cells, and non-hematopoietic healthy tissues. It can also be expressed on tumor cells and tumor stroma. In cancer, the expression of the inhibitory receptor PD-1 is considered as a hallmark of exhausted T cells, which exhibit a dysfunctional phenotype due to persistent antigenic and inflammatory stimulation. Furthermore, it has been shown that upregulation of PD-L1 in the tumor microenvironment allows tumors to evade the host immune system, by interacting with PD-1 on T cells. Multiple studies have reported that PD-L1 is expressed in a variety of tumor tissues, either on tumor cells or immune-infiltrating cells or on both. In patients, blocking the interaction of PD-1 with PD-L1 using monoclonal antibodies has proved to be a successful therapy in a range of cancer indications and is widely thought to enhance antitumor T-cell responses by reversing or preventing the onset of T-cell exhaustion, but also by promoting the expansion of T-cells during T-cell priming in the tumor draining lymph nodes. However, despite the considerable improvement in patient outcome that has been achieved with PD-1/PD-L1 checkpoint inhibitors, durable responses to these therapies are observed in only a minority of patients, and intrinsic or acquired resistances are common.

Accordingly, there exists a need for novel antibodies and therapeutics that enable dual targeting of CD47 and PD-L1 to overcome these obstacles.

SUMMARY OF THE INVENTION

The invention also provides bispecific antibodies that specifically bind to CD47 and PD-L1.

In some aspects, the disclosure provides a bispecific antibody comprising: i) a heavy chain; ii) a first light chain; and iii) a second light chain. In some embodiments, the bispecific antibody disclosed herein comprises a first antigen binding region comprising a heavy chain and a first light chain that specifically binds to CD47 and a second antigen binding region comprising a heavy chain and a second light chain that specifically binds to Programmed Death-ligand 1 (PD-L1).

In some embodiments, the heavy chain comprises a heavy chain complementarity determining region 1 (CDRH1) comprising an amino acid sequence of SEQ ID NO: 1; a heavy chain complementarity determining region 2 (CDRH2) comprising an amino acid sequence of SEQ ID NO: 2; and a heavy chain complementarity determining region 3 (CDRH3) comprising an amino acid sequence of SEQ ID NO: 3.

In some embodiments, a portion of the first light chain is of the kappa type and at least a portion of the second light chain is of the lambda type. In some embodiments, the first light chain comprises at least a Kappa constant region. In some embodiments, the first light chain further comprises a Kappa variable region. In some embodiments, the first light chain further comprises a Lambda variable region.

In some embodiments, the second light chain comprises at least a Lambda constant region. In some embodiments, the second light chain further comprises a Lambda variable region. In some embodiments, the second light chain further comprises a Kappa variable region.

In some embodiments the first light chain comprises a Kappa constant region and a Kappa variable region, and wherein the second light chain comprises a Lambda constant region and a Lambda variable region.

In some embodiments, the first light chain comprises: a light chain complementarity determining region 1 (CDRL1) comprising an amino acid sequence of SEQ ID NO: 89; a light chain complementarity determining region 2 (CDRL2) comprising an amino acid sequence of SEQ ID NO: 217; and a light chain complementarity determining region 3 (CDRL3) comprising an amino acid sequence of SEQ ID NO: 96.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 97.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 98.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 99.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 100.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 101.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 102.

In some embodiments, the first light chain comprises: a light chain complementarity determining region 1 (CDRL1) comprising an amino acid sequence of SEQ ID NO: 89; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 96.

In some embodiments, the first light chain comprises: a light chain complementarity determining region 1 (CDRL1) comprising an amino acid sequence of SEQ ID NO: 91; a light chain complementarity determining region 2 (CDRL2) comprising an amino acid sequence of SEQ ID NO: 95; and a light chain complementarity determining region 3 (CDRL3) comprising an amino acid sequence of SEQ ID NO: 96.

In some embodiments, the first light chain comprises: a light chain complementarity determining region 1 (CDRL1) comprising an amino acid sequence of SEQ ID NO: 92; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 96.

In some embodiments, the first light chain comprises: a light chain complementarity determining region 1 (CDRL1) comprising an amino acid sequence of SEQ ID NO: 90; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 211.

In some embodiments, the first light chain comprises: a light chain complementarity determining region 1 (CDRL1) comprising an amino acid sequence of SEQ ID NO: 213; a light chain complementarity determining region 2 (CDRL2) comprising an amino acid sequence of SEQ ID NO: 215; and a light chain complementarity determining region 3 (CDRL3) comprising an amino acid sequence of SEQ ID NO: 96.

In some embodiments, the first light chain comprises: a light chain complementarity determining region 1 (CDRL1) comprising an amino acid sequence of SEQ ID NO: 213; a light chain complementarity determining region 2 (CDRL2) comprising an amino acid sequence of SEQ ID NO: 94; and a light chain complementarity determining region 3 (CDRL3) comprising an amino acid sequence of SEQ ID NO: 211.

In some embodiments, the first light chain comprises: a light chain complementarity determining region 1 (CDRL1) comprising an amino acid sequence of SEQ ID NO: 214; a light chain complementarity determining region 2 (CDRL2) comprising an amino acid sequence of SEQ ID NO: 216; and a light chain complementarity determining region 3 (CDRL3) comprising an amino acid sequence of SEQ ID NO: 212.

In some embodiments, the second light chain comprises: a CDRL1 comprising an amino acid sequence of SEQ ID NO: 8; a CDRL2 comprising an amino acid sequence of SEQ ID NO: 15; and a CDRL3 comprising an amino acid sequence of SEQ ID NO: 20.

In some embodiments, the second light chain comprises: a CDRL1 comprising an amino acid sequence of SEQ ID NO: 8; a CDRL2 comprising an amino acid sequence of SEQ ID NO: 15; and a CDRL3 comprising an amino acid sequence of SEQ ID NO: 21.

In some embodiments, the second light chain comprises: a CDRL1 comprising an amino acid sequence of SEQ ID NO: 8; a CDRL2 comprising an amino acid sequence of SEQ ID NO: 15; and a CDRL3 comprising an amino acid sequence of SEQ ID NO: 22.

In some embodiments, the second light chain comprises: a CDRL1 comprising an amino acid sequence of SEQ ID NO: 9; a CDRL2 comprising an amino acid sequence of SEQ ID NO: 16; and a CDRL3 comprising an amino acid sequence of SEQ ID NO: 23.

In some embodiments, the second light chain comprises: a CDRL1 comprising an amino acid sequence of SEQ ID NO: 9; a CDRL2 comprising an amino acid sequence of SEQ ID NO: 16; and a CDRL3 comprising an amino acid sequence of SEQ ID NO: 24.

In some embodiments, the second light chain comprises: a CDRL1 comprising an amino acid sequence of SEQ ID NO: 9; a CDRL2 comprising an amino acid sequence of SEQ ID NO: 16; and a CDRL3 comprising an amino acid sequence of SEQ ID NO: 25.

In some embodiments, the second light chain comprises: a CDRL1 comprising an amino acid sequence of SEQ ID NO: 10; a CDRL2 comprising an amino acid sequence of SEQ ID NO: 17; and a CDRL3 comprising an amino acid sequence of SEQ ID NO: 147.

In some embodiments, the second light chain comprises: a CDRL1 comprising an amino acid sequence of SEQ ID NO: 10; a CDRL2 comprising an amino acid sequence of SEQ ID NO: 17; and a CDRL3 comprising an amino acid sequence of SEQ ID NO: 148.

In some embodiments, the second light chain comprises: a CDRL1 comprising an amino acid sequence of SEQ ID NO: 11; a CDRL2 comprising an amino acid sequence of SEQ ID NO: 18; and a CDRL3 comprising an amino acid sequence of SEQ ID NO: 147.

In some embodiments, the second light chain comprises: a CDRL1 comprising an amino acid sequence of SEQ ID NO: 12; a CDRL2 comprising an amino acid sequence of SEQ ID NO: 19; and a CDRL3 comprising an amino acid sequence of SEQ ID NO: 26.

In some embodiments, the second light chain comprises: a CDRL1 comprising an amino acid sequence of SEQ ID NO: 13; a CDRL2 comprising an amino acid sequence of SEQ ID NO: 19; and a CDRL3 comprising an amino acid sequence of SEQ ID NO: 26.

In some embodiments, the second light chain comprises: a CDRL1 comprising an amino acid sequence of SEQ ID NO: 14; a CDRL2 comprising an amino acid sequence of SEQ ID NO: 19; and a CDRL3 comprising an amino acid sequence of SEQ ID NO: 27.

In some embodiments, the second light chain comprises: a CDRL1 comprising an amino acid sequence of SEQ ID NO: 14; a CDRL2 comprising an amino acid sequence of SEQ ID NO: 19; and a CDRL3 comprising an amino acid sequence of SEQ ID NO: 28.

In some embodiments, the bispecific antibody is human antibody. In some embodiments, the isolated bispecific antibody is isolated. In some embodiments, the bispecific antibody is an IgG1 antibody. In some embodiments, the bispecific antibody is an IgG4 antibody.

In some embodiments, the bispecific antibody has a S228P mutation when numbered in accordance to SEQ ID NO: 232. In some embodiments, the bispecific antibody has a R409K mutation when numbered in accordance to SEQ ID NO: 232. In some embodiments, the bispecific antibody has a S228P and a R409K mutation when numbered in accordance to SEQ ID NO: 232.

The disclosure provides a composition comprising the bispecific antibody described herein and a pharmaceutically acceptable carrier.

The disclosure provides a method of reducing the proliferation of and/or killing a tumor cell comprising contacting the cell with the composition comprising the bispecific antibody described herein. The disclosure provides a method of treating a cancer in a subject comprising administering to the subject the composition comprising the bispecific antibody described herein.

In some aspects, the disclosure provides the use of a composition comprising the bispecific antibody described herein for treating, preventing, or delaying the progression of pathologies associated with aberrant CD47 expression or activity, or associated with aberrant CD47-SIRPα expression or activity. In some embodiments, the pathology is cancer. In some embodiments, the cancer is a solid tumor. In some embodiments, the solid tumor is or is derived from breast cancer, ovarian cancer, head and neck cancer, bladder cancer, melanoma, mesothelioma, colorectal cancer, cholangiocarcinoma, pancreatic cancer, lung cancer, leiomyoma, leiomyosarcoma, kidney cancer, glioma, glioblastoma, endometrial cancer, esophageal cancer, biliary gastric cancer, prostate cancer, or combinations thereof.

BRIEF DESCRIPTION OF THE DRAWINGS

FIG. 1A shows binding to recombinant human PD-L1 determined by ELISA assay. FIG. 1B shows binding to recombinant cynomolgus monkey PD-L1 determined by ELISA assay. FIG. 1C shows binding to recombinant mouse PD-L1 determined by ELISA assay. FIG. 1D shows binding to recombinant human PD-L2 determined by ELISA assay. FIG. 1E shows a graph depicting monovalent blockade of soluble hPD-1 binding to hPD-L1-transfected CHO (hamster) cells of exemplary CD47×PD-L1 bispecific antibodies compared to hIgG4 isotype control antibody, anti-PD-L1 mAbs atezolizumab and avelumab, and an anti-PD-L2 mAb, determined by a competitive binding cell-based assay.

FIG. 2A shows binding to recombinant human CD47 determined by ELISA assay. FIG. 2B shows binding to cynomolgus monkey CD47 determined by ELISA assay. FIG. 2C shows binding to recombinant mouse CD47, determined by ELISA assay.

FIG. 2D shows binding to human Raji $CD47^+PD\text{-}L1^-$ tumor cells evaluated by flow cytometry. FIG. 2E shows binding to human Nalm-6 $CD47^+$ $PD\text{-}L1^-$ tumor cells evaluated by flow cytometry. hIgG4 isotype control antibody and anti-CD47 5F9 analog were evaluated for comparison. FIG. 2F shows a graph depicting SIRPa blocking activity of exemplary CD47×PD-L1 bispecific antibody to human $CD47^+$ $PD\text{-}L1^-$ Nalm-6 tumor cells compared to anti-CD47 5F9 analog in a cell-based competitive binding assay.

FIG. 4A shows binding of exemplary CD47×PD-L1 bispecific antibodies (K33×S79, K38×S79, K106×S79) to $CD47^+/PD\text{-}L1^+$ human HT-1080 tumor cells. hIgG4 isotype control, anti-CD47 5F9 analog, anti-PD-L1 avelumab, anti-PD-L1 atezolizumab and S79 control antibodies were evaluated for comparison. FIG. 4B shows binding of CD47×PD-L1 bispecific antibody K38×S79 compared to monovalent CD47 and PD-L1 controls, K38 and S79 respectively.

FIG. 5A shows blockade of soluble hPD-1 binding to human $CD47^+/PD\text{-}L1^+$ HT-1080 tumor cells using exemplary CD47-PD-L1 bispecific antibodies (K33×S79, K38×S79, K106×S79). hIgG4 isotype control antibody, anti-CD47 5F9 analog, anti-PD-L1 mAb avelumab, anti-PD-L1 mAb atezolizumab and S79 as well as monovalent CD47 (K38) and PD-L1 (S79) controls were tested for comparison. FIG. 5B shows blockade of soluble SIRPa binding to human $CD47^+/PD\text{-}L1^+$ HT-1080 tumor cells using exemplary CD47-PD-L1 bispecific antibodies (K33×S79, K38×S79). hIgG4 isotype control antibody, anti-CD47 5F9 analog, and monovalent CD47 (K38) controls were tested for comparison.

In FIG. 6B, a constant concentration of 67 nM of IgG4 control, 5F9 analog or the CD47×PD-L1 bsAbs were combined with different concentrations of the IgG1 anti-CD19 mAb. IgG4 isotype control antibody, anti-CD47 5F9 analog, and monovalent PD-L1 S79 antibody controls were tested for comparison.

FIG. 7A shows average tumor volume. FIG. 7B shows individual tumor growth curves. hIgG4 isotype control antibody and anti-CD47 5F9 analog controls were tested for comparison.

FIG. 8A shows average tumor volume. FIG. 8B shows individual tumor growth curves. hIgG4 isotype control antibody and anti-CD47 5F9 analog controls were tested for comparison.

FIG. 9A shows average tumor volume. FIG. 9B shows individual tumor growth curves. hIgG4 isotype control antibody and anti-CD47 5F9 analog controls were tested for comparison.

FIG. 11A shows expression of human CD47 on humanized mice red blood cells (RBC) versus human RBC isolated from whole blood assessed by flow cytometry. The gray histograms correspond to the analysis of human RBC while the empty histograms correspond to humanized mice RBC. Anti-CD47 and isotype control staining are depicted in dotted and solid line histograms respectively. FIG. 11B shows percentage of DO body weight of mice administered with exemplary IgG4 CD47×PD-L1 bispecific antibodies (K33×S79, K38×S79, K106×S79), at different timepoints after treatment injection. FIG. 11C shows average red blood cell (RBC) count in mice administered exemplary IgG4 CD47×PD-L1 bispecific antibodies (K33×S79, K38×S79, K106×S79), at different timepoints after treatment injection. FIG. 11D shows platelet count in mice administered exemplary IgG4 CD47×PD-L1 bispecific antibodies (K33×S79, K38×S79, K106×S79), at different timepoints after treatment injection. Absolute counts were determined at different timepoints after treatment injection with a hematology analyzer. hIgG4 isotype control antibody and anti-CD47 5F9 analog controls were tested for comparison in each experiment.

DETAILED DESCRIPTION

Figure 1A:
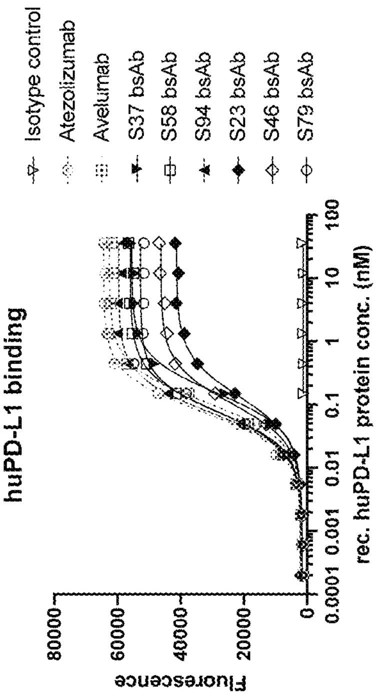
FIGS. 1A-1E shows a series of graphs depicting binding, cross-reactivity, and specificity of exemplary CD47×PD-L1 bispecific antibodies of the invention (S37, S58, S94, S23, S46 and S79) to PD-L1 isolated from various species.

The present disclosure provides bispecific antibodies that bind to CD47 and PD-L1. Specifically, the bispecific antibody includes a first antigen binding region that binds CD47 and block the SIRPa/CD47 interaction and a second antigen binding region that binds PD-L1 and block PD-1/PD-L1 interaction.

Cancer cells adopt multiple mechanisms to escape immune surveillance. Several studies demonstrated that CD47 and PD-L1 expression on tumor cells was concomitantly regulated to suppress immune response. Thus, activating innate or adaptive immunity alone may be insufficient to eradicate tumors and harnessing both immune responses may present a more effective strategy to induce durable anti-tumor activity. Therefore, combinations between anti-PD-L1 or anti-PD-1 antibodies and anti-CD47 antibodies are currently being explored in the clinic. However, the expression of CD47 on many healthy cells such as hematopoietic cells, red blood cell and platelets provides a strong antigen sink that affects the pharmacokinetics and compromised safety profile of these agents.

One way to overcome the ubiquity of CD47 expression is provided by dual-targeting bispecific antibodies (bsAbs), which bind to two different antigens on the surface of the same cell. The bispecific antibodies bind their targets (i.e. CD47 and PD-L1) with high affinity in a monovalent engagement. By high affinity it is meant an affinity of about 0.01 nM-25 nM However, when both targets are expressed on the same cell, the bispecific antibodies can simultaneously block interaction with their respective antigen (i.e., SIRPa and PD-1). This co-engagement results in additive or synergistic increase of affinity due to avidity. As a consequence, co-engagement confers high selectivity towards cells expressing both antigens as compared to cells that express just one single antigen.

Additionally, the bispecific antibodies described herein require a Fc portion with reduced binding to FcγR to reduce Fc-mediated effector function and further avoid safety concerns linked to potential ubiquitous binding to CD47. Thus, the bispecific antibodies are of the present invention have a superior safety profile compared to bispecific antibodies know on the art.

The bispecific antibody is of the IgG4 isotype. Bispecific antibodies of the IgG4 isotype, result in reduced binding to the FcγR thereby reducing Fc-mediated effector functions.

CD47

CD47 or Integrin-Associated-Protein (IAP) is a ubiquitous 50 kDa transmembrane glycoprotein with multiple functions in cell-cell communication. It interacts with multiple ligands, such as, for example, integrins, and/or SIRPα. In the context of the innate immune system, CD47 functions as a marker of self, transmitting an inhibitory "don't kill me" signal through binding to SIRPα expressed by myeloid cells, such as macrophages, neutrophils, and dendritic cells but also NK cells (Deuse T et al., The SIRPα-CD47 immune checkpoint in NK cells, J Exp Med 2021 Vol. 218 No. 3). The role of widespread expression of CD47 in the physiological situation is therefore to protect healthy cells against the elimination by the innate immune system Tumor cells hijack this immunosuppressive mechanism by overexpressing CD47, which efficiently helps them to escape immune surveillance and killing by innate immune cells. CD47 expression is upregulated in most human cancers (e.g., NHL, AML, breast, colon, glioblastoma, glioma, ovarian, bladder and prostate cancers) and increased levels of CD47 expression clearly correlate with aggressive disease and poor survival. Thus, targeting CD47 would be useful in treating, delaying the progression of, or otherwise ameliorating a symptom of cancer.

However, the widespread expression of CD47 in healthy tissues brings the question of treatment safety and efficacy: First, targeting CD47 with a neutralizing monoclonal antibody (mAb) could affect healthy cells, resulting in severe hematological toxicities (anemia and thrombocytopenia) as shown in preclinical studies with mice and cynomolgus monkeys. Second, even if severe toxicities could be avoided or mitigated by using alternative antibody formats broad expression of CD47 could still cause a rapid elimination of CD47-binding molecules through target-mediated drug disposition resulting in poor pharmacokinetics and decreased efficacy.

Programmed Cell Death Ligand-1 (PD-L1)

Programmed cell death ligand-1 (PD-L1), also referred to as B7-H1 and CD274, is a transmembrane protein constitutively expressed on both hematopoietic cells, in particular myeloid cells, and non-hematopoietic healthy tissues. It can also be expressed on tumor cells and tumor stroma. Various inflammatory stimuli, such as IFNγ, TNFα or LPS, induce PD-L1 expression on immune cells, endothelial cells and epithelial lineages, including tumor cells deriving from these lineages. PD-L1 acts both as a ligand of Programmed cell death-1 (PD-1), which is expressed on the surface of activated lymphocytes, and of B7.1 (also known as CD80), expressed by antigen-presenting cells, especially dendritic cells and macrophages. The engagement of PD-1 by PD-L1 on T cells is considered as an immune checkpoint, by counteracting T cell-activating signals, results in the inhibition of proliferation, cytokine production and release and cytotoxicity of T-cells. In fact, PD-1 has been shown to suppress T-cell activation at least in part through the inhibition of CD28 signaling, a major co-stimulatory pathway required for optimal activation of T cells. Therefore, the PD-1/PD-L1 pathway, by regulating the magnitude and the functional activity of the T-cell response, play a critical role in physiological conditions in limiting tissue damage during inflammatory reactions, and in maintaining self-tolerance. In pathological circumstances, it is involved in the development of tumor immunity and autoimmune diseases.

In cancer, the expression of the inhibitory receptor PD-1 is considered as a hallmark of exhausted T cells, which exhibit a dysfunctional phenotype due to persistent antigenic and inflammatory stimulation. Furthermore, it has been shown that upregulation of PD-L1 in the tumor microenvironment allows tumors to evade the host immune system, by interacting with PD-1 on T cells. Multiple studies have reported that PD-L1 is expressed in a variety of tumor tissues, either on tumor cells or immune-infiltrating cells or on both. In patients, blocking the interaction of PD-1 with PD-L1 using monoclonal antibodies has proved to be a successful therapy in a range of cancer indications and is widely thought to enhance antitumor T-cell responses by reversing or preventing the onset of T-cell exhaustion, but also by promoting the expansion of T-cells during T-cell priming in the tumor draining lymph nodes. However, despite the considerable improvement in patient outcome that has been achieved with PD-1/PD-L1 checkpoint inhibitors, durable responses to these therapies are observed in only a minority of patients, and intrinsic or acquired resistances are common.

Exemplary Bispecific Antibodies that Bind to CD47 and PD-L1

The bispecific antibodies of the invention have one antigen binding region that is specific for CD47 and a second antigen binding region that is specific for PD-L1. But another way the bispecific antibodies are monovalent for CD47 and PD-L1. The bispecific antibodies share a common heavy chain.

In some embodiments, the heavy chains are native heavy chains (i.e., does not contain any mutations). In some embodiments, the heavy chains comprise mutations relative to the native heavy chain. In some embodiments, the heavy chains are of the IgG4 type which effector functions (ADCC and/or C1q binding) are of low potency. Optionally, the bispecific antibodies have light chains of different types. For example, one light chain is a kappa and the other light chain is a lambda light chain (i.e., κλ-body). Differing light chains allows the bispecific to be purified easily using kappa and lambda select resins.

Exemplary CD47 antibodies from which the CD47 antigen binding region can be derived from include the K26 antibody, the K30 antibody, the K31 antibody, the K32 antibody, the K34 antibody, the K35 antibody, the K36 antibody, the K37 antibody, the K40 antibody, the K41 antibody, the K43 antibody, the K33 antibody, the K38 antibody, the K91 antibody and the K106 antibody. Exemplary, PD-L1 antibodies from which the PD-L1 antigen binding region can be derived from include the S8 antibody, the S9 antibody, the S37 antibody, the S14 antibody, the S15 antibody, the S17 antibody, the S57 antibody, the S58 antibody, the S28 antibody, the S30 antibody, the S94 antibody, the S23 antibody, the S46 antibody, the S71 antibody, and the S79 antibody.

In some embodiments, exemplary bispecific antibodies of the invention that include at least a first antigen binding region that binds CD47 include a combination of heavy chain and complementarity determining regions and light chain complementarity determining regions (CDRs) selected from the CDR sequences shown in Tables 1, 2 and 3. The CDRs shown in Tables 1, 2 and 3 are defined according to the IMGT nomenclature (See IMGT®, the international ImMunoGeneTics information System®.

In some embodiments, exemplary bispecific antibodies of the invention that includes a heavy chain comprising a combination of heavy chain CDR amino acid sequences selected from the CDRH1, CDRH2 and CDRH3 amino acid sequences shown in Table 1, at least a first light chain with a set of first light chain CDR amino acid sequences selected from the CDRL1, CDRL2 and CDRL3 amino acid sequences shown in Tables 2 and at least a second light chain with a set of second light chain CDR amino acid sequences selected form from CDRL1, CDRL2 and CDRL3 sequences Table 3.

In some embodiments, exemplary bispecific antibodies of the invention that include a first antigen binding region that binds CD47 and a second antigen binding region that binds PD-L1, wherein the first antigen binding region includes the combination of heavy chain complementarity determining regions (CDRs) shown in Table 1 and a combination of the light chain CDRs selected from the CDR sequences shown in Table 2, and wherein the second antigen binding region includes the combination of heavy chain complementarity determining regions (CDRs) shown in Table 1 and a combination of the light chain CDRs selected from the CDR sequences shown in Table 3.

TABLE 1

Common Heavy Chain CDRs

| CDRH1 | CDRH2 | CDRH3 |
|---|---|---|
| GFTFSSYA (SEQ ID NO: 1) | ISGSGGST (SEQ ID NO: 2) | AKSYGAFDY (SEQ ID NO: 3) |

TABLE 2

Anti-CD47 Kappa Light Chain CDRs

| Kappa Chain | CDRL1 | CDRL2 | CDRL3 |
|---|---|---|---|
| K26 | QDINKY (SEQ ID NO: 89) | GAS (SEQ ID NO: 217) | QQMHPRAPKT (SEQ ID NO: 96) |
| K30 | QSISSY (SEQ ID NO: 90) | AAS (SEQ ID NO: 94) | QQMHPRSPKI (SEQ ID NO: 97) |
| K31 | QSISSY (SEQ ID NO: 90) | AAS (SEQ ID NO: 94) | QQMHPRANKI (SEQ ID NO: 98) |
| K32 | QSISSY (SEQ ID NO: 90) | AAS (SEQ ID NO: 94) | QQMHPRTAKQ (SEQ ID NO: 99) |
| K34 | QSISSY (SEQ ID NO: 90) | AAS (SEQ ID NO: 94) | QQFHPRAPKQ (SEQ ID NO: 100) |
| K35 | QSISSY (SEQ ID NO: 90) | AAS (SEQ ID NO: 94) | QQMHPRSHKQ (SEQ ID NO: 101) |
| K36 | QSISSY (SEQ ID NO: 90) | AAS (SEQ ID NO: 94) | QQFHPRAAKN (SEQ ID NO: 102) |
| K37 | QDINKY (SEQ ID NO: 89) | AAS (SEQ ID NO: 94) | QQMHPRAPKT (SEQ ID NO: 96) |
| K40 | QAIDKF (SEQ ID NO: 91) | ASS (SEQ ID NO: 95) | QQMHPRAPKT (SEQ ID NO: 96) |
| K41 | QTIDKF (SEQ ID NO: 92) | AAS (SEQ ID NO: 94) | QQMHPRAPKT (SEQ ID NO: 96) |
| K43 | QTIDKF (SEQ ID NO: 92) | AAS (SEQ ID NO: 94) | QQMHPRAPKT (SEQ ID NO: 96) |
| K33 | QSISSY (SEQ ID NO: 90) | AAS (SEQ ID NO: 94) | QQMHPRAPKT (SEQ ID NO: 211) |

TABLE 2-continued

Anti-CD47 Kappa Light Chain CDRs

| Kappa Chain | CDRL1 | CDRL2 | CDRL3 |
|---|---|---|---|
| K38 | QVIANW (SEQ ID NO: 213) | AGS (SEQ ID NO: 215) | QQMHPRAPKT (SEQ ID NO: 96) |
| K91 | QVIANW (SEQ ID NO: 213) | AAS (SEQ ID NO: 94) | QQMHPRAPKT (SEQ ID NO: 211) |
| K106 | QGIPSY (SEQ ID NO: 214) | GNS (SEQ ID NO: 216) | QQHTIGTRTNT (SEQ ID NO: 212) |

TABLE 3

Anti-PD-L1 Lambda Light Chain CDRs

| Lambda Light Chain | CDRL1 | CDRL2 | CDRL3 |
|---|---|---|---|
| S8 | SSNIRDSF (SEQ ID NO: 8) | ATN (SEQ ID NO: 15) | AAWHPYYTL (SEQ ID NO: 20) |
| S9 | SSNIRDSF (SEQ ID NO: 8) | ATN (SEQ ID NO: 15) | ASWWPYGTV (SEQ ID NO: 21) |
| S37 | SSNIRDSF (SEQ ID NO: 8) | ATN (SEQ ID NO: 15) | ASWWPFGTV (SEQ ID NO: 22) |
| S14 | SSDVVKNNF (SEQ ID NO: 9) | FGS (SEQ ID NO: 16) | SSWDMPALF (SEQ ID NO: 23) |
| S15 | SSDVVKNNF (SEQ ID NO: 9) | FGS (SEQ ID NO: 16) | SSWDEPDRP (SEQ ID NO: 24) |
| S17 | SSDVVKNNF (SEQ ID NO: 9) | FGS (SEQ ID NO: 16) | SSWDLPFLM (SEQ ID NO: 25) |
| S57 | SSDVVKNNF (SEQ ID NO: 9) | FGS (SEQ ID NO: 16) | SSWDEPDRP (SEQ ID NO: 24) |
| S58 | SSDVVKNNF (SEQ ID NO: 9) | FGS (SEQ ID NO: 16) | SSWDEPDRP (SEQ ID NO: 24) |
| S28 | SSNIAHKP (SEQ ID NO: 10) | HDN (SEQ ID NO: 17) | AAWDFATWPATEV (SEQ ID NO: 147) |
| S30 | SSNIAHKP (SEQ ID NO: 10) | HDN (SEQ ID NO: 17) | AAWDFSRWPATEV (SEQ ID NO: 148) |
| S94 | SVDIAHKP (SEQ ID NO: 11) | HDT (SEQ ID NO: 18) | AAWDFATWPATEV (SEQ ID NO: 147) |
| S23 | SSDVAKIPL (SEQ ID NO: 12) | FAS (SEQ ID NO: 19) | SSWDNAGDGHV (SEQ ID NO: 26) |
| S46 | SSDVLRPPL (SEQ ID NO: 13) | FAS (SEQ ID NO: 19) | SSWDNAGDGHV (SEQ ID NO: 26) |

TABLE 3-continued

| Anti-PD-L1 Lambda Light Chain CDRs | | | |
|---|---|---|---|
| Lambda Light Chain | CDRL1 | CDRL2 | CDRL3 |
| S71 | SSDVFRPPL (SEQ ID NO: 14) | FAS (SEQ ID NO: 19) | SSWDQSGDGHV (SEQ ID NO: 27) |
| S79 | SSDVFRPPL (SEQ ID NO: 14) | FAS (SEQ ID NO: 19) | SSWDHTGDGHV (SEQ ID NO: 28) |

In some embodiments, the K26×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K26×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 31 encoded by the nucleic acid sequence of SEQ ID NO: 32.

In some embodiments, the K26×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 29 encoded by the nucleic acid sequence shown in SEQ ID NO: 30.

In some embodiments, the K26×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K26×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 35 encoded by the nucleic acid sequence of SEQ ID NO: 36.

In some embodiments, the K26×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 33 encoded by the nucleic acid sequence shown in SEQ ID NO: 34.

In some embodiments, the K26×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K26×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 39 encoded by the nucleic acid sequence of SEQ ID NO: 40.

In some embodiments, the K26×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 37 encoded by the nucleic acid sequence shown in SEQ ID NO: 38.

In some embodiments, the K26×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K26×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 43 encoded by the nucleic acid sequence of SEQ ID NO: 44.

In some embodiments, the K26×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 41 encoded by the nucleic acid sequence shown in SEQ ID NO: 42.

In some embodiments, the K26×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K26×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 47 encoded by the nucleic acid sequence of SEQ ID NO: 48.

In some embodiments, the K26×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 45 encoded by the nucleic acid sequence shown in SEQ ID NO: 46.

In some embodiments, the K26×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K26×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 51 encoded by the nucleic acid sequence of SEQ ID NO: 52.

In some embodiments, the K26×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 49 encoded by the nucleic acid sequence shown in SEQ ID NO: 50.

In some embodiments, the K26×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K26×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 55 encoded by the nucleic acid sequence of SEQ ID NO: 56.

In some embodiments, the K26×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 53 encoded by the nucleic acid sequence shown in SEQ ID NO: 54.

In some embodiments, the K26×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K26×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 59 encoded by the nucleic acid sequence of SEQ ID NO: 60.

In some embodiments, the K26×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 57 encoded by the nucleic acid sequence shown in SEQ ID NO: 58.

In some embodiments, the K26×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K26×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 63 encoded by the nucleic acid sequence of SEQ ID NO: 64.

In some embodiments, the K26×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 61 encoded by the nucleic acid sequence shown in SEQ ID NO: 62.

In some embodiments, the K26×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K26×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 67 encoded by the nucleic acid sequence of SEQ ID NO: 68.

In some embodiments, the K26×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 65 encoded by the nucleic acid sequence shown in SEQ ID NO: 66.

In some embodiments, the K26×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K26×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 71 encoded by the nucleic acid sequence of SEQ ID NO: 72.

In some embodiments, the K26×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 69 encoded by the nucleic acid sequence shown in SEQ ID NO: 70.

In some embodiments, the K26×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K26×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 75 encoded by the nucleic acid sequence of SEQ ID NO: 76.

In some embodiments, the K26×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 73 encoded by the nucleic acid sequence shown in SEQ ID NO: 74.

In some embodiments, the K26×S46 bispecific antibody has a heavy chain comprising a CDRH1 comprising the amino acid sequence of SEQ ID NO: 1, a CDRH2 comprisinging the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K26×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 79 encoded by the nucleic acid sequence of SEQ ID NO: 80.

In some embodiments, the K26×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 77 encoded by the nucleic acid sequence shown in SEQ ID NO: 78.

In some embodiments, the K26×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K26×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 83 encoded by the nucleic acid sequence of SEQ ID NO: 84.

In some embodiments, the K26×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 81 encoded by the nucleic acid sequence shown in SEQ ID NO: 82.

In some embodiments, the K26×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 217, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K26×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 105 encoded by the nucleic acid sequence of SEQ ID NO: 106, and a lambda light chain variable region comprising the amino acid sequence of SEQ ID NO: 87 encoded by the nucleic acid sequence of SEQ ID NO: 88.

In some embodiments, the K26×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 103 encoded by the nucleic acid sequence of SEQ ID NO: 104, and a lambda light chain comprising the amino acid sequence of SEQ ID NO: 85 encoded by the nucleic acid sequence shown in SEQ ID NO: 86.

In some embodiments, the K30×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K30×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 31 encoded by the nucleic acid sequence of SEQ ID NO: 32.

In some embodiments, the K30×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 29 encoded by the nucleic acid sequence shown in SEQ ID NO: 30.

In some embodiments, the K30×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K30×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 35 encoded by the nucleic acid sequence of SEQ ID NO: 36.

In some embodiments, the K30×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 33 encoded by the nucleic acid sequence shown in SEQ ID NO: 34.

In some embodiments, the K30×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K30×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 39 encoded by the nucleic acid sequence of SEQ ID NO: 40.

In some embodiments, the K30×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 37 encoded by the nucleic acid sequence shown in SEQ ID NO: 38.

In some embodiments, the K30×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K30×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 43 encoded by the nucleic acid sequence of SEQ ID NO: 44.

In some embodiments, the K30×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 41 encoded by the nucleic acid sequence shown in SEQ ID NO: 42.

In some embodiments, the K30×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K30×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 47 encoded by the nucleic acid sequence of SEQ ID NO: 48.

In some embodiments, the K30×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 45 encoded by the nucleic acid sequence shown in SEQ ID NO: 46.

In some embodiments, the K30×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K30×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 51 encoded by the nucleic acid sequence of SEQ ID NO: 52.

In some embodiments, the K30×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 49 encoded by the nucleic acid sequence shown in SEQ ID NO: 50.

In some embodiments, the K30×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K30×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 55 encoded by the nucleic acid sequence of SEQ ID NO: 56.

In some embodiments, the K30×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 53 encoded by the nucleic acid sequence shown in SEQ ID NO: 54.

In some embodiments, the K30×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K30×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 59 encoded by the nucleic acid sequence of SEQ ID NO: 60.

In some embodiments, the K30×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 57 encoded by the nucleic acid sequence shown in SEQ ID NO: 58.

In some embodiments, the K30×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K30×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 63 encoded by the nucleic acid sequence of SEQ ID NO: 64.

In some embodiments, the K30×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 61 encoded by the nucleic acid sequence shown in SEQ ID NO: 62.

In some embodiments, the K30×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K30×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO:

110, and a lambda light chain variable region comprising the amino acid sequence of SEQ ID NO: 67 encoded by the nucleic acid sequence of SEQ ID NO: 68.

In some embodiments, the K30×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 65 encoded by the nucleic acid sequence shown in SEQ ID NO: 66.

In some embodiments, the K30×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K30×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 71 encoded by the nucleic acid sequence of SEQ ID NO: 72.

In some embodiments, the K30×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 69 encoded by the nucleic acid sequence shown in SEQ ID NO: 70.

In some embodiments, the K30×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K30×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 75 encoded by the nucleic acid sequence of SEQ ID NO: 76.

In some embodiments, the K30×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 73 encoded by the nucleic acid sequence shown in SEQ ID NO: 74.

In some embodiments, the K30×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K30×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 79 encoded by the nucleic acid sequence of SEQ ID NO: 80.

In some embodiments, the K30×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 77 encoded by the nucleic acid sequence shown in SEQ ID NO: 78.

In some embodiments, the K30×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K30×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 83 encoded by the nucleic acid sequence of SEQ ID NO: 84.

In some embodiments, the K30×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 81 encoded by the nucleic acid sequence shown in SEQ ID NO: 82.

In some embodiments, the K30×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 97, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K30×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 109 encoded by the nucleic acid sequence of SEQ ID NO: 110, and a lambda light chain variable region comprising the amino acid sequence of SEQ ID NO: 87 encoded by the nucleic acid sequence of SEQ ID NO: 88.

In some embodiments, the K30×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 107 encoded by the nucleic acid sequence of SEQ ID NO: 108, and a lambda light chain comprising the amino acid sequence of SEQ ID NO: 85 encoded by the nucleic acid sequence shown in SEQ ID NO: 86.

In some embodiments, the K31×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K31×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 31 encoded by the nucleic acid sequence of SEQ ID NO: 32.

In some embodiments, the K31×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 29 encoded by the nucleic acid sequence shown in SEQ ID NO: 30.

In some embodiments, the K31×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K31×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 35 encoded by the nucleic acid sequence of SEQ ID NO: 36.

In some embodiments, the K31×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 33 encoded by the nucleic acid sequence shown in SEQ ID NO: 34.

In some embodiments, the K31×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K31×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 39 encoded by the nucleic acid sequence of SEQ ID NO: 40.

In some embodiments, the K31×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 37 encoded by the nucleic acid sequence shown in SEQ ID NO: 38.

In some embodiments, the K31×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K31×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 43 encoded by the nucleic acid sequence of SEQ ID NO: 44.

In some embodiments, the K31×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 41 encoded by the nucleic acid sequence shown in SEQ ID NO: 42.

In some embodiments, the K31×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K31×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 47 encoded by the nucleic acid sequence of SEQ ID NO: 48.

In some embodiments, the K31×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 45 encoded by the nucleic acid sequence shown in SEQ ID NO: 46.

In some embodiments, the K31×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K31×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 51 encoded by the nucleic acid sequence of SEQ ID NO: 52.

In some embodiments, the K31×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 49 encoded by the nucleic acid sequence shown in SEQ ID NO: 50.

In some embodiments, the K31×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K31×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 55 encoded by the nucleic acid sequence of SEQ ID NO: 56.

In some embodiments, the K31×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 53 encoded by the nucleic acid sequence shown in SEQ ID NO: 54.

In some embodiments, the K31×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K31×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 59 encoded by the nucleic acid sequence of SEQ ID NO: 60.

In some embodiments, the K31×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 57 encoded by the nucleic acid sequence shown in SEQ ID NO: 58.

In some embodiments, the K31×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K31×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 63 encoded by the nucleic acid sequence of SEQ ID NO: 64.

In some embodiments, the K31×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 61 encoded by the nucleic acid sequence shown in SEQ ID NO: 62.

In some embodiments, the K31×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 25.

In some embodiments, the K31×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 67 encoded by the nucleic acid sequence of SEQ ID NO: 68.

In some embodiments, the K31×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 65 encoded by the nucleic acid sequence shown in SEQ ID NO: 66.

In some embodiments, the K31×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K31×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 71 encoded by the nucleic acid sequence of SEQ ID NO: 72.

In some embodiments, the K31×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 69 encoded by the nucleic acid sequence shown in SEQ ID NO: 70.

In some embodiments, the K31×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K31×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 75 encoded by the nucleic acid sequence of SEQ ID NO: 76.

In some embodiments, the K31×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 73 encoded by the nucleic acid sequence shown in SEQ ID NO: 74.

In some embodiments, the K31×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K31×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 79 encoded by the nucleic acid sequence of SEQ ID NO: 80.

In some embodiments, the K31×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 77 encoded by the nucleic acid sequence shown in SEQ ID NO: 78.

In some embodiments, the K31×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K31×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 83 encoded by the nucleic acid sequence of SEQ ID NO: 84.

In some embodiments, the K31×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 81 encoded by the nucleic acid sequence shown in SEQ ID NO: 82.

In some embodiments, the K31×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 98, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K31×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 113 encoded by the nucleic acid sequence of SEQ ID NO: 114, and a lambda light chain variable region comprising the amino acid sequence of SEQ ID NO: 87 encoded by the nucleic acid sequence of SEQ ID NO: 88.

In some embodiments, the K31×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 111 encoded by the nucleic acid sequence of SEQ ID NO: 112, and a lambda light chain comprising the amino acid sequence of SEQ ID NO: 85 encoded by the nucleic acid sequence shown in SEQ ID NO: 86.

In some embodiments, the K32×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K32×S8 bispecific antibody has a heavy chain variable region comprising the amino acid sequence of SEQ ID NO: 6 encoded by the nucleic acid sequence sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 31 encoded by the nucleic acid sequence of SEQ ID NO: 32.

In some embodiments, the K32×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 29 encoded by the nucleic acid sequence shown in SEQ ID NO: 30.

In some embodiments, the K32×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K32×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 35 encoded by the nucleic acid sequence of SEQ ID NO: 36.

In some embodiments, the K32×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 33 encoded by the nucleic acid sequence shown in SEQ ID NO: 34.

In some embodiments, the K32×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K32×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 39 encoded by the nucleic acid sequence of SEQ ID NO: 40.

In some embodiments, the K32×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 37 encoded by the nucleic acid sequence shown in SEQ ID NO: 38.

In some embodiments, the K32×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K32×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 43 encoded by the nucleic acid sequence of SEQ ID NO: 44.

In some embodiments, the K32×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 41 encoded by the nucleic acid sequence shown in SEQ ID NO: 42.

In some embodiments, the K32×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K32×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 47 encoded by the nucleic acid sequence of SEQ ID NO: 48.

In some embodiments, the K32×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 45 encoded by the nucleic acid sequence shown in SEQ ID NO: 46.

In some embodiments, the K32×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K32×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 51 encoded by the nucleic acid sequence of SEQ ID NO: 52.

In some embodiments, the K32×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 49 encoded by the nucleic acid sequence shown in SEQ ID NO: 50.

In some embodiments, the K32×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K32×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 55 encoded by the nucleic acid sequence of SEQ ID NO: 56.

In some embodiments, the K32×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 53 encoded by the nucleic acid sequence shown in SEQ ID NO: 54.

In some embodiments, the K32×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K32×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 59 encoded by the nucleic acid sequence of SEQ ID NO: 60.

In some embodiments, the K32×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 57 encoded by the nucleic acid sequence shown in SEQ ID NO: 58.

In some embodiments, the K32×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K32×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 63 encoded by the nucleic acid sequence of SEQ ID NO: 64.

In some embodiments, the K32×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 61 encoded by the nucleic acid sequence shown in SEQ ID NO: 62.

In some embodiments, the K32×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K32×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 67 encoded by the nucleic acid sequence of SEQ ID NO: 68.

In some embodiments, the K32×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 65 encoded by the nucleic acid sequence shown in SEQ ID NO: 66.

In some embodiments, the K32×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K32×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 71 encoded by the nucleic acid sequence of SEQ ID NO: 72.

In some embodiments, the K32×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 69 encoded by the nucleic acid sequence shown in SEQ ID NO: 70.

In some embodiments, the K32×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K32×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 75 encoded by the nucleic acid sequence of SEQ ID NO: 76.

In some embodiments, the K32×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 73 encoded by the nucleic acid sequence shown in SEQ ID NO: 74.

In some embodiments, the K32×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K32×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 79 encoded by the nucleic acid sequence of SEQ ID NO: 80.

In some embodiments, the K32×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 77 encoded by the nucleic acid sequence shown in SEQ ID NO: 78.

In some embodiments, the K32×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K32×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 83 encoded by the nucleic acid sequence of SEQ ID NO: 84.

In some embodiments, the K32×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 81 encoded by the nucleic acid sequence shown in SEQ ID NO: 82.

In some embodiments, the K32×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 99, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K32×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 117 encoded by the nucleic acid sequence of SEQ ID NO: 118, and a lambda light chain variable region comprising the amino acid sequence of SEQ ID NO: 87 encoded by the nucleic acid sequence of SEQ ID NO: 88.

In some embodiments, the K32×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 115 encoded by the nucleic acid sequence of SEQ ID NO: 116, and a lambda light chain comprising the amino acid sequence of SEQ ID NO: 85 encoded by the nucleic acid sequence shown in SEQ ID NO: 86.

In some embodiments, the K34×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K34×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 31 encoded by the nucleic acid sequence of SEQ ID NO: 32.

In some embodiments, the K34×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 29 encoded by the nucleic acid sequence shown in SEQ ID NO: 30.

In some embodiments, the K34×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K34×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 35 encoded by the nucleic acid sequence of SEQ ID NO: 36.

In some embodiments, the K34×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 33 encoded by the nucleic acid sequence shown in SEQ ID NO: 34.

In some embodiments, the K34×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K34×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 39 encoded by the nucleic acid sequence of SEQ ID NO: 40.

In some embodiments, the K34×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 37 encoded by the nucleic acid sequence shown in SEQ ID NO: 38.

In some embodiments, the K34×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K34×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 43 encoded by the nucleic acid sequence of SEQ ID NO: 44.

In some embodiments, the K34×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 41 encoded by the nucleic acid sequence shown in SEQ ID NO: 42.

In some embodiments, the K34×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K34×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 47 encoded by the nucleic acid sequence of SEQ ID NO: 48.

In some embodiments, the K34×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 45 encoded by the nucleic acid sequence shown in SEQ ID NO: 46.

In some embodiments, the K34×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K34×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 51 encoded by the nucleic acid sequence of SEQ ID NO: 52.

In some embodiments, the K34×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 49 encoded by the nucleic acid sequence shown in SEQ ID NO: 50.

In some embodiments, the K34×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K34×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 55 encoded by the nucleic acid sequence of SEQ ID NO: 56.

In some embodiments, the K34×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 53 encoded by the nucleic acid sequence shown in SEQ ID NO: 54.

In some embodiments, the K34×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K34×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 59 encoded by the nucleic acid sequence of SEQ ID NO: 60.

In some embodiments, the K34×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 57 encoded by the nucleic acid sequence shown in SEQ ID NO: 58.

In some embodiments, the K34×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K34×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 63 encoded by the nucleic acid sequence of SEQ ID NO: 64.

In some embodiments, the K34×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 61 encoded by the nucleic acid sequence shown in SEQ ID NO: 62.

In some embodiments, the K34×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K34×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 67 encoded by the nucleic acid sequence of SEQ ID NO: 68.

In some embodiments, the K34×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 65 encoded by the nucleic acid sequence shown in SEQ ID NO: 66.

In some embodiments, the K34×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K34×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO:

122, and a lambda light chain variable region comprising the amino acid sequence of SEQ ID NO: 71 encoded by the nucleic acid sequence of SEQ ID NO: 72.

In some embodiments, the K34×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 69 encoded by the nucleic acid sequence shown in SEQ ID NO: 70.

In some embodiments, the K34×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K34×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 75 encoded by the nucleic acid sequence of SEQ ID NO: 76.

In some embodiments, the K34×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 73 encoded by the nucleic acid sequence shown in SEQ ID NO: 74.

In some embodiments, the K34×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K34×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 79 encoded by the nucleic acid sequence of SEQ ID NO: 80.

In some embodiments, the K34×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 77 encoded by the nucleic acid sequence shown in SEQ ID NO: 78.

In some embodiments, the K34×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K34×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 83 encoded by the nucleic acid sequence of SEQ ID NO: 84.

In some embodiments, the K34×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 81 encoded by the nucleic acid sequence shown in SEQ ID NO: 82.

In some embodiments, the K34×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 100, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K34×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 121 encoded by the nucleic acid sequence of SEQ ID NO: 122, and a lambda light chain variable region comprising the amino acid sequence of SEQ ID NO: 87 encoded by the nucleic acid sequence of SEQ ID NO: 88.

In some embodiments, the K34×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 119 encoded by the nucleic acid sequence of SEQ ID NO: 120, and a lambda light chain comprising the amino acid sequence of SEQ ID NO: 85 encoded by the nucleic acid sequence shown in SEQ ID NO: 86.

In some embodiments, the K35×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K35×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 31 encoded by the nucleic acid sequence of SEQ ID NO: 32.

In some embodiments, the K35×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 29 encoded by the nucleic acid sequence shown in SEQ ID NO: 30.

In some embodiments, the K35×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K35×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 35 encoded by the nucleic acid sequence of SEQ ID NO: 36.

In some embodiments, the K35×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 33 encoded by the nucleic acid sequence shown in SEQ ID NO: 34.

In some embodiments, the K35×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K35×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 39 encoded by the nucleic acid sequence of SEQ ID NO: 40.

In some embodiments, the K35×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 37 encoded by the nucleic acid sequence shown in SEQ ID NO: 38.

In some embodiments, the K35×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K35×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 43 encoded by the nucleic acid sequence of SEQ ID NO: 44.

In some embodiments, the K35×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 41 encoded by the nucleic acid sequence shown in SEQ ID NO: 42.

In some embodiments, the K35×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K35×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 47 encoded by the nucleic acid sequence of SEQ ID NO: 48.

In some embodiments, the K35×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 45 encoded by the nucleic acid sequence shown in SEQ ID NO: 46.

In some embodiments, the K35×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K35×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 51 encoded by the nucleic acid sequence of SEQ ID NO: 52.

In some embodiments, the K35×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 49 encoded by the nucleic acid sequence shown in SEQ ID NO: 50.

In some embodiments, the K35×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K35×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 55 encoded by the nucleic acid sequence of SEQ ID NO: 56.

In some embodiments, the K35×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 53 encoded by the nucleic acid sequence shown in SEQ ID NO: 54.

In some embodiments, the K35×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K35×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 59 encoded by the nucleic acid sequence of SEQ ID NO: 60.

In some embodiments, the K35×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 57 encoded by the nucleic acid sequence shown in SEQ ID NO: 58.

In some embodiments, the K35×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K35×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 63 encoded by the nucleic acid sequence of SEQ ID NO: 64.

In some embodiments, the K35×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 61 encoded by the nucleic acid sequence shown in SEQ ID NO: 62.

In some embodiments, the K35×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K35×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 67 encoded by the nucleic acid sequence of SEQ ID NO: 68.

In some embodiments, the K35×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 65 encoded by the nucleic acid sequence shown in SEQ ID NO: 66.

In some embodiments, the K35×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K35×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 71 encoded by the nucleic acid sequence of SEQ ID NO: 72.

In some embodiments, the K35×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 69 encoded by the nucleic acid sequence shown in SEQ ID NO: 70.

In some embodiments, the K35×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K35×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 75 encoded by the nucleic acid sequence of SEQ ID NO: 76.

In some embodiments, the K35×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 73 encoded by the nucleic acid sequence shown in SEQ ID NO: 74.

In some embodiments, the K35×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K35×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 79 encoded by the nucleic acid sequence of SEQ ID NO: 80.

In some embodiments, the K35×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 77 encoded by the nucleic acid sequence shown in SEQ ID NO: 78.

In some embodiments, the K35×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K35×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 83 encoded by the nucleic acid sequence of SEQ ID NO: 84.

In some embodiments, the K35×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 81 encoded by the nucleic acid sequence shown in SEQ ID NO: 82.

In some embodiments, the K35×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 101, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K35×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 125 encoded by the nucleic acid sequence of SEQ ID NO: 126, and a lambda light chain variable region comprising the amino acid sequence of SEQ ID NO: 87 encoded by the nucleic acid sequence of SEQ ID NO: 88.

In some embodiments, the K35×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 123 encoded by the nucleic acid sequence of SEQ ID NO: 124, and a lambda light chain comprising the amino acid sequence of SEQ ID NO: 85 encoded by the nucleic acid sequence shown in SEQ ID NO: 86.

In some embodiments, the K36×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K36×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 31 encoded by the nucleic acid sequence of SEQ ID NO: 32.

In some embodiments, the K36×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 29 encoded by the nucleic acid sequence shown in SEQ ID NO: 30.

In some embodiments, the K36×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K36×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 35 encoded by the nucleic acid sequence of SEQ ID NO: 36.

In some embodiments, the K36×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 33 encoded by the nucleic acid sequence shown in SEQ ID NO: 34.

In some embodiments, the K36×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K36×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 39 encoded by the nucleic acid sequence of SEQ ID NO: 40.

In some embodiments, the K36×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 37 encoded by the nucleic acid sequence shown in SEQ ID NO: 38.

In some embodiments, the K36×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K36×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 43 encoded by the nucleic acid sequence of SEQ ID NO: 44.

In some embodiments, the K36×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 41 encoded by the nucleic acid sequence shown in SEQ ID NO: 42.

In some embodiments, the K36×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K36×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 47 encoded by the nucleic acid sequence of SEQ ID NO: 48.

In some embodiments, the K36×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 45 encoded by the nucleic acid sequence shown in SEQ ID NO: 46.

In some embodiments, the K36×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K36×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 51 encoded by the nucleic acid sequence of SEQ ID NO: 52.

In some embodiments, the K36×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 49 encoded by the nucleic acid sequence shown in SEQ ID NO: 50.

In some embodiments, the K36×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K36×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 55 encoded by the nucleic acid sequence of SEQ ID NO: 56.

In some embodiments, the K36×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 53 encoded by the nucleic acid sequence shown in SEQ ID NO: 54.

In some embodiments, the K36×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K36×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 59 encoded by the nucleic acid sequence of SEQ ID NO: 60.

In some embodiments, the K36×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 57 encoded by the nucleic acid sequence shown in SEQ ID NO: 58.

In some embodiments, the K36×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K36×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 63 encoded by the nucleic acid sequence of SEQ ID NO: 64.

In some embodiments, the K36×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 61 encoded by the nucleic acid sequence shown in SEQ ID NO: 62.

In some embodiments, the K36×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K36×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 67 encoded by the nucleic acid sequence of SEQ ID NO: 68.

In some embodiments, the K36×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 65 encoded by the nucleic acid sequence shown in SEQ ID NO: 66.

In some embodiments, the K36×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K36×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 71 encoded by the nucleic acid sequence of SEQ ID NO: 72.

In some embodiments, the K36×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 69 encoded by the nucleic acid sequence shown in SEQ ID NO: 70.

In some embodiments, the K36×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K36×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 75 encoded by the nucleic acid sequence of SEQ ID NO: 76.

In some embodiments, the K36×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 73 encoded by the nucleic acid sequence shown in SEQ ID NO: 74.

In some embodiments, the K36×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K36×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 79 encoded by the nucleic acid sequence of SEQ ID NO: 80.

In some embodiments, the K36×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 77 encoded by the nucleic acid sequence shown in SEQ ID NO: 78.

In some embodiments, the K36×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K36×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 83 encoded by the nucleic acid sequence of SEQ ID NO: 84.

In some embodiments, the K36×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 81 encoded by the nucleic acid sequence shown in SEQ ID NO: 82.

In some embodiments, the K36×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 102, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K36×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 129 encoded by the nucleic acid sequence of SEQ ID NO: 130, and a lambda light chain variable region comprising the amino acid sequence of SEQ ID NO: 87 encoded by the nucleic acid sequence of SEQ ID NO: 88.

In some embodiments, the K36×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 127 encoded by the nucleic acid sequence of SEQ ID NO: 128, and a lambda light chain comprising the amino acid sequence of SEQ ID NO: 85 encoded by the nucleic acid sequence shown in SEQ ID NO: 86.

In some embodiments, the K37×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K37×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 31 encoded by the nucleic acid sequence of SEQ ID NO: 32.

In some embodiments, the K37×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 29 encoded by the nucleic acid sequence shown in SEQ ID NO: 30.

In some embodiments, the K37×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K37×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 35 encoded by the nucleic acid sequence of SEQ ID NO: 36.

In some embodiments, the K37×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 33 encoded by the nucleic acid sequence shown in SEQ ID NO: 34.

In some embodiments, the K37×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K37×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 39 encoded by the nucleic acid sequence of SEQ ID NO: 40.

In some embodiments, the K37×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 37 encoded by the nucleic acid sequence shown in SEQ ID NO: 38.

In some embodiments, the K37×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K37×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 43 encoded by the nucleic acid sequence of SEQ ID NO: 44.

In some embodiments, the K37×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 41 encoded by the nucleic acid sequence shown in SEQ ID NO: 42.

In some embodiments, the K37×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K37×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 47 encoded by the nucleic acid sequence of SEQ ID NO: 48.

In some embodiments, the K37×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 45 encoded by the nucleic acid sequence shown in SEQ ID NO: 46.

In some embodiments, the K37×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K37×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 51 encoded by the nucleic acid sequence of SEQ ID NO: 52.

In some embodiments, the K37×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 49 encoded by the nucleic acid sequence shown in SEQ ID NO: 50.

In some embodiments, the K37×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K37×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 55 encoded by the nucleic acid sequence of SEQ ID NO: 56.

In some embodiments, the K37×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 53 encoded by the nucleic acid sequence shown in SEQ ID NO: 54.

In some embodiments, the K37×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K37×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 59 encoded by the nucleic acid sequence of SEQ ID NO: 60.

In some embodiments, the K37×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 57 encoded by the nucleic acid sequence shown in SEQ ID NO: 58.

In some embodiments, the K37×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K37×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 63 encoded by the nucleic acid sequence of SEQ ID NO: 64.

In some embodiments, the K37×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 61 encoded by the nucleic acid sequence shown in SEQ ID NO: 62.

In some embodiments, the K37×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K37×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 67 encoded by the nucleic acid sequence of SEQ ID NO: 68.

In some embodiments, the K37×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 65 encoded by the nucleic acid sequence shown in SEQ ID NO: 66.

In some embodiments, the K37×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K37×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 71 encoded by the nucleic acid sequence of SEQ ID NO: 72.

In some embodiments, the K37×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 69 encoded by the nucleic acid sequence shown in SEQ ID NO: 70.

In some embodiments, the K37×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K37×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO:

134, and a lambda light chain variable region comprising the amino acid sequence of SEQ ID NO: 75 encoded by the nucleic acid sequence of SEQ ID NO: 76.

In some embodiments, the K37×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 73 encoded by the nucleic acid sequence shown in SEQ ID NO: 74.

In some embodiments, the K37×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K37×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 79 encoded by the nucleic acid sequence of SEQ ID NO: 80.

In some embodiments, the K37×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 77 encoded by the nucleic acid sequence shown in SEQ ID NO: 78.

In some embodiments, the K37×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K37×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 83 encoded by the nucleic acid sequence of SEQ ID NO: 84.

In some embodiments, the K37×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 81 encoded by the nucleic acid sequence shown in SEQ ID NO: 82.

In some embodiments, the K37×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 89, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K37×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 133 encoded by the nucleic acid sequence of SEQ ID NO: 134, and a lambda light chain variable region comprising the amino acid sequence of SEQ ID NO: 87 encoded by the nucleic acid sequence of SEQ ID NO: 88.

In some embodiments, the K37×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 131 encoded by the nucleic acid sequence of SEQ ID NO: 132, and a lambda light chain comprising the amino acid sequence of SEQ ID NO: 85 encoded by the nucleic acid sequence shown in SEQ ID NO: 86.

In some embodiments, the K40×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K40×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 31 encoded by the nucleic acid sequence of SEQ ID NO: 32.

In some embodiments, the K40×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 29 encoded by the nucleic acid sequence shown in SEQ ID NO: 30.

In some embodiments, the K40×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K40×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 35 encoded by the nucleic acid sequence of SEQ ID NO: 36.

In some embodiments, the K40×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 33 encoded by the nucleic acid sequence shown in SEQ ID NO: 34.

In some embodiments, the K40×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K40×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 39 encoded by the nucleic acid sequence of SEQ ID NO: 40.

In some embodiments, the K40×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 37 encoded by the nucleic acid sequence shown in SEQ ID NO: 38.

In some embodiments, the K40×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K40×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 43 encoded by the nucleic acid sequence of SEQ ID NO: 44.

In some embodiments, the K40×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 41 encoded by the nucleic acid sequence shown in SEQ ID NO: 42.

In some embodiments, the K40×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K40×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 47 encoded by the nucleic acid sequence of SEQ ID NO: 48.

In some embodiments, the K40×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 45 encoded by the nucleic acid sequence shown in SEQ ID NO: 46.

In some embodiments, the K40×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K40×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 51 encoded by the nucleic acid sequence of SEQ ID NO: 52.

In some embodiments, the K40×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 49 encoded by the nucleic acid sequence shown in SEQ ID NO: 50.

In some embodiments, the K40×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K40×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 55 encoded by the nucleic acid sequence of SEQ ID NO: 56.

In some embodiments, the K40×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 53 encoded by the nucleic acid sequence shown in SEQ ID NO: 54.

In some embodiments, the K40×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K40×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 59 encoded by the nucleic acid sequence of SEQ ID NO: 60.

In some embodiments, the K40×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 57 encoded by the nucleic acid sequence shown in SEQ ID NO: 58.

In some embodiments, the K40×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K40×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 63 encoded by the nucleic acid sequence of SEQ ID NO: 64.

In some embodiments, the K40×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 61 encoded by the nucleic acid sequence shown in SEQ ID NO: 62.

In some embodiments, the K40×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K40×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 67 encoded by the nucleic acid sequence of SEQ ID NO: 68.

In some embodiments, the K40×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 65 encoded by the nucleic acid sequence shown in SEQ ID NO: 66.

In some embodiments, the K40×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K40×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 71 encoded by the nucleic acid sequence of SEQ ID NO: 72.

In some embodiments, the K40×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 69 encoded by the nucleic acid sequence shown in SEQ ID NO: 70.

In some embodiments, the K40×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K40×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 75 encoded by the nucleic acid sequence of SEQ ID NO: 76.

In some embodiments, the K40×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 73 encoded by the nucleic acid sequence shown in SEQ ID NO: 74.

In some embodiments, the K40×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K40×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 79 encoded by the nucleic acid sequence of SEQ ID NO: 80.

In some embodiments, the K40×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 77 encoded by the nucleic acid sequence shown in SEQ ID NO: 78.

In some embodiments, the K40×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K40×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 83 encoded by the nucleic acid sequence of SEQ ID NO: 84.

In some embodiments, the K40×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 81 encoded by the nucleic acid sequence shown in SEQ ID NO: 82.

In some embodiments, the K40×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 91, a CDRL2 comprising the amino acid sequence of SEQ ID NO: 95, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K40×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 137 encoded by the nucleic acid sequence of SEQ ID NO: 138, and a lambda light chain variable region comprising the amino acid sequence of SEQ ID NO: 87 encoded by the nucleic acid sequence of SEQ ID NO: 88.

In some embodiments, the K40×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 135 encoded by the nucleic acid sequence of SEQ ID NO: 136, and a lambda light chain comprising the amino acid sequence of SEQ ID NO: 85 encoded by the nucleic acid sequence shown in SEQ ID NO: 86.

In some embodiments, the K41×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K41×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 31 encoded by the nucleic acid sequence of SEQ ID NO: 32.

In some embodiments, the K41×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 29 encoded by the nucleic acid sequence shown in SEQ ID NO: 30.

In some embodiments, the K41×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K41×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 35 encoded by the nucleic acid sequence of SEQ ID NO: 36.

In some embodiments, the K41×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 33 encoded by the nucleic acid sequence shown in SEQ ID NO: 34.

In some embodiments, the K41×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K41×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 39 encoded by the nucleic acid sequence of SEQ ID NO: 40.

In some embodiments, the K41×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 37 encoded by the nucleic acid sequence shown in SEQ ID NO: 38.

In some embodiments, the K41×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K41×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 43 encoded by the nucleic acid sequence of SEQ ID NO: 44.

In some embodiments, the K41×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 41 encoded by the nucleic acid sequence shown in SEQ ID NO: 42.

In some embodiments, the K41×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K41×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 47 encoded by the nucleic acid sequence of SEQ ID NO: 48.

In some embodiments, the K41×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 45 encoded by the nucleic acid sequence shown in SEQ ID NO: 46.

In some embodiments, the K41×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K41×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 51 encoded by the nucleic acid sequence of SEQ ID NO: 52.

In some embodiments, the K41×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 49 encoded by the nucleic acid sequence shown in SEQ ID NO: 50.

In some embodiments, the K41×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K41×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 55 encoded by the nucleic acid sequence of SEQ ID NO: 56.

In some embodiments, the K41×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 53 encoded by the nucleic acid sequence shown in SEQ ID NO: 54.

In some embodiments, the K41×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K41×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 59 encoded by the nucleic acid sequence of SEQ ID NO: 60.

In some embodiments, the K41×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 57 encoded by the nucleic acid sequence shown in SEQ ID NO: 58.

In some embodiments, the K41×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K41×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 63 encoded by the nucleic acid sequence of SEQ ID NO: 64.

In some embodiments, the K41×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 61 encoded by the nucleic acid sequence shown in SEQ ID NO: 62.

In some embodiments, the K41×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K41×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 67 encoded by the nucleic acid sequence of SEQ ID NO: 68.

In some embodiments, the K41×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 65 encoded by the nucleic acid sequence shown in SEQ ID NO: 66.

In some embodiments, the K41×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K41×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 71 encoded by the nucleic acid sequence of SEQ ID NO: 72.

In some embodiments, the K41×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 69 encoded by the nucleic acid sequence shown in SEQ ID NO: 70.

In some embodiments, the K41×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K41×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 75 encoded by the nucleic acid sequence of SEQ ID NO: 76.

In some embodiments, the K41×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 73 encoded by the nucleic acid sequence shown in SEQ ID NO: 74.

In some embodiments, the K41×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K41×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 79 encoded by the nucleic acid sequence of SEQ ID NO: 80.

In some embodiments, the K41×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 77 encoded by the nucleic acid sequence shown in SEQ ID NO: 78.

In some embodiments, the K41×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K41×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 83 encoded by the nucleic acid sequence of SEQ ID NO: 84.

In some embodiments, the K41×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 81 encoded by the nucleic acid sequence shown in SEQ ID NO: 82.

In some embodiments, the K41×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K41×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 141 encoded by the nucleic acid sequence of SEQ ID NO: 142, and a lambda light chain variable region comprising the amino acid sequence of SEQ ID NO: 87 encoded by the nucleic acid sequence of SEQ ID NO: 88.

In some embodiments, the K41×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 139 encoded by the nucleic acid sequence of SEQ ID NO: 140, and a lambda light chain comprising the amino acid sequence of SEQ ID NO: 85 encoded by the nucleic acid sequence shown in SEQ ID NO: 86.

In some embodiments, the K43×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K43×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 31 encoded by the nucleic acid sequence of SEQ ID NO: 32.

In some embodiments, the K43×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 29 encoded by the nucleic acid sequence shown in SEQ ID NO: 30.

In some embodiments, the K43×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K43×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 35 encoded by the nucleic acid sequence of SEQ ID NO: 36.

In some embodiments, the K43×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 33 encoded by the nucleic acid sequence shown in SEQ ID NO: 34.

In some embodiments, the K43×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K43×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 39 encoded by the nucleic acid sequence of SEQ ID NO: 40.

In some embodiments, the K43×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 37 encoded by the nucleic acid sequence shown in SEQ ID NO: 38.

In some embodiments, the K43×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K43×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 43 encoded by the nucleic acid sequence of SEQ ID NO: 44.

In some embodiments, the K43×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 41 encoded by the nucleic acid sequence shown in SEQ ID NO: 42.

In some embodiments, the K43×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K43×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 47 encoded by the nucleic acid sequence of SEQ ID NO: 48.

In some embodiments, the K43×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 45 encoded by the nucleic acid sequence shown in SEQ ID NO: 46.

In some embodiments, the K43×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K43×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 51 encoded by the nucleic acid sequence of SEQ ID NO: 52.

In some embodiments, the K43×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 49 encoded by the nucleic acid sequence shown in SEQ ID NO: 50.

In some embodiments, the K43×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K43×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 55 encoded by the nucleic acid sequence of SEQ ID NO: 56.

In some embodiments, the K43×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 53 encoded by the nucleic acid sequence shown in SEQ ID NO: 54.

In some embodiments, the K43×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K43×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 59 encoded by the nucleic acid sequence of SEQ ID NO: 60.

In some embodiments, the K43×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 57 encoded by the nucleic acid sequence shown in SEQ ID NO: 58.

In some embodiments, the K43×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K43×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 63 encoded by the nucleic acid sequence of SEQ ID NO: 64.

In some embodiments, the K43×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 61 encoded by the nucleic acid sequence shown in SEQ ID NO: 62.

In some embodiments, the K43×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K43×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 67 encoded by the nucleic acid sequence of SEQ ID NO: 68.

In some embodiments, the K43×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 65 encoded by the nucleic acid sequence shown in SEQ ID NO: 66.

In some embodiments, the K43×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K43×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 71 encoded by the nucleic acid sequence of SEQ ID NO: 72.

In some embodiments, the K43×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 69 encoded by the nucleic acid sequence shown in SEQ ID NO: 70.

In some embodiments, the K43×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K43×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 75 encoded by the nucleic acid sequence of SEQ ID NO: 76.

In some embodiments, the K43×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 73 encoded by the nucleic acid sequence shown in SEQ ID NO: 74.

In some embodiments, the K43×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K43×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO:

146, and a lambda light chain variable region comprising the amino acid sequence of SEQ ID NO: 79 encoded by the nucleic acid sequence of SEQ ID NO: 80.

In some embodiments, the K43×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 77 encoded by the nucleic acid sequence shown in SEQ ID NO: 78.

In some embodiments, the K43×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K43×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 83 encoded by the nucleic acid sequence of SEQ ID NO: 84.

In some embodiments, the K43×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 81 encoded by the nucleic acid sequence shown in SEQ ID NO: 82.

In some embodiments, the K43×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 92, a CDRL2 comprising the amino acid sequence of SEQ ID NO: 94, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K43×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 145 encoded by the nucleic acid sequence of SEQ ID NO: 146, and a lambda light chain variable region comprising the amino acid sequence of SEQ ID NO: 87 encoded by the nucleic acid sequence of SEQ ID NO: 88.

In some embodiments, the K43×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 143 encoded by the nucleic acid sequence of SEQ ID NO: 144, and a lambda light chain comprising the amino acid sequence of SEQ ID NO: 85 encoded by the nucleic acid sequence shown in SEQ ID NO: 86.

In some embodiments, the K33×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K33×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 31 encoded by the nucleic acid sequence of SEQ ID NO: 32.

In some embodiments, the K33×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 29 encoded by the nucleic acid sequence shown in SEQ ID NO: 30.

In some embodiments, the K33×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K33×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 35 encoded by the nucleic acid sequence of SEQ ID NO: 36.

In some embodiments, the K33×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 33 encoded by the nucleic acid sequence shown in SEQ ID NO: 34.

In some embodiments, the K33×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K33×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 39 encoded by the nucleic acid sequence of SEQ ID NO: 40.

In some embodiments, the K33×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 37 encoded by the nucleic acid sequence shown in SEQ ID NO: 38.

In some embodiments, the K33×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K33×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 43 encoded by the nucleic acid sequence of SEQ ID NO: 44.

In some embodiments, the K33×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 41 encoded by the nucleic acid sequence shown in SEQ ID NO: 42.

In some embodiments, the K33×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K33×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 47 encoded by the nucleic acid sequence of SEQ ID NO: 48.

In some embodiments, the K33×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 45 encoded by the nucleic acid sequence shown in SEQ ID NO: 46.

In some embodiments, the K33×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K33×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 51 encoded by the nucleic acid sequence of SEQ ID NO: 52.

In some embodiments, the K33×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 49 encoded by the nucleic acid sequence shown in SEQ ID NO: 50.

In some embodiments, the K33×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K33×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 55 encoded by the nucleic acid sequence of SEQ ID NO: 56.

In some embodiments, the K33×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 53 encoded by the nucleic acid sequence shown in SEQ ID NO: 54.

In some embodiments, the K33×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K33×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 59 encoded by the nucleic acid sequence of SEQ ID NO: 60.

In some embodiments, the K33×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 57 encoded by the nucleic acid sequence shown in SEQ ID NO: 58.

In some embodiments, the K33×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K33×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 63 encoded by the nucleic acid sequence of SEQ ID NO: 64.

In some embodiments, the K33×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 61 encoded by the nucleic acid sequence shown in SEQ ID NO: 62.

In some embodiments, the K33×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K33×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 67 encoded by the nucleic acid sequence of SEQ ID NO: 68.

In some embodiments, the K33×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 65 encoded by the nucleic acid sequence shown in SEQ ID NO: 66.

In some embodiments, the K33×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K33×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 71 encoded by the nucleic acid sequence of SEQ ID NO: 72.

In some embodiments, the K33×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 69 encoded by the nucleic acid sequence shown in SEQ ID NO: 70.

In some embodiments, the K33×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K33×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 75 encoded by the nucleic acid sequence of SEQ ID NO: 76.

In some embodiments, the K33×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 73 encoded by the nucleic acid sequence shown in SEQ ID NO: 74.

In some embodiments, the K33×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K33×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 79 encoded by the nucleic acid sequence of SEQ ID NO: 80.

In some embodiments, the K33×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 77 encoded by the nucleic acid sequence shown in SEQ ID NO: 78.

In some embodiments, the K33×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K33×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 83 encoded by the nucleic acid sequence of SEQ ID NO: 84.

In some embodiments, the K33×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 81 encoded by the nucleic acid sequence shown in SEQ ID NO: 82.

In some embodiments, the K33×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 90, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K33×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 222 encoded by the nucleic acid sequence of SEQ ID NO: 223, and a lambda light chain variable region comprising the amino acid sequence of SEQ ID NO: 87 encoded by the nucleic acid sequence of SEQ ID NO: 88.

In some embodiments, the K33×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 220 encoded by the nucleic acid sequence of SEQ ID NO: 221, and a lambda light chain comprising the amino acid sequence of SEQ ID NO: 85 encoded by the nucleic acid sequence shown in SEQ ID NO: 86.

In some embodiments, the K38×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K38×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 31 encoded by the nucleic acid sequence of SEQ ID NO: 32.

In some embodiments, the K38×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 29 encoded by the nucleic acid sequence shown in SEQ ID NO: 30.

In some embodiments, the K38×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K38×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 35 encoded by the nucleic acid sequence of SEQ ID NO: 36.

In some embodiments, the K38×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 33 encoded by the nucleic acid sequence shown in SEQ ID NO: 34.

In some embodiments, the K38×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K38×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 39 encoded by the nucleic acid sequence of SEQ ID NO: 40.

In some embodiments, the K38×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 37 encoded by the nucleic acid sequence shown in SEQ ID NO: 38.

In some embodiments, the K38×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K38×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 43 encoded by the nucleic acid sequence of SEQ ID NO: 44.

In some embodiments, the K38×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 41 encoded by the nucleic acid sequence shown in SEQ ID NO: 42.

In some embodiments, the K38×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K38×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 47 encoded by the nucleic acid sequence of SEQ ID NO: 48.

In some embodiments, the K38×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 45 encoded by the nucleic acid sequence shown in SEQ ID NO: 46.

In some embodiments, the K38×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K38×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 51 encoded by the nucleic acid sequence of SEQ ID NO: 52.

In some embodiments, the K38×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 49 encoded by the nucleic acid sequence shown in SEQ ID NO: 50.

In some embodiments, the K38×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K38×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 55 encoded by the nucleic acid sequence of SEQ ID NO: 56.

In some embodiments, the K38×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 53 encoded by the nucleic acid sequence shown in SEQ ID NO: 54.

In some embodiments, the K38×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K38×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 59 encoded by the nucleic acid sequence of SEQ ID NO: 60.

In some embodiments, the K38×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 57 encoded by the nucleic acid sequence shown in SEQ ID NO: 58.

In some embodiments, the K38×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K38×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 63 encoded by the nucleic acid sequence of SEQ ID NO: 64.

In some embodiments, the K38×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 61 encoded by the nucleic acid sequence shown in SEQ ID NO: 62.

In some embodiments, the K38×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K38×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 67 encoded by the nucleic acid sequence of SEQ ID NO: 68.

In some embodiments, the K38×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 65 encoded by the nucleic acid sequence shown in SEQ ID NO: 66.

In some embodiments, the K38×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K38×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 71 encoded by the nucleic acid sequence of SEQ ID NO: 72.

In some embodiments, the K38×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 69 encoded by the nucleic acid sequence shown in SEQ ID NO: 70.

In some embodiments, the K38×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K38×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 75 encoded by the nucleic acid sequence of SEQ ID NO: 76.

In some embodiments, the K38×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 73 encoded by the nucleic acid sequence shown in SEQ ID NO: 74.

In some embodiments, the K38×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K38×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 79 encoded by the nucleic acid sequence of SEQ ID NO: 80.

In some embodiments, the K38×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 77 encoded by the nucleic acid sequence shown in SEQ ID NO: 78.

In some embodiments, the K38×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K38×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 83 encoded by the nucleic acid sequence of SEQ ID NO: 84.

In some embodiments, the K38×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 81 encoded by the nucleic acid sequence shown in SEQ ID NO: 82.

In some embodiments, the K38×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 215, and a CDRL3 comprising the amino acid sequence of SEQ ID NO: 96, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K38×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 226 encoded by the nucleic acid sequence of SEQ ID NO: 227, and a lambda light chain variable region comprising the amino acid sequence of SEQ ID NO: 87 encoded by the nucleic acid sequence of SEQ ID NO: 88.

In some embodiments, the K38×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 224 encoded by the nucleic acid sequence of SEQ ID NO: 225, and a lambda light chain comprising the amino acid sequence of SEQ ID NO: 85 encoded by the nucleic acid sequence shown in SEQ ID NO: 86.

In some embodiments, the K91×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K91×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 31 encoded by the nucleic acid sequence of SEQ ID NO: 32.

In some embodiments, the K91×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 29 encoded by the nucleic acid sequence shown in SEQ ID NO: 30.

In some embodiments, the K91×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K91×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 35 encoded by the nucleic acid sequence of SEQ ID NO: 36.

In some embodiments, the K91×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 33 encoded by the nucleic acid sequence shown in SEQ ID NO: 34.

In some embodiments, the K91×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K91×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 39 encoded by the nucleic acid sequence of SEQ ID NO: 40.

In some embodiments, the K91×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 37 encoded by the nucleic acid sequence shown in SEQ ID NO: 38.

In some embodiments, the K91×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K91×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 43 encoded by the nucleic acid sequence of SEQ ID NO: 44.

In some embodiments, the K91×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 41 encoded by the nucleic acid sequence shown in SEQ ID NO: 42.

In some embodiments, the K91×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K91×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 47 encoded by the nucleic acid sequence of SEQ ID NO: 48.

In some embodiments, the K91×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 45 encoded by the nucleic acid sequence shown in SEQ ID NO: 46.

In some embodiments, the K91×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K91×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 51 encoded by the nucleic acid sequence of SEQ ID NO: 52.

In some embodiments, the K91×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 49 encoded by the nucleic acid sequence shown in SEQ ID NO: 50.

In some embodiments, the K91×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K91×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 55 encoded by the nucleic acid sequence of SEQ ID NO: 56.

In some embodiments, the K91×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 53 encoded by the nucleic acid sequence shown in SEQ ID NO: 54.

In some embodiments, the K91×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K91×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 59 encoded by the nucleic acid sequence of SEQ ID NO: 60.

In some embodiments, the K91×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 57 encoded by the nucleic acid sequence shown in SEQ ID NO: 58.

In some embodiments, the K91×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K91×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 63 encoded by the nucleic acid sequence of SEQ ID NO: 64.

In some embodiments, the K91×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 61 encoded by the nucleic acid sequence shown in SEQ ID NO: 62.

In some embodiments, the K91×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K91×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 67 encoded by the nucleic acid sequence of SEQ ID NO: 68.

In some embodiments, the K91×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 65 encoded by the nucleic acid sequence shown in SEQ ID NO: 66.

In some embodiments, the K91×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K91×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 71 encoded by the nucleic acid sequence of SEQ ID NO: 72.

In some embodiments, the K91×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 69 encoded by the nucleic acid sequence shown in SEQ ID NO: 70.

In some embodiments, the K91×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K91×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 75 encoded by the nucleic acid sequence of SEQ ID NO: 76.

In some embodiments, the K91×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 73 encoded by the nucleic acid sequence shown in SEQ ID NO: 74.

In some embodiments, the K91×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K91×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 79 encoded by the nucleic acid sequence of SEQ ID NO: 80.

In some embodiments, the K91×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 77 encoded by the nucleic acid sequence shown in SEQ ID NO: 78.

In some embodiments, the K91×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K91×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO:

241, and a lambda light chain variable region comprising the amino acid sequence of SEQ ID NO: 83 encoded by the nucleic acid sequence of SEQ ID NO: 84.

In some embodiments, the K91×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 81 encoded by the nucleic acid sequence shown in SEQ ID NO: 82.

In some embodiments, the K91×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 213, a CDRL2 comprising the amino acid sequence of SEQ ID NO: 94, and a CDRL3 comprising the amino acid sequence of SEQ ID NO: 211, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K91×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 240 encoded by the nucleic acid sequence of SEQ ID NO: 241, and a lambda light chain variable region comprising the amino acid sequence of SEQ ID NO: 87 encoded by the nucleic acid sequence of SEQ ID NO: 88.

In some embodiments, the K91×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 238 encoded by the nucleic acid sequence of SEQ ID NO: 239, and a lambda light chain comprising the amino acid sequence of SEQ ID NO: 85 encoded by the nucleic acid sequence shown in SEQ ID NO: 86.

In some embodiments, the K106×S8 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 20.

In some embodiments, the K106×S8 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 31 encoded by the nucleic acid sequence of SEQ ID NO: 32.

In some embodiments, the K106×S8 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 29 encoded by the nucleic acid sequence shown in SEQ ID NO: 30.

In some embodiments, the K106×S9 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 21.

In some embodiments, the K106×S9 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 35 encoded by the nucleic acid sequence of SEQ ID NO: 36.

In some embodiments, the K106×S9 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 33 encoded by the nucleic acid sequence shown in SEQ ID NO: 34.

In some embodiments, the K106×S37 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 8, a CDRL2 comprising the amino acid sequence of SEQ ID NO: 15, and a CDRL3 comprising the amino acid sequence of SEQ ID NO: 22.

In some embodiments, the K106×S37 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 39 encoded by the nucleic acid sequence of SEQ ID NO: 40.

In some embodiments, the K106×S37 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 37 encoded by the nucleic acid sequence shown in SEQ ID NO: 38.

In some embodiments, the K106×S14 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 23.

In some embodiments, the K106×S14 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 43 encoded by the nucleic acid sequence of SEQ ID NO: 44.

In some embodiments, the K106×S14 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 41 encoded by the nucleic acid sequence shown in SEQ ID NO: 42.

In some embodiments, the K106×S15 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K106×S15 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 47 encoded by the nucleic acid sequence of SEQ ID NO: 48.

In some embodiments, the K106×S15 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 45 encoded by the nucleic acid sequence shown in SEQ ID NO: 46.

In some embodiments, the K106×S17 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 25.

In some embodiments, the K106×S17 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 51 encoded by the nucleic acid sequence of SEQ ID NO: 52.

In some embodiments, the K106×S17 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 49 encoded by the nucleic acid sequence shown in SEQ ID NO: 50.

In some embodiments, the K106×S57 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K106×S57 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 55 encoded by the nucleic acid sequence of SEQ ID NO: 56.

In some embodiments, the K106×S57 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 53 encoded by the nucleic acid sequence shown in SEQ ID NO: 54.

In some embodiments, the K106×S58 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 9, a CDRL2 comprising the amino acid sequence of SEQ ID NO: 16, and a CDRL3 comprising the amino acid sequence of SEQ ID NO: 24.

In some embodiments, the K106×S58 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 59 encoded by the nucleic acid sequence of SEQ ID NO: 60.

In some embodiments, the K106×S58 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 57 encoded by the nucleic acid sequence shown in SEQ ID NO: 58.

In some embodiments, the K106×S28 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 147.

In some embodiments, the K106×S28 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 63 encoded by the nucleic acid sequence of SEQ ID NO: 64.

In some embodiments, the K106×S28 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 61 encoded by the nucleic acid sequence shown in SEQ ID NO: 62.

In some embodiments, the K106×S30 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 10, a CDRL2 comprising the amino acid sequence of SEQ ID NO: 17, and a CDRL3 comprising the amino acid sequence of SEQ ID NO: 148.

In some embodiments, the K106×S30 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 67 encoded by the nucleic acid sequence of SEQ ID NO: 68.

In some embodiments, the K106×S30 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 65 encoded by the nucleic acid sequence shown in SEQ ID NO: 66.

In some embodiments, the K106×S94 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 11, a CDRL2 comprising the amino acid sequence of SEQ ID NO: 18, and a CDRL3 comprising the amino acid sequence of SEQ ID NO: 147.

In some embodiments, the K106×S94 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 71 encoded by the nucleic acid sequence of SEQ ID NO: 72.

In some embodiments, the K106×S94 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 69 encoded by the nucleic acid sequence shown in SEQ ID NO: 70.

In some embodiments, the K106×S23 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 12, a CDRL2 comprising the amino acid sequence of SEQ ID NO: 19, and a CDRL3 comprising the amino acid sequence of SEQ ID NO: 26.

In some embodiments, the K106×S23 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 75 encoded by the nucleic acid sequence of SEQ ID NO: 76.

In some embodiments, the K106×S23 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 73 encoded by the nucleic acid sequence shown in SEQ ID NO: 74.

In some embodiments, the K106×S46 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 13, a CDRL2 comprising the amino acid sequence of SEQ ID NO: 19, and a CDRL3 comprising the amino acid sequence of SEQ ID NO: 26.

In some embodiments, the K106×S46 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 79 encoded by the nucleic acid sequence of SEQ ID NO: 80.

In some embodiments, the K106×S46 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 77 encoded by the nucleic acid sequence shown in SEQ ID NO: 78.

In some embodiments, the K106×S71 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 27.

In some embodiments, the K106×S71 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 83 encoded by the nucleic acid sequence of SEQ ID NO: 84.

In some embodiments, the K106×S71 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 81 encoded by the nucleic acid sequence shown in SEQ ID NO: 82.

In some embodiments, the K106×S79 bispecific antibody has a heavy chain comprising a CDRH1 comprising the amino acid sequence of SEQ ID NO: 1, a CDRH2 comprising the amino acid sequence of SEQ ID NO: 2, a CDRH3 comprising the amino acid sequence of SEQ ID NO: 3, a kappa light chain comprising a CDRL1 comprising the amino acid sequence of SEQ ID NO: 214, a CDRL2 comprising the amino acid sequence of SEQ ID NO: 216, and a CDRL3 comprising the amino acid sequence of SEQ ID NO: 212, and a lambda light chain comprising a CDRL1 comprising the amino acid sequence of SEQ ID NO: 14, a CDRL2 comprising the amino acid sequence of SEQ ID NO: 19, and a CDRL3 comprising the amino acid sequence of SEQ ID NO: 28.

In some embodiments, the K106×S79 bispecific antibody has a heavy chain variable region comprising the amino acid sequence of SEQ ID NO: 6 encoded by the nucleic acid sequence of SEQ ID NO: 7, a kappa light chain variable region comprising the amino acid sequence of SEQ ID NO: 230 encoded by the nucleic acid sequence of SEQ ID NO: 231, and a lambda light chain variable region comprising the amino acid sequence of SEQ ID NO: 87 encoded by the nucleic acid sequence of SEQ ID NO: 88.

In some embodiments, the K106×S79 bispecific antibody has a heavy chain variable and constant region comprising the amino acid sequence of SEQ ID NO: 4 encoded by the nucleic acid sequence of SEQ ID NO: 5, a kappa light chain comprising the amino acid sequence of SEQ ID NO: 228 encoded by the nucleic acid sequence of SEQ ID NO: 229, and a lambda light chain comprising the amino acid sequence of SEQ ID NO: 85 encoded by the nucleic acid sequence shown in SEQ ID NO: 86.

Each of the exemplary anti-CD47, anti-PD-L1, monospecific and the anti-CD47 and anti-PD-L1 bispecific antibodies described herein include a common heavy chain (HC), one kappa chain or one lambda chain for anti-CD47 and anti-PD-L1 antibodies, one kappa and one lambda light chains (LC) for monospecific bispecific antibodies, as shown in the amino acid and corresponding nucleic acid sequences listed below. Each of the exemplary anti-CD47, anti-PD-L1, monospecific and bispecific antibodies described below includes a heavy chain variable domain (VH), one kappa light chain variable domain or one lambda light chain variable domain for anti-CD47 and anti-PD-L1 antibodies, one kappa light chain variable domain and one lambda light chain variable domains (VL) for monospecific and bispecific antibodies, as shown in the amino acid and corresponding nucleic acid sequences listed below.

While antibody sequences below are provided herein as examples, it is to be understood that these sequences can be used to generate bispecific antibodies using any of a variety of art-recognized techniques. Examples of bispecific formats include but are not limited to bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46) or knob-into-hole (Ridgway J B et al., Protein Eng. 1996 9(7):617-21) or other sets of mutations preventing homodimer formation (Von Kreudenstein T S et al., 2013 MAbs. 5(5):646-54); fragment based bispecific formats such as tandem scFv (such as BiTEs) (Wolf E et al., 2005 Drug Discov. Today 10(18):1237-44); bispecific tetravalent antibodies (Pörtner L M et al., 2012 Cancer Immunol Immunother. 61(10):1869-75); dual affinity retargeting molecules (Moore P A et al., 2011 Blood. 117(17):4542-51), diabodies (Kontermann R E et al., Nat Biotechnol. 1997 15(7):629-31).

It is to be understood that bispecific antibodies of the invention can be further mutated using any variety of art-recognized techniques to produce antibodies with improved characteristics (e.g. increased stability, reduced sensitivity to low pH and decreased aggregation). For example, the R409K mutation in the CH3 domain of a heavy chain causes increased stability of IgG4 antibodies, reduced sensitivity to low pH, and inhibition of aggregate formation. (Namisaki et al. R409K mutation prevents acid-induced aggregation of human IgG4. Plos One 2020, Dunet et al. Insights into the IgG heavy chain engineering patent landscape as applied to IgG4 antibody development. mAbs 2019, Takahashi N, Yoshida D. Stabilized human IgG4 antibodies. European Patent. 2015. EP1810979B1. Goulet and Atkins. Considerations for the Design of Antibody-Based Therapeutics. Journal of Pharmaceutical Sciences 2020)

In some embodiments, the heavy chain comprises, consists of or consists essentially of the IGHV3-23 (Immunoglobulin Heavy Variable 3-23). In some embodiments, the heavy chain is derived from the IGHV3-23 (Immunoglobulin Heavy Variable 3-23). In some embodiments, the CH3 domain of the heavy chain comprises a S228P mutation. In some embodiments, the CH3 domain of the heavy chain comprises a R409K mutation. In some embodiments, the CH3 domain of the heavy chain comprises a S228P and a R409K mutation.

Exemplary anti-CD47, anti-PD-L1, monospecific and bispecific antibodies include a heavy chain variable region and constant region comprising an amino acid sequence of SEQ ID NO: 4 which is encoded by the nucleic acid sequence of SEQ ID NO: 5. CDR sequences are shown in bolded underlined text. S228P position is shown in bolded text.

```
>VHCH IGHV3-23-S228P hIgG4-AA
                                      (SEQ ID NO: 4)
EVQLLESGGGLVQPGGSLRLSCAASGFTFSSYAMSWVRQAPGKGLEWVSA

ISFSFFSTYYADSVKGRFTISRDNSKNTLYLQMNSLRAEDTAVYYC

AKSYGAFDYWGQGTLVTVSSASTKGPSVFPLAPCSRSTSESTAALGCLVK
```

-continued

```
DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLG

>VHCH IGHV3-23-S228P hIgG4-NT
                                      (SEQ ID NO: 5)
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

GGTGCTTTTGACTACTGGGGCCAGGGAACCCTGGTCACAGTCTCGAGCGC

CTCCACCAAGGGCCCATCCGTCTTCCCCCTGGCGCCCTGCTCCAGGAGCA

CCTCCGAGAGCACAGCCGCCCTGGGCTGCCTGGTCAAGGACTACTTCCCC

GAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCG

TGGTGACCGTGCCCTCCAGCAGCTTGGGCACGAAGACCTACACTTGCAAC

GTAGATCACAAGCCCAGCAACACCAAGGTGGACAAGAGAGTTGAGTCCAA

ATATGGTCCCCCATGCCCACCATGCCCAGCACCTGAGTTCCTGGGGGGAC

CATCAGTCTTCCTGTTCCCCCCAAAACCCAAGGACACTCTCATGATCTCC

CGGACCCCTGAGGTCACGTGCGTGGTGGTGGACGTGAGCCAGGAAGACCC

CGAGGTCCAGTTCAACTGGTACGTGGATGGCGTGGAGGTGCATAATGCCA

AGACAAAGCCGCGGGAGGAGCAGTTCAACAGCACGTACCGTGTGGTCAGC

GTCCTCACCGTCCTGCACCAGGACTGGCTGAACGGCAAGGAGTACAAGTG

CAAGGTCTCCAACAAAGGCCTCCCGTCCTCCATCGAGAAAACCATCTCCA

AAGCCAAAGGGCAGCCCCGAGAGCCACAGGTGTACACCCTGCCCCCATCC

CAGGAGGAGATGACCAAGAACCAGGTCAGCCTGACTTGCCTGGTCAAAGG

CTTCTACCCCAGCGACATCGCCGTGGAGTGGGAGAGCAACGGGCAGCCGG

AGAACAACTACAAGACCACGCCTCCCGTGCTGGACTCCGACGGCTCCTTC

TTCCTCTACAGCAGGCTAACCGTGGACAAGTCCAGGTGGCAGGAGGGGAA

TGTCTTCTCATGCTCCGTGATGCATGAGGCTCTGCACAACCACTACACAC

AGAAGAGCCTCTCCCTGTCTCTGGGTTAA
```

The exemplary anti-CD47, anti-PD-L1, monovalent and bispecific antibodies include a heavy chain variable region comprising an amino acid sequence of SEQ ID NO: 6 which is encoded by the nucleic acid sequence of SEQ ID NO: 7.

>VH IGHV3-23-S228P hIgG4-AA (SEQ ID NO: 6)

EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYC

AKSYGAFDYWGQGTLVTVSS

>VH IGHV3-23-S228P hIgG4-NT (SEQ ID NO: 7)

GAGGTGCAGCTGTTGGAGTCTGGGGGAGGCTTGGTACAGCCTGGGGGGT

CCCTGAGACTCTCCTGTGCAGCCTCTGGATTCACCTTTAGCAGCTATGC

CATGAGCTGGGTCCGCCAGGCTCCAGGGAAGGGGCTGGAGTGGGTCTCA

GCTATTAGTGGTAGTGGTGGTAGCACATACTACGCAGACTCCGTGAAGG

GCCGGTTCACCATCTCCAGAGACAATTCCAAGAACACGCTGTATCTGCA

AATGAACAGCCTGAGAGCCGAGGACACGGCCGTATATTACTGTGCGAAA

AGTTATGGTGCTTTTGACTACTGGGGCCAGGGAACCCTGGTCACAGTCT

CGAGC

In some embodiments, the exemplary anti-CD47, anti-PD-L1, monospecific and bispecific antibodies include a heavy chain variable region and constant region comprising an amino acid sequence of SEQ ID NO: 232 which is encoded by the nucleic acid sequence of SEQ ID NO: 233. CDR sequences are shown in bolded underlined text. S228P and R409K positions are shown in bolded text.

>VHCH IGHV3-23-S228P-R409K hIgG4-AA (SEQ ID NO: 232)

EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYC

AKSYGAFDYWGQGTLVTVSSASTKGPSVFPLAPCSRSTSESTAALGCLV

KDYFPEPVTVSWNSGALTSGVHTFPAVLQSSGLYSLSSVVTVPSSSLGT

KTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQF

NSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTT

PPVLDSDGSFFLYSKLTVDKSRWQEGNVFSCSVMHEALHNHYTQKSLSL

SLG

>VHCH IGHV3-23-S228P-R409K hIgG4-NT (SEQ ID NO: 233)

GAGGTGCAGCTGTTGGAGTCTGGGGGAGGCTTGGTACAGCCTGGGGGGT

CCCTGAGACTCTCCTGTGCAGCCTCTGGATTCACCTTTAGCAGCTATGC

CATGAGCTGGGTCCGCCAGGCTCCAGGGAAGGGGCTGGAGTGGGTCTCA

GCTATTAGTGGTAGTGGTGGTAGCACATACTACGCAGACTCCGTGAAGG

GCCGGTTCACCATCTCCAGAGACAATTCCAAGAACACGCTGTATCTGCA

AATGAACAGCCTGAGAGCCGAGGACACGGCCGTATATTACTGTGCGAAA

AGTTATGGTGCTTTTGACTACTGGGGCCAGGGAACCCTGGTCACAGTCT

CGAGCGCCTCCACCAAGGGCCCATCCGTCTTCCCCCTGGCGCCCTGCTC

CAGGAGCACCTCCGAGAGCACAGCCGCCCTGGGCTGCCTGGTCAAGGAC

TACTTCCCCGAACCGGTGACGGTGTCGTGGAACTCAGGCGCCCTGACCA

-continued

GCGGCGTGCACACCTTCCCGGCTGTCCTACAGTCCTCAGGACTCTACTC

CCTCAGCAGCGTGGTGACCGTGCCCTCCAGCAGCTTGGGCACGAAGACC

TACACTTGCAACGTAGATCACAAGCCCAGCAACACCAAGGTGGACAAGA

GAGTTGAGTCCAAATATGGTCCCCCATGCCCACCATGCCCAGCACCTGA

GTTCCTGGGGGGACCATCAGTCTTCCTGTTCCCCCCAAAACCCAAGGAC

ACTCTCATGATCTCCCGGACCCCTGAGGTCACGTGCGTGGTGGTGGACG

TGAGCCAGGAAGACCCCGAGGTCCAGTTCAACTGGTACGTGGATGGCGT

GGAGGTGCATAATGCCAAGACAAAGCCGCGGGAGGAGCAGTTCAACAGC

ACGTACCGTGTGGTCAGCGTCCTCACCGTCCTGCACCAGGACTGGCTGA

ACGGCAAGGAGTACAAGTGCAAGGTCTCCAACAAAGGCCTCCCGTCCTC

CATCGAGAAAACCATCTCCAAAGCCAAAGGGCAGCCCCGAGAGCCACAG

GTGTACACCCTGCCCCCATCCCAGGAGGAGATGACCAAGAACCAGGTCA

GCCTGACTTGCCTGGTCAAAGGCTTCTACCCCAGCGACATCGCCGTGGA

GTGGGAGAGCAACGGGCAGCCGGAGAACAACTACAAGACCACGCCTCCC

GTGCTGGACTCCGACGGCTCCTTCTTCCTCTACAGCAAGCTAACCGTGG

ACAAGTCCAGGTGGCAGGAGGGGAATGTCTTCTCATGCTCCGTGTGCAT

GAGGCTCTGCACAACCACTACACACAGAAGAGCCTCTCCCTGTCTCTGG

GTTAA

In some embodiments, the exemplary anti-CD47, anti-PD-L1, monovalent and bispecific antibodies include a heavy chain variable region comprising an amino acid sequence of SEQ ID NO: 234 which is encoded by the nucleic acid sequence of SEQ ID NO: 235. CDR sequences are shown in bolded underlined text.

>VH IGHV3-23-S228P-R409K hIgG4-AA (SEQ ID NO: 234)

EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYC

AKSYGAFDYWGQGTLVTVSS

>VH IGHV3-23-S228P-R409K hIgG4-NT (SEQ ID NO: 235)

GAGGTGCAGCTGTTGGAGTCTGGGGGAGGCTTGGTACAGCCTGGGGGGT

CCCTGAGACTCTCCTGTGCAGCCTCTGGATTCACCTTTAGCAGCTATGC

CATGAGCTGGGTCCGCCAGGCTCCAGGGAAGGGGCTGGAGTGGGTCTCA

GCTATTAGTGGTAGTGGTGGTAGCACATACTACGCAGACTCCGTGAAGG

GCCGGTTCACCATCTCCAGAGACAATTCCAAGAACACGCTGTATCTGCA

AATGAACAGCCTGAGAGCCGAGGACACGGCCGTATATTACTGTGCGAAA

AGTTATGGTGCTTTTGACTACTGGGGCCAGGGAACCCTGGTCACAGTCT

CGAGC

In some embodiments, the heavy chain further comprises a leader sequence comprising an amino acid sequence of SEQ ID NO: 236, which is encoded by the nucleic acid sequence of SEQ ID NO: 237.

>Leader sequence-AA
(SEQ ID NO: 236)
MEWSWVFLFFLSVTTGVHS

>Leader sequence-NT
(SEQ ID NO: 237)
ATGGAATGGAGCTGGGTCTTTCTCTTCTTCCTGTCAGTAACTACAGGTG
TCCACTCC Anti-CD47 Antibodies Exemplary anti-CD47 antibody sequences are shown below. Light chain variable regions are shown in italicized underlined text. CDR sequences are shown in bolded underlined text.

The “K26” or “K26_K5A3_1C5 VKCK aCD47 IGKV1-33” antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 103, which is encoded by a nucleic acid sequence of SEQ ID NO: 104.

>K26_K5A3_1C5 VKCK aCD47 IGKV1-33-AA
(SEQ ID NO: 103)
*DIQMTQSPSSLSASVGDRVTITCQVSQDINKYLNWYQQKPGKAPKLLIY*
*GASRLETGVPSRFSGSGSGTDFTFTISSLQPEDIATYYCQQMHPRAPKT*
*FGQGTKVEIK*RTVAAPSVFIFPPSDEQLKSGTASVVCLLNNFYPREAKV
QWKVDNALQSGNSQESVTEQDSKDSTYSLSSTLTLSKADYEKHKVYACE
VTHQGLSSPVTKSFNRGEC

>K26_K5A3_1C5 VKCK aCD47 IGKV1-33-NT
(SEQ ID NO: 104)
GACATCCAGATGACCCAGTCTCCATCCTCCCTGTCTGCATCTGTAGGAG
ACAGAGTCACCATCACTTGCCAGGTGAGTCAGGACATTAATAAGTATTT
AAATTGGTATCAGCAGAAACCAGGGAAAGCCCCTAAGCTCCTGATCTAC
GGTGCATCCAGGTTGGAAACAGGGGTCCCATCAAGGTTCAGTGGAAGTG
GATCTGGGACAGATTTTACTTTCACCATCAGCAGCCTGCAGCCTGAAGA
TATTGCAACATATTACTGTCAGCAGATGCACCCGCGCGCCCCGAAGACC
TTCGGCCAAGGGACCAAGGTGGAAATCAAACGTACGGTGGCTGCACCAT
CTGTCTTCATCTTCCCGCCATCTGATGAGCAGTTGAAATCTGGAACTGC
CTCTGTTGTGTGCCTGCTGAATAACTTCTATCCCAGAGAGGCCAAAGTA
CAGTGGAAGGTGGATAACGCCCTCCAATCGGGTAACTCCCAGGAGAGTG
TCACAGAGCAGGACAGCAAGGACAGCACCTACAGCCTCAGCAGCACCCT
GACGCTGAGCAAAGCAGACTACGAGAAACACAAAGTCTACGCCTGCGAA
GTCACCCATCAGGGCCTGAGCTCGCCCGTCACAAAGAGCTTCAACAGGG
GAGAGTGTTAA

The “K26” or “K26_K5A3_1C5 VKCK aCD47 IGKV1-33” antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 105 which is encoded by a nucleic acid sequence of SEQ ID NO: 106.

>K26_K5A3_1CK VKCK aCD47 IGKV1-33-AA
(SEQ ID NO: 105)
DIQMTQSPSSLSASVGDRVTITCQVSQDINKYLNWYQQKPGKAPKLLIY
GASRLETGVPSRFSGSGSGTDFTFTISSLQPEDIATYYC
QQMHPRAPKTFGQGTKVEIK

>K26_K5A3_1C5 VKCK aCD47 IGKV1-33-NT
(SEQ ID NO: 106)
GACATCCAGATGACCCAGTCTCCATCCTCCCTGTCTGCATCTGTAGGAG
ACAGAGTCACCATCACTTGCCAGGTGAGTCAGGACATTAATAAGTATTT
AAATTGGTATCAGCAGAAACCAGGGAAAGCCCCTAAGCTCCTGATCTAC
GGTGCATCCAGGTTGGAAACAGGGGTCCCATCAAGGTTCAGTGGAAGTG
GATCTGGGACAGATTTTACTTTCACCATCAGCAGCCTGCAGCCTGAAGA
TATTGCAACATATTACTGTCAGCAGATGCACCCGCGCGCCCCGAAGACC
TTCGGCCAAGGGACCAAGGTGGAAATCAAA

The “K30” or “K30_Ke8_1E3 VKCK αCD47 IGKV1-39” antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 107, which is encoded by a nucleic acid sequence of SEQ ID NO: 108.

>K30_Ke8_1E3 VKCK αCD47 IGKV1-39-AA
(SEQ ID NO: 107)
*DIQPITQSPSSLSASVGDRVTITCRASQSISSYLNWYQQKPGKAPKLLIY*
*AASSLQSGVPSRFSGSGSGTDFTLTISSLQPEDFATYYCQQMHPRSPKIF*
*GQGTKVEIK*RTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC

>K30_Ke8_1E3 VKCK αCD47 IGKV1-39-NT
(SEQ ID NO: 108)
GACATCCAGATGACCCAGTCTCCATCCTCCCTGTCTGCATCTGTAGGAGA
CAGAGTCACCATCACTTGCCGGGCAAGTCAGAGCATTAGCAGCTATTTAA
ATTGGTATCAGCAGAAACCAGGGAAAGCCCCTAAGCTCCTGATCTATGCT
GCATCCAGTTTGCAAAGTGGGGTCCCATCAAGGTTCAGTGGCAGTGGATC
TGGGACAGATTTCACTCTCACCATCAGCAGTCTGCAACCTGAAGATTTTG
CAACTTACTACTGTCAGCAGATGCACCCGCGGTCGCCGAAGATCTTCGGC
CAAGGGACCAAGGTGGAAATCAAACGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGTTAA

The “K30” or “K30_Ke8_1E3 VKCK αCD47 IGKV1-39” antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 109 which is encoded by a nucleic acid sequence of SEQ ID NO: 110.

>K30_Ke8_1E3 VKCK αCD47 IGKV1-39-AA
(SEQ ID NO: 109)
DIQMTQSPSSLSASVGDRVTITCRASQSISSYLNWYQQKPGKAPKLLIYA

AASLQSGVPSRFSGSGSGTDFTLTISSLQPEDFATYYCQQMHPRSPKIFG

QGTKVEIK

>K30_Ke8_1E3 VKCK αCD47 IGKV1-39-NT
(SEQ ID NO: 110)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGGTCGCCGAAGATCTTCGGC

CAAGGGACCAAGGTGGAAATCAAA (SEQ ID NO: XXX)

The "K31" or "K31_Ke8_1H2 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 111, which is encoded by a nucleic acid sequence of SEQ ID NO: 112.

>K31_Ke8_1H2 VKCK aCD47 IGKV1-39-AA
(SEQ ID NO: 111)
*DIQMTQSPSSLSASVGDRVTITCRASQSISSYLNWYQQKPGKAPKLLIYA*

*ASSLQSGVPSRFSGSGSGTDFTLTISSLQPEDFATYYCQQMHPRANKIFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>K31_Ke8_1H2 VKCK aCD47 IGKV1-39-NT
(SEQ ID NO: 112)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCCCGCGCCAACAAAATCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

The "K31" or "K31_Ke8_1H2 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 113 which is encoded by a nucleic acid sequence of SEQ ID NO: 114.

>K31_Ke8_1H2 VKCK aCD47 IGKV1-39-AA
(SEQ ID NO: 113)
DIQMTQSPSSLSASVGDRVTITCRASQSISSYLNWYQQKPGKAPKLLIY

AASSLQSGVPSRFSGSGSGTDFTLTISSLQPEDFATYYCQQMHPRTAKQ

FGQGTKVEIK

>K31_Ke8_1H2 VKCK aCD47 IGKV1-39-NT
(SEQ ID NO: 114)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCCCGCGCCAACAAAATC

TTCGGCCAAGGGACCAAGGTGGAAATCAAA

The "K32" or "K32_Ke8_1H9 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 115, which is encoded by a nucleic acid sequence of SEQ ID NO: 116.

>K32_Ke8_1H9 VKCK aCD47 IGKV1-39-AA
(SEQ ID NO: 115)
*DIQMTQSPSSLSASVGDRVTITCRASQSISSYLNWYQQKPGKAPKLLIYA*

*ASSLQSGVPSRFSGSGSGTDFTLTISSLQPEDFATYYCQQMHPRTAKQFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>K32_Ke8_1H9 VKCK aCD47 IGKV1-39-NT
(SEQ ID NO: 116)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCGCGGACGGCCAAGCAG

TTCGGCCAAGGGACCAAGGTGGAAATCAAACGTACGGTGGCTGCACCAT

CTGTCTTCATCTTCCCGCCATCTGATGAGCAGTTGAAATCTGGAACTGC

CTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCCT

-continued

GACGCTGAGCAAAGCAGACTACGAGAAACACAAAGTCTACGCCTGCGAA

GTCACCCATCAGGGCCTGAGCTCGCCCGTCACAAAGAGCTTCAACAGGG

GAGAGTGTTAA

The "K32" or "K32_Ke8_1H9 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 117 which is encoded by a nucleic acid sequence of SEQ ID NO: 118.

>K32_Ke8_1H9 VKCK aCD47 IGKV1-39-AA
(SEQ ID NO: 117)
DIQMTQSPSSLSASVGDRVTITCRASQSISSYLNWYQQKPGKAPKLLIY

AASSLQSGVPSRFSGSGSGTDFTLTISSLQPEDFATYYCQQMHPRANKI

FGQGTKVEIK

>K32_Ke8_1H9 VKCK aCD47 IGKV1-39-NT
(SEQ ID NO: 118)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCGCGGACGGCCAAGCAG

TTCGGCCAAGGGACCAAGGTGGAAATCAAA

The "K34" or "K34_Ke8_2G11 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 119, which is encoded by a nucleic acid sequence of SEQ ID NO: 120.

>K34_Ke8_2G11 VKCK aCD47 IGKV1-39-AA
(SEQ ID NO: 119)
*DIQMTQSPSSLSASVGDRVTITCRASQSISSYLNWYQQKPGKAPKLLIYA*

*ASSLQSGVPSRFSGSGSGTDFTLTISSLQPEDFATYYCQQFHPRAPKQFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>K34_Ke8_2G11 VKCK aCD47 IGKV1-39-NT
(SEQ ID NO: 120)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGTTTCACCCGCGGGCGCCCAAGCAG

TTCGGCCAAGGGACCAAGGTGGAAATCAAACGTACGGTGGCTGCACCAT

-continued

CTGTCTTCATCTTCCCGCCATCTGATGAGCAGTTGAAATCTGGAACTGC

CTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCCT

GACGCTGAGCAAAGCAGACTACGAGAAACACAAAGTCTACGCCTGCGAA

GTCACCCATCAGGGCCTGAGCTCGCCCGTCACAAAGAGCTTCAACAGGG

GAGAGTGTTAA

The "K34" or "K34_Ke8_2G11 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 121 which is encoded by a nucleic acid sequence of SEQ ID NO: 122.

>K34_Ke8_2G11 VKCK aCD47 IGKV1-39-AA
(SEQ ID NO: 121)
DIQMTQSPSSLSASVGDRVTITCRASQSISSYLNWYQQKPGKAPKLLIY

AASSLQSGVPSRFSGSGSGTDFTLTISSLQPEDFATYYCQQFHPRAPKQ

FGQGTKVEIK

>K34_Ke8_2G11 VKCK aCD47 IGKV1-39-NT
(SEQ ID NO: 122)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGTTTCACCCGCGGGCGCCCAAGCAG

TTCGGCCAAGGGACCAAGGTGGAAATCAAA

The "K35" or "K35_Ke8_2H3 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 123, which is encoded by a nucleic acid sequence of SEQ ID NO: 124.

>K35_Ke8_2H3 VKCK aCD47 IGKV1-39-AA
(SEQ ID NO: 123)
*DIQMTQSPSSLSASVGDRVTITCRASQSISSYLNWYQQKPGKAPKLLIYA*

*ASSLQSGVPSRFSGSGSGTDFTLTISSLQPEDFATYYCQQMHPRSHKQFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>K35_Ke8_2H3 VKCK aCD47 IGKV1-39-NT
(SEQ ID NO: 124)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

-continued

GATCTGGGACAGATTTCACTCTCACCATCAGCAGTCTGCAACCTGAAGA

TTTTGCAACTTACTACTGTCAGCAGATGCACCCGCGGAGCCACAAGCAG

TTCGGCCAAGGGACCAAGGTGGAAATCAAACGTACGGTGGCTGCACCAT

CTGTCTTCATCTTCCCGCCATCTGATGAGCAGTTGAAATCTGGAACTGC

CTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCCT

GACGCTGAGCAAAGCAGACTACGAGAAACACAAAGTCTACGCCTGCGAA

GTCACCCATCAGGGCCTGAGCTCGCCCGTCACAAAGAGCTTCAACAGGG

GAGAGTGTTAA

The "K35" or "K35_Ke8_2H3 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 125 which is encoded by a nucleic acid sequence of SEQ ID NO: 126.

>K35_Ke8_2H3 VKCK aCD47 IGKV1-39-AA
(SEQ ID NO: 125)
DIQMTQSPSSLSASVGDRVTITCRASQSISSYLNWYQQKPGKAPKLLIY

AASSLQSGVPSRFSGSGSGTDFTLTISSLQPEDFATYYCQQMHPRSHKQ

FGQGTKVEIK

>K35_Ke8_2H3 VKCK aCD47 IGKV1-39-NT
(SEQ ID NO: 126)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGGAGCCACAAGCAGTTCGGC

CAAGGGACCAAGGTGGAAATCAAA

The "K36" or "K36_Ke8_D11 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 127, which is encoded by a nucleic acid sequence of SEQ ID NO: 128.

>K36_Ke8_D11 VKCK aCD47 IGKV1-39-AA
(SEQ ID NO: 127)
*DIQMTQSPSSLSASVGDRVTITCRASQSISSYLNWYQQKPGKAPKLLIYA*

*ASSLQSGVPSRFSGSGSGTDFTLTISSLQPEDFATYYCQQFHPRAAKNFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

-continued

>K36_Ke8_D11 VKCK aCD47 IGKV1-39-NT
(SEQ ID NO: 128)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGTTTCACCCGCGGGCGGCCAAGAAC

TTCGGCCAAGGGACCAAGGTGGAAATCAAACGTACGGTGGCTGCACCAT

CTGTCTTCATCTTCCCGCCATCTGATGAGCAGTTGAAATCTGGAACTGC

CTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCCT

GACGCTGAGCAAAGCAGACTACGAGAAACACAAAGTCTACGCCTGCGAA

GTCACCCATCAGGGCCTGAGCTCGCCCGTCACAAAGAGCTTCAACAGGG

GAGAGTGTTAA

The "K36" or "K36_Ke8_D11 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 129 which is encoded by a nucleic acid sequence of SEQ ID NO: 130.

>K36_Ke8_D11 VKCK aCD47 IGKV1-39-AA
(SEQ ID NO: 129)
DIQMTQSPSSLSASVGDRVTITCRASQSISSYLNWYQQKPGKAPKLLIY

AASSLQSGVPSRFSGSGSGTDFTLTISSLQPEDFATYYCQQFHPRAAKN

FGQGTKVEIK

>K36_Ke8_D11 VKCK aCD47 IGKV1-39-NT
(SEQ ID NO: 130)
GACATCCAGATGACCCAGTCTCCATCCTCCCTGTCTGCATCTGTAGGAG

ACAGAGTCACCATCACTTGCCGGGCAAGTCAGAGCATTAGCAGCTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGTTTCACCCGCGGGCGGCCAAGAAC

TTCGGCCAAGGGACCAAGGTGGAAATCAAA

The "K37" or "K37_Ke8_1B1 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 131, which is encoded by a nucleic acid sequence of SEQ ID NO: 132.

>K37_Ke8_1B1 VKCK aCD47 IGKV1-39-AA (SEQ ID NO: 131)

*DIQMTQSPSSLSASVGDRVTITCQASQDINKYLNWYQQKPGKAPKLLIYA*

*ASSLQSGVPSRFSGSGSGTDFTLTISSLQPEDFATYYCQQMHPRAPKTFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>K37_Ke8_1B1 VKCK aCD47 IGKV1-39-NT (SEQ ID NO: 132)

GACATCCAGATGACCCAGTCTCCATCCTCCCTGTCTGCATCTGTAGGAG

ACAGAGTCACCATCACTTGCCAGGCGAGTCAGGACATTAATAAGTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCGCGCGCCCCGAAGACC

TTCGGCCAAGGGACCAAGGTGGAAATCAAACGTACGGTGGCTGCACCAT

CTGTCTTCATCTTCCCGCCATCTGATGAGCAGTTGAAATCTGGAACTGC

CTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCCT

GACGCTGAGCAAAGCAGACTACGAGAAACACAAAGTCTACGCCTGCGAA

GTCACCCATCAGGGCCTGAGCTCGCCCGTCACAAAGAGCTTCAACAGGG

GAGAGTGTTAA

The "K37" or "K37_Ke8_1B1 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 133 which is encoded by a nucleic acid sequence of SEQ ID NO: 134.

>K37_Ke8_1B1 VKCK aCD47 IGKV1-39-AA (SEQ ID NO: 133)

DIQMTQSPSSLSASVGDRVTITCRASQDINKYLNWYQQKPGKAPKLLIY

AASSLQSGVPSRFSGSGSGTDFTLTISSLQPEDFATYYCQQMHPRAPKT

FGQGTKVEIK

>K37_Ke8_1B1 VKCK aCD47 IGKV1-39-NT (SEQ ID NO: 134)

GACATCCAGATGACCCAGTCTCCATCCTCCCTGTCTGCATCTGTAGGAG

ACAGAGTCACCATCACTTGCCAGGCGAGTCAGGACATTAATAAGTATTT

AAATTGGTATCAGCAGAAACCAGGGAAAGCCCCTAAGCTCCTGATCTAT

GCTGCATCCAGTTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCGCGCGCCCCGAAGACC

TTCGGCCAAGGGACCAAGGTGGAAATCAAA

The "K40" or "K40_Ke8_1H8 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 135, which is encoded by a nucleic acid sequence of SEQ ID NO: 136.

>K40_Ke8_1H8 VKCK aCD47 IGKV1-39-AA (SEQ ID NO: 135)

*DIQMTQSPSSLSASVGDRVTITCRASQAIDKFLNWYQQKPGKAPKLLIYA*

*SSRLQSGVPSRFSGSGSGTDFTLTISSLQPEDFATYYCQQMHPRAPKTFG*

*QGTKVEIK*RTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

>K40_Ke8_1H8 VKCK aCD47 IGKV1-39-NT (SEQ ID NO: 136)

GACATCCAGATGACCCAGTCTCCATCCTCCCTGTCTGCATCTGTAGGAG

ACAGAGTCACCATCACTTGCCGGGCAAGTCAGGCTATTGATAAGTTTTT

AAATTGGTATCAGCAGAAACCAGGGAAAGCCCCTAAGCTCCTGATCTAT

GCGTCTTCCAGGTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCGCGCGCCCCGAAGACC

TTCGGCCAAGGGACCAAGGTGGAAATCAAACGTACGGTGGCTGCACCAT

CTGTCTTCATCTTCCCGCCATCTGATGAGCAGTTGAAATCTGGAACTGC

CTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTG

TCACAGAGCAGGACAGCAAGGACAGCACCTACAGCCTCAGCAGCACCCT

GACGCTGAGCAAAGCAGACTACGAGAAACACAAAGTCTACGCCTGCGAA

GTCACCCATCAGGGCCTGAGCTCGCCCGTCACAAAGAGCTTCAACAGGG

GAGAGTGTTAA

The "K40" or "K40_Ke8_1H8 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 137 which is encoded by a nucleic acid sequence of SEQ ID NO: 138.

>K40_Ke8_1H8 VKCK aCD47 IGKV1-39-AA (SEQ ID NO: 137)

DIQMTQSPSSLSASVGDRVTITCRASQAIDKFLNWYQQKPGKAPKLLIY

AASSLQSGVPSRFSGSGSGTDFTLTISSLQPEDFATYYCQQMHPRAPKT

FGQGTKVEIK

>K40_Ke8_1H8 VKCK aCD47 IGKV1-39-NT (SEQ ID NO: 138)

GACATCCAGATGACCCAGTCTCCATCCTCCCTGTCTGCATCTGTAGGAG

ACAGAGTCACCATCACTTGCCGGGCAAGTCAGGCTATTGATAAGTTTTT

AAATTGGTATCAGCAGAAACCAGGGAAAGCCCCTAAGCTCCTGATCTAT

GCGTCTTCCAGGTTGCAAAGTGGGGTCCCATCAAGGTTCAGTGGCAGTG

GATCTGGGACAGATTTCACTCTCACCATCAGCAGTCTGCAACCTGAAGA

TTTTGCAACTTACTACTGTCAGCAGATGCACCCGCGCGCCCCGAAGACC

TTCGGCCAAGGGACCAAGGTGGAAATCAAA

The "K41" or "K41_Ke8_2D6 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 139, which is encoded by a nucleic acid sequence of SEQ ID NO: 140.

```
>K41_Ke8_2D6 VKCK aCD47 IGKV1-39-AA
                                        (SEQ ID NO: 139)
DIQMTQSPSSLSASVGDRVTITCRASQTIDKFLNWYQQKPGKAPKLLIYA
ASRLQSGVPSRFSGSGSGTDFTLTISSLQPEDFATYYCQQMHPRAPKTFG
QGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
```

```
>K41_Ke8_2D6 VKCK aCD47 IGKV1-39-NT
                                        (SEQ ID NO: 140)
GACATCCAGATGACCCAGTCTCCATCCTCCCTGTCTGCATCTGTAGGAG
ACAGAGTCACCATCACTTGCCGGGCAAGTCAGACGATTGATAAGTTTTT
AAATTGGTATCAGCAGAAACCAGGGAAAGCCCCTAAGCTCCTGATCTAT
GCGGCTTCCAGGTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAGCAGATGCACCCGCGCGCCCCGAAGACC
TTCGGCCAAGGGACCAAGGTGGAAATCAAACGTACGGTGGCTGCACCAT
CTGTCTTCATCTTCCCGCCATCTGATGAGCAGTTGAAATCTGGAACTGC
CTCTGTTGTGTGCCTGCTGAATAACTTCTATCCCAGAGAGGCCAAAGTA
CAGTGGAAGGTGGATAACGCCCTCCAATCGGGTAACTCCCAGGAGAGTG
TCACAGAGCAGGACAGCAAGGACAGCACCTACAGCCTCAGCAGCACCCT
GACGCTGAGCAAAGCAGACTACGAGAAACACAAAGTCTACGCCTGCGAA
GTCACCCATCAGGGCCTGAGCTCGCCCGTCACAAAGAGCTTCAACAGGG
GAGAGTGTTAA
```

The "K41" or "K41_Ke8_2D6 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 141 which is encoded by a nucleic acid sequence of SEQ ID NO: 142.

```
>K41_Ke8_2D6 VKCK aCD47 IGKV1-39-AA
                                        (SEQ ID NO: 141)
DIQMTQSPSSLSASVGDRVTITCRASQTIDKFLNWY
QQKPGKAPKLLIYAASRLQSGVPSRFSGSGSGTDFT
LTISSLQPEDFATYYCQQMHPRAPKTFGQGTKVEIK
```

```
>K41_Ke8_2D6 VKCK aCD47 IGKV1-39-NT
                                        (SEQ ID NO: 142)
GACATCCAGATGACCCAGTCTCCATCCTCCCTGTC
TGCATCTGTAGGAGACAGAGTCACCATCACTTGCC
GGGCAAGTCAGACGATTGATAAGTTTTTAAATTGG
TATCAGCAGAAACCAGGGAAAGCCCCTAAGCTCCT
```

-continued

```
GATCTATGCGGCTTCCAGGTTGCAAAGTGGGGTCC
CATCAAGGTTCAGTGGCAGTGGATCTGGGACAGAT
TTCACTCTCACCATCAGCAGTCTGCAACCTGAAGA
TTTTGCAACTTACTACTGTCAGCAGATGCACCCGC
GCGCCCCGAAGACCTTCGGCCAAGGGACCAAGGTG
GAAATCAAA
```

The "K43" or "K43_Ke8_C10 VKCK aCD47 IGKV1-39" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 143, which is encoded by a nucleic acid sequence of SEQ ID NO: 144.

```
>K43_Ke8_C10 VKCK aCD47 IGKV1-39-AA
                                        (SEQ ID NO: 143)
DIQMTQSPSSLSASVGDRVTITCRASQTIDKFLNW
YQQKPGKAPKLLIYAASILQATGVPSRFSGSGSGT
DFTLTISSLQPEDFATYYCQQMHPRAPKTFGQGTK
VEIKRTVAAPSVFIFPPSDEQLKSGTASVVCLLNN
FYPREAKVQWKVDNALQSGNSQESVTEQDSKDSTY
SLSSTLTLSKADYEKHKVYACEVTHQGLSSPVTKS
FNRGEC
```

```
>K43_Ke8_C10 VKCK aCD47 IGKV1-39-NT
                                        (SEQ ID NO: 144)
GACATCCAGATGACCCAGTCTCCATCCTCCCTGTC
TGCATCTGTAGGAGACAGAGTCACCATCACTTGCC
GGGCAAGTCAGACTATTGATAAGTTTTTAAATTGG
TATCAGCAGAAACCAGGGAAAGCCCCTAAGCTCCT
GATCTATGCTGCGTCCATTTTGCAAAATGGGGTCC
CATCAAGGTTCAGTGGCAGTGGATCTGGGACAGAT
TTCACTCTCACCATCAGCAGTCTGCAACCTGAAGA
TTTTGCAACTTACTACTGTCAGCAGATGCACCCGC
GCGCCCCGAAGACCTTCGGCCAAGGGACCAAGGTG
GAAATCAAACGTACGGTGGCTGCACCATCTGTCTT
CATCTTCCCGCCATCTGATGAGCAGTTGAAATCTG
GAACTGCCTCTGTTGTGTGCCTGCTGAATAACTTC
TATCCCAGAGAGGCCAAAGTACAGTGGAAGGTGGA
TAACGCCCTCCAATCGGGTAACTCCCAGGAGAGTG
TCACAGAGCAGGACAGCAAGGACAGCACCTACAGC
CTCAGCAGCACCCTGACGCTGAGCAAAGCAGACTA
CGAGAAACACAAAGTCTACGCCTGCGAAGTCACCC
ATCAGGGCCTGAGCTCGCCCGTCACAAAGAGCTTC
AACAGGGGAGAGTGTTAA
```

The "K43" or "K43_Ke8_C10 VKCK aCD47 IGKV1-39" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 145 which is encoded by a nucleic acid sequence of SEQ ID NO: 146.

```
>K43_Ke8_C10 VKCK aCD47 IGKV1-39-AA
                                   (SEQ ID NO: 145)
DIQMTQSPSSLSASVGDRVTITCRASQTIDKFLNW

YQQKPGKAPKLLIYAASILQNGVPSRFSGSGSGTD

FTLTISSLQPEDFATYYCQQMHPRAPKTFGQGTKV

EIK

>K43_Ke8_C10 VKCK aCD47 IGKV1-39-NT
                                   (SEQ ID NO: 146)
GACATCCAGATGACCCAGTCTCCATCCTCCCTGTC

TGCATCTGTAGGAGACAGAGTCACCATCACTTGCC

GGGCAAGTCAGACTATTGATAAGTTTTTAAATTGG

TATCAGCAGAAACCAGGGAAAGCCCCTAAGCTCCT

GATCTATGCTGCGTCCATTTTGCAAAATGGGGTCC

CATCAAGGTTCAGTGGCAGTGGATCTGGGACAGAT

TTCACTCTCACCATCAGCAGTCTGCAACCTGAAGA

TTTTGCAACTTACTACTGTCAGCAGATGCACCCGC

GCGCCCCGAAGACCTTCGGCCAAGGGACCAAGGTG

GAAATCAAA
```

The “K33” or “K33_IgG_Ke8_2C4 VKCK” antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 220, which is encoded by a nucleic acid sequence of SEQ ID NO: 221.

```
>K33_IgG_Ke8_2C4 VKCK-AA
                                   (SEQ ID NO: 220)
DIQMTQSPSSLSASVGDRVTITCRASQSISSYLNW

YQQKPGKAPKLLIYAASSLQSGVPSRFSGSGSGTD

FTLTISSLQPEDFATYYCQQFHKRSPQKFGQGTKV

EIKRTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC

>K33_IgG_Ke8_2C4 VKCK-NT
                                   (SEQ ID NO: 221)
GACATCCAGATGACCCAGTCTCCATCCTCCCTGTC

TGCATCTGTAGGAGACAGAGTCACCATCACTTGCC

GGGCAAGTCAGAGCATTAGCAGCTATTTAAATTGG

TATCAGCAGAAACCAGGGAAAGCCCCTAAGCTCCT

GATCTATGCTGCATCCAGTTTGCAAAGTGGGGTCC

CATCAAGGTTCAGTGGCAGTGGATCTGGGACAGAT

TTCACTCTCACCATCAGCAGTCTGCAACCTGAAGA
```

-continued

```
TTTTGCAACTTACTACTGTCAGCAGTTTCACAAGC

GGTCCCCGCAGAAGTTCGGCCAAGGGACCAAGGTG

GAAATCAAACGTACGGTGGCTGCACCATCTGTCTT

CATCTTCCCGCCATCTGATGAGCAGTTGAAATCTG

GAACTGCCTCTGTTGTGTGCCTGCTGAATAACTTC

TATCCCAGAGAGGCCAAAGTACAGTGGAAGGTGGA

TAACGCCCTCCAATCGGGTAACTCCCAGGAGAGTG

TCACAGAGCAGGACAGCAAGGACAGCACCTACAGC

CTCAGCAGCACCCTGACGCTGAGCAAAGCAGACTA

CGAGAAACACAAAGTCTACGCCTGCGAAGTCACCC

ATCAGGGCCTGAGCTCGCCCGTCACAAAGAGCTTC

AACAGGGGAGAGTGTTAA
```

The “K33” or “K33_IgG_Ke8_2C4 VKCK” antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 222 which is encoded by a nucleic acid sequence of SEQ ID NO: 223.

```
>K33_IgG_Ke8_2C4 VKCK-AA
                                   (SEQ ID NO: 222)
DIQMTQSPSSLSASVGDRVTITCRASQSISSYLNW

YQQKPGKAPKLLIYAASSLQSGVPSRFSGSGSGTD

FTLTISSLQPEDFATYYCQQFHKRSPQKFGQGTKV

EIK

>K33_IgG_Ke8_2C4 VKCK-NT
                                   (SEQ ID NO: 223)
GACATCCAGATGACCCAGTCTCCATCCTCCCTGTC

TGCATCTGTAGGAGACAGAGTCACCATCACTTGCC

GGGCAAGTCAGAGCATTAGCAGCTATTTAAATTGG

TATCAGCAGAAACCAGGGAAAGCCCCTAAGCTCCT

GATCTATGCTGCATCCAGTTTGCAAAGTGGGGTCC

CATCAAGGTTCAGTGGCAGTGGATCTGGGACAGAT

TTCACTCTCACCATCAGCAGTCTGCAACCTGAAGA

TTTTGCAACTTACTACTGTCAGCAGTTTCACAAGC

GGTCCCCGCAGAAGTTCGGCCAAGGGACCAAGGTG

GAAATCAAA
```

The “K38” or “K38_IgG_Ke8_1B4 VKCK” antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 224, which is encoded by a nucleic acid sequence of SEQ ID NO: 225.

>K38_IgG_Ke8_1B4_VKCK-AA
(SEQ ID NO: 224)
*DIQMTQSPSSLSASVGDRVTITCRASQVIANWLNW*
*YQQKPGKAPKLLIYAGSHLQSGVPSRFSGSGSGTD*
*FTLTISSLQPEDFATYYCQQMHPRAPKTFGQGTKV*
*EIK*RTVAAPSVFIFPPSDEQLKSGTASVVCLLNNF
YPREAKVQWKVDNALQSGNSQESVTEQDSKDSTYS
LSSTLTLSKADYEKHKVYACEVTHQGLSSPVTKSF
NRGEC

>K38_IgG_Ke8_1B4_VKCK-NT
(SEQ ID NO: 225)
GACATCCAGATGACCCAGTCTCCATCCTCCCTGTC
TGCATCTGTAGGAGACAGAGTCACCATCACTTGCC
GGGCAAGTCAGGTTATTGCTAATTGGTTAAATTGG
TATCAGCAGAAACCAGGGAAAGCCCCTAAGCTCCT
GATCTATGCTGGGTCCCATTTGCAAAGTGGGGTCC
CATCAAGGTTCAGTGGCAGTGGATCTGGGACAGAT
TTCACTCTCACCATCAGCAGTCTGCAACCTGAAGA
TTTTGCAACTTACTACTGTCAGCAGATGCACCCGC
GCGCCCCGAAGACCTTCGGCCAAGGGACCAAGGTG
GAAATCAAACGTACGGTGGCTGCACCATCTGTCTT
CATCTTCCCGCCATCTGATGAGCAGTTGAAATCTG
GAACTGCCTCTGTTGTGTGCCTGCTGAATAACTTC
TATCCCAGAGAGGCCAAAGTACAGTGGAAGGTGGA
TAACGCCCTCCAATCGGGTAACTCCCAGGAGAGTG
TCACAGAGCAGGACAGCAAGGACAGCACCTACAGC
CTCAGCAGCACCCTGACGCTGAGCAAAGCAGACTA
CGAGAAACACAAAGTCTACGCCTGCGAAGTCACCC
ATCAGGGCCTGAGCTCGCCCGTCACAAAGAGCTTC
AACAGGGGAGAGTGTTAA

The “K38” or “K38_IgG_Ke8_1B4 VKCK” antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 226 which is encoded by a nucleic acid sequence of SEQ ID NO: 227.

>K38_IgG_Ke8_1B4_VKCK-AA
(SEQ ID NO: 226)
DIQMTQSPSSLSASVGDRVTITCRASQVIANWLNW
YQQKPGKAPKLLIYAGSHLQSGVPSRFSGSGSGTD
FTLTISSLQPEDFATYYCQQMHPRAPKTFGQGTKV
EIK

-continued

>K38_IgG_Ke8_1B4_VKCK-NT
(SEQ ID NO: 227)
GACATCCAGATGACCCAGTCTCCATCCTCCCTGTC
TGCATCTGTAGGAGACAGAGTCACCATCACTTGCC
GGGCAAGTCAGGTTATTGCTAATTGGTTAAATTGG
TATCAGCAGAAACCAGGGAAAGCCCCTAAGCTCCT
GATCTATGCTGGGTCCCATTTGCAAAGTGGGGTCC
CATCAAGGTTCAGTGGCAGTGGATCTGGGACAGAT
TTCACTCTCACCATCAGCAGTCTGCAACCTGAAGA
TTTTGCAACTTACTACTGTCAGCAGATGCACCCGC
GCGCCCCGAAGACCTTCGGCCAAGGGACCAAGGTG
GAAATCAAA

The “K106” or “K106_IgGKh5_1A1 VKCK” antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 228, which is encoded by a nucleic acid sequence of SEQ ID NO: 229.

>K106_IgG_Ke8_2C4 VKCK-AA
(SEQ ID NO: 228)
*DIQMTQSPSSLSASVGDRVTITCQASQGIPSYLNW*
*YQCKPGKAPKLLIYGNSKLETGVPSRFSGSGSGTD*
*FTFTISSLQPEDIATYYCQQHTIGTRTNTFGQGTK*
*VEIK*RTVAAPSVFIFPPSDEQLKSGTASVVCLLNN
FYPREAKVQWKVDNALQSGNSQESVTEQDSKDSTY
SLSSTLTLSKADYEKHKVYACEVTHQGLSSPVTKS
FNRGEC

>K106_IgG_Ke8_2C4 VKCK-NT
(SEQ ID NO: 229)
GACATCCAGATGACCCAGTCTCCATCCTCCCTGTC
TGCATCTGTAGGAGACAGAGTCACCATCACTTGCC
AGGCGAGTCAGGGTATTCCTAGTTATTTAAATTGG
TATCAGCAGAAACCAGGGAAAGCCCCTAAGCTCCT
GATCTACGGTAATTCCAAGTTGGAAACAGGGGTCC
CATCAAGGTTCAGTGGAAGTGGATCTGGGACAGAT
TTTACTTTCACCATCAGCAGCCTGCAGCCTGAAGA
TATTGCAACATATTACTGTCAGCAGCATACTATTG
GTACTAGGACTAATACCTTCGGCCAAGGGACCAAG
GTGGAAATCAAACGTACGGTGGCTGCACCATCTGT
CTTCATCTTCCCGCCATCTGATGAGCAGTTGAAAT
CTGGAACTGCCTCTGTTGTGTGCCTGCTGAATAAC
TTCTATCCCAGAGAGGCCAAAGTACAGTGGAAGGT
GGATAACGCCCTCCAATCGGGTAACTCCCAGGAGA
GTGTCACAGAGCAGGACAGCAAGGACAGCACCTAC

AGCCTCAGCAGCACCCTGACGCTGAGCAAAGCAGA

CTACGAGAAACACAAAGTCTACGCCTGCGAAGTCA

CCCATCAGGGCCTGAGCTCGCCCGTCACAAAGAGC

TTCAACAGGGGAGAGTGTTAA

The "K106" or "K106_IgG_Kh5_1A1 VKCK" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 230 which is encoded by a nucleic acid sequence of SEQ ID NO: 231.

>K106_IgG_Ke8_2C4 VKCK-AA
(SEQ ID NO: 230)
DIQMTQSPSSLSASVGDRVTITCQASQGIPSYLNW

YQQKPGKAPKLLIYGNSKLETGVPSRFSGSGSGTD

FTFTISSLQPEDIATYYCQQHTIGTRTNTFGQGTK

VEIK

>K106_IgG_Ke8_2C4 VKCK-NT
(SEQ ID NO: 231)
GACATCCAGATGACCCAGTCTCCATCCTCCCTGTC

TGCATCTGTAGGAGACAGAGTCACCATCACTTGCC

AGGCGAGTCAGGGTATTCCTAGTTATTTAAATTGG

TATCAGCAGAAACCAGGGAAAGCCCCTAAGCTCCT

GATCTACGGTAATTCCAAGTTGGAAACAGGGGTCC

CATCAAGGTTCAGTGGAAGTGGATCTGGGACAGAT

TTTACTTTCACCATCAGCAGCCTGCAGCCTGAAGA

TATTGCAACATATTACTGTCAGCAGCATACTATTG

GTACTAGGACTAATACCTTCGGCCAAGGGACCAAG

GTGGAAATCAAA

The "K91" or "K91_IgG_Ke8_2D4 VKCK" antibody has a heavy chain variable region and heavy chain constant region comprising an amino acid sequence of SEQ ID NO: 4, which is encoded by a nucleic acid sequence of SEQ ID NO: 5, and a kappa light chain comprising an amino acid sequence of SEQ ID NO: 238, which is encoded by a nucleic acid sequence of SEQ ID NO: 239.

>K91_IgG_Ke8_2D4 VKCK-AA
(SEQ ID NO: 238)
*DIQMTQSPSSLSASVGDRVTITCNVDQVIANWLNW*

*ITQKPGKAPKLLIYAASSLQSGVPSRFSGSGSGTD*

*FTLTISSLQPEDFATYYCQQMHPRAPKQFGQGTKV*

*EIK*RTVAAPSVFIFPPSDEQLKSGTASVVCLLNNF

YPREAKVQWKVDNALQSGNSQESVTEQDSKDSTYS

LSSTLTLSKADYEKHKVYACEVTHQGLSSPVTKSF

NRGEC

>K91_IgG_Ke8_2D4 VKCK-NT
(SEQ ID NO: 239)
GACATCCAGATGACCCAGTCTCCATCCTCCCTGTC

TGCATCTGTAGGAGACAGAGTCACCATCACTTGCA

ATGTTGATCAGGTTATTGCTAATTGGTTAAATTGG

TATCAGCAGAAACCAGGGAAAGCCCCTAAGCTCCT

GATCTATGCTGCATCCAGTTTGCAAAGTGGGGTCC

CATCAAGGTTCAGTGGCAGTGGATCTGGGACAGAT

TTCACTCTCACCATCAGCAGTCTGCAACCTGAAGA

TTTTGCAACTTACTACTGTCAGCAGATGCACCCGC

GCGCTCCGAAGCAGTTCGGCCAAGGGACCAAGGTG

GAAATCAAACGTACGGTGGCTGCACCATCTGTCTT

CATCTTCCCGCCATCTGATGAGCAGTTGAAATCTG

GAACTGCCTCTGTTGTGTGCCTGCTGAATAACTTC

TATCCCAGAGAGGCCAAAGTACAGTGGAAGGTGGA

TAACGCCCTCCAATCGGGTAACTCCCAGGAGAGTG

TCACAGAGCAGGACAGCAAGGACAGCACCTACAGC

CTCAGCAGCACCCTGACGCTGAGCAAAGCAGACTA

CGAGAAACACAAAGTCTACGCCTGCGAAGTCACCC

ATCAGGGCCTGAGCTCGCCCGTCACAAAGAGCTTC

AACAGGGGAGAGTGTTAA

The "K91" or "K91_IgG_Ke8_2D4 VKCK" antibody has a heavy chain variable region comprising an amino acid sequence of SEQ ID NO: 6 which is encoded by a nucleic acid sequence of SEQ ID NO: 7 and a kappa light chain variable region comprising an amino acid sequence of SEQ ID NO: 240 which is encoded by a nucleic acid sequence of SEQ ID NO: 241.

>K91_IgG_Ke8_2D4 VKCK-AA
(SEQ ID NO: 240)
DIQMTQSPSSLSASVGDRVTITCNVDQVIANWLNW

YQQKPGKAPKLLIYAASSLQSGVPSRFSGSGSGTD

FTLTISSLQPEDFATYYCQQMHPRAPKQFGQGTKV

EIK

>K91_IgG_Ke8_2D4 VKCK-NT
(SEQ ID NO: 241)
GACATCCAGATGACCCAGTCTCCATCCTCCCTGTC

TGCATCTGTAGGAGACAGAGTCACCATCACTTGCA

ATGTTGATCAGGTTATTGCTAATTGGTTAAATTGG

TATCAGCAGAAACCAGGGAAAGCCCCTAAGCTCCT

GATCTATGCTGCATCCAGTTTGCAAAGTGGGGTCC

CATCAAGGTTCAGTGGCAGTGGATCTGGGACAGAT

TTCACTCTCACCATCAGCAGTCTGCAACCTGAAGA

TTTTGCAACTTACTACTGTCAGCAGATGCACCCGC

GCGCTCCGAAGCAGTTCGGCCAAGGGACCAAGGTG

GAAATCAAA

Anti-PD-L1 Antibodies

Exemplary anti-PD-L1 antibody sequences are shown below. Light chain variable regions are shown in italicized underlined text. CDR sequences are shown in bolded underlined text.

The "S8" or "S8_Sa10_1A9_VLCL2 aPDL1 IGLV1-44" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 29, which is encoded by a nucleic acid sequence of SEQ ID NO: 30.

```
>S8_Sa10_1A9 VLCL2 aPDL1 IGLV1-44-AA
                                  (SEQ ID NO: 29)
QSVLTQPPSASGTPGQRVTISCSGSSSNIRDSFVN
WYQQLPGTAPKLLIYATNIRPSGVPDRFSGSKSGT
SASLAISGLQSEDEADYYCAAWHPYYTLFGGGTKL
TVLGQPKAAPSVTLFPPSSEELQANKATLVCLISD
FYPGAVTVAWKADSSPVKAGVETTTPSKQSNNKYA
ASSYLSLTPEQWKSHRSYSCQVTHEGSTVEKTVAP
TECS
```

```
>S8_Sa10_1A9 VLCL2 aPDL1 IGLV1-44-NT
                                  (SEQ ID NO: 30)
CAGTCTGTGCTGACTCAGCCACCCTCAGCGTCTGG
GACCCCCGGGCAGAGGGTCACCATCTCTTGTTCTG
GAAGCAGCTCCAACATCAGGGATAGTTTTGTAAAC
TGGTACCAGCAGCTCCCAGGAACGGCCCCCAAACT
CCTCATCTATGCTACGAATATTCGGCCCTCAGGGG
TCCCTGACCGATTCTCTGGCTCCAAGTCTGGCACC
TCAGCCTCCCTGGCCATCAGTGGGCTCCAGTCTGA
GGATGAGGCTGATTATTACTGTGCAGCATGGCACC
CGTATTACACGTTGTTCGGCGGAGGGACCAAGCTG
ACCGTCCTAGGTCAGCCCAAGGCTGCCCCCTCGGT
CACTCTGTTCCCGCCCTCCTCTGAGGAGCTTCAAG
CCAACAAGGCCACACTGGTGTGTCTCATAAGTGAC
TTCTACCCGGGAGCCGTGACAGTGGCTTGGAAAGC
AGATAGCAGCCCCGTCAAGGCGGGAGTGGAGACCA
CCACACCCTCCAAACAAAGCAACAACAAGTACGCG
GCCAGCAGCTATCTGAGCCTGACGCCTGAGCAGTG
GAAGTCCCACAGAAGCTACAGCTGCCAGGTCACGC
ATGAAGGGAGCACCGTGGAGAAGACAGTGGCCCCT
ACAGAATGTTCA
```

The "S8" or "S8_Sa10_1A9_VLCL2 aPDL1 IGLV1-44" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 31 which is encoded by a nucleic acid sequence of SEQ ID NO: 32.

```
>S8_Sa10_1A9 VLCL2 aPDL1 IGLV1-44-AA
                                  (SEQ ID NO: 31)
QSVLTQPPSASGTPGQRVTISCSGSSSNIRDSFVN
WYQQLPGTAPKLLIYATNIRPSGVPDRFSGSKSGT
SASLAISGLQSEDEADYYCAAWHPYYTLFGGGTKL
TVLGQPKAAPSVTL
```

```
>S8_Sa10_1A9 VLCL2 aPDL1 IGLV1-44-NT
                                  (SEQ ID NO: 32)
CAGTCTGTGCTGACTCAGCCACCCTCAGCGTCTGG
GACCCCCGGGCAGAGGGTCACCATCTCTTGTTCTG
GAAGCAGCTCCAACATCAGGGATAGTTTTGTAAAC
TGGTACCAGCAGCTCCCAGGAACGGCCCCCAAACT
CCTCATCTATGCTACGAATATTCGGCCCTCAGGGG
TCCCTGACCGATTCTCTGGCTCCAAGTCTGGCACC
TCAGCCTCCCTGGCCATCAGTGGGCTCCAGTCTGA
GGATGAGGCTGATTATTACTGTGCAGCATGGCACC
CGTATTACACGTTGTTCGGCGGAGGGACCAAGCTG
ACCGTCCTAGGTCAGCCCAAGGCTGCCCCCTCGGT
CACTCTG
```

The "S9" or "S9_Sa10_1D9_VLCL2 aPDL1 IGLV1-44-AA" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 33, which is encoded by a nucleic acid sequence of SEQ ID NO: 34.

```
>S9_Sa10_1D9 VLCL2 aPDL1 IGLV1-44-AA
                                  (SEQ ID NO: 33)
QSVLTQPPSASGTPGQRVTISCSGSSSNIRDSFVN
WYQQLPGTAPKLLIYATNIRPSGVPDRFSGSKSGT
SASLAISGLQSEDEADYYCASWWPYGTVFGGGTKL
TVLGQPKAAPSVTLFPPSSEELQANKATLVCLISD
FYPGAVTVAWKADSSPVKAGVETTTPSKQSNNKYA
ASSYLSLTPEQWKSHRSYSCQVTHEGSTVEKTVAP
TECS
```

```
>S9_Sa10_1D9 VLCL2 aPDL1 IGLV1-44-NT
                                  (SEQ ID NO: 34)
CAGTCTGTGCTGACTCAGCCACCCTCAGCGTCTGG
GACCCCCGGGCAGAGGGTCACCATCTCTTGTTCTG
GAAGCAGCTCCAACATCAGGGATAGTTTTGTAAAC
TGGTACCAGCAGCTCCCAGGAACGGCCCCCAAACT
CCTCATCTATGCTACGAATATTCGGCCCTCAGGGG
TCCCTGACCGATTCTCTGGCTCCAAGTCTGGCACC
TCAGCCTCCCTGGCCATCAGTGGGCTCCAGTCTGA
GGATGAGGCTGATTATTACTGTGCATCGTGGTGGC
CGTACGGTACTGTGTTCGGCGGAGGGACCAAGCTG
```

-continued

ACCGTCCTAGGTCAGCCCAAGGCTGCCCCCTCGGT
CACTCTGTTCCCGCCCTCCTCTGAGGAGCTTCAAG
CCAACAAGGCCACACTGGTGTGTCTCATAAGTGAC
TTCTACCCGGGAGCCGTGACAGTGGCTTGGAAAGC
AGATAGCAGCCCCGTCAAGGCGGGAGTGGAGACCA
CCACACCCTCCAAACAAAGCAACAACAAGTACGCG
GCCAGCAGCTATCTGAGCCTGACGCCTGAGCAGTG
GAAGTCCCACAGAAGCTACAGCTGCCAGGTCACGC
ATGAAGGGAGCACCGTGGAGAAGACAGTGGCCCCT
ACAGAATGTTCA

The "S9" or "S9_Sa10_1D9_VLCL2 aPDL1 IGLV1-44-AA" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 35 which is encoded by a nucleic acid sequence of SEQ ID NO: 36.

>S9_Sa10_1D9 VLCL2 aPDL1 IGLV1-44-AA
(SEQ ID NO: 35)
QSVLTQPPSASGTPGQRVTISCSGSSNIRDSFVN
WYQQLPGTAPKLLIYATNIRPSGVPDRFSGSKSGT
SASLAISGLQSEDEADYYCASWWPYGTVFGGGTKL
TVLGQPKAAPSVTL

>S9_Sa10_1D9 VLCL2 aPDL1 IGLV1-44-NT
(SEQ ID NO: 36)
CAGTCTGTGCTGACTCAGCCACCCTCAGCGTCTGG
GACCCCCGGGCAGAGGGTCACCATCTCTTGTTCTG
GAAGCAGCTCCAACATCAGGGATAGTTTTGTAAAC
TGGTACCAGCAGCTCCCAGGAACGGCCCCCAAACT
CCTCATCTATGCTACGAATATTCGGCCCTCAGGGG
TCCCTGACCGATTCTCTGGCTCCAAGTCTGGCACC
TCAGCCTCCCTGGCCATCAGTGGGCTCCAGTCTGA
GGATGAGGCTGATTATTACTGTGCATCGTGGTGGC
CGTACGGTACTGTGTTCGGCGGAGGGACCAAGCTG
ACCGTCCTAGGTCAGCCCAAGGCTGCCCCCTCGGT
CACTCTG

The "S37" or "S37_Sa10_1D7_VLCL2 aPDL1 IGLV1-44" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 37, which is encoded by a nucleic acid sequence of SEQ ID NO: 38.

>S37_ Sa10_1D7_VLCL2 aPDL1 IGLV1-44-AA
(SEQ ID NO: 37)
*QSVLTQPPSASGTPGQRVTISCSGSSSNIRDSFVNWYQQLPGTAPKLLIY*
*ATNIRPSGVPDRFSGSKSGTSASLAISGLQSEDEADYYCASWWPFGTVFG*

-continued

*GGTKLTVLGQPKAAPSVTL*FPPSSEELQANKATLVCLISDFYPGAVTVAW
KADSSPVKAGVETTTPSKQSNNKYAASSYLSLTPEQWKSHRSYSCQVTHE
GSTVEKTVAPTECS

>S37_ Sa10_1D7_VLCL2 aPDL1 IGLV1-44-NT
(SEQ ID NO: 38)
CAGTCTGTGCTGACTCAGCCACCCTCAGCGTCTGGGACCCCCGGGCAGAG
GGTCACCATCTCTTGTTCTGGAAGCAGCTCCAACATCAGGGATAGTTTTG
TAAACTGGTACCAGCAGCTCCCAGGAACGGCCCCCAAACTCCTCATCTAT
GCTACGAATATTCGGCCCTCAGGGGTCCCTGACCGATTCTCTGGCTCCAA
GTCTGGCACCTCAGCCTCCCTGGCCATCAGTGGGCTCCAGTCTGAGGATG
AGGCTGATTATTACTGTGCATCCTGGTGGCCGTTCGGTACTGTGTTCGGC
GGAGGGACCAAGCTGACCGTCCTAGGTCAGCCCAAGGCTGCCCCCTCGGT
CACTCTGTTCCCGCCCTCCTCTGAGGAGCTTCAAGCCAACAAGGCCACAC
TGGTGTGTCTCATAAGTGACTTCTACCCGGGAGCCGTGACAGTGGCTTGG
AAAGCAGATAGCAGCCCCGTCAAGGCGGGAGTGGAGACCACCACACCCTC
CAAACAAAGCAACAACAAGTACGCGGCCAGCAGCTATCTGAGCCTGACGC
CTGAGCAGTGGAAGTCCCACAGAAGCTACAGCTGCCAGGTCACGCATGAA
GGGAGCACCGTGGAGAAGACAGTGGCCCCTACAGAATGTTCA

The "S37" or "S37_Sa10_1D7_VLCL2 aPDL1 IGLV1-44" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 39 which is encoded by a nucleic acid sequence of SEQ ID NO: 40.

>S37_ Sa10_1D7_VLCL2 aPDL1 IGLV1-44-AA
(SEQ ID NO: 39)
QSVLTQPPSASGTPGQRVTISCSGSSSNIRDSFVNWYQQLPGTAPKLLIY
ATNIRPSGVPDRFSGSKSGTSASLAISGLQSEDEADYYC
ASWWPFGTVFGGGTKLTVLGQPKAAPSVTL

>S37_ Sa10_1D7_VLCL2 aPDL1 IGLV1-44-NT
(SEQ ID NO: 40)
CAGTCTGTGCTGACTCAGCCACCCTCAGCGTCTGGGACCCCCGGGCAGAG
GGTCACCATCTCTTGTTCTGGAAGCAGCTCCAACATCAGGGATAGTTTTG
TAAACTGGTACCAGCAGCTCCCAGGAACGGCCCCCAAACTCCTCATCTAT
GCTACGAATATTCGGCCCTCAGGGGTCCCTGACCGATTCTCTGGCTCCAA
GTCTGGCACCTCAGCCTCCCTGGCCATCAGTGGGCTCCAGTCTGAGGATG
AGGCTGATTATTACTGTGCATCCTGGTGGCCGTTCGGTACTGTGTTCGGC
GGAGGGACCAAGCTGACCGTCCTAGGTCAGCCCAAGGCTGCCCCCTCGGT
CACTCTG

The "S14" or "S14 Sh3_1C6_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 41, which is encoded by a nucleic acid sequence of SEQ ID NO: 42.

>S14_ Sh3_1C6_VLCL2 aPDL1 IGLV2-23-AA
(SEQ ID NO: 41)
*QSALTQPASVSGSPGQSITISCTGTSSDVVKNNFVSWYQQHPGKAPKLMI*

*YFGSVRPSGVSNRFSGKSGNTASLTISGLQAEDEADYYCSSWDMPALFFG*

*GGTKLTVLGQPKAAPSVTL*FPPSSEELQANKATLVCLISDFYPGAVTVAW

KADSSPVKAGVETTTPSKQSNNKYAASSYLSLTPEQWKSHRSYSCQVTHE

GSTVEKTVAPTECS

>S14_ Sh3_1C6_VLCL2 aPDL1 IGLV2-23-NT
(SEQ ID NO: 42)
CAGTCTGCCCTGACTCAGCCTGCCTCCGTGTCTGGGTCTCCTGGACAGTC

GATCACCATCTCCTGCACTGGAACCAGCAGTGACGTTGTTAAGAATAATT

TTGTCTCCTGGTACCAACAGCACCCAGGCAAAGCCCCCAAACTCATGATT

TATTTTGGGAGTGTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATATGCCTGCGCTTTTCTTC

GGCGGAGGGACCAAGCTGACCGTCCTAGGTCAGCCCAAGGCTGCCCCCTC

GGTCACTCTGTTCCCGCCCTCCTCTGAGGAGCTTCAAGCCAACAAGGCCA

CACTGGTGTGTCTCATAAGTGACTTCTACCCGGGAGCCGTGACAGTGGCT

TGGAAAGCAGATAGCAGCCCCGTCAAGGCGGGAGTGGAGACCACCACACC

CTCCAAACAAAGCAACAACAAGTACGCGGCCAGCAGCTATCTGAGCCTGA

CGCCTGAGCAGTGGAAGTCCCACAGAAGCTACAGCTGCCAGGTCACGCAT

GAAGGGAGCACCGTGGAGAAGACAGTGGCCCCTACAGAATGTTCA

The "S14" or "S14_Sh3_1C6_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 43 which is encoded by a nucleic acid sequence of SEQ ID NO: 44.

>S14_ Sh3_1C6_VLCL2 aPDL1 IGLV2-23-AA
(SEQ ID NO: 43)
QSALTQPASVSGSPGQSITISCTGTSSDVVKNNFVSWYQQHPGKAPKLMIY

FGSVRPSGVSNRFSGKSGNTASLTISGLQAEDEADYYCSSWDMPALF

FGGGTKLTVLGQPKAAPSVTL

>S14_ Sh3_1C6_VLCL2 aPDL1 IGLV2-23-NT
(SEQ ID NO: 44)
CAGTCTGCCCTGACTCAGCCTGCCTCCGTGTCTGGGTCTCCTGGACAGTC

GATCACCATCTCCTGCACTGGAACCAGCAGTGACGTTGTTAAGAATAATT

TTGTCTCCTGGTACCAACAGCACCCAGGCAAAGCCCCCAAACTCATGATT

TATTTTGGGAGTGTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATATGCCTGCGCTTTTCTTC

GGCGGAGGGACCAAGCTGACCGTCCTAGGTCAGCCCAAGGCTGCCCCCTC

GGTCACTCTG

The "S15" or "S15_Sh3_1E2_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 45, which is encoded by a nucleic acid sequence of SEQ ID NO: 46.

>S15_ Sh3_1E2_VLCL2 aPDL1 IGLV2-23-AA
(SEQ ID NO: 45)
*QSALTQPASVSGSPGQSITISCTGTSSDVVKNNFVSWYQQHPGKAPKLMI*

*YFGSVRPSGVSNRFSGSKSGNTASLTISGLQAEDEADYYCSSWDEPDRPF*

*GGGTKLTVLGQPKAAPSVTL*FPPSSEELQANKATLVCLISDFYPGAVTVA

WKADSSPVKAGVETTTPSKQSNNKYAASSYLSLTPEQWKSHRSYSCQVTH

EGSTVEKTVAPTECS

>S15_ Sh3_1E2_VLCL2 aPDL1 IGLV2-23-NT
(SEQ ID NO: 46)
CAGTCTGCCCTGACTCAGCCTGCCTCCGTGTCTGGGTCTCCTGGACAGTC

GATCACCATCTCCTGCACTGGAACCAGCAGTGACGTTGTTAAGAATAATT

TTGTCTCCTGGTACCAACAGCACCCAGGCAAAGCCCCCAAACTCATGATT

TATTTTGGGAGTGTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATGAGCCGGACAGGCCCTTC

GGCGGAGGGACCAAGCTGACCGTCCTAGGTCAGCCCAAGGCTGCCCCCTC

GGTCACTCTGTTCCCGCCCTCCTCTGAGGAGCTTCAAGCCAACAAGGCCA

CACTGGTGTGTCTCATAAGTGACTTCTACCCGGGAGCCGTGACAGTGGCT

TGGAAAGCAGATAGCAGCCCCGTCAAGGCGGGAGTGGAGACCACCACACC

CTCCAAACAAAGCAACAACAAGTACGCGGCCAGCAGCTATCTGAGCCTGA

CGCCTGAGCAGTGGAAGTCCCACAGAAGCTACAGCTGCCAGGTCACGCAT

GAAGGGAGCACCGTGGAGAAGACAGTGGCCCCTACAGAATGTTCA

The "S15" or "S15_Sh3_1E2_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 47 which is encoded by a nucleic acid sequence of SEQ ID NO: 48.

>S15_ Sh3_1E2_VLCL2 aPDL1 IGLV2-23-AA
(SEQ ID NO: 47)
QSALTQPASVSGSPGQSITISCTGTSSDVVKNNFVSWYQQHPGKAPKLMIY

FGSVRPSGVSNRFSGSKSGNTASLTISGLQAEDEADYYCSSWDEPDRP

FGGGTKLTVLGQPKAAPSVTL

>S15_ Sh3_1E2_VLCL2 aPDL1 IGLV2-23-NT
(SEQ ID NO: 48)
CAGTCTGCCCTGACTCAGCCTGCCTCCGTGTCTGGGTCTCCTGGACAGTC

GATCACCATCTCCTGCACTGGAACCAGCAGTGACGTTGTTAAGAATAATT

TTGTCTCCTGGTACCAACAGCACCCAGGCAAAGCCCCCAAACTCATGATT

TATTTTGGGAGTGTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATGAGCCGGACAGGCCCTTC

GGCGGAGGGACCAAGCTGACCGTCCTAGGTCAGCCCAAGGCTGCCCCCTC

GGTCACTCTG

The "S17" or "S17_Sh3_1D9_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 49, which is encoded by a nucleic acid sequence of SEQ ID NO: 50.

>S17_ Sh3_1D9_VLCL2 aPDL1 IGLV2-23-AA
(SEQ ID NO: 49)
QSALTQPASVSGSPGQSITISCTGTSSDVVKNNFVSWYQQHPGKAPKPMI

YFGSVRPSGVSNRFSGSKSGNTASLTISGLQAEDEADYYCSSWDLPFLMF

GXGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

>S17_ Sh3_1D9_VLCL2 aPDL1 IGLV2-23-NT
(SEQ ID NO: 50)
CAGTCTGCCCTGACTCAGCCTGCCTCCGTGTCTGGGTCTCCTGGACAGTC

GATCACCATCTCCTGCACTGGAACCAGCAGTGACGTTGTTAAGAATAATT

TTGTCTCCTGGTACCAACAGCACCCAGGCAAAGCCCCCAAACCCATGATT

TATTTTGGGAGTGTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATCTCCCTTTCCTTATGTTC

GGCGGRGGGACCAAGCTGACCGTCCTAGGTCAGCCCAAGGCTGCCCCCTC

GGTCACTCTGTTCCCGCCCTCCTCTGAGGAGCTTCAAGCCAACAAGGCCA

CACTGGTGTGTCTCATAAGTGACTTCTACCCGGGAGCCGTGACAGTGGCT

TGGAAAGCAGATAGCAGCCCCGTCAAGGCGGGAGTGGAGACCACCACACC

CTCCAAACAAAGCAACAACAAGTACGCGGCCAGCAGCTATCTGAGCCTGA

CGCCTGAGCAGTGGAAGTCCCACAGAAGCTACAGCTGCCAGGTCACGCAT

GAAGGGAGCACCGTGGAGAAGACAGTGGCCCCTACAGAATGTTCA

The "S17" or "S17_Sh3_1D9_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 51 which is encoded by a nucleic acid sequence of SEQ ID NO: 52.

>S17_ Sh3_1D9_VLCL2 aPDL1 IGLV2-23-AA
(SEQ ID NO: 51)
QSALTQPASVSGSPGQSITISCTGTSSDVVKNNFVSWYQQHPGKAPKPMIY

FGSVRPSGVSNRFSGSKSGNTASLTISGLQAEDEADYYCSSWDLPFLM

FGXGTKLTVLGQPKAAPSVTL

>S17_ Sh3_1D9_VLCL2 aPDL1 IGLV2-23-NT
(SEQ ID NO: 52)
CAGTCTGCCCTGACTCAGCCTGCCTCCGTGTCTGGGTCTCCTGGACAGTC

GATCACCATCTCCTGCACTGGAACCAGCAGTGACGTTGTTAAGAATAATT

TTGTCTCCTGGTACCAACAGCACCCAGGCAAAGCCCCCAAACCCATGATT

TATTTTGGGAGTGTTCGGCCCTCAGGGGTTTCTAATCGCTTCTCTGGCTC

CAAGTCTGGCAACACGGCCTCCCTGACCATCTCTGGGCTCCAGGCTGAGG

-continued

ACGAGGCTGATTATTACTGCAGCTCATGGGATCTCCCTTTCCTTATGTTC

GGCGGRGGGACCAAGCTGACCGTCCTAGGTCAGCCCAAGGCTGCCCCCTC

GGTCACTCTG

The "S57" or "S57_Sh3_2D9_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 53, which is encoded by a nucleic acid sequence of SEQ ID NO: 54.

>S57_ Sh3_2D9_VLCL2 aPDL1 IGLV2-23-AA
(SEQ ID NO: 53)
QSALTQPASVSGSPGQSITISCTSISSDVVKNNFVSWYQQHPGKAPKLMI

YFGSVTADGVSNRFSGSKSGNTASLTISGLQAEDEADYYCSSWDEPDRPF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

>S57_ Sh3_2D9_VLCL2 aPDL1 IGLV2-23-NT
(SEQ ID NO: 54)
CAGTCTGCCCTGACTCAGCCTGCCTCCGTGTCTGGGTCTCCTGGACAGTC

GATCACCATCTCCTGCACTAGTATTAGCAGTGACGTTGTTAAGAATAATT

TTGTCTCTTGGTACCAACAGCACCCAGGCAAAGCCCCCAAACTCATGATT

TATTTTGGGAGTGTTACTGCTGATGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATGAGCCGGACAGGCCCTTC

GGCGGAGGGACCAAGCTGACCGTCCTAGGTCAGCCCAAGGCTGCCCCCTC

GGTCACTCTGTTCCCGCCCTCCTCTGAGGAGCTTCAAGCCAACAAGGCCA

CACTGGTGTGTCTCATAAGTGACTTCTACCCGGGAGCCGTGACAGTGGCT

TGGAAAGCAGATAGCAGCCCCGTCAAGGCGGGAGTGGAGACCACCACACC

CTCCAAACAAAGCAACAACAAGTACGCGGCCAGCAGCTATCTGAGCCTGA

CGCCTGAGCAGTGGAAGTCCCACAGAAGCTACAGCTGCCAGGTCACGCAT

GAAGGGAGCACCGTGGAGAAGACAGTGGCCCCTACAGAATGTTCA

The "S57" or "S57_Sh3_2D9_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 55 which is encoded by a nucleic acid sequence of SEQ ID NO: 56.

>S57_ Sh3_2D9_VLCL2 aPDL1 IGLV2-23-AA
(SEQ ID NO: 55)
QSALTQPASVSGSPGQSITISCTSISSDVVKNNFVSWYQQHPGKAPKLMIY

FGSVTADGVSNRFSGSKSGNTASLTISGLQAEDEADYYCSSWDEPDRP

FGGGTKLTVLGQPKAAPSVTL

>S57_ Sh3_2D9_VLCL2 aPDL1 IGLV2-23-NT
(SEQ ID NO: 56)
CAGTCTGCCCTGACTCAGCCTGCCTCCGTGTCTGGGTCTCCTGGACAGTC

GATCACCATCTCCTGCACTAGTATTAGCAGTGACGTTGTTAAGAATAATT

-continued

TTGTCTCTTGGTACCAACAGCACCCAGGCAAAGCCCCCAAACTCATGATT

TATTTTGGGAGTGTTACTGCTGATGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATGAGCCGGACAGGCCCTTC

GGCGGAGGGACCAAGCTGACCGTCCTAGGTCAGCCCAAGGCTGCCCCCTC

GGTCACTCTG

The "S58" or "S58_Sh3_1G5_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 57, which is encoded by a nucleic acid sequence of SEQ ID NO: 58.

>S58_ Sh3_1G5_VLCL2 aPDL1 IGLV2-23-AA
(SEQ ID NO: 57)
*QSALTQPASVSGSPGQSITISCNSPSSDVVKNNFVSWYQQHPGKAPKLMI*

*YFGSVTGPGVSNRFSGSKSGNTASLTISGLQAEDEADYYCSSWDEPDRPF*

*GGGTKLTVLGQPKAAPSVTL*FPPSSEELQANKATLVCLISDFYPGAVTVA

WKADSSPVKAGVETTTPSKQSNNKYAASSYLSLTPEQWKSHRSYSCQVTH

EGSTVEKTVAPTECS

>S58_ Sh3_1G5_VLCL2 aPDL1 IGLV2-23-NT
(SEQ ID NO: 58)
CAGTCTGCCCTGACTCAGCCTGCCTCCGTGTCTGGGTCTCCTGGACAGTC

GATCACCATCTCCTGCAATAGTCCTAGCAGTGACGTTGTTAAGAATAATT

TTGTCTCTTGGTACCAACAGCACCCAGGCAAAGCCCCCAAACTCATGATT

TATTTTGGGAGTGTTACTGGTCCTGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATGAGCCGGACAGGCCCTTC

GGCGGAGGGACCAAGCTGACCGTCCTAGGTCAGCCCAAGGCTGCCCCCTC

GGTCACTCTGTTCCCGCCCTCCTCTGAGGAGCTTCAAGCCAACAAGGCCA

CACTGGTGTGTCTCATAAGTGACTTCTACCCGGGAGCCGTGACAGTGGCT

TGGAAAGCAGATAGCAGCCCCGTCAAGGCGGGAGTGGAGACCACCACACC

CTCCAAACAAAGCAACAACAAGTACGCGGCCAGCAGCTATCTGAGCCTGA

CGCCTGAGCAGTGGAAGTCCCACAGAAGCTACAGCTGCCAGGTCACGCAT

GAAGGGAGCACCGTGGAGAAGACAGTGGCCCCTACAGAATGTTCA

The "S58" or "S58_Sh3_1G5_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 59 which is encoded by a nucleic acid sequence of SEQ ID NO: 60.

>S58_ Sh3_1G5_VLCL2 aPDL1 IGLV2-23-AA
(SEQ ID NO: 59)
QSALTQPASVSGSPGQSITISCNSPSSDVVKNNFVSWYQQHPGKAPKLMIY

-continued

FGSVTGPGVSNRFSGSKSGNTASLTISGLQAEDEADYYCSSWDEPDRP

FGGGTKLTVLGQPKAAPSVTL

>S58_ Sh3_1G5_VLCL2 aPDL1 IGLV2-23-NT
(SEQ ID NO: 60)
CAGTCTGCCCTGACTCAGCCTGCCTCCGTGTCTGGGTCTCCTGGACAGTC

GATCACCATCTCCTGCAATAGTCCTAGCAGTGACGTTGTTAAGAATAATT

TTGTCTCTTGGTACCAACAGCACCCAGGCAAAGCCCCCAAACTCATGATT

TATTTTGGGAGTGTTACTGGTCCTGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATGAGCCGGACAGGCCCTTC

GGCGGAGGGACCAAGCTGACCGTCCTAGGTCAGCCCAAGGCTGCCCCCTC

GGTCACTCTG

The "S28" or "S28_Sa2_1G7_VLCL2 aPDL1 IGLV2-44" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 61, which is encoded by a nucleic acid sequence of SEQ ID NO: 62.

>S28_Sa2_1G7_VLCL2 aPDL1 IGLV2-44-AA
(SEQ ID NO: 61)
*QSVLTQPPSASGTPGQRVTISCSGSSSNIAHKPVNWYQQLPGTAPKLLIY*

*HDNSRPSGVPDRFSGSKSGTSASLAISGLQSEDEADYYCAAWDFATWPAT*

*EVFGGGTKLTVLGQPKAAPSVTL*FPPSSEELQANKATLVCLISDFYPGAV

TVAWKADSSPVKAGVETTTPSKQSNNKYAASSYLSLTPEQWKSHRSYSCQ

VTHEGSTVEKTVAPTECS

>S28_Sa2_1G7_VLCL2 aPDL1 IGLV2-44-NT
(SEQ ID NO: 62)
CAGTCTGTGCTGACTCAGCCACCCTCAGCGTCTGGGACCCCCGGGCAGAG

GGTCACCATCTCTTGTTCTGGAAGCAGCTCCAACATCGCTCATAAGCCTG

TAAACTGGTACCAGCAGCTCCCAGGAACGGCCCCCAAACTCCTCATCTAT

CATGATAATTCTCGGCCCTCAGGGGTCCCTGACCGATTCTCTGGCTCCAA

GTCTGGCACCTCAGCCTCCCTGGCCATCAGTGGGCTCCAGTCTGAGGATG

AGGCTGATTATTACTGTGCAGCATGGGATTTCGCGACGTGGCCGGCTACT

GAGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCA

The "S28" or "S28_Sa2_1G7_VLCL2 aPDL1 IGLV2-44" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 63 which is encoded by a nucleic acid sequence of SEQ ID NO: 64.

>S28_Sa2_1G7_VLCL2 aPDL1 IGLV2-44-AA
(SEQ ID NO: 63)
QSVLTQPPSASGTPGQRVTISCSGSSSNIAHKPVNWYQQLPGTAPKLLIY
HDNSRPSGVPDRFSGSKSGTSASLAISGLQSEDEADYYC
AAWDFATWPATEVFGGGTKLTVLGQPKAAPSVTL

>S28_Sa2_1G7_VLCL2 aPDL1 IGLV2-44-NT
(SEQ ID NO: 64)
CAGTCTGTGCTGACTCAGCCACCCTCAGCGTCTGGGACCCCCGGGCAGAG
GGTCACCATCTCTTGTTCTGGAAGCAGCTCCAACATCGCTCATAAGCCTG
TAAACTGGTACCAGCAGCTCCCAGGAACGGCCCCCAAACTCCTCATCTAT
CATGATAATTCTCGGCCCTCAGGGGTCCCTGACCGATTCTCTGGCTCCAA
GTCTGGCACCTCAGCCTCCCTGGCCATCAGTGGGCTCCAGTCTGAGGATG
AGGCTGATTATTACTGTGCAGCATGGGATTTCGCGACGTGGCCGGCTACT
GAGGTGTTCGGCGGAGGGACCAAGCTGACCGTCCTAGGTCAGCCCAAGGC
TGCCCCCTCGGTCACTCTG

The "S30" or "S30_Sa2_C10_VLCL2 aPDL1 IGLV2-44" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 65, which is encoded by a nucleic acid sequence of SEQ ID NO: 66.

>S30_ Sa2_C10_VLCL2 aPDL1 IGLV2-44-AA
(SEQ ID NO: 65)
*QSVLTQPPSASGTPGQRVTISCSGSSSNIAHKPVNWYQQLPGTAPKLLIY*
*HDNSRPSGVPDRFSGSRSGTSASLAISGLQSEDEADYYCAAWDFSRWPAT*
*EVFGGGTKLTVLGQPKAAPSVTL*FPPSSEELQANKATLVCLISDFYPGAV
TVAWKADSSPVKAGVETTTPSKQSNNKYAASSYLSLTPEQWKSHRSYSCQ
VTHEGSTVEKTVAPTECS

>S30_ Sa2_C10_VLCL2 aPDL1 IGLV2-44-NT
(SEQ ID NO: 66)
CAGTCTGTGCTGACTCAGCCACCCTCAGCGTCTGGGACCCCCGGGCAGAG
GGTCACCATCTCTTGTTCTGGAAGCAGCTCCAACATCGCTCATAAGCCTG
TAAACTGGTACCAGCAGCTCCCAGGAACGGCCCCCAAACTCCTCATCTAT
CATGATAATTCTCGGCCCTCAGGGGTCCCTGACCGATTCTCTGGCTCCAG
GTCTGGCACCTCAGCCTCCCTGGCCATCAGTGGGCTCCAGTCTGAGGATG
AGGCTGATTATTACTGTGCAGCATGGGATTTCAGCCGCTGGCCGGCTACT
GAGGTGTTCGGCGGAGGGACCAAGCTGACCGTCCTAGGTCAGCCCAAGGC
TGCCCCCTCGGTCACTCTGTTCCCGCCCTCCTCTGAGGAGCTTCAAGCCA
ACAAGGCCACACTGGTGTGTCTCATAAGTGACTTCTACCCGGGAGCCGTG
ACAGTGGCTTGGAAAGCAGATAGCAGCCCCGTCAAGGCGGGAGTGGAGAC
CACCACACCCTCCAAACAAAGCAACAACAAGTACGCGGCCAGCAGCTATC
TGAGCCTGACGCCTGAGCAGTGGAAGTCCCACAGAAGCTACAGCTGCCAG
GTCACGCATGAAGGGAGCACCGTGGAGAAGACAGTGGCCCCTACAGAATG
TTCA

The "S30" or "S30_Sa2_C10_VLCL2 aPDL1 IGLV2-44" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 67 which is encoded by a nucleic acid sequence of SEQ ID NO: 68.

>S30_ Sa2_C10_VLCL2 aPDL1 IGLV2-44-AA
(SEQ ID NO: 67)
QSVLTQPPSASGTPGQRVTISCSGSSSNIAHKPVNWYQQLPGTAPKLLI
YHDNSRPSGVPDRFSGSRSGTSASLAISGLQSEDEADYYC
AAWDFSRWPATEVFGGGTKLTVLGQPKAAPSVTL

>S30_ Sa2_C10_VLCL2 aPDL1 IGLV2-44-NT
(SEQ ID NO: 68)
CAGTCTGTGCTGACTCAGCCACCCTCAGCGTCTGGGACCCCCGGGCAGAG
GGTCACCATCTCTTGTTCTGGAAGCAGCTCCAACATCGCTCATAAGCCTG
TAAACTGGTACCAGCAGCTCCCAGGAACGGCCCCCAAACTCCTCATCTAT
CATGATAATTCTCGGCCCTCAGGGGTCCCTGACCGATTCTCTGGCTCCAG
GTCTGGCACCTCAGCCTCCCTGGCCATCAGTGGGCTCCAGTCTGAGGATG
AGGCTGATTATTACTGTGCAGCATGGGATTTCAGCCGCTGGCCGGCTACT
GAGGTGTTCGGCGGAGGGACCAAGCTGACCGTCCTAGGTCAGCCCAAGGC
TGCCCCCTCGGTCACTCTG

The "S94" or "S94_Sa2_G11_VLCL2 aPDL1 IGLV1-44" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 69, which is encoded by a nucleic acid sequence of SEQ ID NO: 70.

>S94_Sa2_G11_VLCL2 aPDL1 IGLV1-44-AA
(SEQ ID NO: 69)
*QSVLTQPPSASGTPGQRVTISCISGSVDIAHKPVNWYQQLPGTAPKLLIY*
*HDTSTPDGVPDRFSGSKSGTSASLAISGLQSEDEADYYCAAWDFATWPAT*
*EVFGGGTKLTVLGQPKAAPSVTL*FPPSSEELQANKATLVCLISDFYPGAV
TVAWKADSSPVKAGVETTTPSKQSNNKYAASSYLSLTPEQWKSHRSYSCQ
VTHEGSTVEKTVAPTECS

>S94_Sa2_G11_VLCL2 aPDL1 IGLV1-44-NT
(SEQ ID NO: 70)
CAGTCTGTGCTGACTCAGCCACCCTCAGCGTCTGGGACCCCCGGGCAGAG
GGTCACCATCTCTTGTATTAGTGGTAGCGTTGATATCGCTCATAAGCCTG
TAAACTGGTACCAGCAGCTCCCAGGAACGGCCCCCAAACTCCTCATCTAT
CATGATACCTCTACTCCTGATGGGGTCCCTGACCGATTCTCTGGCTCCAA
GTCTGGCACCTCAGCCTCCCTGGCCATCAGTGGGCTCCAGTCTGAGGATG
AGGCTGATTATTACTGTGCAGCATGGGATTTCGCGACGTGGCCGGCTACT
GAGGTGTTCGGCGGAGGGACCAAGCTGACCGTCCTAGGTCAGCCCAAGGC
TGCCCCCTCGGTCACTCTGTTCCCGCCCTCCTCTGAGGAGCTTCAAGCCA
ACAAGGCCACACTGGTGTGTCTCATAAGTGACTTCTACCCGGGAGCCGTG
ACAGTGGCTTGGAAAGCAGATAGCAGCCCCGTCAAGGCGGGAGTGGAGAC
CACCACACCCTCCAAACAAAGCAACAACAAGTACGCGGCCAGCAGCTATC
TGAGCCTGACGCCTGAGCAGTGGAAGTCCCACAGAAGCTACAGCTGCCAG

-continued

GTCACGCATGAAGGGAGCACCGTGGAGAAGACAGTGGCCCCTACAGAATG

TTCATAA

The "S94" or "S94_Sa2_G11_VLCL2 aPDL1 IGLV1-44" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 71 which is encoded by a nucleic acid sequence of SEQ ID NO: 72.

>S94_Sa2_G11_VLCL2 aPDL1 IGLV1-44-AA
(SEQ ID NO: 71)
QSVLTQPPSASGTPGQRVTISCISGSVDIAHKPVNWYQQLPGTAPKLLI

YHDTSTPDGVPDRFSGSKSGTSASLAISGLQSEDEADYYC

AAWDFATWPATEVFGGGTKLTVLGQPKAAPSVTL

>S94_Sa2_G11_VLCL2 aPDL1 IGLV1-44-NT
(SEQ ID NO: 72)
CAGTCTGTGCTGACTCAGCCACCCTCAGCGTCTGGGACCCCCGGGCAGAG

GGTCACCATCTCTTGTATTAGTGGTAGCGTTGATATCGCTCATAAGCCTG

TAAACTGGTACCAGCAGCTCCCAGGAACGGCCCCCAAACTCCTCATCTAT

CATGATACCTCTACTCCTGATGGGGTCCCTGACCGATTCTCTGGCTCCAA

GTCTGGCACCTCAGCCTCCCTGGCCATCAGTGGGCTCCAGTCTGAGGATG

AGGCTGATTATTACTGTGCAGCATGGGATTTCGCGACGTGGCCGGCTACT

GAGGTGTTCGGCGGAGGGACCAAGCTGACCGTCCTAGGTCAGCCCAAGGC

TGCCCCCTCGGTCACTCTG

The "S23" or "S23_Sc3_1H4_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 73, which is encoded by a nucleic acid sequence of SEQ ID NO: 74.

>S23_ Sc3_1H4_VLCL2 aPDL1 IGLV2-23-AA
(SEQ ID NO: 73)
*QSALTQPASVSGSPGQSITISCTGTSSDVAKIPLVSWYQQHPGKAPKLMI*

*YFASLRPSGVSNRFSGSKSGNTASLTISGLQAEDEADYYCSSWDNAGDGH*

*VFGGGTKLTVLGQPKAAPSVTL*FPPSSEELQANKATLVCLISDFYPGAVT

VAWKADSSPVKAGVETTTPSKQSNNKYAASSYLSLTPEQWKSHRSYSCQV

THEGSTVEKTVAPTECS

>S23_ Sc3_1H4_VLCL2 aPDL1 IGLV2-23-NT
(SEQ ID NO: 74)
CAGTCTGCCCTGACTCAGCCTGCCTCCGTGTCTGGGTCTCCTGGACAGTC

GATCACCATCTCCTGCACTGGAACCAGCAGTGACGTTGCTAAGATTCCTC

TTGTCTCCTGGTACCAACAGCACCCAGGCAAAGCCCCCAAACTCATGATT

TATTTTGCTAGTCTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATAATGCTGGTGATGGGCAT

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

-continued

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

A

The "S23" or "S23_Sc3_1H4_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 75 which is encoded by a nucleic acid sequence of SEQ ID NO: 76.

>S23_ Sc3_1H4_VLCL2 aPDL1 IGLV2-23-AA
(SEQ ID NO: 75)
QSALTQPASVSGSPGQSITISCTGTSSDVAKIPLVSWYQQHPGKAPKLMI

YFASLRPSGVSNRFSGSKSGNTASLTISGLQAEDEADYYC

SSWDNAGDGHVFGGGTKLTVLGQPKAAPSVTL

>S23_ Sc3_1H4_VLCL2 aPDL1 IGLV2-23-NT
(SEQ ID NO: 76)
CAGTCTGCCCTGACTCAGCCTGCCTCCGTGTCTGGGTCTCCTGGACAGTC

GATCACCATCTCCTGCACTGGAACCAGCAGTGACGTTGCTAAGATTCCTC

TTGTCTCCTGGTACCAACAGCACCCAGGCAAAGCCCCCAAACTCATGATT

TATTTTGCTAGTCTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATAATGCTGGTGATGGGCAT

GTGTTCGGCGGAGGGACCAAGCTGACCGTCCTAGGTCAGCCCAAGGCTGC

CCCCTCGGTCACTCTG

The "S46" or "S46_Sc3_1E4_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 77, which is encoded by a nucleic acid sequence of SEQ ID NO: 78.

>S46_ Sc3_1E4_VLCL2 aPDL1 IGLV2-23-AA
(SEQ ID NO: 77)
*QSALTQPASVSGSPGQSITISCTGTSSDVLRPPLVSWYQQHPGKAPKLMI*

*YFASLRPSGVSNRFSGSKSGNTASLTISGLQAEDEADYYCSSWDNAGDGH*

*VFGGGTKLTVLGQPKAAPSVTL*FPPSSEELQANKATLVCLISDFYPGAVT

VAWKADSSPVKAGVETTTPSKQSNNKYAASSYLSLTPEQWKSHRSYSCQV

THEGSTVEKTVAPTECS

>S46_ Sc3_1E4_VLCL2 aPDL1 IGLV2-23-NT
(SEQ ID NO: 78)
CAGTCTGCCCTGACTCAGCCTGCCTCCGTGTCTGGGTCTCCTGGACAGTC

GATCACCATCTCCTGCACTGGAACCAGCAGTGACGTTCTTAGGCCTCCTC

TTGTCTCCTGGTACCAACAGCACCCAGGCAAAGCCCCCAAACTCATGATT

-continued

TATTTTGCTAGTCTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATAATGCTGGTGATGGGCAT

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

A

The "S46" or "S46_Sc3_1E4_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 79 which is encoded by a nucleic acid sequence of SEQ ID NO: 80.

>S46_ Sc3_1E4_VLCL2 aPDL1 IGLV2-23-AA (SEQ ID NO: 79)

QSALTQPASVSGSPGQSITISCTGTSSDVLRPPLVSWYQQHPGKAPKLM

IYFASLRPSGVSNRFSGSKSGNTASLTISGLQAEDEADYYC

SSWDNAGDGHVFGGGTKLTVLGQPKAAPSVTL

>S46_ Sc3_1E4_VLCL2 aPDL1 IGLV2-23-NT (SEQ ID NO: 80)

CAGTCTGCCCTGACTCAGCCTGCCTCCGTGTCTGGGTCTCCTGGACAGTC

GATCACCATCTCCTGCACTGGAACCAGCAGTGACGTTCTTAGGCCTCCTC

TTGTCTCCTGGTACCAACAGCACCCAGGCAAAGCCCCCAAACTCATGATT

TATTTTGCTAGTCTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATAATGCTGGTGATGGGCAT

GTGTTCGGCGGAGGGACCAAGCTGACCGTCCTAGGTCAGCCCAAGGCTGC

CCCCTCGGTCACTCTG

The "S71" or "S71_Sc3_2C6_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 81, which is encoded by a nucleic acid sequence of SEQ ID NO: 82.

>S71_ Sc3_2C6_VLCL2 aPDL1 IGLV2-23-AA (SEQ ID NO: 81)

*QSALTQPASVSGSPGQSITISCTGTSSDVFRPPLVSWYQQHPGKAPKLMI*

*YFASLRPSGVSNRFSGSKSGNTASLTISGLQAEDEADYYCSSWDQSGDGH*

*VFGGGTKLTVLGQPKAAPSVTL*FPPSSEELQANKATLVCLISDFYPGAVT

VAWKADSSPVKAGVETTTPSKQSNNKYAASSYLSLTPEQWKSHRSYSCQV

THEGSTVEKTVAPTECS

-continued

>S71_ Sc3_2C6_VLCL2 aPDL1 IGLV2-23-NT (SEQ ID NO: 82)

CAGTCTGCCCTGACTCAGCCTGCCTCCGTGTCTGGGTCTCCTGGACAGTC

GATCACCATCTCCTGCACTGGAACCAGCAGTGACGTTTTTAGGCCTCCTC

TTGTCTCCTGGTACCAACAGCACCCAGGCAAAGCCCCCAAACTCATGATT

TATTTTGCTAGTCTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATCAGTCCGGGGACGGCCAT

GTGTTCGGCGGAGGGACCAAGCTGACCGTCCTAGGTCAGCCCAAGGCTGC

CCCCTCGGTCACTCTGTTCCCGCCCTCCTCTGAGGAGCTTCAAGCCAACA

AGGCCACACTGGTGTGTCTCATAAGTGACTTCTACCCGGGAGCCGTGACA

GTGGCTTGGAAAGCAGATAGCAGCCCCGTCAAGGCGGGAGTGGAGACCAC

CACACCCTCCAAACAAAGCAACAACAAGTACGCGGCCAGCAGCTATCTGA

GCCTGACGCCTGAGCAGTGGAAGTCCCACAGAAGCTACAGCTGCCAGGTC

ACGCATGAAGGGAGCACCGTGGAGAAGACAGTGGCCCCTACAGAATGTTC

A

The "S71" or "S71_Sc3_2C6_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 83 which is encoded by a nucleic acid sequence of SEQ ID NO: 84.

>S71_ Sc3_2C6_VLCL2 aPDL1 IGLV2-23-AA (SEQ ID NO: 83)

*QSALTQPASVSGSPGQSITISCTGTSSDVFRPPLVSWYQQHPGKAPKLMI*

*YFASLRPSGVSNRFSGSKSGNTASLTISGLQAEDEADYYC*

*SSWDQSGDGHVFGGGTKLTVLGQPKAAPSVTL*

>S71_ Sc3_2C6_VLCL2 aPDL1 IGLV2-23-NT (SEQ ID NO: 84)

CAGTCTGCCCTGACTCAGCCTGCCTCCGTGTCTGGGTCTCCTGGACAGTC

GATCACCATCTCCTGCACTGGAACCAGCAGTGACGTTTTTAGGCCTCCTC

TTGTCTCCTGGTACCAACAGCACCCAGGCAAAGCCCCCAAACTCATGATT

TATTTTGCTAGTCTTCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATGGGATCAGTCCGGGGACGGCCAT

GTGTTCGGCGGAGGGACCAAGCTGACCGTCCTAGGTCAGCCCAAGGCTGC

CCCCTCGGTCACTCTG

The "S79" or "S79_Sc3_1G7_VLCL2 aPDL1 IGLV2-23" antibody has a heavy chain variable region and heavy chain constant region comprising an amino acid sequence of SEQ ID NO: 4, which is encoded by a nucleic acid sequence of SEQ ID NO: 5, and a lambda light chain comprising an amino acid sequence of SEQ ID NO: 85, which is encoded by a nucleic acid sequence of SEQ ID NO: 86.

>S79_ Sc3_1G7_VLCL2 aPDL1 IGLV2-23-AA
(SEQ ID NO: 85)
*QSALTQPASVSGSPGQSITISCTGTSSDVFRPPLVSWYQQHPGKAPKLMI*
*YFASLRPSGVSNRFSGSKSGNTASLTISGLQAEDEADYYCSSWDHTGDGH*
*VFGGGTKLTVLGQPKAAPSVTL*FPPSSEELQANKATLVCLISDFYPGAVT
VAWKADSSPVKAGVETTTPSKQSNNKYAASSYLSLTPEQWKSHRSYSCQV
THEGSTVEKTVAPTECS

>S79_ Sc3_1G7_VLCL2 aPDL1 IGLV2-23-NT
(SEQ ID NO: 86)
CAGTCTGCCCTGACTCAGCCTGCCTCCGTGTCTGGGTCTCCTGGACAGTC
GATCACCATCTCCTGCACTGGAACCAGCAGTGACGTTTTTAGGCCTCCTC
TTGTCTCCTGGTACCAACAGCACCCAGGCAAAGCCCCCAAACTCATGATT
TATTTTGCTAGTCTTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATGGGATCACACGGGCGATGGGCAT
GTCTTCGGCGGAGGGACCAAGCTGACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCTTGGAAAGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
A

The "S79" or "S79_Sc3_1G7_VLCL2 aPDL1 IGLV2-23" antibody has a heavy chain variable region comprising an amino acid sequence of SEQ ID NO: 6 which is encoded by a nucleic acid sequence of SEQ ID NO: 7 and a lambda light chain variable region comprising an amino acid sequence of SEQ ID NO: 87 which is encoded by a nucleic acid sequence of SEQ ID NO: 88.

>S79_ Sc3_1G7_VLCL2 aPDL1 IGLV2-23-AA
(SEQ ID NO: 87)
QSALTQPASVSGSPGQSITISCTGTSSDVFRPPLVSWYQQHPGKAPKLM
IYFASLRPSGVSNRFSGSKSGNTASLTISGLQAEDEADYYC
SSWDHTGDGHVFGGGTKLTVLGQPKAAPSVTL

>S79_ Sc3_1G7_VLCL2 aPDL1 IGLV2-23-NT
(SEQ ID NO: 88)
CAGTCTGCCCTGACTCAGCCTGCCTCCGTGTCTGGGTCTCCTGGACAGTC
GATCACCATCTCCTGCACTGGAACCAGCAGTGACGTTTTTAGGCCTCCTC
TTGTCTCCTGGTACCAACAGCACCCAGGCAAAGCCCCCAAACTCATGATT
TATTTTGCTAGTCTTCGGCCCTCAGGGGTTTCTAATCGCTTCTCTGGCTC
CAAGTCTGGCAACACGGCCTCCCTGACCATCTCTGGGCTCCAGGCTGAGG
ACGAGGCTGATTATTACTGCAGCTCATGGGATCACACGGGCGATGGGCAT
GTCTTCGGCGGAGGGACCAAGCTGACCGTCCTAGGTCAGCCCAAGGCTGC
CCCCTCGGTCACTCTG

Dummy Light Chains

The Dummy light chain 1 (SEQ ID NO: 242) is encoded by the nucleic acid sequence shown in SEQ ID NO: 243.

>DUMMY-LC1-NT
(SEQ ID NO: 243)
CAGTCTGTGTTGACGCAGCCGCCCTCAGTGTCTGCGGCCCCAGGACAGAA
GGTCACCATCTCCTGCTCTGGAAGCAGCTCCAATATTGAGACTGGTTCTG
TATCCTGGTACCAGCAGCTCCCAGGAACAGCCCCCAAACTCCTCATTTAT
GACAATAATAAGCGACCCTCAGGGATTCCTGACCGATTCTCTGGCTCCAA
GTCTGGCACGTCAGCCACCCTGGGCATCACCGGACTCCAGACTGGGGACG
AGGCCGATTATTACTGCGGAACATGGGATGACAGCCTGCCTGGATGGGTG
TTCGGCGGAGGGACCAAGCTGACCGTCCTAGGTCAGCCCAAGGCTGCCCC
CTCGGTCACTCTGTTCCCGCCCTCCTCTGAGGAGCTTCAAGCCAACAAGG
CCACACTGGTGTGTCTCATAAGTGACTTCTACCCGGGAGCCGTGACAGTG
GCTTGGAAAGCAGATAGCAGCCCCGTCAAGGCGGGAGTGGAGACCACCAC
ACCCTCCAAACAAAGCAACAACAAGTACGCGGCCAGCAGCTATCTGAGCC
TGACGCCTGAGCAGTGGAAGTCCCACAGAAGCTACAGCTGCCAGGTCACG
CATGAAGGGAGCACCGTGGAGAAGACAGTGGCCCCTACAGAATGTTCATA
A

>DUMMY-LC1-AA
(SEQ ID NO: 242)
QSVLTQPPSVSAAPGQKVTISCSGSSSNIETGSVSWYQQLPGTAPKLLIY
DNNKRPSGIPDRFSGSKSGTSATLGITGLQTGDEADYYCGTWDDSLPGWV
FGGGTKLTVLGQPKAAPSVTLFPPSSEELQANKATLVCLISDFYPGAVTV
AWKADSSPVKAGVETTTPSKQSNNKYAASSYLSLTPEQWKSHRSYSCQVT
HEGSTVEKTVAPTECS

The Dummy variable light domain 1 (SEQ ID NO: 206) is encoded by the nucleic acid sequence shown in SEQ ID NO: 205.

>DUMMY-VL1-NT
(SEQ ID NO: 205)
CAGTCTGTGTTGACGCAGCCGCCCTCAGTGTCTGCGGCCCCAGGACAGAA
GGTCACCATCTCCTGCTCTGGAAGCAGCTCCAATATTGAGACTGGTTCTG
TATCCTGGTACCAGCAGCTCCCAGGAACAGCCCCCAAACTCCTCATTTAT
GACAATAATAAGCGACCCTCAGGGATTCCTGACCGATTCTCTGGCTCCAA
GTCTGGCACGTCAGCCACCCTGGGCATCACCGGACTCCAGACTGGGGACG
AGGCCGATTATTACTGCGGAACATGGGATGACAGCCTGCCTGGATGGGTG
TTCGGCGGAGGGACCAAGCTGACCGTCCTA

>DUMMY-VL1-AA
(SEQ ID NO: 206)
QSVLTQPPSVSAAPGQKVTISCSGSSSNIETGSVSWYQQLPGTAPKLLIY
DNNKRPSGIPDRFSGSKSGTSATLGITGLQTGDEADYYCGTWDDSLPGWV
FGGGTKLTVL

The Dummy light chain 2 (SEQ ID NO: 208) is encoded by the nucleic acid sequence shown in SEQ ID NO: 207.

>DUMMY-LC2-NT (SEQ ID NO: 207)

GAAATAGTGATGACGCAGTCTCCAGCCACCCTGTCTGTGTCTCCAGGGGA

AAGAGCCACCCTCTCCTGCAGGGCCAGTCAGACGGTTAAGAATAATTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAACAACTGGTTGCCCATCAACCCCTAT

ACCTTCGGCCAAGGGACCAAGGTGGAAATCAAACGTACGGTGGCTGCACC

ATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGT

CACAGAGCAGGACAGCAAGGACAGCACCTACAGCCTCAGCAGCACCCTGA

CGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGA

GTGTTAA

>DUMMY-LC2-AA (SEQ ID NO: 208)

EIVMTQSPATLSVSPGERATLSCRASQTVKNNLAWYQQKPGQAPRLLIYG

ASTRATGIPARFSGSGSGTEFTLTISSLQSEDFAVYYCQQYNNWLPINPY

TFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

The Dummy variable light domain 2 (SEQ ID NO: 210) is encoded by the nucleic acid sequence shown in SEQ ID NO: 209.

>DUMMY-VL2-NT (SEQ ID NO: 209)

GAAATAGTGATGACGCAGTCTCCAGCCACCCTGTCTGTGTCTCCAGGGGA

AAGAGCCACCCTCTCCTGCAGGGCCAGTCAGACGGTTAAGAATAATTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAACAACTGGTTGCCCATCAACCCCTAT

ACCTTCGGCCAAGGGACCAAGGTGGAAATCAAA

>DUMMY-VL2-AA (SEQ ID NO: 210)

EIVMTQSPATLSVSPGERATLSCRASQTVKNNLAWYQQKPGQAPRLLIYG

ASTRATGIPARFSGSGSGTEFTLTISSLQSEDFAVYYCQQYNNWLPINPY

TFGQGTKVEIK

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library. Antibodies with high affinity such as the antibodies described herein have an affinity of about 0.01 nM-25 nM.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$ and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen binding region" or "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." Various methods are known in the art for numbering the amino acids sequences of antibodies and identification of the complementary determining regions. For example, the Kabat numbering system (See Kabat, E. A., et al., Sequences of Protein of immunological interest, Fifth Edition, US Department of Health and Human Services, US Government Printing Office (1991)) or the IMGT numbering system (See IMGT®, the international ImMunoGeneTics information System®). The IMGT numbering system is routinely used and accepted as a reliable and accurate system in the art to determine amino acid positions in coding sequences, alignment of alleles, and to easily compare sequences in immunoglobulin (IG) and T-cell receptor (TR) from all vertebrate species. The accuracy and the consistency of the IMGT data are based on IMGT-ONTOLOGY, the first, and so far unique, ontology for immunogenetics and immunoinformatics (See Lefranc. M. P. et al., Biomolecules, 2014 December; 4(4), 1102-1139). IMGT tools and databases run against IMGT reference directories built from a large repository of sequences. In the IMGT system the IG V-DOMAIN and IG C-DOMAIN are delimited taking into account the exon delimitation, whenever appropriate. Therefore, the availability of more sequences to the IMGT database, the IMGT exon numbering system can be and "is used" by those skilled in the art reliably to determine amino acid positions in coding sequences and for alignment of alleles. Additionally, correspondences between the IMGT unique numbering with other numberings (i.e., Kabat) are available in the IMGT Scientific chart (See Lefranc. M. P. et al., Biomolecules, 2014 December; 4(4), 1102-1139).

The term "hypervariable region" or "variable region" refers to the amino acid residues of an antibody that are typically responsible for antigen-binding. The hypervariable region generally comprises amino acid residues from a "complementarity determining region" or "CDR" (e.g., around about residues 24-34 (LI), 50-56 (L2) and 89-97 (L3) in the $V_L$, and around about 31-35 (HI), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (LI), 50-56 (L2) and 89-97 (L3) in the $V_L$, and 26-32 (HI), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop" VCDR (e.g., residues 27-38 (LI), 56-65 (L2) and 105-120 (L3) in the $V_L$, and 27-38 (HI), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally, the antibody has symmetrical insertions at one or more of the following points 28, 36 (LI), 63, 74-75 (L2) and 123 (L3) in the $V_L$, and 28, 36 (HI), 63, 74-75 (H2) and 123 (H3) in the $V_H$ when numbered in accordance with AHo; Honneger, A. and Plunkthun, A. J. Mol. Biol. 309:657-670 (2001)).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is the to specifically bind an antigen when the dissociation constant is ≤1 μM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is the to specifically bind to its target, when the equilibrium binding constant ($K_d$) is ≤1 μM, e.g., ≤100 nM, preferably ≤10 nM, and more preferably ≤1 nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Various procedures known within the art may be used for the production of polyclonal or monoclonal antibodies directed against a given target, such as, for example, CD47, a tumor associated antigen or other target, or against derivatives, fragments, analogs homologs or orthologs thereof. (See, for example. Antibodies: A Laboratory Manual, Harlow E, and Lane D, 1988, Cold Spring Harbor Laboratory Press, Cold Spring Harbor, NY, incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia PA, Vol. 14, No. 8 (Apr. 17, 2000), pp. 25-28).

In some embodiments, the antibodies of the invention are monoclonal antibodies. Monoclonal antibodies are generated, for example, by using the procedures set forth in the Examples provided herein. Antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose® (agarose bead), hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', $F(ab')_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icy) infusion using a minipump infusion system, such as a SynchroMed™ Infusion System (implantable infusion pump). A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Bispecific antibodies are antibodies that have binding specificities for at least two different antigens. In the present case, one of the binding specificities is for a target such as CD47 or any fragment thereof. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Bispecific and/or monospecific antibodies of the invention can be made using any of a variety of art-recognized techniques, including those disclosed in co-pending application WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the invention by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof. (See, e.g., Antibodies: A Laboratory Manual, Harlow E, and Lane D, 1988, Cold Spring Harbor Laboratory Press, Cold Spring Harbor, NY, incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies and Cancer Therapy, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies and Cancer Therapy, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of techniques are well-known in the art for producing xenogenic non-human animals. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The methods disclosed in co-pending application WO 2012/023053 overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in co-pending applications WO 2010/135558 and WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the invention. The bispecific antibodies of the invention can be of different Isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the invention. (see for example Strohl, WR Curr Opin Biotechnol 2009 (6):685-91; U.S. Pat. No. 6,528,624; PCT/US2009/0191199 filed Jan. 9, 2009). The methods of the invention can also be used to generate bispecific antibodies and antibody mixtures in a F(ab')2 format that lacks the Fc portion.

The common heavy chain and two different light chains are co-expressed into a single cell to allow for the assembly of a bispecific antibody of the invention. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore, a means to modulate the relative expression of the different polypeptides is used to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Samow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CaptureSelect® Fab Kappa and CaptureSelect® Fab Lambda affinity matrices (BAC BV, Holland). This multi-step affinity chromatography purification approach is efficient and generally applicable to antibodies of the invention. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

Other suitable purification methods include those disclosed in co-pending application PCT/IB2012/003028, filed on Oct. 19, 2012, published as WO2013/088259, the contents of which are hereby incorporated by reference in their entirety.

In other embodiments of producing bispecific antibodies, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating cancer and/or other diseases and disorders associated with aberrant CD47 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985);

Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Methods of Use

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an antibody of the invention, are used to treat or alleviate a symptom associated with a cancer, such as, by way of non-limiting example, leukemias, lymphomas, breast cancer, colon cancer, ovarian cancer, bladder cancer, prostate cancer, glioma, lung & bronchial cancer, colorectal cancer, pancreatic cancer, esophageal cancer, liver cancer, urinary bladder cancer, kidney and renal pelvis cancer, oral cavity & pharynx cancer, uterine corpus cancer, and/or melanoma The present invention also provides methods of treating or alleviating a symptom associated with a cancer. A therapeutic regimen is carried out by identifying a subject, e.g., a human patient suffering from (or at risk of developing) a cancer, using standard methods.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against a target such as CD47, PD-L1, or a combination thereof (or a fragment thereof), may be used in methods known within the art relating to the localization and/or quantitation of these targets, e.g., for use in measuring levels of these targets within appropriate physiological samples, for use in diagnostic methods, for use in imaging the protein, and the like). In a given embodiment, antibodies specific any of these targets, or derivative, fragment, analog or homolog thereof, that contain the antibody derived antigen binding domain, are utilized as pharmacologically active compounds (referred to hereinafter as "Therapeutics").

An antibody of the invention can be used to isolate a particular target using standard techniques, such as immunoaffinity, chromatography or immunoprecipitation. Antibodies of the invention (or a fragment thereof) can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and neutralizes or otherwise inhibits the interaction between CD47 and SIRPα.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a given target (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R Crowther (Ed.) Human Press, Totowa, NJ, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies of the invention (also referred to herein as "active compounds"), and derivatives, fragments, analogs and homologs thereof, can be incorporated into pharmaceutical compositions suitable for administration. Such compositions typically comprise the antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1: Phage Display Selection of PD-L1 or CD47 Fvs Using Human scFv Libraries Containing Fixed Variable Heavy Chain General procedures for construction and handling of human scFv libraries displayed on M13 bacteriophage are described in Vaughan et al., (Nat. Biotech. 1996, 14:309-314), hereby incorporated by reference in its entirety. The libraries for selection and screening encode scFv that all share the same VH domain and are solely diversified in the VL domain. Methods for the generation of fixed VH libraries and their use for the identification and assembly of bispecific antibodies are described in US 2012/0184716 and WO 2012/023053, each of which is hereby incorporated by reference in its entirety. The procedures to identify scFv binding to human PD-L1 are described below.

Protein Selections

Aliquots of scFv phage libraries ($10^{12}$ Pfu) are blocked with PBS containing 3% (w/v) skimmed milk for one hour at room temperature on a rotary mixer. Blocked phage is deselected on streptavidin magnetic beads (Dynabeads™ M-280) for one hour at room temperature on a rotary mixer. For selections against CD47, in some cases, $10^8$ purified red blood cells were added to the beads for deselection. Deselected phage is incubated with 100 nM of biotinylated human PD-L1 or CD47 extracellular domain captured on streptavidin magnetic beads for two hours at room temperature on a rotary mixer. For improving the binding affinity decreasing concentrations of PD-L1 or CD47 are used at each round of selection (from 10 nM to 0.01 nM). Beads are captured using a magnetic stand followed by five washes with PBS/0.1% Tween® 20 (detergent) and two washes with PBS. Phage is eluted with 100 nM TEA for 30 minutes at room temperature on a rotary mixer. Eluted phage and beads are neutralized with Tris-HCl (buffer) 1M pH 7.4 and directly added to 10 ml of exponentially growing TG1 cells and incubated for one hour at 37° C. with slow shaking (90 rpm). An aliquot of the infected TG1 is serial diluted to titer the selection output. The remaining infected TG1 are spun at 3800 rpm for 10 minutes and resuspended in 2 ml 2×TY and spread on 2×TYAG (2×TY medium containing 100 μg/ml ampicillin and 2% glucose) agar Bioassay plates. After overnight incubation at 30° C., 10 ml of 2×TY is added to the plates and the cells are scraped from the surface and transferred to a 50 ml polypropylene tube. 50% glycerol solution is added to the cell suspension to obtain a final concentration of 17% glycerol. Aliquots of the selection rounds are kept at −80° C.

Phage Rescue

50 μl of cell suspension obtained from previous selection rounds are added to 50 ml of 2×TYAG and grown at 37° C. with agitation (240 rpm) until an $OD_{600}$ of 0.3 to 0.5 is reached. The culture is then super-infected with $1.2\times10^{11}$ M13K07 helper phage and incubated for one hour at 37° C. (90 rpm). The medium is changed by centrifuging the cells at 3800 rpm for 10 minutes, removing the medium and resuspending the pellet in 50 ml of 2×TYAK (2×TY medium containing 100 μg/ml ampicillin; 50 μg/ml kanamycin). The culture is then grown overnight at 30° C. (240 rpm). The next day, the phage containing supernatant is used for the next round of selection.

Cell Surface Selections (for PD-L1 Only)

Phage containing supernatants were blocked with PBS containing 3% (w/v) skimmed milk for one hour at room temperature on a rotary mixer. Blocked phages were deselected for one hour on $10^7$ MKN-45 cells that do not express human PD-L1. Deselected phages were incubated with $10^7$ A431 or THP-1 cells pre-incubated for 24 h with IFNγ to boost PD-L1 expression (blocked in PBS 3% BSA, 0.1% $NaN_3$) for two hours at room temperature with gentle shaking. Cells were pelleted and washed six times with PBS. Bound phages were eluted with 76 mM citric acid and shaking for 10 minutes. After neutralization with Tris-HCl (buffer) 1 M pH 8, the eluates with the cells were added directly to 10 ml of exponentially growing TG1 and incubated for one hour at 37° C. with slow shaking. Infected TG1 were spread on a 2×TYAG agar Bioassay plate. After overnight incubation at 30° C., the cells were scraped from the surface with 10 ml 2×TY. 50% glycerol solution was added to the cell suspension to obtain a final concentration of 17% glycerol. Aliquots of the selection rounds were kept at −80° C.

Example 2: Screening for scFv Binding to PD-L1 or CD47 scFv Periplasmic Preparation for Binding and Functional Tests

Individual infected TG1 clones are inoculated into a deep-well 96-well plate containing 0.9 ml per well of 2×TYAG medium (2×TY medium containing 100 μg/ml ampicillin, 0.1% glucose) and grown at 37° C. for 5-6 hours (240 rpm). IPTG 0.2 mM in 2×TY medium was added to give a final concentration of 0.02 mM. The plate is incubated overnight at 30° C. with shaking at 240 rpm. The deep-well plate is centrifuged at 3200 rpm for 10 minutes at 4° C. and the supernatant carefully removed. The pellets are resuspended in 150 μl TES buffer (50 mM Tris-HCl (buffer) (pH 8), 1 mM EDTA (pH 8), 20% sucrose). A hypotonic shock is produced by adding 150 μl of diluted TES buffer (1:5 TES:water dilution) and incubation on ice for 30 minutes. The plate is centrifuged at 4000 rpm for 10 minutes at 4° C. to pellet cells and debris. The supernatants are carefully transferred into a 96-well microtiter plate and kept on ice for immediate testing in functional assays or binding assays.

Binding

Screening of scFv for binding to PD-L1 or CD47 was tested in a homogenous assay using CellInsight™ technology. The following reagents were mixed in each well of a 384 clear bottom well plate (Corning): 30 μl of a streptavidin polystyrene bead suspension (Polysciences; 3000 beads/well) coated with biotinylated PD-L1 or CD47 or a biotinylated irrelevant protein as a control protein; 60 μl of blocked scFv periplasmic preparation; 10 μl of detection buffer (PBS containing human anti-c-myc antibody at 2 μg/ml; anti-human IgG Fc AlexaFluor® 647 diluted 1:500). After shaking at 600 rpm for 5 minutes, the 384-well plate was incubated at room temperature and read after 2 hours on a CellInsight™ CX5 High-Content Screening platform (ThermoFisher Scientific). Clones expressing scFv giving a specific signal on PD-L1 or CD47 and not on the control protein were selected for further analysis or sequencing.

Inhibition of PD-1/PD-L1 Interaction

ScFv targeting PD-L1 were screened for their capacity to inhibit the interaction between PD-1 and PD-L1 in a bead based homogenous assay using the CellInsight™ technology. The following reagents were mixed in each well of a 384 clear bottom well plate (Corning): 30 μl of a streptavidin polystyrene bead suspension (Polysciences; 3000 beads/well) coated with biotinylated PD-L1, 0.1 μg/ml PD-1-huFc (ACROBiosystems), anti-human IgG Fc AlexaFluor® 647 diluted 1:2000 and 50 μl of scFv periplasmic preparation.

After shaking at 600 rpm for 5 minutes, the 384-well plate was incubated at room temperature and read after 2 hours on a CellInsight™ CX5 High-Content Screening platform (ThermoFisher Scientific). Control wells containing an irrelevant scFv not binding to PD-L1 were included in each plate so that clones expressing scFv leading to a reduction of the PD-1/PD-L1 signal measured in controls were selected for further analysis or sequencing.

Inhibition of CD47/SIRPa Interaction

ScFv targeting CD47 were screened for their capacity to inhibit the interaction between SIRPa and CD47 in a bead based homogenous assay using FMAT® technology. Protein A coated polystyrene beads (Spherotech) were incubated with 5 μg/ml of goat anti-human IgG (Fcγ specific) (Jackson ImmunoResearch). After washing the beads, 5 μg/mL SIRPa-Fc (R&D Systems) was added and captured at the bead surface for one hour. The beads were blocked with PBS, 2% BSA and 30 μl/well were transferred in a 384-well optical plate (Costar)(3000 beads/well). In a separate 96-well plate, 120 μl of scFv periplasmic preparation were mixed with 24 μl of biotinylated CD47 (300 ng/ml) and incubated at room temperature. After 50 minutes incubation, 24 μl/well of Streptavidin Cy5 (1 μg/ml; Invitrogen) were added to the 96-well plate and 70 μl/well of this final mix were transferred to the 384-well plate containing the blocked beads. After 3 hours incubation at room temperature, the plate was read on an FMAT® 8200 Cellular Detection System (Applied Biosystems). Control wells containing an irrelevant scFv not binding to CD47 were used as references to identify the clones expressing scFv reducing the CD47 binding signal. These clones were selected for further analysis.

Example 3: Expression and Purification of Bispecific Antibodies Carrying a Lambda and a Kappa Light Chain The simultaneous expression of one heavy chain and two light chains in the same cell can lead to the assembly of three different antibodies. Simultaneous expression can be achieved in different ways such as the transfection of multiple vectors expressing one of the chains to be co-expressed or by using vectors that drive multiple gene expression. A vector pNovi κHλ was previously generated to allow for the co-expression of one heavy chain, one kappa light chain and one lambda light chain as described in US 2012/0184716 and WO 2012/023053, each of which is hereby incorporated by reference in its entirety. The expression of the three genes is driven by human cytomegalovirus promoters (hCMV), and the vector also contains a glutamine synthetase gene (GS) that enables the selection and establishment of stable cell lines. The VL genes of the anti-hPD-L1 IgGλ or the anti-hCD47 IgGκ were cloned in the vector pNovi κHκ, for transient expression in mammalian cells. Expi293™ cells (Gibco) were amplified and split in Erlenmeyer flask at a concentration of $3\times10^6$ cells per mL in 50 mL of Expi293™ culture medium (Gibco). 62.5 μg of plasmid DNA were transfected into the cells using polyethylenimine transfection reagent (PEI, Polyscience) according to manufacturer's instructions. IgG concentration in supernatant of transfected cells was measured during the production using the Bio-Layer Interferometry (BLI) technology. An Octet® RED96 (biomolecule detection) instrument and Protein A biosensors were used for quantitation (Sartorius). Biosensors were pre-conditioned and regenerated using 10 mM glycine pH 1.7 and IgG calibrators diluted in conditioned cell medium were prepared for standard curve generation. Concentrations were determined using the dose response 5PL unweighted Y standard curve equation and an initial slope binding rate equation. According to antibody concentration, supernatants were harvested 7 to 10 days after transfection and clarified by filtration after addition of diatomaceous earth (Sartorius). The purification process was composed of three steps using affinity resins from Thermo Fisher Scientific. First, the CaptureSelect® FcXL resin was washed with PBS and then added to the clarified supernatant. After incubation overnight at +4° C. and 15 rpm, supernatants were centrifuged at 600 g for 10 min, flow through was stored until the end of the purification process and resin washed twice with PBS. Then, the resin was transferred on Amicon® Pro (protein purification) columns (Merck Millipore) and a solution containing 50 mM glycine at pH 3 was used for elution. Several elution fractions were generated, neutralized with 1/10 Tris HCl (buffer) pH7.5 (Invitrogen) and pooled. The purified product, containing total human IgGs, was quantified using a Nanodrop® spectrophotometer (NanoDrop® Technologies). A small aliquot was stored for further analysis and the remaining sample incubated for 30 min at RT and 15 rpm with the appropriate volume of CaptureSelect® Kappa XL affinity matrix. Incubation, resin recovery, elution and neutralization steps were performed as described previously. The last affinity purification step was performed using the CaptureSelect® LC-lambda (Hu) affinity matrix applying the same process as for the two previous purifications. The pool of elution fractions was desalted against 25 mM histidine/125 mM NaCl pH6.0 using 50 kDa Amicon® (protein purification) centrifugal units (Merck Millipore). Purified κλ bodies were quantified using the Nanodrop® (spectrophotometer) and analyzed by capillary electrophoresis in denaturing and reducing conditions using the Agilent 2100 Bioanalyzer and Protein 80 kit as described by the manufacturer (Agilent Technologies). An aliquot from the first purification step (containing the bispecific antibody and both monospecific mAbs) and an aliquot of the final product (containing the purified KX body) were loaded on an IsoElectric Focusing (IEF) gel to evaluate the purity of the final purified bispecific antibody (absence of mAb contamination). The aggregate level was determined by SEC-HPLC. Finally, all samples were tested for endotoxin contamination using the Limulus Amebocyte Lysate test (LAL; Charles River Laboratories).

Example 4: Characterization of CD47×PD-L1 Bispecific Antibodies

The CD47×PD-L1 bispecific antibodies (bsAbs) were generated by pairing various CD47 and PD-L1 arms that were described in the previous sections. All the bsAbs were reformatted with a human IgG4 Fc domain.

A. Binding to Recombinant Human PD-L1 Protein and Cross-Reactivity

Figure 1B:
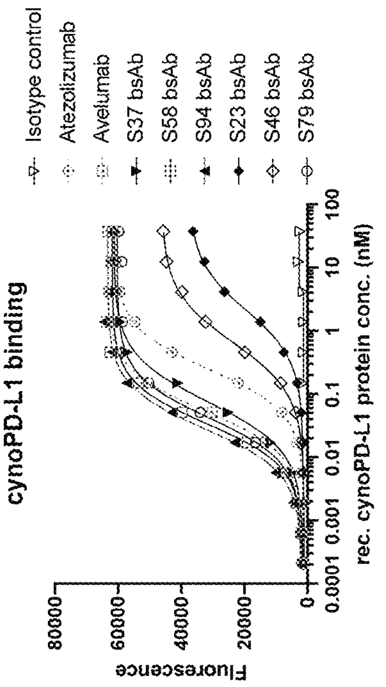
Figure 1C:
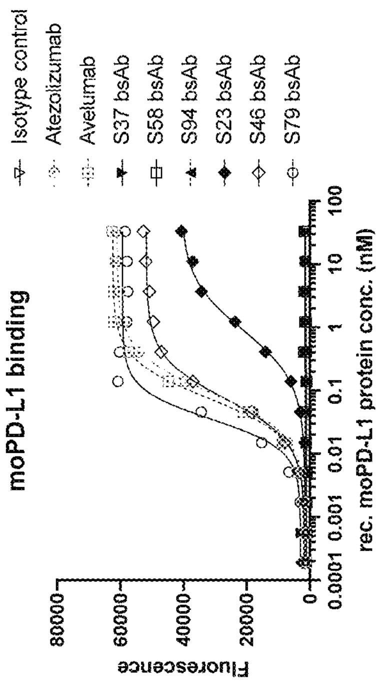

The ability of selected CD47×PD-L1 bsAbs to bind recombinant human PD-L1 (ACROBiosystems), cynomolgus monkey PD-L1 (Sino Biological) and mouse PD-L1 (in-house production) soluble proteins was assessed by a sandwich ELISA assay. Briefly, a goat anti-human Fc capture antibody (Jackson ImmunoResearch), diluted in PBS at 5 μg/ml, was coated O/N at 4° C. in a MaxiSorp™ (hydrophilic surface treatment) 96-well black plate (Nunc). The plate was blocked with blocking reagent (PBS Buffer/BSA 3%/Tween® (detergent) 0.05%) for one hour at room temperature. After 3 washes with PBS Buffer-Tween® (detergent) 0.05%, a fixed concentration of the bsAbs was added and incubated for one hour at room temperature, and 3 more washes were performed. After washing, increasing concentrations of biotinylated human, cynomolgus or mouse recombinant PD-L1 proteins were added and incubated for one hour at room temperature. Finally, after one hour incubation with Streptavidin-HRP, Amplex red detection reagent was added and incubated at room temperature for 20 minutes in the dark and the fluorescence signal was detected using a plate reader. FIG. 1A shows various monovalent binding to human PD-L1 of selected bsAbs as compared to anti-PD-L1 benchmarks atezolizumab and avelumab. FIG. 1B highlights that all the PD-L1 arms tested are cross-reactive to cynomolgus PD-L1 while FIG. 1C shows that only some PD-L1 arms are cross-reactive with mouse PD-L1 (S23, S46 and S79).

B. PD-L1 Specificity

Figure 1D:
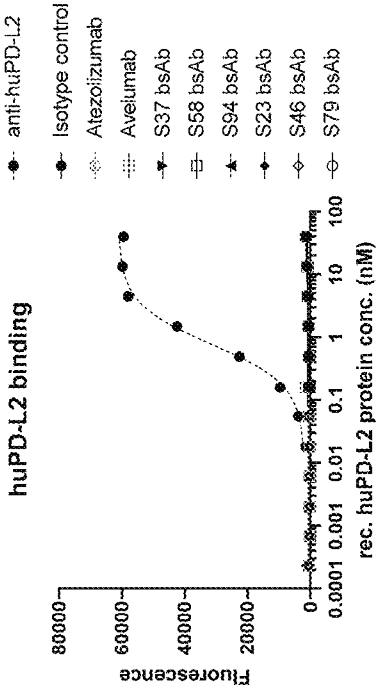

The specificity of exemplary CD47×PD-L1 bsAbs to PD-L1 was determined by evaluating their absence of binding to human PD-L2 by ELISA. Human PD-L2 has 34% of sequence identity with human PD-L1. The ability of the bsAbs to bind recombinant human PD-L2 soluble protein (ACROBiosystems) was assessed by a sandwich ELISA assay. Briefly, a goat anti-mouse Fc capture antibody (Jackson ImmunoResearch), diluted in PBS at 5 μg/ml, was coated O/N at 4° C. in a MaxiSorp™ (hydrophilic surface treatment) 96-well black plate (Nunc). The plate was blocked with blocking reagent (PBS Buffer/BSA 3%/Tween® (detergent) 0.05%) for one hour at room temperature. After 3 washes with PBS Buffer-Tween® (detergent) 0.05%, a fixed concentration of the bsAbs was added and incubated for one hour at room temperature. After washing, increasing concentrations of biotinylated human recombinant PD-L2 protein were added and incubated for one hour at room temperature. Finally, after one hour incubation with Streptavidin-HRP, Amplex red detection reagent was added and incubated at room temperature for 20 minutes in the dark and the fluorescence signal was detected using a plate reader. An isotype control antibody was used as a negative control, and a commercially available mouse anti-human PD-L2 IgG (R&D system) served as a positive control. As shown in FIG. 1D, none of the CD47×PD-L1 bsAbs tested cross-react with human PD-L2.

C. PD-1/PD-L1 Blocking Activity on PD-L1 Transfected CHO Cells

Figure 1E:
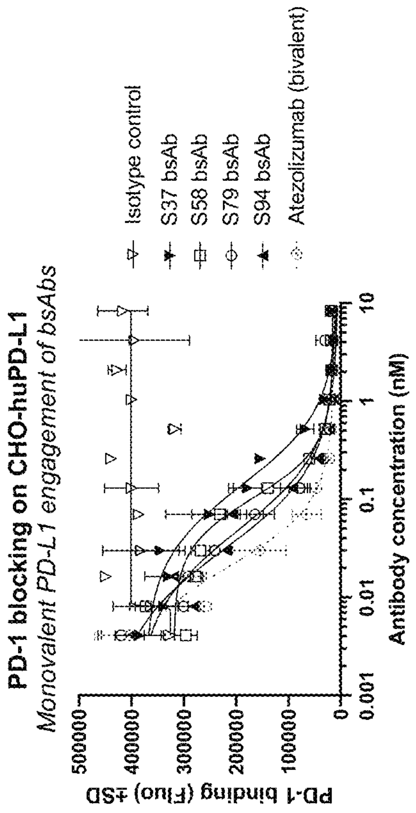

The PD-1 blocking activity of the CD47×PD-L1 bsAbs was evaluated in the PD-1/PD-L1 competitive binding cell-based assay. Human PD-L1-transfected CHO cells (negative for human CD47), pre-stained with Cell Trace Violet (Invitrogen), were incubated with various concentrations of bsAbs for 1 hour at room temperature. As detection reagent, a mix of a human PD-1-moFc protein (ACROBiosystem, final concentration 100 ng/ml) and an anti-mouse Fc AF647 (Jackson ImmunoResearch) were added for 3 hours at room temperature. Finally, the plate was read using the CellInsight™ CX5 High Content Screening Platform. FIG. 1E shows that the selected bsAbs block monovalently (i.e. without CD47 co-engagement) the interaction between PD-1 and PD-L1 with various potencies (Table 4). The bivalent anti-PD-L1 atezolizumab was used as a reference.

TABLE 4

PD-1 blocking potency of selected CD47xPD-L1 bispecific antibodies and anti-PD-L1 atezolizumab on human PD-L1 transfected CHO cells

| Antibody name | PD-1 inhibition potency (IC50 in nM) |
|---|---|
| Atezolizumab (bivalent anti-PD-L1) | 0.02 |
| S37 bsAb | 0.14 |
| S58 bsAb | 0.10 |
| S79 bsAb | 0.03 |
| S94 bsAb | 0.05 |

D. Binding to Recombinant CD47

Figure 2A:
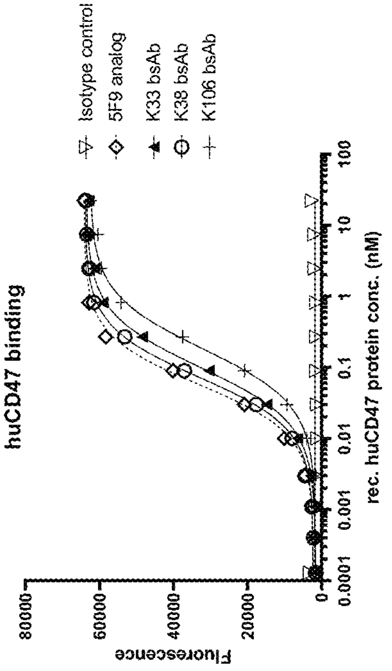
FIGS. 2A-2C shows a series of graphs depicting binding of exemplary CD47×PD-L1 bispecific antibodies of the invention to CD47 isolated from various species.
Figure 2B:
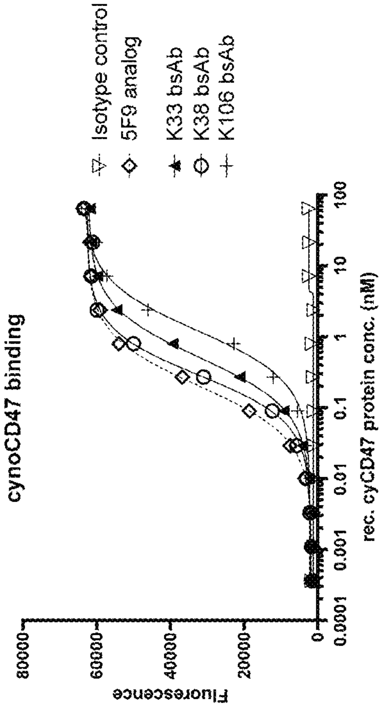
Figure 2C:
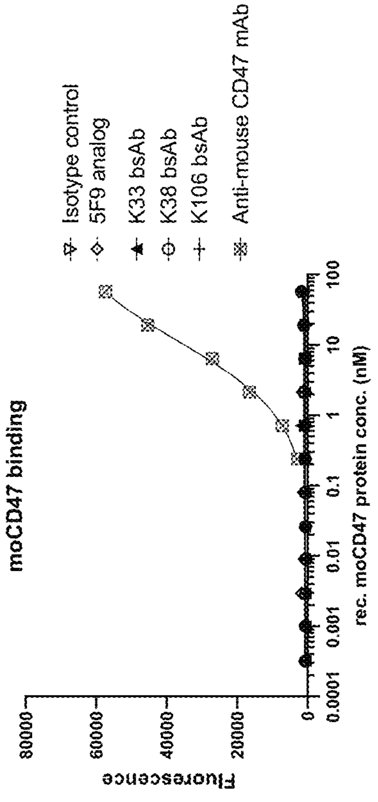

The ability of exemplary CD47×PD-L1 bsAbs to bind recombinant human CD47 (in-house), cynomolgus monkey CD47 (Sino Biological) and mouse CD47 (ACROBiosystems) soluble proteins was assessed by a sandwich ELISA assay. A goat anti-human Fc capture antibody (Jackson ImmunoResearch), diluted in PBS at 5 μg/ml, was coated O/N at 4° C. in a MaxiSorp™ (hydrophilic surface treatment) 96-well black plate (Nunc). The plate was blocked with blocking reagent (PBS Buffer/BSA 3%/Tween® (detergent) 0.05%) for 1 hour at room temperature. After 3 washes with PBS Buffer-Tween® (detergent) 0.05%, a fixed concentration of the bsAbs was added and incubated for 1 hour at room temperature. After washing, increasing concentrations of biotinylated human, cynomolgus or mouse recombinant CD47 proteins were added and incubated for 1 hour at room temperature. Finally, after 1 hour incubation with Streptavidin-HRP, Amplex red detection reagent was added and incubated at room temperature for 20 minutes in the dark and the fluorescence signal was detected using a plate reader. FIG. 2A shows monovalent binding to human CD47 of selected CD47×PD-L1 bsAbs as compared to the anti-CD47 mAb 5F9 analog. FIG. 2B demonstrates that all the bsAbs tested are cross-reactive to cynomolgus CD47 while none of them are cross-reactive to mouse CD47, as depicted in FIG. 2C.

E. Binding to CD47-Positive Tumor Cells

The CD47 binding on cells of selected CD47×PD-L1 bsAbs was studied by flow cytometry using human Raji (ATCC; CCL-86) and Nalm-6 (ATCC; CRL-3273) tumor cell lines and CHO cells as a negative control. Both Raji and Nalm-6 cell lines express very low levels or do not express PD-L1 (Table 5) allowing the evaluation of monovalent CD47 binding of the bsAbs.

Antibodies were incubated for 15 minutes at 4° C. at various concentrations with the cells previously resuspended in PBS/BSA 2%. After two washes, bound Abs were detected using a AF647 conjugated anti-human Fc F(ab')2 (Jackson ImmunoResearch). After incubation for 15 minutes at 4° C., followed by 2 washing steps, cells were analyzed by flow cytometry.

TABLE 5

Target density of PD-L1 and CD47 at the cell surface of Raji and Nalm-6 human tumor cell lines

| Cell line | Origin | PD-L1 binding sites | CD47 binding sites |
|---|---|---|---|
| Raji | Burkitt's lymphoma | 700 | 44'000 |
| Nalm-6 | Acute lymphoblastic leukemia | <100 | 53'000 |

Figure 2D:
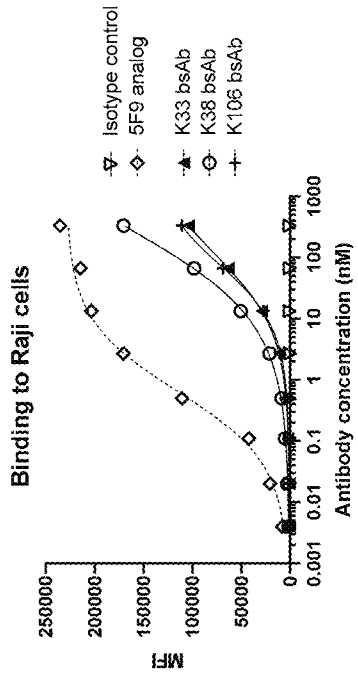
FIGS. 2D-2F shows a series of graphs depicting binding of exemplary CD47×PD-L1 bispecific antibodies to human $CD47^+PD\text{-}L1^-$ tumor cell lines.
Figure 2E:
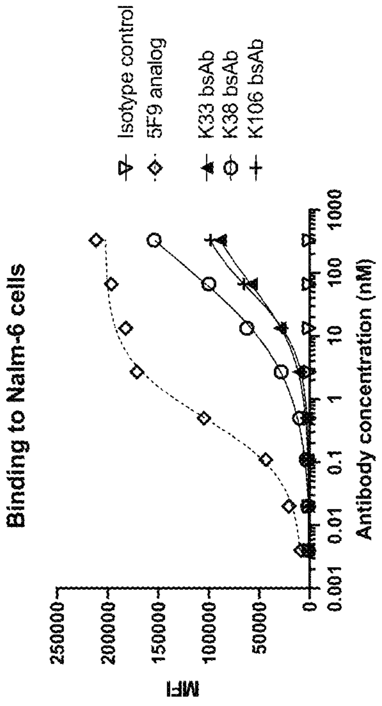

FIGS. 2D and 2E show various binding profile of the CD47 arms of selected CD47×PD-L1 bsAbs and bivalent anti-CD47 5F9 analog on Raji and Nalm-6 tumor cells, respectively. The different binding profiles are consistent between both tumor cell lines. The K38, K33 and K106 arms show significantly lower binding as compared to 5F9 analog. No binding of any of the molecules tested was observed on CHO cells (data not shown).

F. CD47/SIRPa Blocking Activity on CD47-Positive Tumor Cells

The SIRPa blocking activity of the CD47×PD-L1 bsAbs was determined in the CD47/SIRPa cell-based competitive binding assay. PD-L1$^{-}$CD47$^{+}$ Nalm-6 tumor cells (Table 5), pre-stained with Cell Trace Violet (Invitrogen), were incubated with various concentrations of bsAbs and controls for 1 hour at room temperature. As detection reagent, a mix of human SIRPa-mouse Fc protein (in-house) and anti-mouse Fc AF647 (Jackson ImmunoResearch) was added for 3 hours at room temperature. Finally, the plate was read using the CellInsight™ CX5 High Content Screening Platform.

Figure 2F:
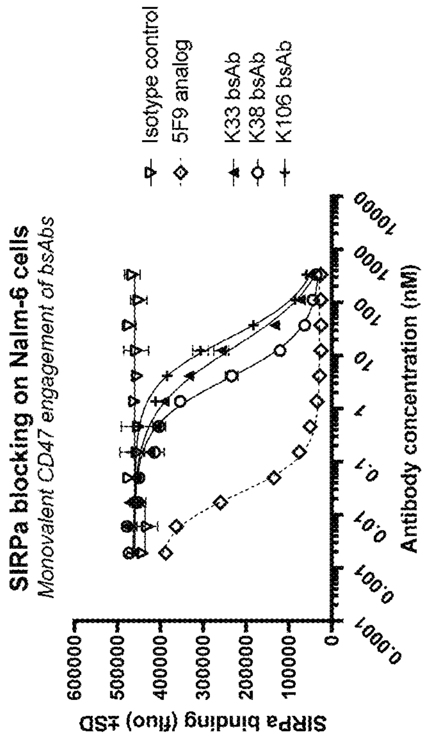

Following monovalent engagement of CD47, the tested bsAbs block the interaction between CD47 and SIRPa with various potencies (Table 6), consistent with their binding properties (FIG. 2F).

TABLE 6

SIRPa blocking potency of selected CD47xPD-L1 bispecific antibodies and benchmark molecules on human PD-L1$^{-}$CD47$^{+}$ Nalm-6 tumor cells

| Antibody name | SIRPα inhibition potency (IC50 in nM) |
|---|---|
| 5F9 mAb analog | 0.025 |
| K33 bsAb | 14.10 |
| K38 bsAb | 3.67 |
| K106 bsAb | 21.2 |

G. Binding to Human Red Blood Cells (RBC)

Human RBC express CD47 target at their cell surface, but not PD-L1, and represent a significant antigen sink for CD47-targeting antibodies, impacting on their safety and pharmacokinetic properties. Therefore, the binding of selected CD47×PD-L1 bsAbs was assessed on human RBC by flow cytometry and compared to the anti-CD47 5F9 analog used as a clinical benchmark molecule.

RBC were isolated from whole blood of healthy donors, resuspended in PBS/BSA 2%, and incubated with antibodies at various concentrations for 15 minutes at 4° C. After two washes, bound bsAbs were detected using an AF647 conjugated anti-human Fc F(ab')2 (Jackson ImmunoResearch). After 15 minutes incubation at 4° C. and 2 washing steps, cells were analyzed by flow cytometry.

Figure 3:
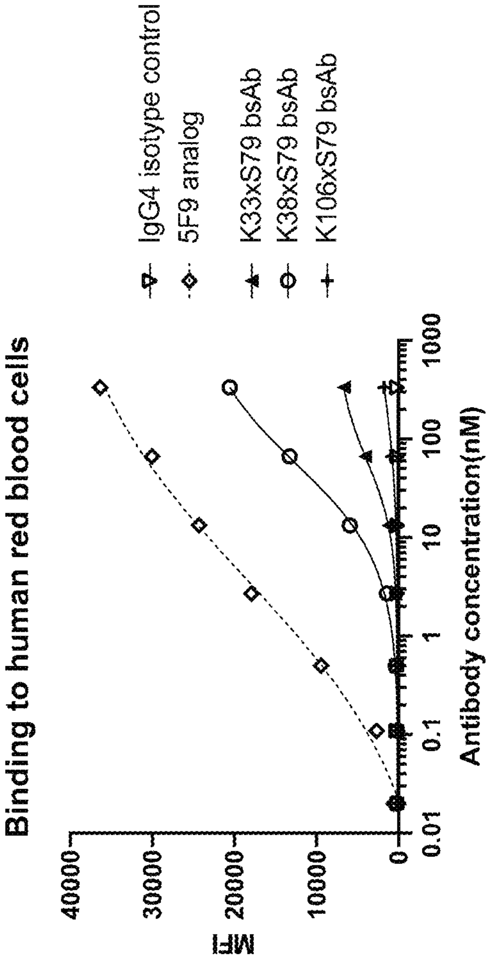
FIG. 3 shows a graph depicting binding of exemplary CD47×PD-L1 bispecific antibodies to human red blood cells isolated from whole blood of healthy donors assessed by flow cytometry. hIgG4 isotype antibody and anti-CD47 5F9 analog controls were tested for comparison.

FIG. 3 shows representative binding profiles of selected CD47×PD-L1 bsAbs and benchmark molecules to human red blood cells. The 3 bsAbs tested, K33×S79, K38×S79 and K106×S79 demonstrate significantly lower binding to RBC as compared to the anti-CD47 mAb 5F9 analog.

H. Binding Affinity of Exemplary Bispecific Antibodies to PD-L1 and CD47 Proteins The affinity of selected CD47×PD-L1 bsAbs to PD-L1 and CD47 recombinant proteins was determined at 30° C. using the Bio-Layer Interferometry technology. An Octet® RED96 (biomolecule detection) instrument was used.

For PD-L1 affinity measurements, after hydration and a baseline step in kinetic buffer (Sartorius, #18-1105; PBS, 0.02% Tween® 20 (detergent), 0.1% BSA, 0.05% sodium azide), streptavidin biosensors (Sartorius, #18-5019) were loaded for 5 min with the biotinylated human, cynomolgus or mouse PD-L1 recombinant protein at 1 μg/mL (Acrobiosystems, #PD1-H82E5, #PD1-C52H4 and #PD1-M5220 respectively) in kinetic buffer. Then, biosensors were dipped into a serial dilution of bsAbs starting from 28.6 nM with a 2-fold dilution factor. The association and the dissociation steps were monitored for 600 secs and 900 secs, respectively. The affinity was measured applying a 1:1 global fitting model on double referenced curves, on the full association and dissociation steps.

For CD47 affinity measurements, after hydration and baseline steps, HIS1K biosensors (Sartorius, #18-5120) were loaded for 5 min with His-tag human CD47 recombinant protein at 2.5 μg/mL (Acrobiosystems, #CD7-H82E9) in kinetic buffer. Then, biosensors were dipped into a serial dilution of bsAbs starting from 200 nM with a 2-fold dilution factor. The association and the dissociation steps were monitored for 120 secs and 300 secs, respectively. The affinity was measured applying a 1:1 global fitting model on double referenced curves, on the full association step and on the first phase of the dissociation step (first 30 secs for K33×S79 and first 100 secs for K38×S79) and on the full dissociation phase for K106×S79, depending on the heterogeneity of the dissociation profile.

The affinity results are shown in Table 7.

TABLE 7

Binding Affinity of selected bsAbs to recombinant PD-L1 and CD47 soluble proteins

| CD47xPD-L1 bsAb | Human PD-L1 $K_D$ (nM) | Cyno PD-L1 $K_D$ (nM) | Mouse PD-L1 $K_D$ (nM) | Human CD47 $K_D$ (nM) | Cyno CD47 $K_D$ (nM) |
|---|---|---|---|---|---|
| K33xS79 | 0.5 ± 0.3 | 1.35 ± 0.02 | 0.52 ± 0.01 | 56 ± 3 | ND |
| K38xS79 | | | | 13.6 ± 3 | 16 ± 0.4 |
| K106xS79 | | | | 99 ± 3 | ND |

ND: not determined

I. Binding to CD47/PD-L1-Positive Tumor Cells

The binding of selected CD47×PD-L1 bsAbs to PD-L1$^{+}$ CD47$^{+}$ human tumor cells was studied by flow cytometry using the HT-1080 tumor cell line (ATCC; CCL-121) pre-activated with IFNg (Table 8). CHO cell line was used as a negative cell line.

Antibodies were incubated at various concentrations with the tumor cells, previously resuspended in PBS/BSA 2%, for 15 minutes at 4° C. After two washes, bound Abs were detected using a AF647 conjugated anti-human Fc F(ab')2 (Jackson ImmunoResearch). After incubation for 15 minutes at 4° C., followed by 2 washing steps, cells were analyzed by flow cytometry.

TABLE 8

Target density of PD-L1 and CD47 at the cell surface of HT-1080 tumor cells after IFNg induction for 24 h

| Cell line | Origin | PD-L1 binding sites | CD47 binding sites | Ratio CD47:PD-L1 |
|---|---|---|---|---|
| HT-1080 | Fibrosarcoma | 55'950 | 159'800 | 2.85 |

Figure 4A:
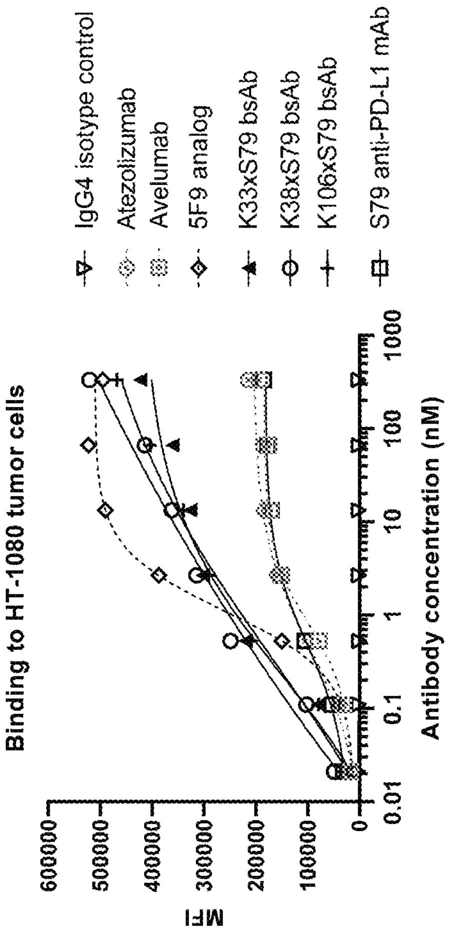
FIGS. 4A-4B shows a series of graphs depicting binding of exemplary CD47×PD-L1 bispecific antibodies of the invention to HT-1080 tumor cells evaluated by flow cytometry.
Figure 4B:
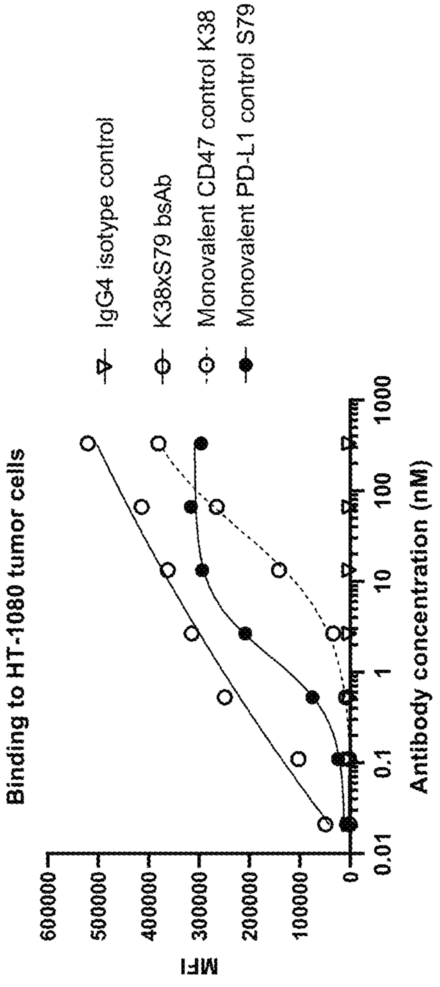

FIG. 4A shows the binding profile of the exemplary CD47×PD-L1 bsAbs as compared to the anti-CD47 5F9 analog and anti-PD-L1 mAbs atezolizumab and S79. FIG. 4B shows the binding of the bsAb K38S79 as compared to the CD47 and PD-L1 monovalent controls, highlighting the contribution of the co-engagement of both target in the binding of the molecule. No binding of any of the molecules tested was observed on CHO cells (data not shown).

J. CD47/SIRPa and PD-1/PD-L1 Blocking Activity on CD47 and PD-L1 Positive Tumor Cells The SIRPa and PD-1 blocking activity of the CD47×PD-L1 bsAbs was assessed in the CD47/SIRPa and PD-1/PD-L1 cell-based competitive binding assay, as compared to various controls. Briefly, PD-L1$^+$CD47$^+$ HT-1080 tumor cells induced with IFNg for 24 h (Table 8), and stained with Cell Trace Violet (Invitrogen), were incubated with various concentrations of antibodies for 1 hour at room temperature. As detection reagent, a mix of human SIRPa-mouse Fc protein (in-house) or human PD-1-moFc protein (ACROBiosystem) and anti-mouse Fc AF647 (Jackson ImmunoResearch) was added for 3 hours at room temperature. Finally, the plate was read using the CellInsight™ CX5 High Content Screening Platform.

Figure 5A:
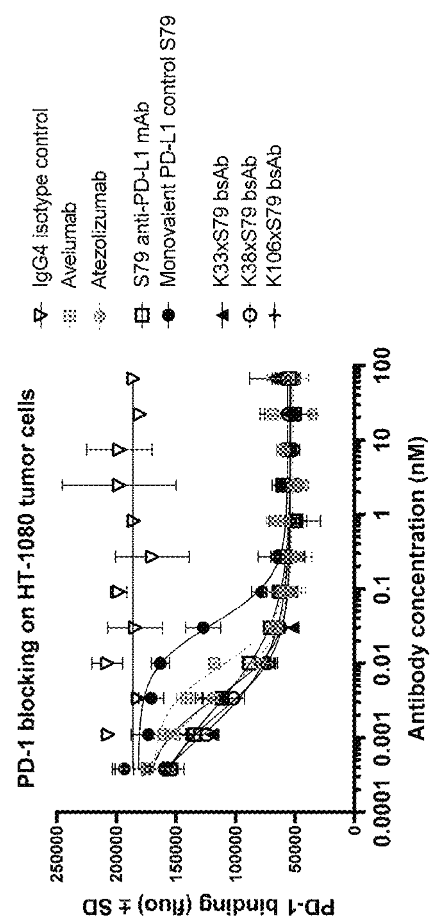
FIGS. 5A-5B shows a series of graphs depicting blocking activity of exemplary CD47×PD-L1 bispecific antibodies in human $CD47^+/PD\text{-}L1^+$ HT-1080 tumor cells.

As depicted in FIG. 5A and Table 9, the selected bsAbs have similar PD-1 blocking properties as compared to the S79 anti-PD-L1 mAb and atezolizumab and improved blockade as compared to avelumab anti-PD-L1 benchmark. Independently of the affinity of the CD47 arm, the co-engagement of CD47 by the bsAbs significantly contributes to PD-1 blockade, as demonstrated by the improved activity of bsAbs over the monovalent PD-L1 control S79.

Figure 5B:
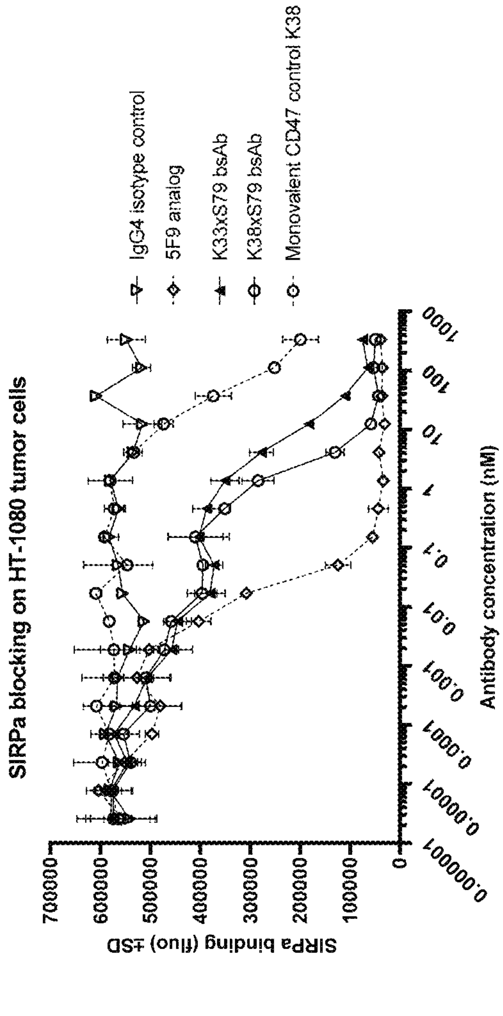

On the other hand, K33×S79 and K38×S79 bsAbs induce strong SIRPa blocking activity as shown in FIG. 5B. As demonstrated by the improved activity of K38×S79 bsAb over its monovalent CD47 control K38, the co-engagement of PD-L1 highly contributes to SIRPa blockade.

TABLE 9

SIRPa and PD-1blocking potency of selected CD47xPD-L1 bispecific antibodies and benchmark molecules on human PD-L1$^+$CD47$^+$ HT-1080 tumor cells

| Antibody name | SIRPa inhibition potency (IC50 in nM) | PD-1 inhibition potency (IC50 in pM) |
|---|---|---|
| Atezolizumab | N/A | 2.96 |
| Avelumab | N/A | 9.11 |
| 5F9 mAb analog | 0.016 | N/A |
| K33xS79 bsAb | ND | 2.19 |
| K38xS79 bsAb | ND | 0.83 |
| Monovalent K38 | 35.99 | N/A |
| K106xS79 bsAb | Not tested | 3.51 |
| Monovalent S79 | N/A | 33.87 |
| S79 mAb | N/A | 2.52 |

N/A: not applicable

ND: not determined due to the presence of a biphasic curve that did not allow determination of IC50

Example 5: Antibody Dependent Cellular Phagocytosis (ADCP) of CD47-Positive Tumor Cells Mediated by CD47×PD-L1 Bispecific Antibodies The in vitro phagocytic activity induced by the CD47 arm of selected CD47×PD-L1 bsAbs was assessed using the Nalm-6 tumor cell line (Table 5). The assay relies on an imaging-based method, which makes use of the CellInsight™ CX5 High Content Screening Platform. The phagocytosis index obtained is defined as the average number of target cells engulfed by 100 macrophages.

A. Preparation of the Macrophages:

Human peripheral blood mononuclear cells (PBMCs) are isolated from buffy coats of healthy donors by Ficoll gradient. Macrophages are generated by culturing PBMCs for 7 to 9 days in complete medium (RPMI 1640, 10% heat-inactivated fetal calf serum, Invitrogen), 2 mM L-glutamine, 1 mM sodium pyruvate, 10 mM HEPES buffer, 25 mg/mL gentamicin (all from Sigma-Aldrich), and 50 mM 2-mercaptoethanol (Thermo Fisher Scientific) in the presence of 20 ng/mL of human macrophage colony-stimulating factor (M-CSF) (PeproTech). Non-adherent cells are subsequently eliminated in the differentiation phase (day+1) by exchanging the cell culture medium, and adherent cells representing macrophages are detached using cell dissociation buffer at day 6 and seeded at 30,000 per well in 96-well optical plate (Costar).

B. Assessment of the Phagocytosis Activity of CD47×PD-L1 bsAbs as Single Agents

Macrophages (stained with calcein red orange) adhering to microplate wells are co-incubated with Calcein AM-labeled target Nalm-6 tumor cells at an effector:target cell ratio of 1:3 for 2.5 hours at 37° C. in the presence of different concentrations of the tested antibodies. At the end of the incubation period, supernatants are replaced by complete culture medium and the microplates are imaged with the CellInsight™ CX5 High Content Screening Platform. 1500 macrophages are acquired and analyzed per well. Phagocytosis is evidenced as double-positive events (macrophage+ tumor cell that are inside macrophages) and the phagocytosis indexes are calculated by the CellInsight™ manufacturer's software.

Figure 6A:
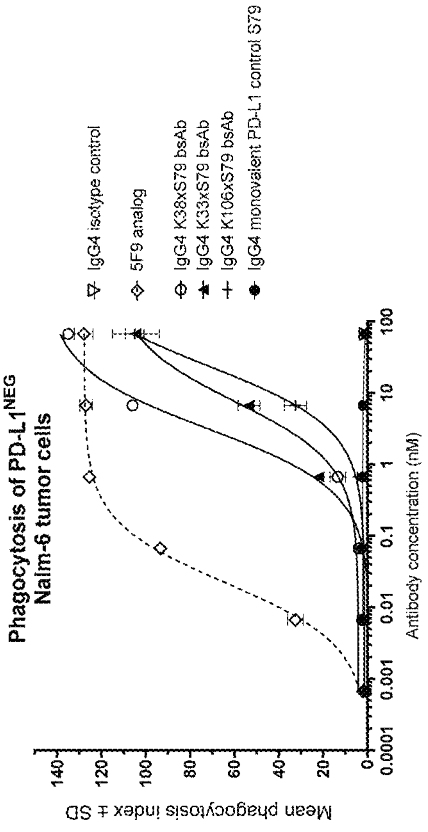
FIGS. 6A-6B shows a series of graphs depicting antibody-dependent cellular phagocytosis (ADCP) of human CD47⁺ PD-L1⁻ Nalm-6 tumor cells by human monocyte-derived macrophages induced or enhanced by exemplary CD47×PD-L1 bispecific antibodies (K33×S79, K38×S79 and/or K106×S79) as single agents and without human IgG (FIG. 6A) or in combination with an IgG1 anti-CD19 mAb in presence of 1 mg/ml of human IgG (FIG. 6B).

FIG. 6A shows representative phagocytic activity of the bsAbs (Donor D #097), as compared to IgG4 anti-CD47 5F9 analog. Overall, the bsAbs induce phagocytosis of Nalm-6 cells in a dose-dependent manner, with potencies correlated to their affinities to CD47 (Table 10).

TABLE 10 in vitro phagocytosis potencies of CD47xPD-L1 bispecific antibodies and benchmark molecules assessed by using the Nalm-6 human cancer cells as target cells, with 4 different macrophage donors (D).

| Macrophage donor | 5F9 analog | K33xS79 bsAb | K38xS79 bsAb | K106xS79 bsAb |
|---|---|---|---|---|
| D#103 | 0.02 | 7.5 | 3.2 | 23.5 |
| D#097 | 0.04 | 16 | 5 | 94 |
| D#096 | 0.06 | 29.2 | 5.6 | 99.2 |
| D#102 | 0.03 | 37.9 | 7.4 | ND |
| Mean (+/−SD) | 0.04 ± 0.02 | 22.6 ± 13.5 | 5.3 ± 1.7 | 72.23 ± 42.3 |

ND: not determined due to low phagocytic activity

C. Enhancement of Phagocytosis Activity of an Antitumor Antibody in Combination with CD47×PD-L1 bsAbs Macrophages (stained with calcein red orange) are incubated with human IgG (1 mg/ml) to saturate high-affinity Fcγ receptors (FcγRI) and thus reduce phagocytosis induced by the IgG4 CD47×PD-L1 bsAb. These experimental conditions allow evaluation of the enhancement of phagocytosis of an antitumor antibody due to the CD47 blockade activity of the IgG4 CD47×PD-L1 bsAb.

After at least 10 min of incubation at 37° C., macrophages are then co-incubated with Calcein AM-labeled Nalm-6 tumor cells at an effector:target cell ratio of 1:3 for 2.5 hours at 37° in the presence of different concentrations of the tested antibodies, as single agents or in combination with an IgG1 anti-CD19 mAb. At the end of the incubation period, supernatants are replaced by complete culture medium and the microplates are imaged with the CellInsight™ CX5 High Content Screening Platform. About 1500 macrophages are acquired and analyzed per well. Phagocytosis is evidenced as double-positive events (macrophage+tumor cell that are inside macrophages) and the phagocytosis indexes are calculated by the CellInsight™ manufacturer's software.

Figure 6B:
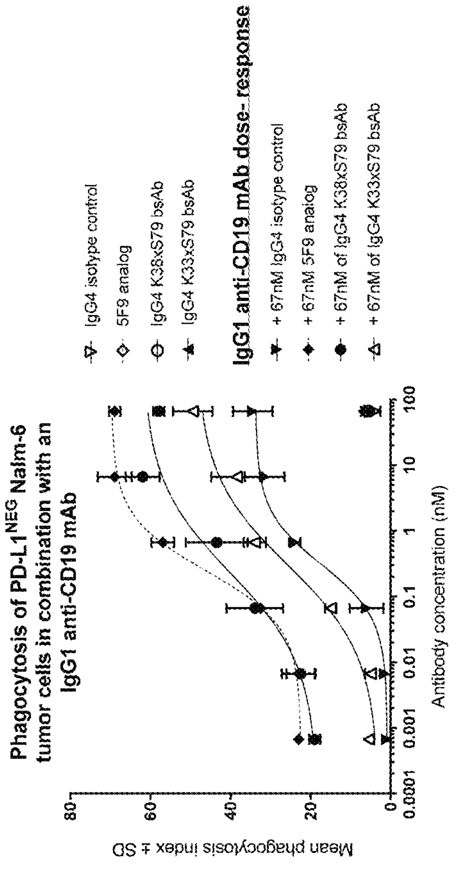

As depicted in FIG. 6B, neither the 5F9 analog or the IgG4 CD47×PD-L1 bsAbs induce ADCP in presence of human IgG at high concentration (67 nM, 10 μg/ml) in the absence of the anti-CD19 mAb, consistent with the low Fc-mediated effector function of the IgG4 Fc. By contrast, the IgG1 anti-CD19 mAb combined with a fixed concentration of the IgG4 isotype control demonstrates concentration-dependent phagocytic activity, that is significantly enhanced once a fixed concentration of 5F9 analog or the CD47×PD-L1 bsAbs is added. Consistent with their CD47/SIRPa blocking potency, a combination with K33×S79 bsAb confers only slight increase in phagocytosis over the level observed with a combination of the IgG4 control and anti-CD19 antibody, while a significant enhancement of phagocytosis is observed for the combination with K38×S79 bsAb or 5F9 analog.

Example 6: Antitumor Activity of Various CD47 Arms of Exemplary CD47×PD-L1 Bispecific Antibodies in a Xenograft Model The monovalent anti-tumor activity of the CD47 arms of selected bsAbs was tested in NOD scid mice bearing the Raji Burkitt lymphoma cell line. Importantly, Raji cells express very low level of human PD-L1 in vitro (Table 5) even after IFNg exposition for 24 h (data not shown), which is known to upregulate PD-L1 expression in many tumor cell lines and mimic inflammatory conditions in the tumor microenvironment. In addition, preliminary analysis by flow cytometry of PD-L1 expression in Raji tumors collected from NOD Scid mice confirmed the absence of PD-L1 expression on the tumor cells. Therefore, this tumor model was considered suitable for the specific assessment of the activity of the CD47 arm of the bsAbs, in absence of PD-L1 co-engagement.

Briefly, 8- to 10-week-old female NOD scid mice were engrafted subcutaneously (s.c.) with $5\times10^6$ (FIGS. 7 and 8) or $3\times10^6$ (FIG. 9) Raji cells. When average tumor volume reached about 250 $mm^3$ (FIG. 9) or 500 $mm^3$ (FIGS. 7 and 8), mice were administered intravenously a single dose (FIG. 9) or weekly doses (FIGS. 7 and 8) of different treatment. Mice received either an IgG4 isotype control, the IgG4 anti-CD47 mAb 5F9 analog or selected CD47×PD-L1 bsAbs at a dose of 10 mg/kg (FIGS. 7 and 8) or 20 mg/kg (FIG. 9). None of the molecule tested cross-react with mouse CD47, but the S79 PD-L1 arm of the bsAbs cross-react with mouse PD-L1 while S28 arm does not.

Figure 7A:
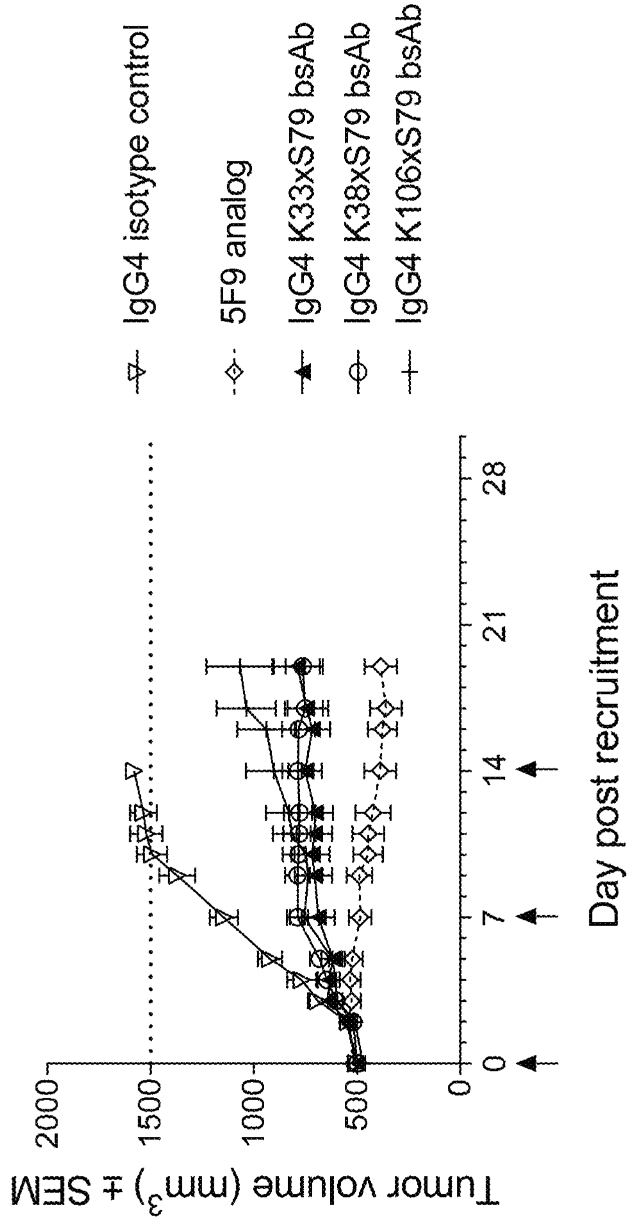
FIGS. 7A-7B. shows a series of graphs depicting anti-tumor activity of exemplary CD47×PD-L1 bispecific antibodies (K33×S79, K38×S79, K106×S79) on high volume ($5\times10^6$ cells) $CD47^+$ $PD\text{-}L1^-$ Raji tumors implanted in immunodeficient NOD Scid mice. Mice were recruited when tumor volume reached about 500 $mm^3$ and treatments were administered intravenously at a dose of 10 mg/kg once/week.
Figure 7B:
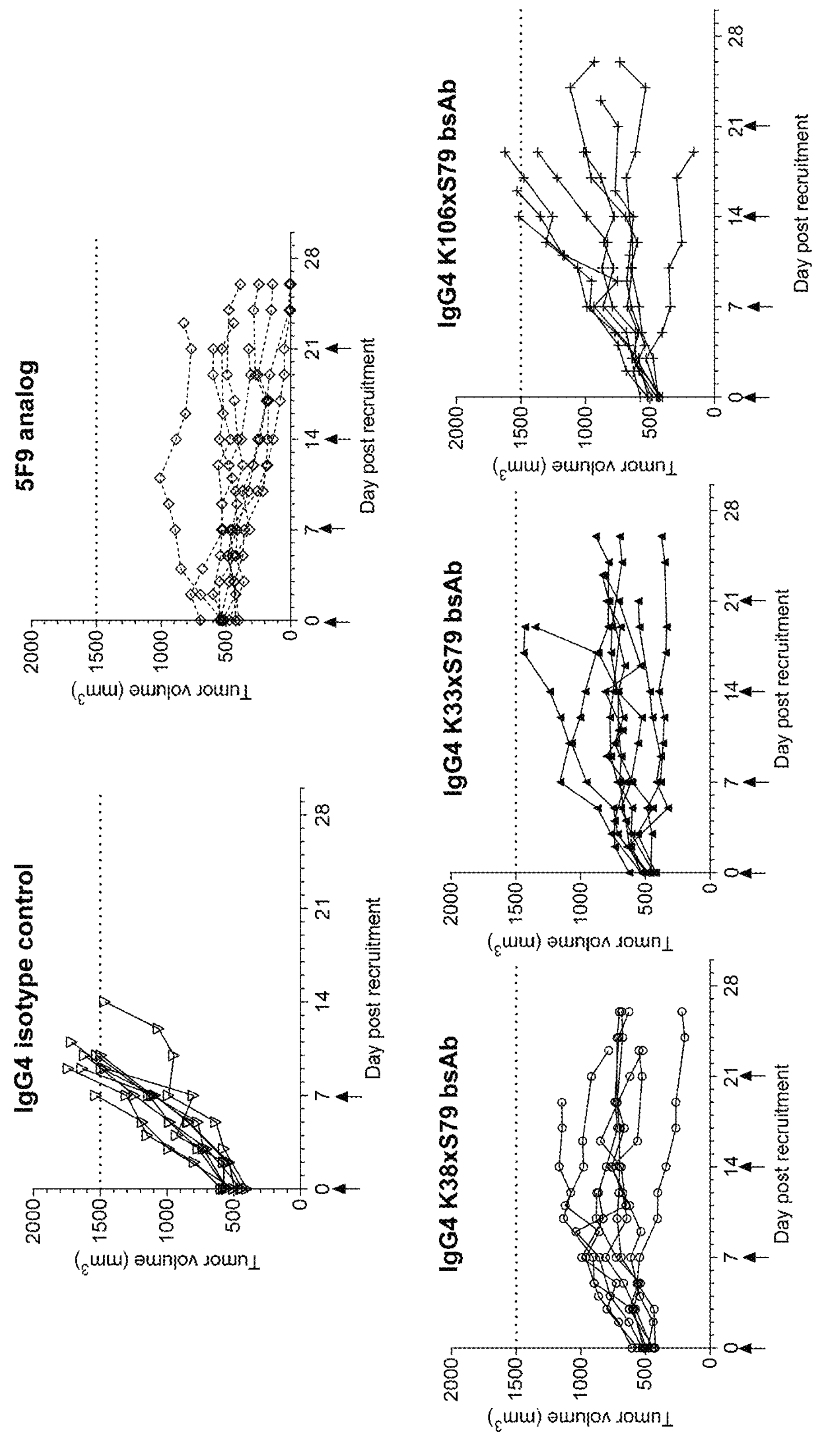
Figure 8A:
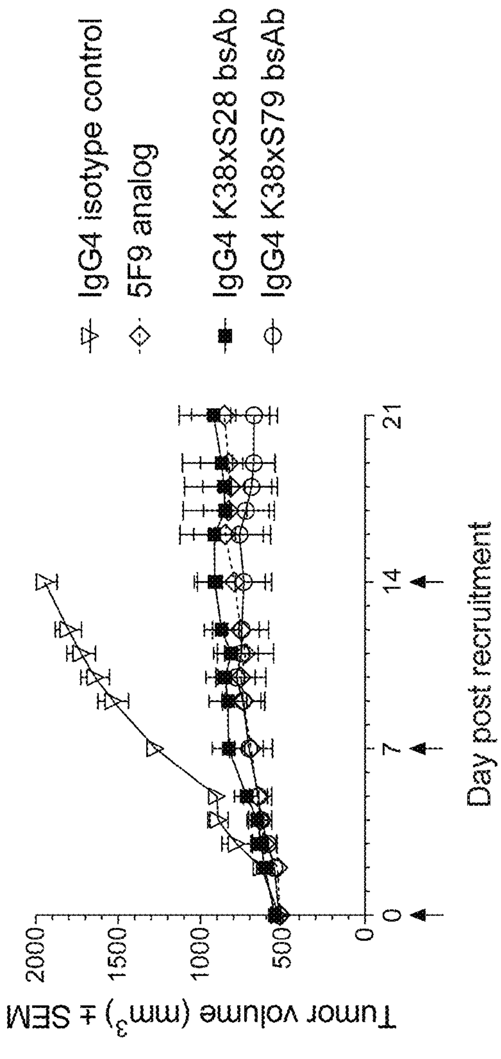
FIGS. 8A-8B. shows a series of graphs depicting anti-tumor activity of mouse PD-L1 cross-reactive and non-cross reactive CD47×PD-L1 bispecific antibodies on high volume ($5\times10^6$ cells) $CD47^+$ $PD\text{-}L1^-$ Raji tumors implanted in immunodeficient NOD Scid mice. Mice were recruited when tumor volume reached about 500 $mm^3$ and treatments were administrated intravenously at a dose of 10 mg/kg once/week.
Figure 8B:
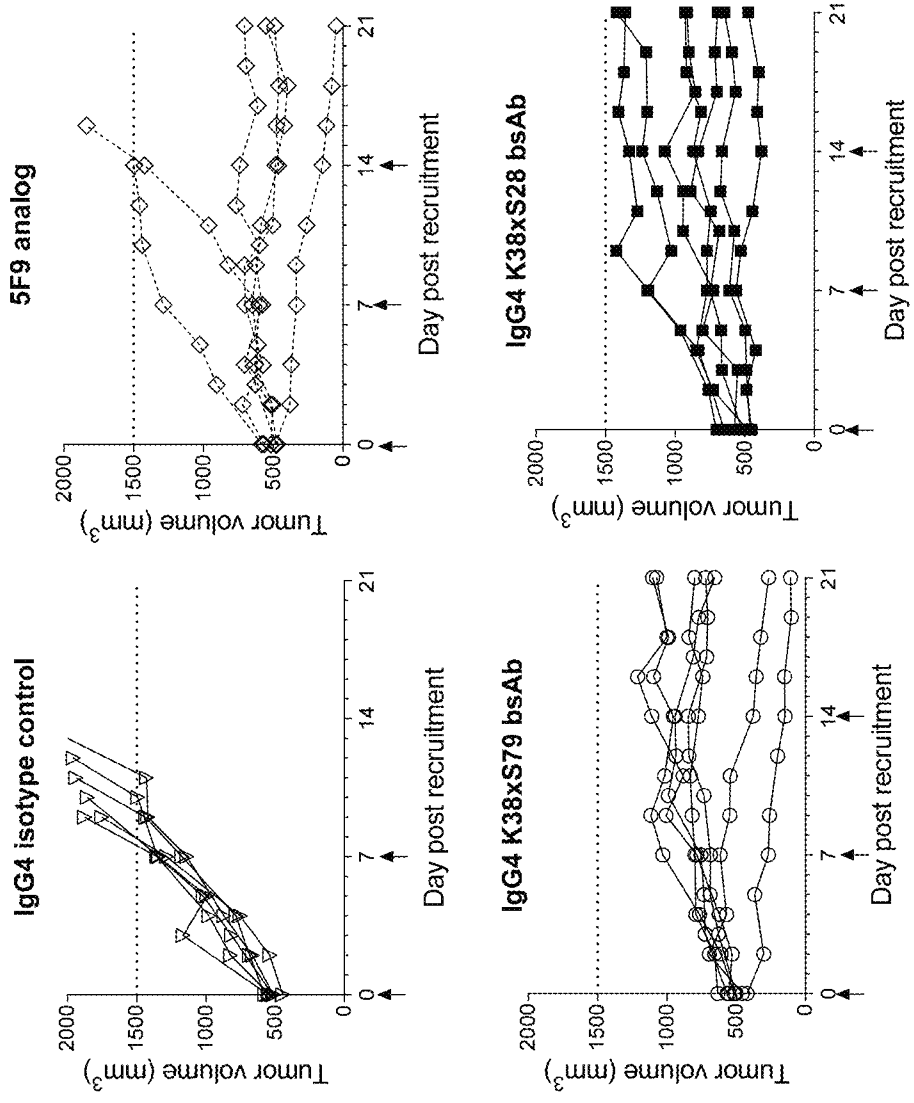

As observed in FIGS. 7A and 7B, all the bsAbs tested show significant antitumor activity on well-established Raji tumors after repeated administrations with K106×S79 producing the lowest activity with several tumors escaping to the treatment after several days, while K33×S79 and K38×S79 produce similar and intermediate antitumor activity leading to tumor stasis. The anti-CD47 5F9 analog leads to tumor regression. FIGS. 8A and 8B confirm that the antitumor activity observed with the bsAbs in the established Raji tumor model is mostly mediated by the monovalent engagement of the CD47 arm. Indeed, although K38×S28 bsAb does not engage mouse PD-L1 (the S28 PD-L1 arm is not cross-reactive to mouse PD-L1), it induces similar effect than the K38×S79 bsAbs that bears the mouse cross-reactive S79 PD-L1 arm.

Figure 9A:
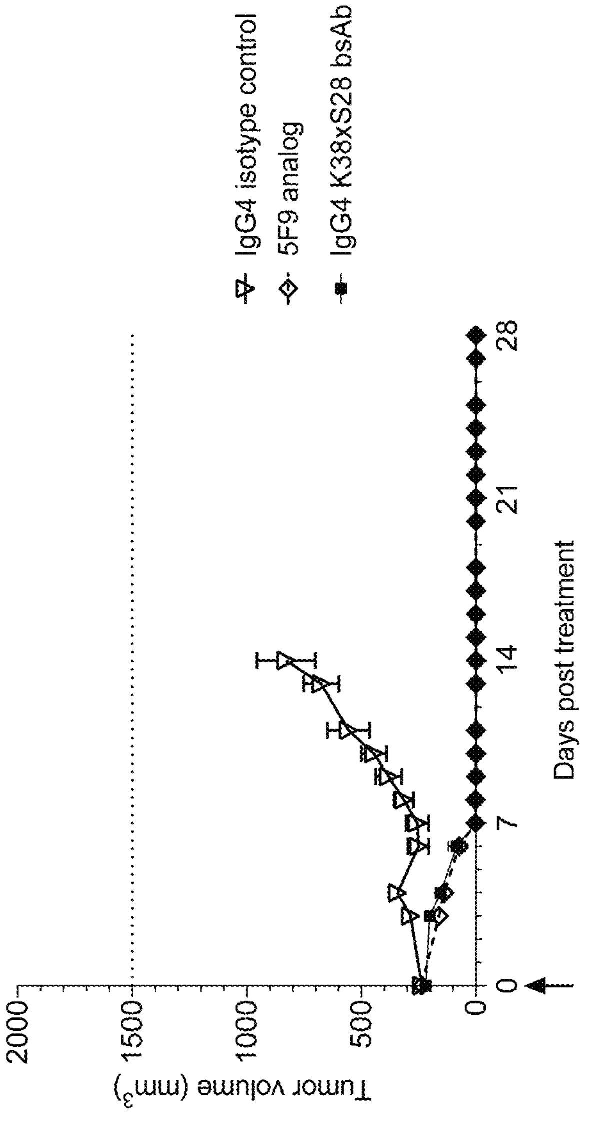
FIGS. 9A-9B shows a series of graphs depicting anti-tumor activity of the CD47×PD-L1 bispecific antibody (K38×S28) on a low volume ($3\times10^6$ cells) $CD47^+$ $PD\text{-}L1^-$ Raji tumors implanted in immunodeficient NOD Scid mice. Mice were administered a single intravenous injection of 20 mg/kg when tumor volume reached about 250 $mm^3$.
Figure 9B:
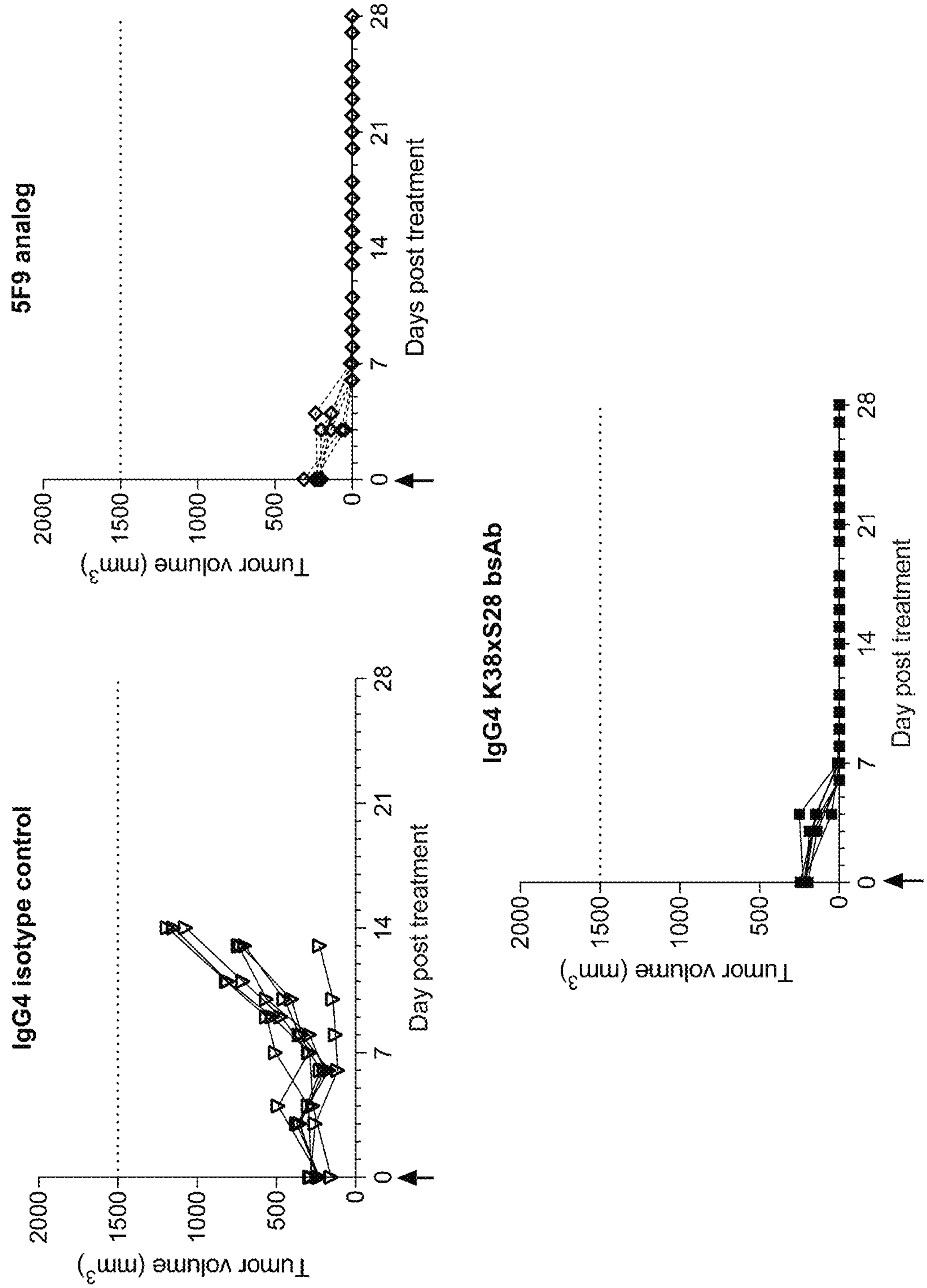

FIGS. 9A and 9B show that a single i.v. administration of 20 mg/kg of the monovalent K38 CD47 arm (K38×S28 bsAb) can induce complete and prolonged tumor regression of established Raji tumors having lower tumor volume, like anti-CD47 5F9 analog.

Example 7: Enhancement of T-Cell Activation by CD47×PD-L1 Bispecific Antibodies

The ability of the CD47×PD-L1 bsAbs to enhance T-cell activation was evaluated by incubating serial dilutions of the bsAbs and various benchmark molecules with human PBMCs in the presence of Staphylococcal enterotoxin A (200 ng/mL; SEA) for 96 hours. Human IL-2 production in the supernatant was measured by ELISA (DuoSET® ELISA (immunoassay kit) R&D system DY2020) and use to determine T-cell activation.

Figure 10:
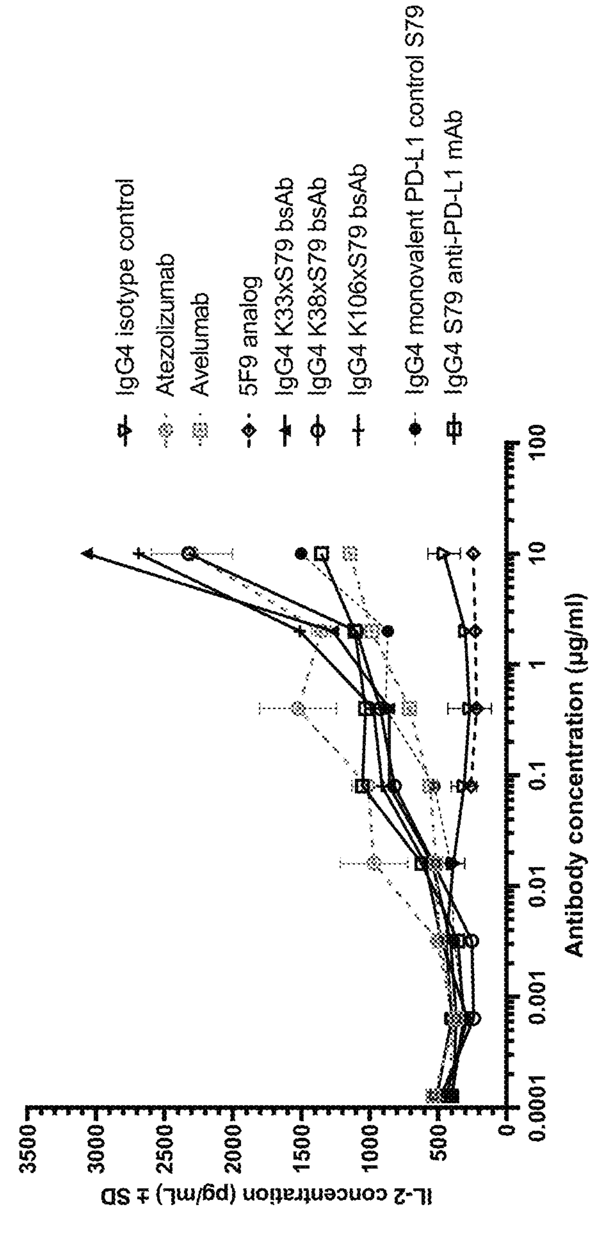
FIG. 10 shows a graph depicting T-cell activation (IL-2 concentration in the supernatant) induced by exemplary CD47×PD-L1 bispecific antibodies assessed in the *Staphylococcus* enterotoxin A (SEA) PBMC stimulation assay and quantified by ELISA. hIgG4 isotype control antibody, anti-CD47 5F9 analog, anti-PD-L1 mAbs avelumab, atezolizumab and S79 as well as monovalent PD-L1 control S79 were tested for comparison.

Results of FIG. 10 show that all the CD47×PD-L1 bsAbs tested enhance T-cell activation in comparable range to the anti-PD-L1 benchmark atezolizumab and the S79 anti-PD-L1 mAb.

Example 8: Tolerability of CD47×PD-L1 Bispecific Antibodies in Humanized CD47/SIRPa Transgenic Mice The development of CD47-targeted agents has been hindered by safety concerns, especially hematological toxicities such as anemia and thrombocytopenia. To evaluate the tolerability of the CD47×PD-L1 bsAbs, mice genetically modified to express the human extracellular domain of CD47 and SIRPa were used (Biocytogen, C57BL/6-$Sirpa^{tm1(SIRPA)}Cd47^{tm1(CD47)}$/Bcgen, #120525). In these mice, the CD47×PD-L1 bsAbs are expected to bind both targets with comparable affinity to human cells (see binding affinities described in Table 7).

Figure 11A:
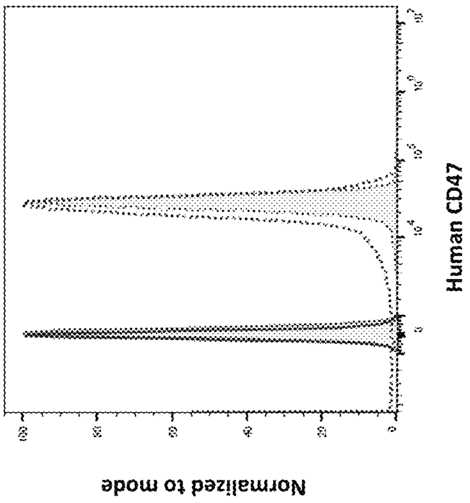
FIGS. 11A-11D shows a series of graphs depicting tolerability and impact on red blood cells and platelets of a single intravenous injection of 10 mg/kg of selected IgG4 CD47×PD-L1 in humanized CD47/SIRPa transgenic C57BL/6 mice.

First, to ensure that the human CD47 expression in the humanized mice was close to the physiological expression found in humans, isolated red blood cells (RBC) from the transgenic mice was stained with an anti-human CD47 mAb and compared by flow cytometry to the expression of human RBC isolated from whole blood of healthy donors. FIG. 11A demonstrates that the expression of human CD47 on transgenic mouse RBC is similar to the expression of human red blood cells.

Then, mice were injected intravenously (bolus) with a single dose of 10 mg/kg of IgG4 isotype control or the IgG4 anti-CD47 mAb 5F9 analog or selected IgG4 CD47×PD-L1 bsAbs. To assess tolerability of treatments, mice were monitored for clinical signs of toxicity following injection (i.e. prostration, hunched posture, etc. . . . ) and body weight was measured every day for 4 days and every 3 days until the end of the study. In addition, red blood cell and platelet counts were analyzed at several time points after injection (6 h, 24 h, 96 h and 168 h after injection) to assess potential impact on blood parameters.

Clinical signs of mild toxicity including prostration and loss of mobility were noted few minutes after the i.v. injection and during 1 hour in the anti-CD47 5F9 analog group. The administration of the K33×S79, K38×S79 and K106×S79 was generally well-tolerated with occurrence of a short prostration and loss of mobility in 2 to 3 mice out of 12 animals during 15 min.

Figure 11B:
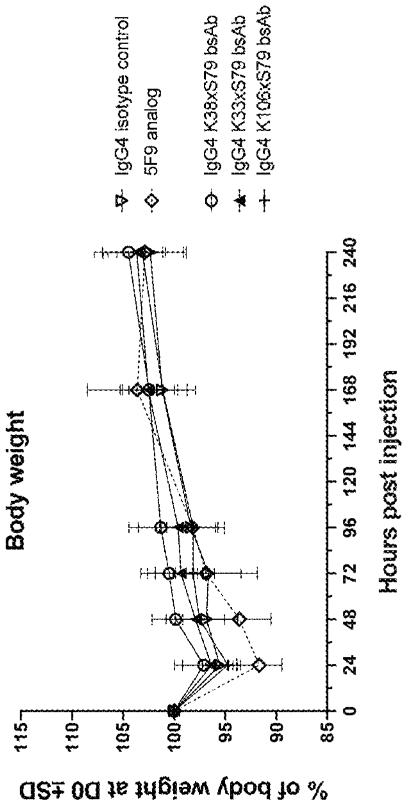
Figure 11C:
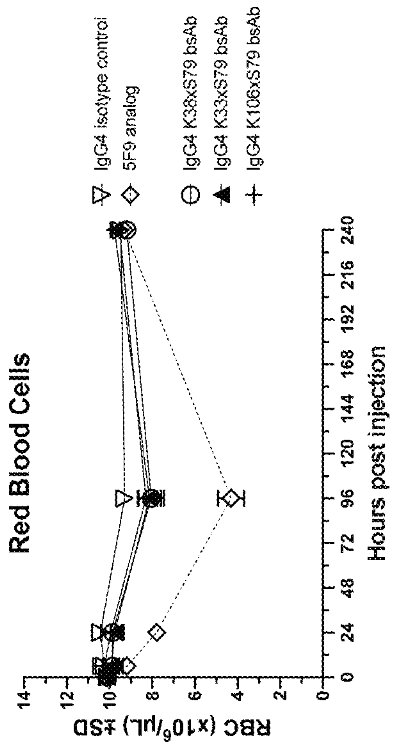
Figure 11D:
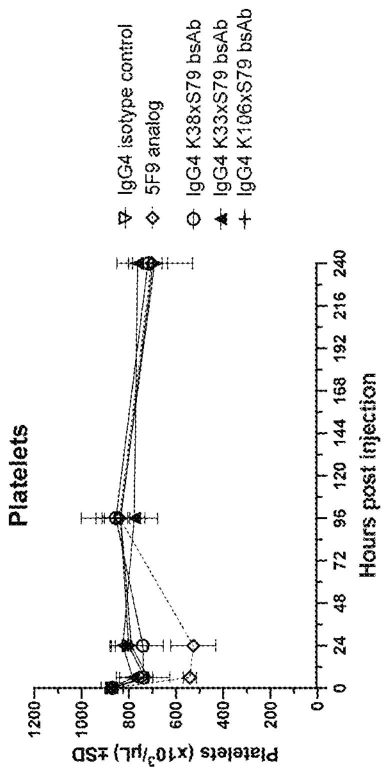

FIG. 11B shows a slight drop of body weight 24 h after the injection, which is obviously not specifically linked to the treatments, as this drop is also observed in the isotype control group. However, it can be highlighted that the drop is more pronounced and prolonged for the 5F9 group. FIG. 11C shows that 5F9 analog induces significant depletion of RBC after administration, reaching a nadir of more than 50% decrease at 96 h, as compared to the IgG4 isotype control. In contrary, the bsAbs only slightly impact on the RBC count (10% decrease at 96 h). The RBC recovered their basal level in all the groups at 240 h post-injection. FIG. 11D also suggests that platelets are significantly impacted at early timepoints after injection (30% decrease at 6 h) 5F9 analog group, while the bsAb treatments do not have a significant impact.

Figure 12:
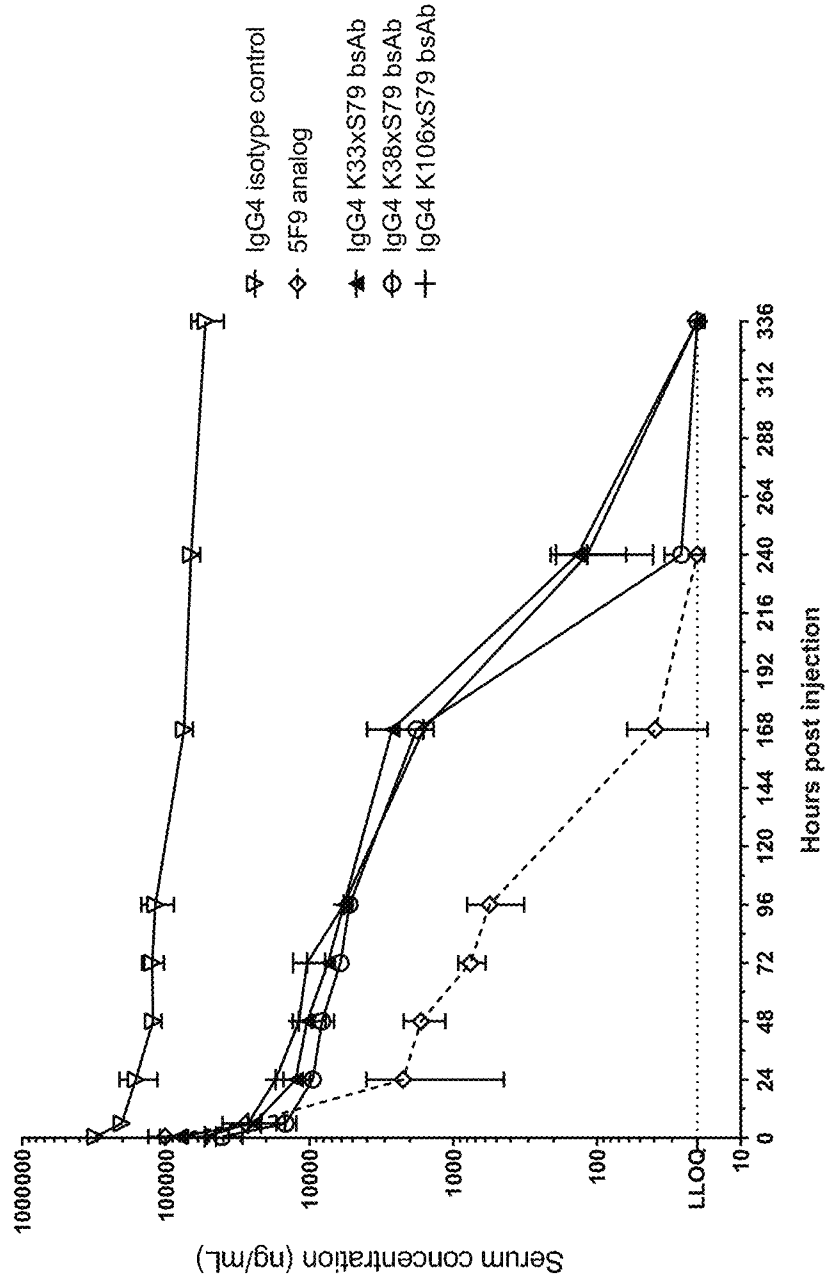
FIG. 12 shows a graph depicting the pharmacokinetic profile of exemplary CD47×PD-L1 bispecific antibodies (K33×S79, K38×S79, K106×S79) in humanized CD47/hSIRP transgenic C57BL/6 mice after a single i.v. administration (bolus) of 10 mg/kg compared to hIgG4 isotype control antibody and anti-CD47 5F9 analog.

Example 9: Single Dose PK of Exemplary CD47×PD-L1 Bispecific Antibodies Comprising Different CD47 Binders in Healthy Humanized CD47/SIRPa Transgenic Mice A single dose pharmacokinetic study was performed in the above described humanized hCD47/hSIRPa transgenic mice to evaluate exposure of selected CD47×PD-L1 bsAbs, as compared to the anti-CD47 mAb 5F9 analog. An intravenous bolus injection of 10 mg/kg was administered to mice and blood samples were collected at various timepoints for pharmacokinetic evaluation. A generic immunoassay was used for measuring total concentrations of the various IgG4 molecules tested. The lower limit of quantification (LLOQ) was defined at 20 ng/ml. FIG. 12 shows that the PK of each CD47-targeting agent is affected by target-mediated drug disposition from different timepoints (96 h for 5F9 analog while from 168 h for the bsAbs). The exposure to the bsAbs is slightly above the one of anti-CD47 5F9 analog, as suggested by the PK profiles and the AUC found in Table 11.

TABLE 11

Area Under Curve (AUC) of PK profile of tested antibodies in humanized hCD47/hSIRPa transgenic C57BL/6 mice depicted in FIG. 12.

| Antibody name | $AUC_{0\text{-}last}$ (μg · h/mL) |
|---|---|
| IgG4 isotype control | 317777 |
| 5F9 mAb analog | 654 |
| K33xS79 bsAb | 1623 |
| K38xS79 bsAb | 1161 |
| K106xS79 bsAb | 1712 |

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bispecific antibody comprising:

i) a heavy chain comprising a heavy chain complementarity determining region 1 (CDRH1) comprising SEQ ID NO: 1;

a heavy chain complementarity determining region 2 (CDRH2) comprising SEQ ID NO: 2; and a heavy chain complementarity determining region 3 (CDRH3) comprising SEQ ID NO: 3;

ii) a first light chain comprising

A) a light chain complementarity determining region 1 (CDRL1) comprising SEQ ID NO: 89;

a light chain complementarity determining region 2 (CDRL2) comprising Gly-Ala-Ser; and a light chain complementarity determining region 3 (CDRL3) comprising SEQ ID NO: 96; or B) a CDRL1 comprising SEQ ID NO: 90;

a CDRL2 comprising Ala-Ala-Ser; and a CDRL3 comprising SEQ ID NO: 97; or

C) a CDRL1 comprising SEQ ID NO: 90;

a CDRL2 comprising Ala-Ala-Ser; and a CDRL3 comprising SEQ ID NO: 98; or

D) a CDRL1 comprising SEQ ID NO: 90;

a CDRL2 comprising Ala-Ala-Ser; and a CDRL3 comprising SEQ ID NO: 99; or

E) a CDRL1 comprising SEQ ID NO: 90;

a CDRL2 comprising Ala-Ala-Ser; and a CDRL3 comprising SEQ ID NO: 100; or

F) a CDRL1 comprising SEQ ID NO: 90;

a CDRL2 comprising Ala-Ala-Ser; and a CDRL3 comprising SEQ ID NO: 101; or

G) a CDRL1 comprising SEQ ID NO: 90;

a CDRL2 comprising Ala-Ala-Ser; and a CDRL3 comprising SEQ ID NO: 102; or

H) a CDRL1 comprising SEQ ID NO: 91;
a CDRL2 comprising Ala-Ser-Ser; and
a CDRL3 comprising SEQ ID NO: 96; or
I) a CDRL1 comprising SEQ ID NO: 92;
a CDRL2 comprising Ala-Ala-Ser; and
a CDRL3 comprising SEQ ID NO: 96; or
J) a CDRL1 comprising SEQ ID NO: 90;
a CDRL2 comprising Ala-Ala-Ser; and
a CDRL3 comprising SEQ ID NO: 244; or
K) a CDRL1 comprising SEQ ID NO: 213;
a CDRL2 comprising Ala-Gly-Ser; and
a CDRL3 comprising SEQ ID NO: 96; or
L) a CDRL1 comprising SEQ ID NO: 213;
a CDRL2 comprising Ala-Ala-Ser; and
a CDRL3 comprising SEQ ID NO: 245; or
M) a CDRL1 comprising SEQ ID NO: 214;
a CDRL2 comprising Gly-Asn-Ser; and
a CDRL3 comprising SEQ ID NO: 212; and
iii) a second light chain comprising:
a) a CDRL1 comprising SEQ ID NO: 8;
a CDRL2 comprising Ala-11r-Asn; and
a CDRL3 comprising SEQ ID NO: 20; or
b) a CDRL1 comprising SEQ ID NO: 8;
a CDRL2 comprising Ala-11r-Asn; and
a CDRL3 comprising SEQ ID NO: 21; or
c) a CDRL1 comprising SEQ ID NO: 8;
a CDRL2 comprising Ala-Thr-Asn; and
a CDRL3 comprising SEQ ID NO: 22; or
d) a CDRL1 comprising SEQ ID NO: 9;
a CDRL2 comprising Phe-Gly-Ser; and
a CDRL3 comprising SEQ ID NO: 23; or
e) a CDRL1 comprising SEQ ID NO: 9;
a CDRL2 comprising Phe-Gly-Ser; and
a CDRL3 comprising SEQ ID NO: 24; or
f) a CDRL1 comprising SEQ ID NO: 9;
a CDRL2 comprising Phe-Gly-Ser; and
a CDRL3 comprising SEQ ID NO: 25; or
g) a CDRL1 comprising SEQ ID NO: 10;
a CDRL2 comprising His-Asp-Asn; and
a CDRL3 comprising SEQ ID NO: 147; or
h) a CDRL1 comprising SEQ ID NO: 10;
a CDRL2 comprising His-Asp-Asn; and
a CDRL3 comprising SEQ ID NO: 148; or
i) a CDRL1 comprising SEQ ID NO: 11;
a CDRL2 comprising His-Asp-Thr; and
a CDRL3 comprising SEQ ID NO: 147; or
j) a CDRL1 comprising SEQ ID NO: 12;
a CDRL2 comprising Phe-Ala-Ser; and
a CDRL3 comprising SEQ ID NO: 26; or
k) a CDRL1 comprising SEQ ID NO: 13;
a CDRL2 comprising Phe-Ala-Ser; and
a CDRL3 comprising SEQ ID NO: 26; or
l) a CDRL1 comprising SEQ ID NO: 14;
a CDRL2 comprising Phe-Ala-Ser; and
a CDRL3 comprising SEQ ID NO: 27; or
m) a CDRL1 comprising SEQ ID NO: 14;
a CDRL2 comprising Phe-Ala-Ser; and
a CDRL3 comprising SEQ ID NO: 28; and
wherein the bispecific antibody comprises a first antigen binding region comprising i) and ii) that specifically binds to CD47 and a second antigen binding region comprising i) and iii) that specifically binds to Programmed Death-ligand 1 (PD-L1).

2. The bispecific antibody of claim 1, comprising:
ii) a first light chain comprising
K) a CDRL1 comprising SEQ ID NO: 213;
a CDRL2 comprising Ala-Gly-Ser; and
a CDRL3 comprising SEQ ID NO: 96; and
iii) a second light chain comprising
m) a CDRL1 comprising SEQ ID NO: 14;
a CDRL2 comprising Phe-Ala-Ser; and
a CDRL3 comprising SEQ ID NO: 28.

3. The bispecific antibody of claim 1, comprising:
ii) a first light chain comprising
M) a CDRL1 comprising SEQ ID NO: 214;
a CDRL2 comprising Gly-Asn-Ser; and
a CDRL3 comprising SEQ ID NO: 212; and
iii) a second light chain comprising
m) a CDRL1 comprising SEQ ID NO: 14;
a CDRL2 comprising Phe-Ala-Ser; and
a CDRL3 comprising SEQ ID NO: 28.

4. The bispecific antibody of claim 1, wherein at least a portion of the first light chain is of the kappa type and at least a portion of the second light chain is of the lambda type.

5. The bispecific antibody of claim 4, wherein the first light chain comprises at least a Kappa constant region.

6. The bispecific antibody of claim 5, wherein the first light chain further comprises a Kappa variable region.

7. The bispecific antibody of claim 5, wherein the first light chain further comprises a Lambda variable region.

8. The bispecific antibody of claim 4, wherein the second light chain comprises at least a Lambda constant region.

9. The bispecific antibody of claim 8, wherein the second light chain further comprises a Lambda variable region.

10. The bispecific antibody of claim 8, wherein the second light chain further comprises a Kappa variable region.

11. The bispecific antibody of claim 4, wherein the first light chain comprises a Kappa constant region and a Kappa variable region, and wherein the second light chain comprises a Lambda constant region and a Lambda variable region.

12. The bispecific antibody of claim 1, wherein the bispecific antibody is a human antibody.

13. The bispecific antibody of claim 1, wherein the bispecific antibody is an IgG4 antibody.

14. The bispecific antibody of claim 13, wherein the bispecific antibody has a heavy chain variable region and a constant region comprising SEQ ID NO: 232.

15. A composition comprising the bispecific antibody of claim 1 and a pharmaceutically acceptable carrier.

16. A method of treating a PD-L1+ and/or CD47+ solid tumor, killing a PD-L1+ and/or CD47+ tumor cell, or reducing the proliferation of a PD-L1+ and/or CD47+ tumor cell comprising, contacting the cell with a bispecific antibody comprising:
(i) a first antigen binding region comprising a heavy chain and a light chain, wherein the first antigen binding region binds CD47 and comprises:
(a) a CDRH1 comprising SEQ ID NO: 1;
a CDRH2 comprising SEQ ID NO: 2;
a CDRH3 comprising SEQ ID NO: 3;
a CDRL1 comprising SEQ ID NO: 213;
a CDRL2 comprising Ala-Gly-Ser; and
a CDRL3 comprising SEQ ID NO: 96;
(b) a CDRH1 comprising SEQ ID NO: 1;
a CDRH2 comprising SEQ ID NO: 2;
a CDRH3 comprising SEQ ID NO: 3;
a CDRL1 comprising SEQ ID NO: 90;
a CDRL2 comprising Ala-Ala-Ser; and
a CDRL3 comprising SEQ ID NO: 244; or (c) a CDRH1 comprising SEQ ID NO: 1;
a CDRH2 comprising SEQ ID NO: 2;
a CDRH3 comprising SEQ ID NO: 3;
a CDRL1 comprising SEQ ID NO: 214;
a CDRL2 comprising Gly-Asn-Ser; and
a CDRL3 comprising SEQ ID NO: 212; and (ii) a second antigen binding region comprising a heavy chain and a light chain, wherein the second antigen binding region binds PD-L1 and comprises:

(a) a CDRH1 comprising SEQ ID NO: 1;
a CDRH2 comprising SEQ ID NO: 2;
a CDRH3 comprising SEQ ID NO: 3;
a CDRL1 comprising SEQ ID NO: 14;
a CDRL2 comprising Phe-Ala-Ser; and
a CDRL3 comprising SEQ ID NO: 28.

17. The method of claim 16, wherein the PD-L1+ and/or CD47+ solid tumor is, or is derived from, breast cancer, ovarian cancer, head and neck cancer, bladder cancer, melanoma, mesothelioma, colorectal cancer, cholangiocarcinoma, pancreatic cancer, lung cancer, leiomyoma, leiomyosarcoma, kidney cancer, glioma, glioblastoma, endometrial cancer, esophageal cancer, biliary gastric cancer, prostate cancer, or combinations thereof.

18. The bispecific antibody of claim 2, wherein at least a portion of the first light chain is of the kappa type and at least a portion of the second light chain is of the lambda type.

19. The bispecific antibody of claim 18, wherein the first light chain comprises at least a Kappa constant region.

20. The bispecific antibody of claim 19, wherein the first light chain further comprises a Kappa variable region.

21. The bispecific antibody of claim 19, wherein the first light chain further comprises a Lambda variable region.

22. The bispecific antibody of claim 18, wherein the second light chain comprises at least a Lambda constant region.

23. The bispecific antibody of claim 22, wherein the second light chain further comprises a Lambda variable region.

24. The bispecific antibody of claim 18, wherein the second light chain further comprises a Kappa variable region.

25. The bispecific antibody of claim 18, wherein the first light chain comprises a Kappa constant region and a Kappa variable region, and wherein the second light chain comprises a Lambda constant region and a Lambda variable region.

26. The bispecific antibody of claim 2, wherein the bispecific antibody is an IgG4 antibody.

27. The bispecific antibody of claim 26, wherein the bispecific antibody has a heavy chain variable region and a constant region comprising SEQ ID NO: 232.

28. The bispecific antibody of claim 2, wherein:

the heavy chain comprises a heavy chain variable region comprising SEQ ID NO: 6;

the first light chain comprises a kappa light chain variable region comprising SEQ ID NO: 226; and the second light chain comprises a lambda light chain variable region comprising SEQ ID NO: 87.

29. The bispecific antibody of claim 28, wherein:

the heavy chain comprises a heavy chain variable region and constant region comprising SEQ ID NO: 4;

the first light chain comprises a kappa light chain comprising SEQ ID NO: 224 the second light chain comprises a lambda light chain comprising SEQ ID NO: 85.

30. A method of treating a PD-L1+ and/or CD47+ solid tumor in a subject, the method comprising administering the bispecific antibody of claim 28 to the subject.

31. The method of claim 30, wherein the PD-L1+ and/or CD47+ solid tumor is, or is derived from, breast cancer, ovarian cancer, head and neck cancer, bladder cancer, melanoma, mesothelioma, colorectal cancer, cholangiocarcinoma, pancreatic cancer, lung cancer, leiomyoma, leiomyosarcoma, kidney cancer, glioma, glioblastoma, endometrial cancer, esophageal cancer, biliary gastric cancer, prostate cancer, or combinations thereof.

32. A method of treating a PD-L1+ and/or CD47+ solid tumor in a subject, the method comprising administering the bispecific antibody of claim 29 to the subject.

33. The method of claim 32, wherein the PD-L1+ and/or CD47+ solid tumor is, or is derived from, breast cancer, ovarian cancer, head and neck cancer, bladder cancer, melanoma, mesothelioma, colorectal cancer, cholangiocarcinoma, pancreatic cancer, lung cancer, leiomyoma, leiomyosarcoma, kidney cancer, glioma, glioblastoma, endometrial cancer, esophageal cancer, biliary gastric cancer, prostate cancer, or combinations thereof.

34. A composition comprising the bispecific antibody of claim 28 and a pharmaceutically acceptable carrier.

35. A composition comprising the bispecific antibody of claim 29 and a pharmaceutically acceptable carrier.

* * * * *

SEQUENCE LISTING

```
<160> NUMBER OF SEQ ID NOS: 245

<210> SEQ ID NO 1
<211> LENGTH: 8
<212> TYPE: PRT
<213> ORGANISM: Artificial Sequence
<220> FEATURE:
<223> OTHER INFORMATION: CDRH1

<400> SEQUENCE: 1

Gly Phe Thr Phe Ser Ser Tyr Ala
1               5


<210> SEQ ID NO 2
<211> LENGTH: 8
<212> TYPE: PRT
<213> ORGANISM: Artificial Sequence
<220> FEATURE:
<223> OTHER INFORMATION: CDRH2

<400> SEQUENCE: 2

Ile Ser Gly Ser Gly Gly Ser Thr
1               5


<210> SEQ ID NO 3
<211> LENGTH: 9
<212> TYPE: PRT
<213> ORGANISM: Artificial Sequence
<220> FEATURE:
<223> OTHER INFORMATION: CDRH3

<400> SEQUENCE: 3

Ala Lys Ser Tyr Gly Ala Phe Asp Tyr
1               5


<210> SEQ ID NO 4
<211> LENGTH: 442
<212> TYPE: PRT
<213> ORGANISM: Artificial Sequence
```

<220> FEATURE:
<223> OTHER INFORMATION: VHCH IGHV3-23-S228P hIgG4-AA

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400
```

```
Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 5
<211> LENGTH: 1329
<212> TYPE: DNA
<213> ORGANISM: Artificial Sequence
<220> FEATURE:
<223> OTHER INFORMATION: VHCH  IGHV3-23-S228P hIgG4-NT

<400> SEQUENCE: 5

gaggtgcagc tgttggagtc tgggggaggc ttggtacagc ctggggggtc cctgagactc     60

tcctgtgcag cctctggatt cacctttagc agctatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaaagttat    300

ggtgcttttg actactgggg ccagggaacc ctggtcacag tctcgagcgc ctccaccaag    360

ggcccatccg tcttccccct ggcgccctgc tccaggagca cctccgagag cacagccgcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cgaagaccta cacttgcaac    600

gtagatcaca agcccagcaa caccaaggtg gacaagagag ttgagtccaa atatggtccc    660

ccatgcccac catgcccagc acctgagttc ctggggggac catcagtctt cctgttcccc    720

ccaaaaccca aggacactct catgatctcc cggacccctg aggtcacgtg cgtggtggtg    780

gacgtgagcc aggaagaccc cgaggtccag ttcaactggt acgtggatgg cgtggaggtg    840

cataatgcca agacaaagcc gcgggaggag cagttcaaca gcacgtaccg tgtggtcagc    900

gtcctcaccg tcctgcacca ggactggctg aacggcaagg agtacaagtg caaggtctcc    960

aacaaaggcc tcccgtcctc catcgagaaa accatctcca aagccaaagg gcagccccga   1020

gagccacagg tgtacaccct gcccccatcc caggaggaga tgaccaagaa ccaggtcagc   1080

ctgacttgcc tggtcaaagg cttctacccc agcgacatcg ccgtggagtg ggagagcaac   1140

gggcagccgg agaacaacta caagaccacg cctcccgtgc tggactccga cggctccttc   1200

ttcctctaca gcaggctaac cgtggacaag tccaggtggc aggaggggaa tgtcttctca   1260

tgctccgtga tgcatgaggc tctgcacaac cactacacac agaagagcct ctccctgtct   1320

ctgggttaa                                                           1329


<210> SEQ ID NO 6
<211> LENGTH: 116
<212> TYPE: PRT
<213> ORGANISM: Artificial Sequence
<220> FEATURE:
<223> OTHER INFORMATION: VH  IGHV3-23-S228P hIgG4-AA

<400> SEQUENCE: 6

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115
```

<210> SEQ ID NO 7
<211> LENGTH: 348
<212> TYPE: DNA
<213> ORGANISM: Artificial Sequence
<220> FEATURE:
<223> OTHER INFORMATION: VH IGHV3-23-S228P hIgG4-NT

<400> SEQUENCE: 7

```
gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agccgaggac acggccgtat attactgtgc gaaaagttat     300

ggtgcttttg actactgggg ccagggaacc ctggtcacag tctcgagc                  348
```

<210> SEQ ID NO 8
<211> LENGTH: 8
<212> TYPE: PRT
<213> ORGANISM: Artificial Sequence
<220> FEATURE:
<223> OTHER INFORMATION: PDL1-CDRL1-1

<400> SEQUENCE: 8

```
Ser Ser Asn Ile Arg Asp Ser Phe
1               5
```

<210> SEQ ID NO 9
<211> LENGTH: 9
<212> TYPE: PRT
<213> ORGANISM: Artificial Sequence
<220> FEATURE:
<223> OTHER INFORMATION: PDL1-CDRL1-2

<400> SEQUENCE: 9

```
Ser Ser Asp Val Val Lys Asn Asn Phe
1               5
```

<210> SEQ ID NO 10
<211> LENGTH: 8
<212> TYPE: PRT
<213> ORGANISM: Artificial Sequence
<220> FEATURE:
<223> OTHER INFORMATION: PDL1-CDRL1-3

<400> SEQUENCE: 10

Ser Ser Asn Ile Ala His Lys Pro
1               5

<210> SEQ ID NO 11
<211> LENGTH: 8
<212> TYPE: PRT
<213> ORGANISM: Artificial Sequence
<220> FEATURE:
<223> OTHER INFORMATION: PDL1-CDRL1-4

<400> SEQUENCE: 11

Ser Val Asp Ile Ala His Lys Pro
1               5

<210> SEQ ID NO 12
<211> LENGTH: 9
<212> TYPE: PRT
<213> ORGANISM: Artificial Sequence
<220> FEATURE:
<223> OTHER INFORMATION: PDL1-CDRL1-5

<400> SEQUENCE: 12

Ser Ser Asp Val Ala Lys Ile Pro Leu
1               5

<210> SEQ ID NO 13
<211> LENGTH: 9
<212> TYPE: PRT
<213> ORGANISM: Artificial Sequence
<220> FEATURE:
<223> OTHER INFORMATION: PDL1-CDRL1-6

<400> SEQUENCE: 13

Ser Ser Asp Val Leu Arg Pro Pro Leu
1               5

<210> SEQ ID NO 14
<211> LENGTH: 9
<212> TYPE: PRT
<213> ORGANISM: Artificial Sequence
<220> FEATURE:
<223> OTHER INFORMATION: PDL1-CDRL1-7

<400> SEQUENCE: 14

Ser Ser Asp Val Phe Arg Pro Pro Leu
1               5

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 9
<212> TYPE: PRT
<213> ORGANISM: Artificial Sequence
<220> FEATURE:
<223> OTHER INFORMATION: PDL1-CDRL3-1

<400> SEQUENCE: 20

Ala Ala Trp His Pro Tyr Tyr Thr Leu
1 5

<210> SEQ ID NO 21
<211> LENGTH: 9
<212> TYPE: PRT
<213> ORGANISM: Artificial Sequence
<220> FEATURE:
<223> OTHER INFORMATION: PDL1-CDRL3-2

<400> SEQUENCE: 21

Ala Ser Trp Trp Pro Tyr Gly Thr Val
1 5

<210> SEQ ID NO 22
<211> LENGTH: 9
<212> TYPE: PRT
<213> ORGANISM: Artificial Sequence
<220> FEATURE:
<223> OTHER INFORMATION: PDL1-CDRL3-3

<400> SEQUENCE: 22

Ala Ser Trp Trp Pro Phe Gly Thr Val
1 5

<210> SEQ ID NO 23
<211> LENGTH: 9
<212> TYPE: PRT
<213> ORGANISM: Artificial Sequence
<220> FEATURE:
<223> OTHER INFORMATION: PDL1-CDRL3-4

<400> SEQUENCE: 23

Ser Ser Trp Asp Met Pro Ala Leu Phe
1 5

<210> SEQ ID NO 24
<211> LENGTH: 9
<212> TYPE: PRT
<213> ORGANISM: Artificial Sequence
<220> FEATURE:
<223> OTHER INFORMATION: PDL1-CDRL3-5

<400> SEQUENCE: 24

Ser Ser Trp Asp Glu Pro Asp Arg Pro
1 5

<210> SEQ ID NO 25
<211> LENGTH: 9

<212> TYPE: PRT
<213> ORGANISM: Artificial Sequence
<220> FEATURE:
<223> OTHER INFORMATION: PDL1-CDRL3-6

<400> SEQUENCE: 25

Ser Ser Trp Asp Leu Pro Phe Leu Met
1               5

<210> SEQ ID NO 26
<211> LENGTH: 11
<212> TYPE: PRT
<213> ORGANISM: Artificial Sequence
<220> FEATURE:
<223> OTHER INFORMATION: PDL1-CDRL3-9

<400> SEQUENCE: 26

Ser Ser Trp Asp Asn Ala Gly Asp Gly His Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: PDL1-CDRL3-10

<400> SEQUENCE: 27

Ser Ser Trp Asp Gln Ser Gly Asp Gly His Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: PDL1-CDRL3-11

<400> SEQUENCE: 28

Ser Ser Trp Asp His Thr Gly Asp Gly His Val
1               5                   10

<210> SEQ ID NO 29
<211> LENGTH: 214
<212> TYPE: PRT
<213> ORGANISM: Artificial Sequence
<220> FEATURE:
<223> OTHER INFORMATION: S8_Sa10_1A9_VLCL2 aPDL1 IGLV1-44-AA

<400> SEQUENCE: 29

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Asp Ser
            20                  25                  30

Phe Val Asn Trp Tyr Gln Gln Leu Pro Gly Thr Ala Pro Lys Leu Leu
        35                  40                  45

Ile Tyr Ala Thr Asn Ile Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp His Pro Tyr Tyr
                85                  90                  95

Thr Leu Phe Gly Gly Gly Thr Lys Leu Thr Val Leu Gly Gln Pro Lys
            100                 105                 110

```
Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 30
<211> LENGTH: 642
<212> TYPE: DNA
<213> ORGANISM: Artificial Sequence
<220> FEATURE:
<223> OTHER INFORMATION: S8_Sa10_1A9_VLCL2 aPDL1 IGLV1-44-NT

<400> SEQUENCE: 30

cagtctgtgc tgactcagcc accctcagcg tctgggaccc ccgggcagag ggtcaccatc     60

tcttgttctg gaagcagctc caacatcagg gatagttttg taaactggta ccagcagctc    120

ccaggaacgg cccccaaact cctcatctat gctacgaata ttcggccctc aggggtccct    180

gaccgattct ctggctccaa gtctggcacc tcagcctccc tggccatcag tgggctccag    240

tctgaggatg aggctgatta ttactgtgca gcatggcacc cgtattacac gttgttcggc    300

ggagggacca agctgaccgt cctaggtcag cccaaggctg ccccctcggt cactctgttc    360

ccgccctcct ctgaggagct tcaagccaac aaggccacac tggtgtgtct cataagtgac    420

ttctacccgg gagccgtgac agtggcttgg aaagcagata gcagccccgt caaggcggga    480

gtggagacca ccacaccctc caaacaaagc aacaacaagt acgcggccag cagctatctg    540

agcctgacgc ctgagcagtg gaagtcccac agaagctaca gctgccaggt cacgcatgaa    600

gggagcaccg tggagaagac agtggcccct acagaatgtt ca                       642


<210> SEQ ID NO 31
<211> LENGTH: 119
<212> TYPE: PRT
<213> ORGANISM: Artificial Sequence
<220> FEATURE:
<223> OTHER INFORMATION: S8_Sa10_1A9_VLCL2 aPDL1 IGLV1-44-AA

<400> SEQUENCE: 31

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Asp Ser
            20                  25                  30

Phe Val Asn Trp Tyr Gln Gln Leu Pro Gly Thr Ala Pro Lys Leu Leu
        35                  40                  45

Ile Tyr Ala Thr Asn Ile Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Ala Ala Trp His Pro Tyr Tyr
                85                  90                  95

Thr Leu Phe Gly Gly Gly Thr Lys Leu Thr Val Leu Gly Gln Pro Lys
            100                 105                 110

Ala Ala Pro Ser Val Thr Leu
        115
```

<210> SEQ ID NO 32
<211> LENGTH: 357
<212> TYPE: DNA
<213> ORGANISM: Artificial Sequence
<220> FEATURE:
<223> OTHER INFORMATION: S8_Sa10_1A9_VLCL2 aPDL1 IGLV1-44-NT

<400> SEQUENCE: 32

```
cagtctgtgc tgactcagcc accctcagcg tctgggaccc ccgggcagag ggtcaccatc     60

tcttgttctg gaagcagctc caacatcagg gatagttttg taaactggta ccagcagctc    120

ccaggaacgg cccccaaact cctcatctat gctacgaata ttcggccctc aggggtccct    180

gaccgattct ctggctccaa gtctggcacc tcagcctccc tggccatcag tgggctccag    240

tctgaggatg aggctgatta ttactgtgca gcatggcacc cgtattacac gttgttcggc    300

ggagggacca agctgaccgt cctaggtcag cccaaggctg ccccctcggt cactctg       357
```

<210> SEQ ID NO 33
<211> LENGTH: 214
<212> TYPE: PRT
<213> ORGANISM: Artificial Sequence
<220> FEATURE:
<223> OTHER INFORMATION: S9_Sa10_1D9_VLCL2 aPDL1 IGLV1-44-AA

<400> SEQUENCE: 33

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Asp Ser
            20                  25                  30

Phe Val Asn Trp Tyr Gln Gln Leu Pro Gly Thr Ala Pro Lys Leu Leu
        35                  40                  45

Ile Tyr Ala Thr Asn Ile Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Trp Pro Tyr Gly
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205
```

```
Ala Pro Thr Glu Cys Ser
    210


<210> SEQ ID NO 34
<211> LENGTH: 642
<212> TYPE: DNA
<213> ORGANISM: Artificial Sequence
<220> FEATURE:
<223> OTHER INFORMATION: S9_Sa10_1D9_VLCL2 aPDL1 IGLV1-44-NT

<400> SEQUENCE: 34

cagtctgtgc tgactcagcc accctcagcg tctgggaccc ccgggcagag ggtcaccatc     60

tcttgttctg gaagcagctc caacatcagg gatagttttg taaactggta ccagcagctc    120

ccaggaacgg cccccaaact cctcatctat gctacgaata ttcggccctc aggggtccct    180

gaccgattct ctggctccaa gtctggcacc tcagcctccc tggccatcag tgggctccag    240

tctgaggatg aggctgatta ttactgtgca tcgtggtggc cgtacggtac tgtgttcggc    300

ggagggacca agctgaccgt cctaggtcag cccaaggctg ccccctcggt cactctgttc    360

ccgccctcct ctgaggagct tcaagccaac aaggccacac tggtgtgtct cataagtgac    420

ttctacccgg gagccgtgac agtggcttgg aaagcagata gcagccccgt caaggcggga    480

gtggagacca ccacaccctc caaacaaagc aacaacaagt acgcggccag cagctatctg    540

agcctgacgc ctgagcagtg gaagtcccac agaagctaca gctgccaggt cacgcatgaa    600

gggagcaccg tggagaagac agtggcccct acagaatgtt ca                       642


<210> SEQ ID NO 35
<211> LENGTH: 119
<212> TYPE: PRT
<213> ORGANISM: Artificial Sequence
<220> FEATURE:
<223> OTHER INFORMATION: S9_Sa10_1D9_VLCL2 aPDL1 IGLV1-44-AA

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Asp Ser
            20                  25                  30

Phe Val Asn Trp Tyr Gln Gln Leu Pro Gly Thr Ala Pro Lys Leu Leu
        35                  40                  45

Ile Tyr Ala Thr Asn Ile Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Trp Pro Tyr Gly
                85                  90                  95

Thr Val Phe Gly Gly Gly Thr Lys Leu Thr Val Leu Gly Gln Pro Lys
            100                 105                 110

Ala Ala Pro Ser Val Thr Leu
        115


<210> SEQ ID NO 36
<211> LENGTH: 357
<212> TYPE: DNA
<213> ORGANISM: Artificial Sequence
<220> FEATURE:
<223> OTHER INFORMATION: S9_Sa10_1D9_VLCL2 aPDL1 IGLV1-44-NT

<400> SEQUENCE: 36
```

cagtctgtgc tgactcagcc accctcagcg tctgggaccc ccgggcagag ggtcaccatc 60
tcttgttctg gaagcagctc caacatcagg gatagttttg taaactggta ccagcagctc 120
ccaggaacgg cccccaaact cctcatctat gctacgaata ttcggccctc aggggtccct 180
gaccgattct ctggctccaa gtctggcacc tcagcctccc tggccatcag tgggctccag 240
tctgaggatg aggctgatta ttactgtgca tcgtggtggc cgtacggtac tgtgttcggc 300
ggagggacca agctgaccgt cctaggtcag cccaaggctg ccccctcggt cactctg 357

<210> SEQ ID NO 37
<211> LENGTH: 214
<212> TYPE: PRT
<213> ORGANISM: Artificial Sequence
<220> FEATURE:
<223> OTHER INFORMATION: S37_ Sa10_1D7_VLCL2 aPDL1 IGLV1-44-AA

<400> SEQUENCE: 37

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Asp Ser
            20                  25                  30

Phe Val Asn Trp Tyr Gln Gln Leu Pro Gly Thr Ala Pro Lys Leu Leu
        35                  40                  45

Ile Tyr Ala Thr Asn Ile Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Trp Pro Phe Gly
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 38
<211> LENGTH: 642
<212> TYPE: DNA
<213> ORGANISM: Artificial Sequence
<220> FEATURE:
<223> OTHER INFORMATION: S37_ Sa10_1D7_VLCL2 aPDL1 IGLV1-44-NT

<400> SEQUENCE: 38
cagtctgtgc tgactcagcc accctcagcg tctgggaccc ccgggcagag ggtcaccatc 60
tcttgttctg gaagcagctc caacatcagg gatagttttg taaactggta ccagcagctc 120

```
ccaggaacgg cccccaaact cctcatctat gctacgaata ttcggccctc aggggtccct    180

gaccgattct ctggctccaa gtctggcacc tcagcctccc tggccatcag tgggctccag    240

tctgaggatg aggctgatta ttactgtgca tcctggtggc cgttcggtac tgtgttcggc    300

ggagggacca agctgaccgt cctaggtcag cccaaggctg ccccctcggt cactctgttc    360

ccgccctcct ctgaggagct tcaagccaac aaggccacac tggtgtgtct cataagtgac    420

ttctacccgg gagccgtgac agtggcttgg aaagcagata gcagccccgt caaggcggga    480

gtggagacca ccacaccctc caaacaaagc aacaacaagt acgcggccag cagctatctg    540

agcctgacgc ctgagcagtg gaagtcccac agaagctaca gctgccaggt cacgcatgaa    600

gggagcaccg tggagaagac agtggcccct acagaatgtt ca                       642
```

<210> SEQ ID NO 39
<211> LENGTH: 119
<212> TYPE: PRT
<213> ORGANISM: Artificial Sequence
<220> FEATURE:
<223> OTHER INFORMATION: S37_ Sa10_1D7_VLCL2 aPDL1 IGLV1-44-AA

<400> SEQUENCE: 39

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Arg Asp Ser
            20                  25                  30

Phe Val Asn Trp Tyr Gln Gln Leu Pro Gly Thr Ala Pro Lys Leu Leu
        35                  40                  45

Ile Tyr Ala Thr Asn Ile Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Trp Pro Phe Gly
                85                  90                  95

Thr Val Phe Gly Gly Gly Thr Lys Leu Thr Val Leu Gly Gln Pro Lys
            100                 105                 110

Ala Ala Pro Ser Val Thr Leu
        115
```

<210> SEQ ID NO 40
<211> LENGTH: 357
<212> TYPE: DNA
<213> ORGANISM: Artificial Sequence
<220> FEATURE:
<223> OTHER INFORMATION: S37_ Sa10_1D7_VLCL2 aPDL1 IGLV1-44-NT

<400> SEQUENCE: 40

```
cagtctgtgc tgactcagcc accctcagcg tctgggaccc ccgggcagag ggtcaccatc     60

tcttgttctg gaagcagctc caacatcagg gatagttttg taaactggta ccagcagctc    120

ccaggaacgg cccccaaact cctcatctat gctacgaata ttcggccctc aggggtccct    180

gaccgattct ctggctccaa gtctggcacc tcagcctccc tggccatcag tgggctccag    240

tctgaggatg aggctgatta ttactgtgca tcctggtggc cgttcggtac tgtgttcggc    300

ggagggacca agctgaccgt cctaggtcag cccaaggctg ccccctcggt cactctg       357
```

<210> SEQ ID NO 41
<211> LENGTH: 214
<212> TYPE: PRT
<213> ORGANISM: Artificial Sequence
<220> FEATURE:
<223> OTHER INFORMATION: S14_ Sh3_1C6_VLCL2 aPDL1 IGLV2-23-AA

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Val Lys Asn
            20                  25                  30

Asn Phe Val Ser Trp Tyr Gln Gln His Pro Gly Lys Ala Pro Lys Leu
        35                  40                  45

Met Ile Tyr Phe Gly Ser Val Arg Pro Ser Gly Val Ser Asn Arg Phe
    50                  55                  60

Ser Gly Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Trp Asp Met Pro Ala
                85                  90                  95

Leu Phe Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 42
<211> LENGTH: 645
<212> TYPE: DNA
<213> ORGANISM: Artificial Sequence
<220> FEATURE:
<223> OTHER INFORMATION: S14_ Sh3_1C6_VLCL2 aPDL1 IGLV2-23-NT

<400> SEQUENCE: 42
cagtctgccc tgactcagcc tgcctccgtg tctgggtctc ctggacagtc gatcaccatc 60
tcctgcactg gaaccagcag tgacgttgtt aagaataatt ttgtctcctg gtaccaacag 120
cacccaggca aagcccccaa actcatgatt tattttggga gtgttcggcc ctcaggggtt 180
tctaatcgct tctctggctc caagtctggc aacacggcct ccctgaccat ctctgggctc 240
caggctgagg acgaggctga ttattactgc agctcatggg atatgcctgc gcttttcttc 300
ggcggaggga ccaagctgac cgtcctaggt cagcccaagg ctgccccctc ggtcactctg 360
ttcccgccct cctctgagga gcttcaagcc aacaaggcca cactggtgtg tctcataagt 420
gacttctacc cgggagccgt gacagtggct tggaaagcag atagcagccc cgtcaaggcg 480
ggagtggaga ccaccacacc ctccaaacaa agcaacaaca agtacgcggc cagcagctat 540
ctgagcctga cgcctgagca gtggaagtcc cacagaagct acagctgcca ggtcacgcat 600
gaagggagca ccgtggagaa gacagtggcc cctacagaat gttca 645

<210> SEQ ID NO 43
<211> LENGTH: 119
<212> TYPE: PRT
<213> ORGANISM: Artificial Sequence
<220> FEATURE:
<223> OTHER INFORMATION: S14_ Sh3_1C6_VLCL2 aPDL1 IGLV2-23-AA

<400> SEQUENCE: 43

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Val Lys Asn
            20                  25                  30

Asn Phe Val Ser Trp Tyr Gln Gln His Pro Gly Lys Ala Pro Lys Leu
        35                  40                  45

Met Ile Tyr Phe Gly Ser Val Arg Pro Ser Gly Val Ser Asn Arg Phe
    50                  55                  60

Ser Gly Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Trp Asp Met Pro Ala
                85                  90                  95

Leu Phe Phe Gly Gly Gly Thr Lys Leu Thr Val Leu Gly Gln Pro Lys
            100                 105                 110

Ala Ala Pro Ser Val Thr Leu
        115
```

<210> SEQ ID NO 44
<211> LENGTH: 360
<212> TYPE: DNA
<213> ORGANISM: Artificial Sequence
<220> FEATURE:
<223> OTHER INFORMATION: S14_ Sh3_1C6_VLCL2 aPDL1 IGLV2-23-NT

<400> SEQUENCE: 44

```
cagtctgccc tgactcagcc tgcctccgtg tctgggtctc ctggacagtc gatcaccatc     60

tcctgcactg gaaccagcag tgacgttgtt aagaataatt ttgtctcctg gtaccaacag    120

cacccaggca aagcccccaa actcatgatt tattttggga gtgttcggcc ctcaggggtt    180

tctaatcgct tctctggctc caagtctggc aacacggcct ccctgaccat ctctgggctc    240

caggctgagg acgaggctga ttattactgc agctcatggg atatgcctgc gcttttcttc    300

ggcggaggga ccaagctgac cgtcctaggt cagcccaagg ctgccccctc ggtcactctg    360
```

<210> SEQ ID NO 45
<211> LENGTH: 215
<212> TYPE: PRT
<213> ORGANISM: Artificial Sequence
<220> FEATURE:
<223> OTHER INFORMATION: S15_ Sh3_1E2_VLCL2 aPDL1 IGLV2-23-AA

<400> SEQUENCE: 45

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Val Lys Asn
            20                  25                  30

Asn Phe Val Ser Trp Tyr Gln Gln His Pro Gly Lys Ala Pro Lys Leu
        35                  40                  45

Met Ile Tyr Phe Gly Ser Val Arg Pro Ser Gly Val Ser Asn Arg Phe
    50                  55                  60

Ser Gly Ser Lys Ser Gly Asn Thr Ala Ser Leu Thr Ile Ser Gly Leu
```

```
65                  70                  75                  80

Gln Ala Glu Asp Glu Ala Asp Tyr Tyr Cys Ser Ser Trp Asp Glu Pro
                85                  90                  95

Asp Arg Pro Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 46
<211> LENGTH: 645
<212> TYPE: DNA
<213> ORGANISM: Artificial Sequence
<220> FEATURE:
<223> OTHER INFORMATION: S15_ Sh3_1E2_VLCL2 aPDL1 IGLV2-23-NT

<400> SEQUENCE: 46

```
cagtctgccc tgactcagcc tgcctccgtg tctgggtctc ctggacagtc gatcaccatc     60

tcctgcactg gaaccagcag tgacgttgtt aagaataatt ttgtctcctg gtaccaacag    120

cacccaggca aagcccccaa actcatgatt tattttggga gtgttcggcc ctcaggggtt    180

tctaatcgct tctctggctc caagtctggc aacacggcct ccctgaccat ctctgggctc    240

caggctgagg acgaggctga ttattactgc agctcatggg atgagccgga caggcccttc    300

ggcggaggga ccaagctgac cgtcctaggt cagcccaagg ctgccccctc ggtcactctg    360

ttcccgccct cctctgagga gcttcaagcc aacaaggcca cactggtgtg tctcataagt    420

gacttctacc cgggagccgt gacagtggct tggaaagcag atagcagccc cgtcaaggcg    480

ggagtggaga ccaccacacc ctccaaacaa agcaacaaca agtacgcggc cagcagctat    540

ctgagcctga cgcctgagca gtggaagtcc cacagaagct acagctgcca ggtcacgcat    600

gaagggagca ccgtggagaa gacagtggcc cctacagaat gttca                     645
```

<210> SEQ ID NO 47
<211> LENGTH: 120
<212> TYPE: PRT
<213> ORGANISM: Artificial Sequence
<220> FEATURE:
<223> OTHER INFORMATION: S15_ Sh3_1E2_VLCL2 aPDL1 IGLV2-23-AA

<400> SEQUENCE: 47

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Val Lys Asn
            20                  25                  30

Asn Phe Val Ser Trp Tyr Gln Gln His Pro Gly Lys Ala Pro Lys Leu
        35                  40                  45
```

Met Ile Tyr Phe Gly Ser Val Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Glu Pro
                85                  90                  95

Asp Arg Pro Phe Gly Gly Gly Thr Lys Leu Thr Val Leu Gly Gln Pro
            100                 105                 110

Lys Ala Ala Pro Ser Val Thr Leu
        115                 120

<210> SEQ ID NO 48
<211> LENGTH: 360
<212> TYPE: DNA
<213> ORGANISM: Artificial Sequence
<220> FEATURE:
<223> OTHER INFORMATION: S15_ Sh3_1E2_VLCL2 aPDL1 IGLV2-23-NT

<400> SEQUENCE: 48
cagtctgccc tgactcagcc tgcctccgtg tctgggtctc ctggacagtc gatcaccatc 60
tcctgcactg gaaccagcag tgacgttgtt aagaataatt ttgtctcctg gtaccaacag 120
cacccaggca aagcccccaa actcatgatt tattttggga gtgttcggcc ctcaggggtt 180
tctaatcgct tctctggctc caagtctggc aacacggcct ccctgaccat ctctgggctc 240
caggctgagg acgaggctga ttattactgc agctcatggg atgagccgga caggcccttc 300
ggcggaggga ccaagctgac cgtcctaggt cagcccaagg ctgccccctc ggtcactctg 360

<210> SEQ ID NO 49
<211> LENGTH: 215
<212> TYPE: PRT
<213> ORGANISM: Artificial Sequence
<220> FEATURE:
<223> OTHER INFORMATION: S17_ Sh3_1D9_VLCL2 aPDL1 IGLV2-23-AA
<220> FEATURE:
<221> NAME/KEY: misc_feature
<222> LOCATION: (102)..(102)
<223> OTHER INFORMATION: Xaa can be any naturally occurring amino acid

<400> SEQUENCE: 49

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Val Lys Asn
            20                  25                  30

Asn Phe Val Ser Trp Tyr Gln Gln His Pro Gly Lys Ala Pro Lys Pro
        35                  40                  45

Met Ile Tyr Phe Gly Ser Val Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Leu Pro
                85                  90                  95

Phe Leu Met Phe Gly Xaa Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

```
Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 50
<211> LENGTH: 645
<212> TYPE: DNA
<213> ORGANISM: Artificial Sequence
<220> FEATURE:
<223> OTHER INFORMATION: S17_ Sh3_1D9_VLCL2 aPDL1 IGLV2-23-NT

<400> SEQUENCE: 50

cagtctgccc tgactcagcc tgcctccgtg tctgggtctc ctggacagtc gatcaccatc     60

tcctgcactg gaaccagcag tgacgttgtt aagaataatt ttgtctcctg gtaccaacag    120

cacccaggca aagcccccaa acccatgatt tattttggga gtgttcggcc ctcaggggtt    180

tctaatcgct tctctggctc caagtctggc aacacggcct ccctgaccat ctctgggctc    240

caggctgagg acgaggctga ttattactgc agctcatggg atctcccttt ccttatgttc    300

ggcggrggga ccaagctgac cgtcctaggt cagcccaagg ctgccccctc ggtcactctg    360

ttcccgccct cctctgagga gcttcaagcc aacaaggcca cactggtgtg tctcataagt    420

gacttctacc cgggagccgt gacagtggct tggaaagcag atagcagccc cgtcaaggcg    480

ggagtggaga ccaccacacc ctccaaacaa agcaacaaca agtacgcggc cagcagctat    540

ctgagcctga cgcctgagca gtggaagtcc cacagaagct acagctgcca ggtcacgcat    600

gaagggagca ccgtggagaa gacagtggcc cctacagaat gttca                    645


<210> SEQ ID NO 51
<211> LENGTH: 120
<212> TYPE: PRT
<213> ORGANISM: Artificial Sequence
<220> FEATURE:
<223> OTHER INFORMATION: S17_ Sh3_1D9_VLCL2 aPDL1 IGLV2-23-AA
<220> FEATURE:
<221> NAME/KEY: misc_feature
<222> LOCATION: (102)..(102)
<223> OTHER INFORMATION: Xaa can be any naturally occurring amino acid

<400> SEQUENCE: 51

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Val Lys Asn
            20                  25                  30

Asn Phe Val Ser Trp Tyr Gln Gln His Pro Gly Lys Ala Pro Lys Pro
        35                  40                  45

Met Ile Tyr Phe Gly Ser Val Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Leu Pro
                85                  90                  95
```

```
Phe Leu Met Phe Gly Xaa Gly Thr Lys Leu Thr Val Leu Gly Gln Pro
            100                 105                 110

Lys Ala Ala Pro Ser Val Thr Leu
        115                 120


<210> SEQ ID NO 52
<211> LENGTH: 360
<212> TYPE: DNA
<213> ORGANISM: Artificial Sequence
<220> FEATURE:
<223> OTHER INFORMATION: S17_ Sh3_1D9_VLCL2 aPDL1 IGLV2-23-NT

<400> SEQUENCE: 52

cagtctgccc tgactcagcc tgcctccgtg tctgggtctc ctggacagtc gatcaccatc      60

tcctgcactg gaaccagcag tgacgttgtt aagaataatt ttgtctcctg gtaccaacag     120

cacccaggca aagcccccaa acccatgatt tattttggga gtgttcggcc ctcaggggtt     180

tctaatcgct tctctggctc caagtctggc aacacggcct ccctgaccat ctctgggctc     240

caggctgagg acgaggctga ttattactgc agctcatggg atctcccttt ccttatgttc     300

ggcggrggga ccaagctgac cgtcctaggt cagcccaagg ctgcccccctc ggtcactctg    360


<210> SEQ ID NO 53
<211> LENGTH: 215
<212> TYPE: PRT
<213> ORGANISM: Artificial Sequence
<220> FEATURE:
<223> OTHER INFORMATION: S57_ Sh3_2D9_VLCL2 aPDL1 IGLV2-23-AA

<400> SEQUENCE: 53

Gln Ser Ala Leu Thr Gln Pro Ala Ser Val Ser Gly Ser Pro Gly Gln
1               5                   10                  15

Ser Ile Thr Ile Ser Cys Thr Ser Ile Ser Ser Asp Val Val Lys Asn
            20                  25                  30

Asn Phe Val Ser Trp Tyr Gln Gln His Pro Gly Lys Ala Pro Lys Leu
        35                  40                  45

Met Ile Tyr Phe Gly Ser Val Thr Ala Asp Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Glu Pro
                85                  90                  95

Asp Arg Pro Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 54
<211> LENGTH: 645
<212> TYPE: DNA
<213> ORGANISM: Artificial Sequence
<220> FEATURE:
<223> OTHER INFORMATION: S57_ Sh3_2D9_VLCL2 aPDL1 IGLV2-23-NT

<400> SEQUENCE: 54
cagtctgccc tgactcagcc tgcctccgtg tctgggtctc ctggacagtc gatcaccatc 60
tcctgcacta gtattagcag tgacgttgtt aagaataatt ttgtctcttg gtaccaacag 120
cacccaggca aagcccccaa actcatgatt tattttggga gtgttactgc tgatggggtt 180
tctaatcgct tctctggctc caagtctggc aacacggcct ccctgaccat ctctgggctc 240
caggctgagg acgaggctga ttattactgc agctcatggg atgagccgga caggcccttc 300
ggcggaggga ccaagctgac cgtcctaggt cagcccaagg ctgccccctc ggtcactctg 360
ttcccgccct cctctgagga gcttcaagcc aacaaggcca cactggtgtg tctcataagt 420
gacttctacc cgggagccgt gacagtggct tggaaagcag atagcagccc cgtcaaggcg 480
ggagtggaga ccaccacacc ctccaaacaa agcaacaaca agtacgcggc cagcagctat 540
ctgagcctga cgcctgagca gtggaagtcc cacagaagct acagctgcca ggtcacgcat 600
gaagggagca ccgtggagaa gacagtggcc cctacagaat gttca 645

<210> SEQ ID NO 55
<211> LENGTH: 120
<212> TYPE: PRT
<213> ORGANISM: Artificial Sequence
<220> FEATURE:
<223> OTHER INFORMATION: S57_ Sh3_2D9_VLCL2 aPDL1 IGLV2-23-AA

<400> SEQUENCE: 55

Gln Ser Ala Leu Thr Gln Pro Ala Ser Val Ser Gly Ser Pro Gly Gln
1 5 10 15

Ser Ile Thr Ile Ser Cys Thr Ser Ile Ser Ser Asp Val Val Lys Asn
20 25 30

Asn Phe Val Ser Trp Tyr Gln Gln His Pro Gly Lys Ala Pro Lys Leu
35 40 45

Met Ile Tyr Phe Gly Ser Val Thr Ala Asp Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Trp Asp Glu Pro
85 90 95

Asp Arg Pro Phe Gly Gly Gly Thr Lys Leu Thr Val Leu Gly Gln Pro
100 105 110

Lys Ala Ala Pro Ser Val Thr Leu
115 120

<210> SEQ ID NO 56
<211> LENGTH: 360
<212> TYPE: DNA
<213> ORGANISM: Artificial Sequence
<220> FEATURE:
<223> OTHER INFORMATION: S57_ Sh3_2D9_VLCL2 aPDL1 IGLV2-23-NT

<400> SEQUENCE: 56
cagtctgccc tgactcagcc tgcctccgtg tctgggtctc ctggacagtc gatcaccatc 60
tcctgcacta gtattagcag tgacgttgtt aagaataatt ttgtctcttg gtaccaacag 120
cacccaggca aagcccccaa actcatgatt tattttggga gtgttactgc tgatggggtt 180
tctaatcgct tctctggctc caagtctggc aacacggcct ccctgaccat ctctgggctc 240
caggctgagg acgaggctga ttattactgc agctcatggg atgagccgga caggcccttc 300
ggcggaggga ccaagctgac cgtcctaggt cagcccaagg ctgcccccctc ggtcactctg 360

<210> SEQ ID NO 57
<211> LENGTH: 215
<212> TYPE: PRT
<213> ORGANISM: Artificial Sequence
<220> FEATURE:
<223> OTHER INFORMATION: S58_ Sh3_1G5_VLCL2 aPDL1 IGLV2-23-AA

<400> SEQUENCE: 57

Gln Ser Ala Leu Thr Gln Pro Ala Ser Val Ser Gly Ser Pro Gly Gln
1 5 10 15

Ser Ile Thr Ile Ser Cys Asn Ser Pro Ser Ser Asp Val Val Lys Asn
20 25 30

Asn Phe Val Ser Trp Tyr Gln Gln His Pro Gly Lys Ala Pro Lys Leu
35 40 45

Met Ile Tyr Phe Gly Ser Val Thr Gly Pro Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Trp Asp Glu Pro
85 90 95

Asp Arg Pro Phe Gly Gly Gly Thr Lys Leu Thr Val Leu Gly Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Thr Val Ala Trp Lys Ala Asp Ser Ser Pro Val Lys Ala
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Arg
180 185 190

Ser Tyr Ser Cys Gln Val Thr His Glu Gly Ser Thr Val Glu Lys Thr
195 200 205

Val Ala Pro Thr Glu Cys Ser
210 215

<210> SEQ ID NO 58
<211> LENGTH: 645
<212> TYPE: DNA
<213> ORGANISM: Artificial Sequence
<220> FEATURE:
<223> OTHER INFORMATION: S58_ Sh3_1G5_VLCL2 aPDL1 IGLV2-23-NT

<400> SEQUENCE: 58
cagtctgccc tgactcagcc tgcctccgtg tctgggtctc ctggacagtc gatcaccatc 60
tcctgcaata gtcctagcag tgacgttgtt aagaataatt ttgtctcttg gtaccaacag 120
cacccaggca aagcccccaa actcatgatt tattttggga gtgttactgg tcctggggtt 180
tctaatcgct tctctggctc caagtctggc aacacggcct ccctgaccat ctctgggctc 240

```
caggctgagg acgaggctga ttattactgc agctcatggg atgagccgga caggcccttc    300

ggcggaggga ccaagctgac cgtcctaggt cagcccaagg ctgccccctc ggtcactctg    360

ttcccgccct cctctgagga gcttcaagcc aacaaggcca cactggtgtg tctcataagt    420

gacttctacc cgggagccgt gacagtggct tggaaagcag atagcagccc cgtcaaggcg    480

ggagtggaga ccaccacacc ctccaaacaa agcaacaaca agtacgcggc cagcagctat    540

ctgagcctga cgcctgagca gtggaagtcc cacagaagct acagctgcca ggtcacgcat    600

gaagggagca ccgtggagaa gacagtggcc cctacagaat gttca                    645
```

<210> SEQ ID NO 59
<211> LENGTH: 120
<212> TYPE: PRT
<213> ORGANISM: Artificial Sequence
<220> FEATURE:
<223> OTHER INFORMATION: S58_ Sh3_1G5_VLCL2 aPDL1 IGLV2-23-AA

<400> SEQUENCE: 59

```
Gln Ser Ala Leu Thr Gln Pro Ala Ser Val Ser Gly Ser Pro Gly Gln
1               5                   10                  15

Ser Ile Thr Ile Ser Cys Asn Ser Pro Ser Ser Asp Val Val Lys Asn
            20                  25                  30

Asn Phe Val Ser Trp Tyr Gln Gln His Pro Gly Lys Ala Pro Lys Leu
        35                  40                  45

Met Ile Tyr Phe Gly Ser Val Thr Gly Pro Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Glu Pro
                85                  90                  95

Asp Arg Pro Phe Gly Gly Gly Thr Lys Leu Thr Val Leu Gly Gln Pro
            100                 105                 110

Lys Ala Ala Pro Ser Val Thr Leu
        115                 120
```

<210> SEQ ID NO 60
<211> LENGTH: 360
<212> TYPE: DNA
<213> ORGANISM: Artificial Sequence
<220> FEATURE:
<223> OTHER INFORMATION: S58_ Sh3_1G5_VLCL2 aPDL1 IGLV2-23-NT

<400> SEQUENCE: 60

```
cagtctgccc tgactcagcc tgcctccgtg tctgggtctc ctggacagtc gatcaccatc     60

tcctgcaata gtcctagcag tgacgttgtt aagaataatt ttgtctcttg gtaccaacag    120

cacccaggca aagcccccaa actcatgatt tattttggga gtgttactgg tcctggggtt    180

tctaatcgct tctctggctc caagtctggc aacacggcct ccctgaccat ctctgggctc    240

caggctgagg acgaggctga ttattactgc agctcatggg atgagccgga caggcccttc    300

ggcggaggga ccaagctgac cgtcctaggt cagcccaagg ctgccccctc ggtcactctg    360
```

<210> SEQ ID NO 61
<211> LENGTH: 218
<212> TYPE: PRT
<213> ORGANISM: Artificial Sequence
<220> FEATURE:
<223> OTHER INFORMATION: S28_Sa2_1G7_VLCL2 aPDL1 IGLV2-44-AA

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Ala His Lys
            20                  25                  30

Pro Val Asn Trp Tyr Gln Gln Leu Pro Gly Thr Ala Pro Lys Leu Leu
        35                  40                  45

Ile Tyr His Asp Asn Ser Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Phe Ala Thr
                85                  90                  95

Trp Pro Ala Thr Glu Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

<210> SEQ ID NO 62
<211> LENGTH: 654
<212> TYPE: DNA
<213> ORGANISM: Artificial Sequence
<220> FEATURE:
<223> OTHER INFORMATION: S28_Sa2_1G7_VLCL2 aPDL1 IGLV2-44-NT

<400> SEQUENCE: 62
cagtctgtgc tgactcagcc accctcagcg tctgggaccc ccgggcagag ggtcaccatc 60
tcttgttctg gaagcagctc caacatcgct cataagcctg taaactggta ccagcagctc 120
ccaggaacgg cccccaaact cctcatctat catgataatt ctcggccctc aggggtccct 180
gaccgattct ctggctccaa gtctggcacc tcagcctccc tggccatcag tgggctccag 240
tctgaggatg aggctgatta ttactgtgca gcatgggatt tcgcgacgtg gccggctact 300
gaggtgttcg gcggagggac caagctgacc gtcctaggtc agcccaaggc tgccccctcg 360
gtcactctgt tcccgccctc ctctgaggag cttcaagcca acaaggccac actggtgtgt 420
ctcataagtg acttctaccc gggagccgtg acagtggctt ggaaagcaga tagcagcccc 480
gtcaaggcgg gagtggagac caccacaccc tccaaacaaa gcaacaacaa gtacgcggcc 540
agcagctatc tgagcctgac gcctgagcag tggaagtccc acagaagcta cagctgccag 600
gtcacgcatg aagggagcac cgtggagaag acagtggccc ctacagaatg ttca 654

<210> SEQ ID NO 63
<211> LENGTH: 123

<212> TYPE: PRT
<213> ORGANISM: Artificial Sequence
<220> FEATURE:
<223> OTHER INFORMATION: S28_Sa2_1G7_VLCL2 aPDL1 IGLV2-44-AA

<400> SEQUENCE: 63

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Ala His Lys
            20                  25                  30

Pro Val Asn Trp Tyr Gln Gln Leu Pro Gly Thr Ala Pro Lys Leu Leu
        35                  40                  45

Ile Tyr His Asp Asn Ser Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Phe Ala Thr
                85                  90                  95

Trp Pro Ala Thr Glu Val Phe Gly Gly Gly Thr Lys Leu Thr Val Leu
            100                 105                 110

Gly Gln Pro Lys Ala Ala Pro Ser Val Thr Leu
        115                 120
```

<210> SEQ ID NO 64
<211> LENGTH: 369
<212> TYPE: DNA
<213> ORGANISM: Artificial Sequence
<220> FEATURE:
<223> OTHER INFORMATION: S28_Sa2_1G7_VLCL2 aPDL1 IGLV2-44-NT

<400> SEQUENCE: 64

```
cagtctgtgc tgactcagcc accctcagcg tctgggaccc ccgggcagag ggtcaccatc      60

tcttgttctg gaagcagctc caacatcgct cataagcctg taaactggta ccagcagctc     120

ccaggaacgg cccccaaact cctcatctat catgataatt ctcggccctc aggggtccct     180

gaccgattct ctggctccaa gtctggcacc tcagcctccc tggccatcag tgggctccag     240

tctgaggatg aggctgatta ttactgtgca gcatgggatt tcgcgacgtg gccggctact     300

gaggtgttcg gcggagggac caagctgacc gtcctaggtc agcccaaggc tgccccctcg     360

gtcactctg                                                             369
```

<210> SEQ ID NO 65
<211> LENGTH: 218
<212> TYPE: PRT
<213> ORGANISM: Artificial Sequence
<220> FEATURE:
<223> OTHER INFORMATION: S30_ Sa2_C10_VLCL2 aPDL1 IGLV2-44-AA

<400> SEQUENCE: 65

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Ala His Lys
            20                  25                  30

Pro Val Asn Trp Tyr Gln Gln Leu Pro Gly Thr Ala Pro Lys Leu Leu
        35                  40                  45

Ile Tyr His Asp Asn Ser Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80
```

```
Ser Glu Asp Glu Ala Asp Tyr Tyr Cys Ala Ala Trp Asp Phe Ser Arg
                85                  90                  95

Trp Pro Ala Thr Glu Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 66
<211> LENGTH: 654
<212> TYPE: DNA
<213> ORGANISM: Artificial Sequence
<220> FEATURE:
<223> OTHER INFORMATION: S30_ Sa2_C10_VLCL2 aPDL1 IGLV2-44-NT

<400> SEQUENCE: 66

```
cagtctgtgc tgactcagcc accctcagcg tctgggaccc ccgggcagag ggtcaccatc     60

tcttgttctg gaagcagctc caacatcgct cataagcctg taaactggta ccagcagctc    120

ccaggaacgg cccccaaact cctcatctat catgataatt ctcggccctc aggggtccct    180

gaccgattct ctggctccag gtctggcacc tcagcctccc tggccatcag tgggctccag    240

tctgaggatg aggctgatta ttactgtgca gcatgggatt tcagccgctg gccggctact    300

gaggtgttcg gcggagggac caagctgacc gtcctaggtc agcccaaggc tgccccctcg    360

gtcactctgt tcccgccctc ctctgaggag cttcaagcca acaaggccac actggtgtgt    420

ctcataagtg acttctaccc gggagccgtg acagtggctt ggaaagcaga tagcagcccc    480

gtcaaggcgg gagtggagac caccacaccc tccaaacaaa gcaacaacaa gtacgcggcc    540

agcagctatc tgagcctgac gcctgagcag tggaagtccc acagaagcta cagctgccag    600

gtcacgcatg aagggagcac cgtggagaag acagtggccc ctacagaatg ttca          654
```

<210> SEQ ID NO 67
<211> LENGTH: 123
<212> TYPE: PRT
<213> ORGANISM: Artificial Sequence
<220> FEATURE:
<223> OTHER INFORMATION: S30_ Sa2_C10_VLCL2 aPDL1 IGLV2-44-AA

<400> SEQUENCE: 67

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Ala His Lys
            20                  25                  30

Pro Val Asn Trp Tyr Gln Gln Leu Pro Gly Thr Ala Pro Lys Leu Leu
        35                  40                  45
```

```
Ile Tyr His Asp Asn Ser Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Phe Ser Arg
                85                  90                  95

Trp Pro Ala Thr Glu Val Phe Gly Gly Gly Thr Lys Leu Thr Val Leu
            100                 105                 110

Gly Gln Pro Lys Ala Ala Pro Ser Val Thr Leu
        115                 120


<210> SEQ ID NO 68
<211> LENGTH: 369
<212> TYPE: DNA
<213> ORGANISM: Artificial Sequence
<220> FEATURE:
<223> OTHER INFORMATION: S30_ Sa2_C10_VLCL2 aPDL1 IGLV2-44-NT

<400> SEQUENCE: 68

cagtctgtgc tgactcagcc accctcagcg tctgggaccc ccgggcagag ggtcaccatc      60

tcttgttctg gaagcagctc caacatcgct cataagcctg taaactggta ccagcagctc     120

ccaggaacgg cccccaaact cctcatctat catgataatt ctcggccctc aggggtccct     180

gaccgattct ctggctccag gtctggcacc tcagcctccc tggccatcag tgggctccag     240

tctgaggatg aggctgatta ttactgtgca gcatgggatt tcagccgctg gccggctact     300

gaggtgttcg gcggagggac caagctgacc gtcctaggtc agcccaaggc tgccccctcg     360

gtcactctg                                                             369


<210> SEQ ID NO 69
<211> LENGTH: 218
<212> TYPE: PRT
<213> ORGANISM: Artificial Sequence
<220> FEATURE:
<223> OTHER INFORMATION: S94_Sa2_G11_VLCL2 aPDL1 IGLV1-44-AA

<400> SEQUENCE: 69

Gln Ser Val Leu Thr Gln Pro Pro Ser Ala Ser Gly Thr Pro Gly Gln
1               5                   10                  15

Arg Val Thr Ile Ser Cys Ile Ser Gly Ser Val Asp Ile Ala His Lys
            20                  25                  30

Pro Val Asn Trp Tyr Gln Gln Leu Pro Gly Thr Ala Pro Lys Leu Leu
        35                  40                  45

Ile Tyr His Asp Thr Ser Thr Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Phe Ala Thr
                85                  90                  95

Trp Pro Ala Thr Glu Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160
```

```
Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215


<210> SEQ ID NO 70
<211> LENGTH: 657
<212> TYPE: DNA
<213> ORGANISM: Artificial Sequence
<220> FEATURE:
<223> OTHER INFORMATION: S94_Sa2_G11_VLCL2 aPDL1 IGLV1-44-NT

<400> SEQUENCE: 70

cagtctgtgc tgactcagcc accctcagcg tctgggaccc ccgggcagag ggtcaccatc     60

tcttgtatta gtggtagcgt tgatatcgct cataagcctg taaactggta ccagcagctc    120

ccaggaacgg cccccaaact cctcatctat catgatacct ctactcctga tggggtccct    180

gaccgattct ctggctccaa gtctggcacc tcagcctccc tggccatcag tgggctccag    240

tctgaggatg aggctgatta ttactgtgca gcatgggatt tcgcgacgtg gccggctact    300

gaggtgttcg gcggagggac caagctgacc gtcctaggtc agcccaaggc tgccccctcg    360

gtcactctgt tcccgccctc ctctgaggag cttcaagcca acaaggccac actggtgtgt    420

ctcataagtg acttctaccc gggagccgtg acagtggctt ggaaagcaga tagcagcccc    480

gtcaaggcgg gagtggagac caccacaccc tccaaacaaa gcaacaacaa gtacgcggcc    540

agcagctatc tgagcctgac gcctgagcag tggaagtccc acagaagcta cagctgccag    600

gtcacgcatg aagggagcac cgtggagaag acagtggccc ctacagaatg ttcataa       657


<210> SEQ ID NO 71
<211> LENGTH: 123
<212> TYPE: PRT
<213> ORGANISM: Artificial Sequence
<220> FEATURE:
<223> OTHER INFORMATION: S94_Sa2_G11_VLCL2 aPDL1 IGLV1-44-AA

<400> SEQUENCE: 71

Gln Ser Val Leu Thr Gln Pro Pro Ser Ala Ser Gly Thr Pro Gly Gln
1               5                   10                  15

Arg Val Thr Ile Ser Cys Ile Ser Gly Ser Val Asp Ile Ala His Lys
            20                  25                  30

Pro Val Asn Trp Tyr Gln Gln Leu Pro Gly Thr Ala Pro Lys Leu Leu
        35                  40                  45

Ile Tyr His Asp Thr Ser Thr Pro Asp Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Phe Ala Thr
                85                  90                  95

Trp Pro Ala Thr Glu Val Phe Gly Gly Gly Thr Lys Leu Thr Val Leu
            100                 105                 110

Gly Gln Pro Lys Ala Ala Pro Ser Val Thr Leu
        115                 120
```

<210> SEQ ID NO 72
<211> LENGTH: 369
<212> TYPE: DNA
<213> ORGANISM: Artificial Sequence
<220> FEATURE:
<223> OTHER INFORMATION: S94_Sa2_G11_VLCL2 aPDL1 IGLV1-44-NT

<400> SEQUENCE: 72
cagtctgtgc tgactcagcc accctcagcg tctgggaccc ccgggcagag ggtcaccatc 60
tcttgtatta gtggtagcgt tgatatcgct cataagcctg taaactggta ccagcagctc 120
ccaggaacgg cccccaaact cctcatctat catgatacct ctactcctga tggggtccct 180
gaccgattct ctggctccaa gtctggcacc tcagcctccc tggccatcag tgggctccag 240
tctgaggatg aggctgatta ttactgtgca gcatgggatt tcgcgacgtg gccggctact 300
gaggtgttcg gcggagggac caagctgacc gtcctaggtc agcccaaggc tgccccctcg 360
gtcactctg 369

<210> SEQ ID NO 73
<211> LENGTH: 217
<212> TYPE: PRT
<213> ORGANISM: Artificial Sequence
<220> FEATURE:
<223> OTHER INFORMATION: S23_ Sc3_1H4_VLCL2 aPDL1 IGLV2-23-AA

<400> SEQUENCE: 73

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Ala Lys Ile
20 25 30

Pro Leu Val Ser Trp Tyr Gln Gln His Pro Gly Lys Ala Pro Lys Leu
35 40 45

Met Ile Tyr Phe Ala Ser Leu Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Trp Asp Asn Ala
85 90 95

Gly Asp Gly His Val Phe Gly Gly Gly Thr Lys Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys
165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

<210> SEQ ID NO 74
<211> LENGTH: 651
<212> TYPE: DNA

<213> ORGANISM: Artificial Sequence
<220> FEATURE:
<223> OTHER INFORMATION: S23_ Sc3_1H4_VLCL2 aPDL1 IGLV2-23-NT

<400> SEQUENCE: 74
cagtctgccc tgactcagcc tgcctccgtg tctgggtctc ctggacagtc gatcaccatc 60
tcctgcactg gaaccagcag tgacgttgct aagattcctc ttgtctcctg gtaccaacag 120
cacccaggca aagcccccaa actcatgatt tattttgcta gtcttcggcc ctcaggggtt 180
tctaatcgct tctctggctc caagtctggc aacacggcct ccctgaccat ctctgggctc 240
caggctgagg acgaggctga ttattactgc agctcatggg ataatgctgg tgatgggcat 300
gtgttcggcg gagggaccaa gctgaccgtc ctaggtcagc ccaaggctgc cccctcggtc 360
actctgttcc cgccctcctc tgaggagctt caagccaaca aggccacact ggtgtgtctc 420
ataagtgact tctacccggg agccgtgaca gtggcttgga aagcagatag cagccccgtc 480
aaggcgggag tggagaccac cacaccctcc aaacaaagca acaacaagta cgcggccagc 540
agctatctga gcctgacgcc tgagcagtgg aagtcccaca gaagctacag ctgccaggtc 600
acgcatgaag ggagcaccgt ggagaagaca gtggccccta cagaatgttc a 651

<210> SEQ ID NO 75
<211> LENGTH: 122
<212> TYPE: PRT
<213> ORGANISM: Artificial Sequence
<220> FEATURE:
<223> OTHER INFORMATION: S23_ Sc3_1H4_VLCL2 aPDL1 IGLV2-23-AA

<400> SEQUENCE: 75

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Ala Lys Ile
20 25 30

Pro Leu Val Ser Trp Tyr Gln Gln His Pro Gly Lys Ala Pro Lys Leu
35 40 45

Met Ile Tyr Phe Ala Ser Leu Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Trp Asp Asn Ala
85 90 95

Gly Asp Gly His Val Phe Gly Gly Gly Thr Lys Leu Thr Val Leu Gly
100 105 110

Gln Pro Lys Ala Ala Pro Ser Val Thr Leu
115 120

<210> SEQ ID NO 76
<211> LENGTH: 366
<212> TYPE: DNA
<213> ORGANISM: Artificial Sequence
<220> FEATURE:
<223> OTHER INFORMATION: S23_ Sc3_1H4_VLCL2 aPDL1 IGLV2-23-NT

<400> SEQUENCE: 76
cagtctgccc tgactcagcc tgcctccgtg tctgggtctc ctggacagtc gatcaccatc 60
tcctgcactg gaaccagcag tgacgttgct aagattcctc ttgtctcctg gtaccaacag 120
cacccaggca aagcccccaa actcatgatt tattttgcta gtcttcggcc ctcaggggtt 180
tctaatcgct tctctggctc caagtctggc aacacggcct ccctgaccat ctctgggctc 240
caggctgagg acgaggctga ttattactgc agctcatggg ataatgctgg tgatgggcat 300
gtgttcggcg gagggaccaa gctgaccgtc ctaggtcagc ccaaggctgc cccctcggtc 360
actctg 366

<210> SEQ ID NO 77
<211> LENGTH: 217
<212> TYPE: PRT
<213> ORGANISM: Artificial Sequence
<220> FEATURE:
<223> OTHER INFORMATION: S46_ Sc3_1E4_VLCL2 aPDL1 IGLV2-23-AA

<400> SEQUENCE: 77

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Leu Arg Pro
            20                  25                  30

Pro Leu Val Ser Trp Tyr Gln Gln His Pro Gly Lys Ala Pro Lys Leu
        35                  40                  45

Met Ile Tyr Phe Ala Ser Leu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Asn Ala
                85                  90                  95

Gly Asp Gly His Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 78
<211> LENGTH: 651
<212> TYPE: DNA
<213> ORGANISM: Artificial Sequence
<220> FEATURE:
<223> OTHER INFORMATION: S46_ Sc3_1E4_VLCL2 aPDL1 IGLV2-23-NT

<400> SEQUENCE: 78
cagtctgccc tgactcagcc tgcctccgtg tctgggtctc ctggacagtc gatcaccatc 60
tcctgcactg gaaccagcag tgacgttctt aggcctcctc ttgtctcctg gtaccaacag 120
cacccaggca aagcccccaa actcatgatt tattttgcta gtcttcggcc ctcaggggtt 180
tctaatcgct tctctggctc caagtctggc aacacggcct ccctgaccat ctctgggctc 240
caggctgagg acgaggctga ttattactgc agctcatggg ataatgctgg tgatgggcat 300

```
gtgttcggcg gagggaccaa gctgaccgtc ctaggtcagc ccaaggctgc cccctcggtc    360

actctgttcc cgccctcctc tgaggagctt caagccaaca aggccacact ggtgtgtctc    420

ataagtgact tctacccggg agccgtgaca gtggcttgga aagcagatag cagccccgtc    480

aaggcgggag tggagaccac cacaccctcc aaacaaagca acaacaagta cgcggccagc    540

agctatctga gcctgacgcc tgagcagtgg aagtcccaca gaagctacag ctgccaggtc    600

acgcatgaag ggagcaccgt ggagaagaca gtggccccta cagaatgttc a             651
```

<210> SEQ ID NO 79
<211> LENGTH: 122
<212> TYPE: PRT
<213> ORGANISM: Artificial Sequence
<220> FEATURE:
<223> OTHER INFORMATION: S46_ Sc3_1E4_VLCL2 aPDL1 IGLV2-23-AA

<400> SEQUENCE: 79

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Leu Arg Pro
            20                  25                  30

Pro Leu Val Ser Trp Tyr Gln Gln His Pro Gly Lys Ala Pro Lys Leu
        35                  40                  45

Met Ile Tyr Phe Ala Ser Leu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Asn Ala
                85                  90                  95

Gly Asp Gly His Val Phe Gly Gly Gly Thr Lys Leu Thr Val Leu Gly
            100                 105                 110

Gln Pro Lys Ala Ala Pro Ser Val Thr Leu
        115                 120
```

<210> SEQ ID NO 80
<211> LENGTH: 366
<212> TYPE: DNA
<213> ORGANISM: Artificial Sequence
<220> FEATURE:
<223> OTHER INFORMATION: S46_ Sc3_1E4_VLCL2 aPDL1 IGLV2-23-NT

<400> SEQUENCE: 80

```
cagtctgccc tgactcagcc tgcctccgtg tctgggtctc ctggacagtc gatcaccatc     60

tcctgcactg gaaccagcag tgacgttctt aggcctcctc ttgtctcctg gtaccaacag    120

cacccaggca aagcccccaa actcatgatt tattttgcta gtcttcggcc ctcaggggtt    180

tctaatcgct tctctggctc caagtctggc aacacggcct ccctgaccat ctctgggctc    240

caggctgagg acgaggctga ttattactgc agctcatggg ataatgctgg tgatgggcat    300

gtgttcggcg gagggaccaa gctgaccgtc ctaggtcagc ccaaggctgc cccctcggtc    360

actctg                                                               366
```

<210> SEQ ID NO 81
<211> LENGTH: 217
<212> TYPE: PRT
<213> ORGANISM: Artificial Sequence
<220> FEATURE:
<223> OTHER INFORMATION: S71_ Sc3_2C6_VLCL2 aPDL1 IGLV2-23-AA

<400> SEQUENCE: 81

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Phe Arg Pro
            20                  25                  30

Pro Leu Val Ser Trp Tyr Gln Gln His Pro Gly Lys Ala Pro Lys Leu
        35                  40                  45

Met Ile Tyr Phe Ala Ser Leu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp Gln Ser
                85                  90                  95

Gly Asp Gly His Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 82
<211> LENGTH: 651
<212> TYPE: DNA
<213> ORGANISM: Artificial Sequence
<220> FEATURE:
<223> OTHER INFORMATION: S71_ Sc3_2C6_VLCL2 aPDL1 IGLV2-23-NT

<400> SEQUENCE: 82

```
cagtctgccc tgactcagcc tgcctccgtg tctgggtctc ctggacagtc gatcaccatc     60

tcctgcactg gaaccagcag tgacgttttt aggcctcctc ttgtctcctg gtaccaacag    120

cacccaggca aagcccccaa actcatgatt tattttgcta gtcttcggcc ctcaggggtt    180

tctaatcgct tctctggctc caagtctggc aacacggcct ccctgaccat ctctgggctc    240

caggctgagg acgaggctga ttattactgc agctcatggg atcagtccgg ggacggccat    300

gtgttcggcg gagggaccaa gctgaccgtc ctaggtcagc ccaaggctgc cccctcggtc    360

actctgttcc cgccctcctc tgaggagctt caagccaaca aggccacact ggtgtgtctc    420

ataagtgact tctacccggg agccgtgaca gtggcttgga aagcagatag cagccccgtc    480

aaggcgggag tggagaccac cacaccctcc aaacaaagca acaacaagta cgcggccagc    540

agctatctga gcctgacgcc tgagcagtgg aagtcccaca gaagctacag ctgccaggtc    600

acgcatgaag ggagcaccgt ggagaagaca gtggccccta cagaatgttc a             651
```

<210> SEQ ID NO 83
<211> LENGTH: 122
<212> TYPE: PRT

<213> ORGANISM: Artificial Sequence
<220> FEATURE:
<223> OTHER INFORMATION: S71_ Sc3_2C6_VLCL2 aPDL1 IGLV2-23-AA

<400> SEQUENCE: 83

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Phe Arg Pro
20 25 30

Pro Leu Val Ser Trp Tyr Gln Gln His Pro Gly Lys Ala Pro Lys Leu
35 40 45

Met Ile Tyr Phe Ala Ser Leu Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Ser Ser Trp Asp Gln Ser
85 90 95

Gly Asp Gly His Val Phe Gly Gly Gly Thr Lys Leu Thr Val Leu Gly
100 105 110

Gln Pro Lys Ala Ala Pro Ser Val Thr Leu
115 120

<210> SEQ ID NO 84
<211> LENGTH: 366
<212> TYPE: DNA
<213> ORGANISM: Artificial Sequence
<220> FEATURE:
<223> OTHER INFORMATION: S71_ Sc3_2C6_VLCL2 aPDL1 IGLV2-23-NT

<400> SEQUENCE: 84
cagtctgccc tgactcagcc tgcctccgtg tctgggtctc ctggacagtc gatcaccatc 60
tcctgcactg gaaccagcag tgacgttttt aggcctcctc ttgtctcctg gtaccaacag 120
cacccaggca aagcccccaa actcatgatt tattttgcta gtcttcggcc ctcaggggtt 180
tctaatcgct tctctggctc caagtctggc aacacggcct ccctgaccat ctctgggctc 240
caggctgagg acgaggctga ttattactgc agctcatggg atcagtccgg ggacggccat 300
gtgttcggcg gagggaccaa gctgaccgtc ctaggtcagc ccaaggctgc cccctcggtc 360
actctg 366

<210> SEQ ID NO 85
<211> LENGTH: 217
<212> TYPE: PRT
<213> ORGANISM: Artificial Sequence
<220> FEATURE:
<223> OTHER INFORMATION: S79_ Sc3_1G7_VLCL2 aPDL1 IGLV2-23-AA

<400> SEQUENCE: 85

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Phe Arg Pro
20 25 30

Pro Leu Val Ser Trp Tyr Gln Gln His Pro Gly Lys Ala Pro Lys Leu
35 40 45

Met Ile Tyr Phe Ala Ser Leu Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

```
Gln Ala Glu Asp Glu Ala Asp Tyr Tyr Cys Ser Ser Trp Asp His Thr
                85                  90                  95

Gly Asp Gly His Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 86
<211> LENGTH: 651
<212> TYPE: DNA
<213> ORGANISM: Artificial Sequence
<220> FEATURE:
<223> OTHER INFORMATION: S79_ Sc3_1G7_VLCL2 aPDL1 IGLV2-23-NT

<400> SEQUENCE: 86

```
cagtctgccc tgactcagcc tgcctccgtg tctgggtctc ctggacagtc gatcaccatc      60

tcctgcactg gaaccagcag tgacgttttt aggcctcctc ttgtctcctg gtaccaacag     120

cacccaggca aagcccccaa actcatgatt tattttgcta gtcttcggcc ctcaggggtt     180

tctaatcgct tctctggctc caagtctggc aacacggcct ccctgaccat ctctgggctc     240

caggctgagg acgaggctga ttattactgc agctcatggg atcacacggg cgatgggcat     300

gtcttcggcg gagggaccaa gctgaccgtc ctaggtcagc ccaaggctgc cccctcggtc     360

actctgttcc cgccctcctc tgaggagctt caagccaaca aggccacact ggtgtgtctc     420

ataagtgact tctacccggg agccgtgaca gtggcttgga aagcagatag cagccccgtc     480

aaggcgggag tggagaccac cacaccctcc aaacaaagca acaacaagta cgcggccagc     540

agctatctga gcctgacgcc tgagcagtgg aagtcccaca gaagctacag ctgccaggtc     600

acgcatgaag ggagcaccgt ggagaagaca gtggccccta cagaatgttc a              651
```

<210> SEQ ID NO 87
<211> LENGTH: 122
<212> TYPE: PRT
<213> ORGANISM: Artificial Sequence
<220> FEATURE:
<223> OTHER INFORMATION: S79_ Sc3_1G7_VLCL2 aPDL1 IGLV2-23-AA

<400> SEQUENCE: 87

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Phe Arg Pro
            20                  25                  30

Pro Leu Val Ser Trp Tyr Gln Gln His Pro Gly Lys Ala Pro Lys Leu
        35                  40                  45

Met Ile Tyr Phe Ala Ser Leu Arg Pro Ser Gly Val Ser Asn Arg Phe
```

```
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Trp Asp His Thr
                85                  90                  95

Gly Asp Gly His Val Phe Gly Gly Gly Thr Lys Leu Thr Val Leu Gly
            100                 105                 110

Gln Pro Lys Ala Ala Pro Ser Val Thr Leu
        115                 120


<210> SEQ ID NO 88
<211> LENGTH: 366
<212> TYPE: DNA
<213> ORGANISM: Artificial Sequence
<220> FEATURE:
<223> OTHER INFORMATION: S79_ Sc3_1G7_VLCL2 aPDL1 IGLV2-23-NT

<400> SEQUENCE: 88

cagtctgccc tgactcagcc tgcctccgtg tctgggtctc ctggacagtc gatcaccatc      60

tcctgcactg gaaccagcag tgacgttttt aggcctcctc ttgtctcctg gtaccaacag     120

cacccaggca aagcccccaa actcatgatt tattttgcta gtcttcggcc ctcaggggtt     180

tctaatcgct tctctggctc caagtctggc aacacggcct ccctgaccat ctctgggctc     240

caggctgagg acgaggctga ttattactgc agctcatggg atcacacggg cgatgggcat     300

gtcttcggcg gagggaccaa gctgaccgtc ctaggtcagc ccaaggctgc cccctcggtc     360

actctg                                                                366


<210> SEQ ID NO 89
<211> LENGTH: 6
<212> TYPE: PRT
<213> ORGANISM: Artificial Sequence
<220> FEATURE:
<223> OTHER INFORMATION: CD47-CDRL1-1

<400> SEQUENCE: 89

Gln Asp Ile Asn Lys Tyr
1               5


<210> SEQ ID NO 90
<211> LENGTH: 6
<212> TYPE: PRT
<213> ORGANISM: Artificial Sequence
<220> FEATURE:
<223> OTHER INFORMATION: CD47-CDRL1-2

<400> SEQUENCE: 90

Gln Ser Ile Ser Ser Tyr
1               5


<210> SEQ ID NO 91
<211> LENGTH: 6
<212> TYPE: PRT
<213> ORGANISM: Artificial Sequence
<220> FEATURE:
<223> OTHER INFORMATION: CD47-CDRL1-3

<400> SEQUENCE: 91

Gln Ala Ile Asp Lys Phe
1               5


<210> SEQ ID NO 92
```

<211> LENGTH: 6
<212> TYPE: PRT
<213> ORGANISM: Artificial Sequence
<220> FEATURE:
<223> OTHER INFORMATION: CD47-CDRL1-4

<400> SEQUENCE: 92

Gln Thr Ile Asp Lys Phe
1               5

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96
<211> LENGTH: 10
<212> TYPE: PRT
<213> ORGANISM: Artificial Sequence
<220> FEATURE:
<223> OTHER INFORMATION: CD47-CDRL3-1

<400> SEQUENCE: 96

Gln Gln Met His Pro Arg Ala Pro Lys Thr
1               5                   10

<210> SEQ ID NO 97
<211> LENGTH: 10
<212> TYPE: PRT
<213> ORGANISM: Artificial Sequence
<220> FEATURE:
<223> OTHER INFORMATION: CD47-CDRL3-2

<400> SEQUENCE: 97

Gln Gln Met His Pro Arg Ser Pro Lys Ile
1               5                   10

<210> SEQ ID NO 98
<211> LENGTH: 10
<212> TYPE: PRT
<213> ORGANISM: Artificial Sequence
<220> FEATURE:
<223> OTHER INFORMATION: CD47-CDRL3-3

<400> SEQUENCE: 98

Gln Gln Met His Pro Arg Ala Asn Lys Ile
1               5                   10

<210> SEQ ID NO 99
<211> LENGTH: 10
<212> TYPE: PRT
<213> ORGANISM: Artificial Sequence
<220> FEATURE:
<223> OTHER INFORMATION: CD47-CDRL3-4

<400> SEQUENCE: 99

Gln Gln Met His Pro Arg Thr Ala Lys Gln
1 5 10

<210> SEQ ID NO 100
<211> LENGTH: 10
<212> TYPE: PRT
<213> ORGANISM: Artificial Sequence
<220> FEATURE:
<223> OTHER INFORMATION: CD47-CDRL3-5

<400> SEQUENCE: 100

Gln Gln Phe His Pro Arg Ala Pro Lys Gln
1 5 10

<210> SEQ ID NO 101
<211> LENGTH: 10
<212> TYPE: PRT
<213> ORGANISM: Artificial Sequence
<220> FEATURE:
<223> OTHER INFORMATION: CD47-CDRL3-6

<400> SEQUENCE: 101

Gln Gln Met His Pro Arg Ser His Lys Gln
1 5 10

<210> SEQ ID NO 102
<211> LENGTH: 10
<212> TYPE: PRT
<213> ORGANISM: Artificial Sequence
<220> FEATURE:
<223> OTHER INFORMATION: CD47-CDRL3-7

<400> SEQUENCE: 102

Gln Gln Phe His Pro Arg Ala Ala Lys Asn
1 5 10

<210> SEQ ID NO 103
<211> LENGTH: 215
<212> TYPE: PRT
<213> ORGANISM: Artificial Sequence
<220> FEATURE:
<223> OTHER INFORMATION: K26_K5A3_1C5 VKCK aCD47 IGKV1-33-AA

<400> SEQUENCE: 103

Asp Ile Gln Met Thr Gln Ser Pro Ser Ser Leu Ser Ala Ser Val Gly
1 5 10 15

Asp Arg Val Thr Ile Thr Cys Gln Val Ser Gln Asp Ile Asn Lys Tyr
20 25 30

Leu Asn Trp Tyr Gln Gln Lys Pro Gly Lys Ala Pro Lys Leu Leu Ile
35 40 45

Tyr Gly Ala Ser Arg Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Met His Pro Arg Ala Pro
85 90 95

Lys Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu 130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 104
<211> LENGTH: 648
<212> TYPE: DNA
<213> ORGANISM: Artificial Sequence
<220> FEATURE:
<223> OTHER INFORMATION: K26_K5A3_1C5 VKCK aCD47 IGKV1-33-NT

<400> SEQUENCE: 104
gacatccaga tgacccagtc tccatcctcc ctgtctgcat ctgtaggaga cagagtcacc 60
atcacttgcc aggtgagtca ggacattaat aagtatttaa attggtatca gcagaaacca 120
gggaaagccc ctaagctcct gatctacggt gcatccaggt tggaaacagg ggtcccatca 180
aggttcagtg gaagtggatc tgggacagat tttactttca ccatcagcag cctgcagcct 240
gaagatattg caacatatta ctgtcagcag atgcacccgc gcgccccgaa gaccttcggc 300
caagggacca aggtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttaa 648

<210> SEQ ID NO 105
<211> LENGTH: 108
<212> TYPE: PRT
<213> ORGANISM: Artificial Sequence
<220> FEATURE:
<223> OTHER INFORMATION: K26_K5A3_1C5 VKCK aCD47 IGKV1-33-AA

<400> SEQUENCE: 105

Asp Ile Gln Met Thr Gln Ser Pro Ser Ser Leu Ser Ala Ser Val Gly
1 5 10 15

Asp Arg Val Thr Ile Thr Cys Gln Val Ser Gln Asp Ile Asn Lys Tyr
20 25 30

Leu Asn Trp Tyr Gln Gln Lys Pro Gly Lys Ala Pro Lys Leu Leu Ile
35 40 45

Tyr Gly Ala Ser Arg Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Met His Pro Arg Ala Pro
85 90 95

Lys Thr Phe Gly Gln Gly Thr Lys Val Glu Ile Lys
100 105

<210> SEQ ID NO 106
<211> LENGTH: 324
<212> TYPE: DNA
<213> ORGANISM: Artificial Sequence
<220> FEATURE:
<223> OTHER INFORMATION: K26_K5A3_1C5 VKCK aCD47 IGKV1-33-NT

<400> SEQUENCE: 106
gacatccaga tgacccagtc tccatcctcc ctgtctgcat ctgtaggaga cagagtcacc 60
atcacttgcc aggtgagtca ggacattaat aagtatttaa attggtatca gcagaaacca 120
gggaaagccc ctaagctcct gatctacggt gcatccaggt tggaaacagg ggtcccatca 180
aggttcagtg gaagtggatc tgggacagat tttactttca ccatcagcag cctgcagcct 240
gaagatattg caacatatta ctgtcagcag atgcacccgc gcgccccgaa gaccttcggc 300
caagggacca aggtggaaat caaa 324

<210> SEQ ID NO 107
<211> LENGTH: 215
<212> TYPE: PRT
<213> ORGANISM: Artificial Sequence
<220> FEATURE:
<223> OTHER INFORMATION: K30_Ke8_1E3 VKCK aCD47 IGKV1-39-AA

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser Pro
                85                  90                  95

Lys Ile Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 108
<211> LENGTH: 648
<212> TYPE: DNA

<213> ORGANISM: Artificial Sequence
<220> FEATURE:
<223> OTHER INFORMATION: K30_Ke8_1E3 VKCK aCD47 IGKV1-39-NT

<400> SEQUENCE: 108
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcagcag atgcacccgc ggtcgccgaa gatcttcggc 300
caagggacca aggtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttaa 648

<210> SEQ ID NO 109
<211> LENGTH: 108
<212> TYPE: PRT
<213> ORGANISM: Artificial Sequence
<220> FEATURE:
<223> OTHER INFORMATION: K30_Ke8_1E3 VKCK aCD47 IGKV1-39-AA

<400> SEQUENCE: 109

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Met His Pro Arg Ser Pro
85 90 95

Lys Ile Phe Gly Gln Gly Thr Lys Val Glu Ile Lys
100 105

<210> SEQ ID NO 110
<211> LENGTH: 324
<212> TYPE: DNA
<213> ORGANISM: Artificial Sequence
<220> FEATURE:
<223> OTHER INFORMATION: K30_Ke8_1E3 VKCK aCD47 IGKV1-39-NT

<400> SEQUENCE: 110
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcagcag atgcacccgc ggtcgccgaa gatcttcggc 300
caagggacca aggtggaaat caaa 324

<210> SEQ ID NO 111
<211> LENGTH: 215
<212> TYPE: PRT
<213> ORGANISM: Artificial Sequence
<220> FEATURE:
<223> OTHER INFORMATION: K31_Ke8_1H2 VKCK aCD47 IGKV1-39-AA

<400> SEQUENCE: 111

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Met His Pro Arg Ala Asn
85 90 95

Lys Ile Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 112
<211> LENGTH: 647
<212> TYPE: DNA
<213> ORGANISM: Artificial Sequence
<220> FEATURE:
<223> OTHER INFORMATION: K31_Ke8_1H2 VKCK aCD47 IGKV1-39-NT

<400> SEQUENCE: 112
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcagcag atgcaccccc gcgccaacaa aatcttcggc 300
caagggacca aggtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480

```
caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgtta                  647
```

```
<210> SEQ ID NO 113
<211> LENGTH: 108
<212> TYPE: PRT
<213> ORGANISM: Artificial Sequence
<220> FEATURE:
<223> OTHER INFORMATION: K31_Ke8_1H2 VKCK aCD47 IGKV1-39-AA

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Asn
                85                  90                  95

Lys Ile Phe Gly Gln Gly Thr Lys Val Glu Ile Lys
            100                 105
```

```
<210> SEQ ID NO 114
<211> LENGTH: 324
<212> TYPE: DNA
<213> ORGANISM: Artificial Sequence
<220> FEATURE:
<223> OTHER INFORMATION: K31_Ke8_1H2 VKCK aCD47 IGKV1-39-NT

<400> SEQUENCE: 114

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag atgcaccccc gcgccaacaa aatcttcggc    300

caagggacca aggtggaaat caaa                                           324
```

```
<210> SEQ ID NO 115
<211> LENGTH: 215
<212> TYPE: PRT
<213> ORGANISM: Artificial Sequence
<220> FEATURE:
<223> OTHER INFORMATION: K32_Ke8_1H9 VKCK aCD47 IGKV1-39-AA

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Thr Ala
                85                  90                  95

Lys Gln Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 116
<211> LENGTH: 648
<212> TYPE: DNA
<213> ORGANISM: Artificial Sequence
<220> FEATURE:
<223> OTHER INFORMATION: K32_Ke8_1H9 VKCK aCD47 IGKV1-39-NT

<400> SEQUENCE: 116

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag atgcacccgc ggacggccaa gcagttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaa                 648
```

<210> SEQ ID NO 117
<211> LENGTH: 108
<212> TYPE: PRT
<213> ORGANISM: Artificial Sequence
<220> FEATURE:
<223> OTHER INFORMATION: K32_Ke8_1H9 VKCK aCD47 IGKV1-39-AA

<400> SEQUENCE: 117

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Thr Ala
                85                  90                  95

Lys Gln Phe Gly Gln Gly Thr Lys Val Glu Ile Lys
            100                 105


<210> SEQ ID NO 118
<211> LENGTH: 324
<212> TYPE: DNA
<213> ORGANISM: Artificial Sequence
<220> FEATURE:
<223> OTHER INFORMATION: K32_Ke8_1H9 VKCK aCD47 IGKV1-39-NT

<400> SEQUENCE: 118

gacatccaga tgacccagtc tccatcctcc ctgtctgcat ctgtaggaga cagagtcacc      60

atcacttgcc gggcaagtca gagcattagc agctatttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcagcag atgcacccgc ggacggccaa gcagttcggc     300

caagggacca aggtggaaat caaa                                            324


<210> SEQ ID NO 119
<211> LENGTH: 215
<212> TYPE: PRT
<213> ORGANISM: Artificial Sequence
<220> FEATURE:
<223> OTHER INFORMATION: K34_Ke8_2G11 VKCK aCD47 IGKV1-39-AA

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Pro Arg Ala Pro
                85                  90                  95

Lys Gln Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 120
<211> LENGTH: 648
<212> TYPE: DNA
<213> ORGANISM: Artificial Sequence
<220> FEATURE:
<223> OTHER INFORMATION: K34_Ke8_2G11 VKCK aCD47 IGKV1-39-NT

<400> SEQUENCE: 120

gacatccaga tgacccagtc tccatcctcc ctgtctgcat ctgtaggaga cagagtcacc      60

atcacttgcc gggcaagtca gagcattagc agctatttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcagcag tttcacccgc gggcgcccaa gcagttcggc     300

caagggacca aggtggaaat caaacgtacg gtggctgcac catctgtctt catcttcccg     360

ccatctgatg agcagttgaa atctggaact gcctctgttg tgtgcctgct gaataacttc     420

tatcccagag aggccaaagt acagtggaag gtggataacg ccctccaatc gggtaactcc     480

caggagagtg tcacagagca ggacagcaag gacagcacct acagcctcag cagcaccctg     540

acgctgagca aagcagacta cgagaaacac aaagtctacg cctgcgaagt cacccatcag     600

ggcctgagct cgcccgtcac aaagagcttc aacaggggag agtgttaa                   648


<210> SEQ ID NO 121
<211> LENGTH: 108
<212> TYPE: PRT
<213> ORGANISM: Artificial Sequence
<220> FEATURE:
<223> OTHER INFORMATION: K34_Ke8_2G11 VKCK aCD47 IGKV1-39-AA

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Pro Arg Ala Pro
                85                  90                  95

Lys Gln Phe Gly Gln Gly Thr Lys Val Glu Ile Lys
            100                 105


<210> SEQ ID NO 122
<211> LENGTH: 324
<212> TYPE: DNA
```

<213> ORGANISM: Artificial Sequence
<220> FEATURE:
<223> OTHER INFORMATION: K34_Ke8_2G11 VKCK aCD47 IGKV1-39-NT

<400> SEQUENCE: 122

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag tttcacccgc gggcgcccaa gcagttcggc    300

caagggacca aggtggaaat caaa                                           324
```

<210> SEQ ID NO 123
<211> LENGTH: 215
<212> TYPE: PRT
<213> ORGANISM: Artificial Sequence
<220> FEATURE:
<223> OTHER INFORMATION: K35_Ke8_2H3 VKCK aCD47 IGKV1-39-AA

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser His
                85                  90                  95

Lys Gln Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 124
<211> LENGTH: 648
<212> TYPE: DNA
<213> ORGANISM: Artificial Sequence
<220> FEATURE:
<223> OTHER INFORMATION: K35_Ke8_2H3 VKCK aCD47 IGKV1-39-NT

<400> SEQUENCE: 124

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag atgcacccgc ggagccacaa gcagttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaa                 648
```

<210> SEQ ID NO 125
<211> LENGTH: 108
<212> TYPE: PRT
<213> ORGANISM: Artificial Sequence
<220> FEATURE:
<223> OTHER INFORMATION: K35_Ke8_2H3 VKCK aCD47 IGKV1-39-AA

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ser His
                85                  90                  95

Lys Gln Phe Gly Gln Gly Thr Lys Val Glu Ile Lys
            100                 105
```

<210> SEQ ID NO 126
<211> LENGTH: 324
<212> TYPE: DNA
<213> ORGANISM: Artificial Sequence
<220> FEATURE:
<223> OTHER INFORMATION: K35_Ke8_2H3 VKCK aCD47 IGKV1-39-NT

<400> SEQUENCE: 126

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag atgcacccgc ggagccacaa gcagttcggc    300

caagggacca aggtggaaat caaa                                           324
```

<210> SEQ ID NO 127
<211> LENGTH: 215

<212> TYPE: PRT
<213> ORGANISM: Artificial Sequence
<220> FEATURE:
<223> OTHER INFORMATION: K36_Ke8_D11 VKCK aCD47 IGKV1-39-AA

<400> SEQUENCE: 127

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Pro Arg Ala Ala
                85                  90                  95

Lys Asn Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 128
<211> LENGTH: 648
<212> TYPE: DNA
<213> ORGANISM: Artificial Sequence
<220> FEATURE:
<223> OTHER INFORMATION: K36_Ke8_D11 VKCK aCD47 IGKV1-39-NT

<400> SEQUENCE: 128

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag tttcacccgc gggcggccaa gaacttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600
```

ggcctgagct cgcccgtcac aaagagcttc aacaggggag agtgttaa 648

<210> SEQ ID NO 129
<211> LENGTH: 108
<212> TYPE: PRT
<213> ORGANISM: Artificial Sequence
<220> FEATURE:
<223> OTHER INFORMATION: K36_Ke8_D11 VKCK aCD47 IGKV1-39-AA

<400> SEQUENCE: 129

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe His Pro Arg Ala Ala
85 90 95

Lys Asn Phe Gly Gln Gly Thr Lys Val Glu Ile Lys
100 105

<210> SEQ ID NO 130
<211> LENGTH: 324
<212> TYPE: DNA
<213> ORGANISM: Artificial Sequence
<220> FEATURE:
<223> OTHER INFORMATION: K36_Ke8_D11 VKCK aCD47 IGKV1-39-NT

<400> SEQUENCE: 130
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcagcag tttcacccgc gggcggccaa gaacttcggc 300
caagggacca aggtggaaat caaa 324

<210> SEQ ID NO 131
<211> LENGTH: 215
<212> TYPE: PRT
<213> ORGANISM: Artificial Sequence
<220> FEATURE:
<223> OTHER INFORMATION: K37_Ke8_1B1 VKCK aCD47 IGKV1-39-AA

<400> SEQUENCE: 131

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Asn Lys Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

```
Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 132
<211> LENGTH: 648
<212> TYPE: DNA
<213> ORGANISM: Artificial Sequence
<220> FEATURE:
<223> OTHER INFORMATION: K37_Ke8_1B1 VKCK aCD47 IGKV1-39-NT

<400> SEQUENCE: 132

gacatccaga tgacccagtc tccatcctcc ctgtctgcat ctgtaggaga cagagtcacc     60

atcacttgcc aggcgagtca ggacattaat aagtatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaa                 648


<210> SEQ ID NO 133
<211> LENGTH: 108
<212> TYPE: PRT
<213> ORGANISM: Artificial Sequence
<220> FEATURE:
<223> OTHER INFORMATION: K37_Ke8_1B1 VKCK aCD47 IGKV1-39-AA

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

<210> SEQ ID NO 134
<211> LENGTH: 324
<212> TYPE: DNA
<213> ORGANISM: Artificial Sequence
<220> FEATURE:
<223> OTHER INFORMATION: K37_Ke8_1B1 VKCK aCD47 IGKV1-39-NT

<400> SEQUENCE: 134

```
gacatccaga tgacccagtc tccatcctcc ctgtctgcat ctgtaggaga cagagtcacc      60

atcacttgcc aggcgagtca ggacattaat aagtatttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcagcag atgcacccgc gcgccccgaa gaccttcggc     300

caagggacca aggtggaaat caaa                                            324
```

<210> SEQ ID NO 135
<211> LENGTH: 215
<212> TYPE: PRT
<213> ORGANISM: Artificial Sequence
<220> FEATURE:
<223> OTHER INFORMATION: K40_Ke8_1H8 VKCK aCD47 IGKV1-39-AA

<400> SEQUENCE: 135

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Lys Phe
            20                  25                  30

Leu Asn Trp Tyr Gln Gln Lys Pro Gly Lys Ala Pro Lys Leu Leu Ile
        35                  40                  45

Tyr Ala Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 136
<211> LENGTH: 648
<212> TYPE: DNA
<213> ORGANISM: Artificial Sequence
<220> FEATURE:
<223> OTHER INFORMATION: K40_Ke8_1H8 VKCK aCD47 IGKV1-39-NT

<400> SEQUENCE: 136

gacatccaga tgacccagtc tccatcctcc ctgtctgcat ctgtaggaga cagagtcacc      60

atcacttgcc gggcaagtca ggctattgat aagtttttaa attggtatca gcagaaacca     120

gggaaagccc ctaagctcct gatctatgcg tcttccaggt tgcaaagtgg ggtcccatca     180

aggttcagtg gcagtggatc tgggacagat ttcactctca ccatcagcag tctgcaacct     240

gaagattttg caacttacta ctgtcagcag atgcacccgc gcgccccgaa gaccttcggc     300

caagggacca aggtggaaat caaacgtacg gtggctgcac catctgtctt catcttcccg     360

ccatctgatg agcagttgaa atctggaact gcctctgttg tgtgcctgct gaataacttc     420

tatcccagag aggccaaagt acagtggaag gtggataacg ccctccaatc gggtaactcc     480

caggagagtg tcacagagca ggacagcaag gacagcacct acagcctcag cagcaccctg     540

acgctgagca aagcagacta cgagaaacac aaagtctacg cctgcgaagt cacccatcag     600

ggcctgagct cgcccgtcac aaagagcttc aacaggggag agtgttaa                  648


<210> SEQ ID NO 137
<211> LENGTH: 108
<212> TYPE: PRT
<213> ORGANISM: Artificial Sequence
<220> FEATURE:
<223> OTHER INFORMATION: K40_Ke8_1H8 VKCK aCD47 IGKV1-39-AA

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Asp Lys Phe
            20                  25                  30

Leu Asn Trp Tyr Gln Gln Lys Pro Gly Lys Ala Pro Lys Leu Leu Ile
        35                  40                  45

Tyr Ala Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105


<210> SEQ ID NO 138
<211> LENGTH: 324
<212> TYPE: DNA
<213> ORGANISM: Artificial Sequence
<220> FEATURE:
<223> OTHER INFORMATION: K40_Ke8_1H8 VKCK aCD47 IGKV1-39-NT

<400> SEQUENCE: 138
```

```
gacatccaga tgacccagtc tccatcctcc ctgtctgcat ctgtaggaga cagagtcacc     60

atcacttgcc gggcaagtca ggctattgat aagtttttaa attggtatca gcagaaacca    120

gggaaagccc ctaagctcct gatctatgcg tcttccaggt tgcaaagtgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaa                                           324
```

<210> SEQ ID NO 139
<211> LENGTH: 215
<212> TYPE: PRT
<213> ORGANISM: Artificial Sequence
<220> FEATURE:
<223> OTHER INFORMATION: K41_Ke8_2D6 VKCK aCD47 IGKV1-39-AA

<400> SEQUENCE: 139

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asp Lys Phe
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 140
<211> LENGTH: 648
<212> TYPE: DNA
<213> ORGANISM: Artificial Sequence
<220> FEATURE:
<223> OTHER INFORMATION: K41_Ke8_2D6 VKCK aCD47 IGKV1-39-NT

<400> SEQUENCE: 140

```
gacatccaga tgacccagtc tccatcctcc ctgtctgcat ctgtaggaga cagagtcacc     60

atcacttgcc gggcaagtca gacgattgat aagtttttaa attggtatca gcagaaacca    120
```

```
gggaaagccc ctaagctcct gatctatgcg gcttccaggt tgcaaagtgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaa                648
```

<210> SEQ ID NO 141
<211> LENGTH: 108
<212> TYPE: PRT
<213> ORGANISM: Artificial Sequence
<220> FEATURE:
<223> OTHER INFORMATION: K41_Ke8_2D6 VKCK aCD47 IGKV1-39-AA

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asp Lys Phe
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

<210> SEQ ID NO 142
<211> LENGTH: 324
<212> TYPE: DNA
<213> ORGANISM: Artificial Sequence
<220> FEATURE:
<223> OTHER INFORMATION: K41_Ke8_2D6 VKCK aCD47 IGKV1-39-NT

<400> SEQUENCE: 142

```
gacatccaga tgacccagtc tccatcctcc ctgtctgcat ctgtaggaga cagagtcacc     60

atcacttgcc gggcaagtca gacgattgat aagtttttaa attggtatca gcagaaacca    120

gggaaagccc ctaagctcct gatctatgcg gcttccaggt tgcaaagtgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaa                                          324
```

<210> SEQ ID NO 143
<211> LENGTH: 215
<212> TYPE: PRT
<213> ORGANISM: Artificial Sequence
<220> FEATURE:
<223> OTHER INFORMATION: K43_Ke8_C10 VKCK aCD47 IGKV1-39-AA

<400> SEQUENCE: 143

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asp Lys Phe
            20                  25                  30

Leu Asn Trp Tyr Gln Gln Lys Pro Gly Lys Ala Pro Lys Leu Leu Ile
        35                  40                  45

Tyr Ala Ala Ser Ile Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 144
<211> LENGTH: 648
<212> TYPE: DNA
<213> ORGANISM: Artificial Sequence
<220> FEATURE:
<223> OTHER INFORMATION: K43_Ke8_C10 VKCK aCD47 IGKV1-39-NT

<400> SEQUENCE: 144

```
gacatccaga tgacccagtc tccatcctcc ctgtctgcat ctgtaggaga cagagtcacc     60

atcacttgcc gggcaagtca gactattgat aagtttttaa attggtatca gcagaaacca    120

gggaaagccc ctaagctcct gatctatgct gcgtccattt tgcaaaatgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaa                 648
```

<210> SEQ ID NO 145
<211> LENGTH: 108

<212> TYPE: PRT
<213> ORGANISM: Artificial Sequence
<220> FEATURE:
<223> OTHER INFORMATION: K43_Ke8_C10 VKCK aCD47 IGKV1-39-AA

<400> SEQUENCE: 145

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asp Lys Phe
            20                  25                  30

Leu Asn Trp Tyr Gln Gln Lys Pro Gly Lys Ala Pro Lys Leu Leu Ile
        35                  40                  45

Tyr Ala Ala Ser Ile Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

<210> SEQ ID NO 146
<211> LENGTH: 324
<212> TYPE: DNA
<213> ORGANISM: Artificial Sequence
<220> FEATURE:
<223> OTHER INFORMATION: K43_Ke8_C10 VKCK aCD47 IGKV1-39-NT

<400> SEQUENCE: 146

```
gacatccaga tgacccagtc tccatcctcc ctgtctgcat ctgtaggaga cagagtcacc     60

atcacttgcc gggcaagtca gactattgat aagtttttaa attggtatca gcagaaacca    120

gggaaagccc ctaagctcct gatctatgct gcgtccattt tgcaaaatgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaa                                           324
```

<210> SEQ ID NO 147
<211> LENGTH: 13
<212> TYPE: PRT
<213> ORGANISM: Artificial Sequence
<220> FEATURE:
<223> OTHER INFORMATION: PDL1-CDRL3-7

<400> SEQUENCE: 147

```
Ala Ala Trp Asp Phe Ala Thr Trp Pro Ala Thr Glu Val
1               5                   10
```

<210> SEQ ID NO 148
<211> LENGTH: 13
<212> TYPE: PRT
<213> ORGANISM: Artificial Sequence
<220> FEATURE:
<223> OTHER INFORMATION: PDL1-CDRL3-8

<400> SEQUENCE: 148

```
Ala Ala Trp Asp Phe Ser Arg Trp Pro Ala Thr Glu Val
1               5                   10
```

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205
<211> LENGTH: 330
<212> TYPE: DNA
<213> ORGANISM: Artificial Sequence
<220> FEATURE:

<223> OTHER INFORMATION: Dummy-VL1-NT

<400> SEQUENCE: 205
cagtctgtgt tgacgcagcc gccctcagtg tctgcggccc caggacagaa ggtcaccatc 60
tcctgctctg gaagcagctc caatattgag actggttctg tatcctggta ccagcagctc 120
ccaggaacag cccccaaact cctcatttat gacaataata agcgaccctc agggattcct 180
gaccgattct ctggctccaa gtctggcacg tcagccaccc tgggcatcac cggactccag 240
actggggacg aggccgatta ttactgcgga acatgggatg acagcctgcc tggatgggtg 300
ttcggcggag ggaccaagct gaccgtccta 330

<210> SEQ ID NO 206
<211> LENGTH: 110
<212> TYPE: PRT
<213> ORGANISM: Artificial Sequence
<220> FEATURE:
<223> OTHER INFORMATION: Dummy-VL1-AA

<400> SEQUENCE: 206

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Glu Thr Gly
20 25 30

Ser Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asp Tyr Tyr Cys Gly Thr Trp Asp Asp Ser Leu
85 90 95

Pro Gly Trp Val Phe Gly Gly Gly Thr Lys Leu Thr Val Leu
100 105 110

<210> SEQ ID NO 207
<211> LENGTH: 657
<212> TYPE: DNA
<213> ORGANISM: Artificial Sequence
<220> FEATURE:
<223> OTHER INFORMATION: DUMMY-LC2-NT

<400> SEQUENCE: 207
gaaatagtga tgacgcagtc tccagccacc ctgtctgtgt ctccagggga aagagccacc 60
ctctcctgca gggccagtca gacggttaag aataatttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataacaact ggttgcccat caacccctat 300
accttcggcc aagggaccaa ggtggaaatc aaacgtacgg tggctgcacc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgttaa 657

<210> SEQ ID NO 208
<211> LENGTH: 218
<212> TYPE: PRT
<213> ORGANISM: Artificial Sequence
<220> FEATURE:
<223> OTHER INFORMATION: DUMMY-LC2-AA

<400> SEQUENCE: 208

Glu Ile Val Met Thr Gln Ser Pro Ala Thr Leu Ser Val Ser Pro Gly
1 5 10 15

Glu Arg Ala Thr Leu Ser Cys Arg Ala Ser Gln Thr Val Lys Asn Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Leu Pro
85 90 95

Ile Asn Pro Tyr Thr Phe Gly Gln Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 209
<211> LENGTH: 333
<212> TYPE: DNA
<213> ORGANISM: Artificial Sequence
<220> FEATURE:
<223> OTHER INFORMATION: DUMMY-VL2-NT

<400> SEQUENCE: 209
gaaatagtga tgacgcagtc tccagccacc ctgtctgtgt ctccagggga aagagccacc 60
ctctcctgca gggccagtca gacggttaag aataatttag cctggtacca gcagaaacct 120
ggccaggctc ccaggctcct catctatggt gcatccacca gggccactgg tatcccagcc 180
aggttcagtg gcagtgggtc tgggacagag ttcactctca ccatcagcag cctgcagtct 240
gaagattttg cagtttatta ctgtcagcag tataacaact ggttgcccat caacccctat 300
accttcggcc aagggaccaa ggtggaaatc aaa 333

<210> SEQ ID NO 210
<211> LENGTH: 111
<212> TYPE: PRT
<213> ORGANISM: Artificial Sequence

<220> FEATURE:
<223> OTHER INFORMATION: DUMMY-VL2-AA

<400> SEQUENCE: 210

Glu Ile Val Met Thr Gln Ser Pro Ala Thr Leu Ser Val Ser Pro Gly
1 5 10 15

Glu Arg Ala Thr Leu Ser Cys Arg Ala Ser Gln Thr Val Lys Asn Asn
20 25 30

Leu Ala Trp Tyr Gln Gln Lys Pro Gly Gln Ala Pro Arg Leu Leu Ile
35 40 45

Tyr Gly Ala Ser Thr Arg Ala Thr Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Leu Pro
85 90 95

Ile Asn Pro Tyr Thr Phe Gly Gln Gly Thr Lys Val Glu Ile Lys
100 105 110

<210> SEQ ID NO 211
<211> LENGTH: 10
<212> TYPE: PRT
<213> ORGANISM: Artificial Sequence
<220> FEATURE:
<223> OTHER INFORMATION: CD47-CDRL3-8

<400> SEQUENCE: 211

Gln Gln Met His Pro Arg Ala Pro Lys Thr
1 5 10

<210> SEQ ID NO 212
<211> LENGTH: 11
<212> TYPE: PRT
<213> ORGANISM: Artificial Sequence
<220> FEATURE:
<223> OTHER INFORMATION: CD47-CDRL3-9

<400> SEQUENCE: 212

Gln Gln His Thr Ile Gly Thr Arg Thr Asn Thr
1 5 10

<210> SEQ ID NO 213
<211> LENGTH: 6
<212> TYPE: PRT
<213> ORGANISM: Artificial Sequence
<220> FEATURE:
<223> OTHER INFORMATION: CD47-CDRL1-5

<400> SEQUENCE: 213

Gln Val Ile Ala Asn Trp
1 5

<210> SEQ ID NO 214
<211> LENGTH: 6
<212> TYPE: PRT
<213> ORGANISM: Artificial Sequence
<220> FEATURE:
<223> OTHER INFORMATION: CD47-CDRL1-6

<400> SEQUENCE: 214

Gln Gly Ile Pro Ser Tyr
1 5

```
<210> SEQ ID NO 215

<400> SEQUENCE: 215

000


<210> SEQ ID NO 216

<400> SEQUENCE: 216

000


<210> SEQ ID NO 217

<400> SEQUENCE: 217

000


<210> SEQ ID NO 218

<400> SEQUENCE: 218

000


<210> SEQ ID NO 219

<400> SEQUENCE: 219

000


<210> SEQ ID NO 220
<211> LENGTH: 215
<212> TYPE: PRT
<213> ORGANISM: Artificial Sequence
<220> FEATURE:
<223> OTHER INFORMATION: K33_IgG_Ke8_2C4 VKCK-AA

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe His Lys Arg Ser Pro
                85                  90                  95

Gln Lys Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 221
<211> LENGTH: 648
<212> TYPE: DNA
<213> ORGANISM: Artificial Sequence
<220> FEATURE:
<223> OTHER INFORMATION: K33_IgG_Ke8_2C4 VKCK-NT

<400> SEQUENCE: 221
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcagcag tttcacaagc ggtccccgca gaagttcggc 300
caagggacca aggtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttaa 648

<210> SEQ ID NO 222
<211> LENGTH: 108
<212> TYPE: PRT
<213> ORGANISM: Artificial Sequence
<220> FEATURE:
<223> OTHER INFORMATION: K33_IgG_Ke8_2C4 VKCK-AA

<400> SEQUENCE: 222

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe His Lys Arg Ser Pro
85 90 95

Gln Lys Phe Gly Gln Gly Thr Lys Val Glu Ile Lys
100 105

<210> SEQ ID NO 223
<211> LENGTH: 324
<212> TYPE: DNA
<213> ORGANISM: Artificial Sequence
<220> FEATURE:
<223> OTHER INFORMATION: K33_IgG_Ke8_2C4 VKCK-NT

<400> SEQUENCE: 223

```
gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcagcag tttcacaagc ggtccccgca gaagttcggc    300

caagggacca aggtggaaat caaa                                            324
```

<210> SEQ ID NO 224
<211> LENGTH: 215
<212> TYPE: PRT
<213> ORGANISM: Artificial Sequence
<220> FEATURE:
<223> OTHER INFORMATION: K38_IgG_Ke8_1B4_VKCK-AA

<400> SEQUENCE: 224

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ala Asn Trp
            20                  25                  30

Leu Asn Trp Tyr Gln Gln Lys Pro Gly Lys Ala Pro Lys Leu Leu Ile
        35                  40                  45

Tyr Ala Gly Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 225
<211> LENGTH: 648
<212> TYPE: DNA
<213> ORGANISM: Artificial Sequence
<220> FEATURE:
<223> OTHER INFORMATION: K38_IgG_Ke8_1B4_VKCK-NT

<400> SEQUENCE: 225

```
gacatccaga tgacccagtc tccatcctcc ctgtctgcat ctgtaggaga cagagtcacc     60

atcacttgcc gggcaagtca ggttattgct aattggttaa attggtatca gcagaaacca    120
```

```
gggaaagccc ctaagctcct gatctatgct gggtcccatt tgcaaagtgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttaa                 648
```

<210> SEQ ID NO 226
<211> LENGTH: 108
<212> TYPE: PRT
<213> ORGANISM: Artificial Sequence
<220> FEATURE:
<223> OTHER INFORMATION: K38_IgG_Ke8_1B4_VKCK -AA

<400> SEQUENCE: 226

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ala Asn Trp
            20                  25                  30

Leu Asn Trp Tyr Gln Gln Lys Pro Gly Lys Ala Pro Lys Leu Leu Ile
        35                  40                  45

Tyr Ala Gly Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105
```

<210> SEQ ID NO 227
<211> LENGTH: 324
<212> TYPE: DNA
<213> ORGANISM: Artificial Sequence
<220> FEATURE:
<223> OTHER INFORMATION: K38_IgG_Ke8_1B4_VKCK -NT

<400> SEQUENCE: 227

```
gacatccaga tgacccagtc tccatcctcc ctgtctgcat ctgtaggaga cagagtcacc     60

atcacttgcc gggcaagtca ggttattgct aattggttaa attggtatca gcagaaacca    120

gggaaagccc ctaagctcct gatctatgct gggtcccatt tgcaaagtgg ggtcccatca    180

aggttcagtg gcagtggatc tgggacagat ttcactctca ccatcagcag tctgcaacct    240

gaagattttg caacttacta ctgtcagcag atgcacccgc gcgccccgaa gaccttcggc    300

caagggacca aggtggaaat caaa                                           324
```

<210> SEQ ID NO 228
<211> LENGTH: 216
<212> TYPE: PRT
<213> ORGANISM: Artificial Sequence
<220> FEATURE:
<223> OTHER INFORMATION: K106_IgG_Ke8_2C4 VKCK-AA

<400> SEQUENCE: 228

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Pro Ser Tyr
            20                  25                  30

Leu Asn Trp Tyr Gln Gln Lys Pro Gly Lys Ala Pro Lys Leu Leu Ile
        35                  40                  45

Tyr Gly Asn Ser Lys Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Thr Ile Gly Thr Arg
                85                  90                  95

Thr Asn Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 229
<211> LENGTH: 651
<212> TYPE: DNA
<213> ORGANISM: Artificial Sequence
<220> FEATURE:
<223> OTHER INFORMATION: K106_IgG_Ke8_2C4 VKCK-NT

<400> SEQUENCE: 229

```
gacatccaga tgacccagtc tccatcctcc ctgtctgcat ctgtaggaga cagagtcacc     60

atcacttgcc aggcgagtca gggtattcct agttatttaa attggtatca gcagaaacca    120

gggaaagccc ctaagctcct gatctacggt aattccaagt tggaaacagg ggtcccatca    180

aggttcagtg gaagtggatc tgggacagat tttactttca ccatcagcag cctgcagcct    240

gaagatattg caacatatta ctgtcagcag catactattg gtactaggac taataccttc    300

ggccaaggga ccaaggtgga aatcaaacgt acggtggctg caccatctgt cttcatcttc    360

ccgccatctg atgagcagtt gaaatctgga actgcctctg ttgtgtgcct gctgaataac    420

ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgtta a             651
```

<210> SEQ ID NO 230
<211> LENGTH: 109

<212> TYPE: PRT
<213> ORGANISM: Artificial Sequence
<220> FEATURE:
<223> OTHER INFORMATION: K106_IgG_Ke8_2C4 VKCK-AA

<400> SEQUENCE: 230

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Pro Ser Tyr
            20                  25                  30

Leu Asn Trp Tyr Gln Gln Lys Pro Gly Lys Ala Pro Lys Leu Leu Ile
        35                  40                  45

Tyr Gly Asn Ser Lys Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Thr Ile Gly Thr Arg
                85                  90                  95

Thr Asn Thr Phe Gly Gln Gly Thr Lys Val Glu Ile Lys
            100                 105
```

<210> SEQ ID NO 231
<211> LENGTH: 327
<212> TYPE: DNA
<213> ORGANISM: Artificial Sequence
<220> FEATURE:
<223> OTHER INFORMATION: K106_IgG_Ke8_2C4 VKCK-NT

<400> SEQUENCE: 231

```
gacatccaga tgacccagtc tccatcctcc ctgtctgcat ctgtaggaga cagagtcacc      60

atcacttgcc aggcgagtca gggtattcct agttatttaa attggtatca gcagaaacca     120

gggaaagccc ctaagctcct gatctacggt aattccaagt tggaaacagg ggtcccatca     180

aggttcagtg gaagtggatc tgggacagat tttactttca ccatcagcag cctgcagcct     240

gaagatattg caacatatta ctgtcagcag catactattg gtactaggac taataccttc     300

ggccaaggga ccaaggtgga aatcaaa                                         327
```

<210> SEQ ID NO 232
<211> LENGTH: 442
<212> TYPE: PRT
<213> ORGANISM: Artificial Sequence
<220> FEATURE:
<223> OTHER INFORMATION: VHCH IGHV3-23-S228P-R409K hIgG4-AA

<400> SEQUENCE: 232

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
```

```
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440


<210> SEQ ID NO 233
<211> LENGTH: 1329
<212> TYPE: DNA
<213> ORGANISM: Artificial Sequence
<220> FEATURE:
<223> OTHER INFORMATION: VHCH IGHV3-23-S228P-R409K hIgG4-NT

<400> SEQUENCE: 233

gaggtgcagc tgttggagtc tgggggaggc ttggtacagc ctggggggtc cctgagactc      60

tcctgtgcag cctctggatt cacctttagc agctatgcca tgagctgggt ccgccaggct     120
```

```
ccagggaagg ggctggagtg ggtctcagct attagtggta gtggtggtag cacatactac    180

gcagactccg tgaagggccg gttcaccatc tccagagaca attccaagaa cacgctgtat    240

ctgcaaatga acagcctgag agccgaggac acggccgtat attactgtgc gaaaagttat    300

ggtgcttttg actactgggg ccagggaacc ctggtcacag tctcgagcgc ctccaccaag    360

ggcccatccg tcttccccct ggcgccctgc tccaggagca cctccgagag cacagccgcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cgaagaccta cacttgcaac    600

gtagatcaca agcccagcaa caccaaggtg gacaagagag ttgagtccaa atatggtccc    660

ccatgcccac catgcccagc acctgagttc ctggggggac catcagtctt cctgttcccc    720

ccaaaaccca aggacactct catgatctcc cggacccctg aggtcacgtg cgtggtggtg    780

gacgtgagcc aggaagaccc cgaggtccag ttcaactggt acgtggatgg cgtggaggtg    840

cataatgcca agacaaagcc gcgggaggag cagttcaaca gcacgtaccg tgtggtcagc    900

gtcctcaccg tcctgcacca ggactggctg aacggcaagg agtacaagtg caaggtctcc    960

aacaaaggcc tcccgtcctc catcgagaaa accatctcca aagccaaagg gcagccccga   1020

gagccacagg tgtacaccct gcccccatcc caggaggaga tgaccaagaa ccaggtcagc   1080

ctgacttgcc tggtcaaagg cttctacccc agcgacatcg ccgtggagtg ggagagcaac   1140

gggcagccgg agaacaacta caagaccacg cctcccgtgc tggactccga cggctccttc   1200

ttcctctaca gcaagctaac cgtggacaag tccaggtggc aggaggggaa tgtcttctca   1260

tgctccgtga tgcatgaggc tctgcacaac cactacacac agaagagcct ctccctgtct   1320

ctgggttaa                                                           1329
```

```
<210> SEQ ID NO 234
<211> LENGTH: 116
<212> TYPE: PRT
<213> ORGANISM: Artificial Sequence
<220> FEATURE:
<223> OTHER INFORMATION: VH IGHV3-23-S228P-R409K hIgG4-AA

<400> SEQUENCE: 234

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115


<210> SEQ ID NO 235
<211> LENGTH: 348
```

<212> TYPE: DNA
<213> ORGANISM: Artificial Sequence
<220> FEATURE:
<223> OTHER INFORMATION: VH IGHV3-23-S228P-R409K hIgG4-NT

<400> SEQUENCE: 235
gaggtgcagc tgttggagtc tgggggaggc ttggtacagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaaagttat 300
ggtgcttttg actactgggg ccagggaacc ctggtcacag tctcgagc 348

<210> SEQ ID NO 236
<211> LENGTH: 19
<212> TYPE: PRT
<213> ORGANISM: Artificial Sequence
<220> FEATURE:
<223> OTHER INFORMATION: Leader sequence-AA

<400> SEQUENCE: 236

Met Glu Trp Ser Trp Val Phe Leu Phe Phe Leu Ser Val Thr Thr Gly
1 5 10 15

Val His Ser

<210> SEQ ID NO 237
<211> LENGTH: 57
<212> TYPE: DNA
<213> ORGANISM: Artificial Sequence
<220> FEATURE:
<223> OTHER INFORMATION: Leader sequence-NT

<400> SEQUENCE: 237
atggaatgga gctgggtctt tctcttcttc ctgtcagtaa ctacaggtgt ccactcc 57

<210> SEQ ID NO 238
<211> LENGTH: 215
<212> TYPE: PRT
<213> ORGANISM: Artificial Sequence
<220> FEATURE:
<223> OTHER INFORMATION: K91_ IgG_Ke8_2D4 VKCK-AA

<400> SEQUENCE: 238

Asp Ile Gln Met Thr Gln Ser Pro Ser Ser Leu Ser Ala Ser Val Gly
1 5 10 15

Asp Arg Val Thr Ile Thr Cys Asn Val Asp Gln Val Ile Ala Asn Trp
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Met His Pro Arg Ala Pro
85 90 95

Lys Gln Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 239
<211> LENGTH: 648
<212> TYPE: DNA
<213> ORGANISM: Artificial Sequence
<220> FEATURE:
<223> OTHER INFORMATION: K91_ IgG_Ke8_2D4 VKCK-NT

<400> SEQUENCE: 239

gacatccaga tgacccagtc tccatcctcc ctgtctgcat ctgtaggaga cagagtcacc      60

atcacttgca atgttgatca ggttattgct aattggttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcagcag atgcacccgc gcgctccgaa gcagttcggc     300

caagggacca aggtggaaat caaacgtacg gtggctgcac catctgtctt catcttcccg     360

ccatctgatg agcagttgaa atctggaact gcctctgttg tgtgcctgct gaataacttc     420

tatcccagag aggccaaagt acagtggaag gtggataacg ccctccaatc gggtaactcc     480

caggagagtg tcacagagca ggacagcaag gacagcacct acagcctcag cagcaccctg     540

acgctgagca aagcagacta cgagaaacac aaagtctacg cctgcgaagt cacccatcag     600

ggcctgagct cgcccgtcac aaagagcttc aacaggggag agtgttaa                  648


<210> SEQ ID NO 240
<211> LENGTH: 108
<212> TYPE: PRT
<213> ORGANISM: Artificial Sequence
<220> FEATURE:
<223> OTHER INFORMATION: K91_ IgG_Ke8_2D4 VKCK-AA

<400> SEQUENCE: 240

Asp Ile Gln Met Thr Gln Ser Pro Ser Ser Leu Ser Ala Ser Val Gly
1               5                   10                  15

Asp Arg Val Thr Ile Thr Cys Asn Val Asp Gln Val Ile Ala Asn Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95
```

```
Lys Gln Phe Gly Gln Gly Thr Lys Val Glu Ile Lys
            100                 105
```

<210> SEQ ID NO 241
<211> LENGTH: 324
<212> TYPE: DNA
<213> ORGANISM: Artificial Sequence
<220> FEATURE:
<223> OTHER INFORMATION: K91_ IgG_Ke8_2D4 VKCK-NT

<400> SEQUENCE: 241

```
gacatccaga tgacccagtc tccatcctcc ctgtctgcat ctgtaggaga cagagtcacc      60

atcacttgca atgttgatca ggttattgct aattggttaa attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcagcag atgcacccgc gcgctccgaa gcagttcggc     300

caagggacca aggtggaaat caaa                                            324
```

<210> SEQ ID NO 242
<211> LENGTH: 216
<212> TYPE: PRT
<213> ORGANISM: Artificial Sequence
<220> FEATURE:
<223> OTHER INFORMATION: Dummy-LC1-AA

<400> SEQUENCE: 242

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Thr Gly
            20                  25                  30

Ser Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asp Ser Leu
                85                  90                  95

Pro Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 243

```
<211> LENGTH: 651
<212> TYPE: DNA
<213> ORGANISM: Artificial Sequence
<220> FEATURE:
<223> OTHER INFORMATION: Dummy-LC1-NT

<400> SEQUENCE: 243

cagtctgtgt tgacgcagcc gccctcagtg tctgcggccc caggacagaa ggtcaccatc     60

tcctgctctg gaagcagctc caatattgag actggttctg tatcctggta ccagcagctc    120

ccaggaacag cccccaaact cctcatttat gacaataata agcgaccctc agggattcct    180

gaccgattct ctggctccaa gtctggcacg tcagccaccc tgggcatcac cggactccag    240

actggggacg aggccgatta ttactgcgga acatgggatg acagcctgcc tggatgggtg    300

ttcggcggag ggaccaagct gaccgtccta ggtcagccca aggctgcccc ctcggtcact    360

ctgttcccgc cctcctctga ggagcttcaa gccaacaagg ccacactggt gtgtctcata    420

agtgacttct acccgggagc cgtgacagtg gcttggaaag cagatagcag ccccgtcaag    480

gcgggagtgg agaccaccac accctccaaa caaagcaaca acaagtacgc ggccagcagc    540

tatctgagcc tgacgcctga gcagtggaag tcccacagaa gctacagctg ccaggtcacg    600

catgaaggga gcaccgtgga gaagacagtg gcccctacag aatgttcata a             651


<210> SEQ ID NO 244
<211> LENGTH: 10
<212> TYPE: PRT
<213> ORGANISM: Artificial Sequence
<220> FEATURE:
<223> OTHER INFORMATION: Synthetic

<400> SEQUENCE: 244

Gln Gln Phe His Lys Arg Ser Pro Gln Lys
1               5                   10


<210> SEQ ID NO 245
<211> LENGTH: 10
<212> TYPE: PRT
<213> ORGANISM: Artificial Sequence
<220> FEATURE:
<223> OTHER INFORMATION: Synthetic

<400> SEQUENCE: 245

Gln Gln Met His Pro Arg Ala Pro Lys Gln
1               5                   10
```